US012583818B2

(12) United States Patent
Im et al.

(10) Patent No.: US 12,583,818 B2
(45) Date of Patent: Mar. 24, 2026

(54) COMPOUND, PREPARATION METHOD THEREOF, AND USE THEREOF

(71) Applicants: DAEGU-GYEONGBUK MEDICAL INNOVATION FOUNDATION, Daegu (KR); PIMEDBIO, INC., Gyeonggi-do (KR)

(72) Inventors: Chun Young Im, Daegu (KR); Sang Hyun Min, Daegu (KR); Ji Hoon Yu, Daegu (KR); Eun Bi Ko, Daegu (KR); So Young Kim, Daegu (KR); Seungyeon Lee, Daegu (KR); Dong Kyu Choi, Daegu (KR); Heejin Lee, Daegu (KR); Ga Young Park, Daegu (KR); Doohyun Lee, Daegu (KR); Eunmi Hong, Daegu (KR); Hui-Jeon Jeon, Daegu (KR); Young-Hoon Park, Daegu (KR); Ye Ri Han, Daegu (KR); Nam Hui Kim, Daegu (KR); Jun Woo Kim, Daegu (KR); Bae Jun Oh, Daegu (KR); Jeong-Eun Park, Daegu (KR); Chang Hoon Seo, Daegu (KR); Minsoo Song, Daegu (KR); Seonggu Ro, Gyeonggi-do (KR); Dongkyu Shin, Gyeonggi-do (KR)

(73) Assignees: DAEGU-GYEONGBUK MEDICAL INNOVATION FOUNDATION, Daegu (KR); PIMEDBIO, INC., Gyeonggi-do (KR)

( * ) Notice: Subject to any disclaimer, the term of this patent is extended or adjusted under 35 U.S.C. 154(b) by 875 days.

(21) Appl. No.: 17/788,440

(22) PCT Filed: Jan. 15, 2021

(86) PCT No.: PCT/KR2021/000614

§ 371 (c)(1),
(2) Date: Jun. 23, 2022

(87) PCT Pub. No.: WO2021/145729

PCT Pub. Date: Jul. 22, 2021

(65) Prior Publication Data

US 2023/0142654 A1 May 11, 2023

(30) Foreign Application Priority Data

Jan. 17, 2020 (KR) ........................ 10-2020-0006739
Dec. 14, 2020 (KR) ........................ 10-2020-0174237

(51) Int. Cl.
*C07D 209/14* (2006.01)
*C07C 311/29* (2006.01)
(Continued)

(52) U.S. Cl.
CPC .......... *C07C 311/29* (2013.01); *C07D 207/27* (2013.01); *C07D 209/14* (2013.01); *C07D 209/16* (2013.01); *C07D 209/86* (2013.01); *C07D 211/10* (2013.01); *C07D 235/06* (2013.01); *C07D 235/14* (2013.01); *C07D 295/12* (2013.01); *C07D 295/14* (2013.01); *C07D 401/12* (2013.01); *C07D 401/14* (2013.01); *C07D 403/12* (2013.01); *C07D 471/04* (2013.01)

(58) Field of Classification Search
CPC .. C07D 209/14; C07D 211/10; C07D 235/06; C07D 401/12; C07D 403/12
See application file for complete search history.

(56) References Cited

U.S. PATENT DOCUMENTS

| | | | | |
|---|---|---|---|---|
| 8,916,553 B2 | 12/2014 | Austin et al. | .............. | 514/235.8 |
| 2003/0130271 A1 | 7/2003 | Pikul et al. | ................ | 514/226.8 |
| 2011/0130387 A1 | 6/2011 | Nunes et al. | ................. | 514/218 |

FOREIGN PATENT DOCUMENTS

| | | |
|---|---|---|
| JP | 2006-514614 | 5/2006 |
| JP | 2009503114 | 1/2009 |

(Continued)

OTHER PUBLICATIONS

Glioblastoma (GBM) [online]; retrieved from the internet on Sep. 1, 2025; URL https://my.clevelandclinic.org/health/diseases/17032-glioblastoma.*

Guo et al: "Design and bio-evaluation of indole derivatives as potent Kv1.5 inhibitors", Bioorganic & Medicinal Chemistry, Elsevier, Amsterdam, NL, vol. 21, No. 21, Aug. 31, 2013 (Aug. 31, 2013), pp. 6466-6476, XP028732741, ISSN: 0968-0896, DOI: 10.1016/J.BMC.2013.08.041.

Hopkins et al., "Synthesis and Identification of Heteroaromatic N-Benzyl Sulfonamides as Potential Anticancer Agents" Organic & Molecular Biology 2019, DOI : 10.1039/C9OB0169E 12 pages.

Jiang et al: "Hypervalent lodine-Mediated Cyclization of Homotryptamine Derivatives", European Journal of Organic Chemistry, WILEY-VCH, DE, vol. 2019, No. 12, Mar. 18, 2019 (Mar. 18, 2019), pp. 2268-2274, XP072119559, ISSN: 1434-193X, DOI: 10.1002/EJOC.201801842; Accepted Manuscript 9 pages.

(Continued)

*Primary Examiner* — Shawquia Jackson
(74) *Attorney, Agent, or Firm* — Licata & Tyrrell P.C.

(57) ABSTRACT

The present invention relates to a method for preparing a biomaterial having selectively functionalized tyrosine, a biomaterial having selectively functionalized tyrosine, and a pharmaceutical composition containing the same as an active ingredient. The method for preparing a biomaterial to which a compound represented by formula 2 is coupled, of the present invention, allows the compound represented by formula 2 to be selectively coupled, in a high yield in a biomaterial, to tyrosine, which is present on the surface of an aqueous solution such that the coupling thereof to amino acids other than tyrosine does not occur and, when only one tyrosine is present, heterogeneous mixtures are not present and the inherent activity of the biomaterial is maintained, and thus the compound can be effectively used as a pharmaceutical composition containing a biomaterial drug as an active ingredient. In addition, the method can selectively functionalize tyrosine, and thus can be effectively used for tyrosine functionalization in a biomaterial.

16 Claims, No Drawings

(51) Int. Cl.

| | |
|---|---|
| ***C07D 207/27*** | (2006.01) |
| ***C07D 209/16*** | (2006.01) |
| ***C07D 209/86*** | (2006.01) |
| ***C07D 211/10*** | (2006.01) |
| ***C07D 235/06*** | (2006.01) |
| ***C07D 235/14*** | (2006.01) |
| ***C07D 295/12*** | (2006.01) |
| ***C07D 295/14*** | (2006.01) |
| ***C07D 401/12*** | (2006.01) |
| ***C07D 401/14*** | (2006.01) |
| ***C07D 403/12*** | (2006.01) |
| ***C07D 471/04*** | (2006.01) |

(56) References Cited

FOREIGN PATENT DOCUMENTS

| | | |
|---|---|---|
| JP | 2013-532688 | 8/2013 |
| KR | 10-2017-0110017 | 10/2017 |
| WO | 2006/034390 | 3/2006 |
| WO | 2006/040646 | 4/2006 |
| WO | 2007/002433 | 1/2007 |
| WO | 2012/015723 | 2/2012 |
| WO | 2018/178384 | 10/2018 |
| WO | 2019/031472 | 2/2019 |
| WO | 2019/099703 | 5/2019 |

OTHER PUBLICATIONS

Jiang et al: "Hypervalent lodine-Mediated Cyclization of Homotryptamine Derivatives", European Journal of Organic Chemistry, WILEY-VCH, DE, vol. 2019, No. 12, Mar. 18, 2019 (Mar. 18, 2019), pp. 2268-2274, XP072119559, ISSN: 1434-193X, DOI: 10.1002/EJOC.201801842.

Kaldrikyan et al: "Arylsulfonic acid derivatives. VIII. Some substituted 4-alkoxybenzenesulfonamides and sulfonylureas", Armyanskii Khimicheskii Zhurnal/ Aikakan Himiakan Amsagir/ Armenian Chemical Journal, Akademiya Nauk Armenii, Erevan, AI, vol. 30, No. 7, 1977, pp. 600-603, XP009544188, ISSN: 0515-9628.

Li Yan et al., "Bioinsipred radical cyclization of tryptamines: synthesis of peroxypyrroloindolenines as potential anti-cancer agents" Chemical communications, vol. 55, No. 1, 2019, pp. 63-66.

Kaldrikian et al. "Arylsulphonic Acid Derivatives" Armyanskii Khimicheskii Zhurnal 1977 30(7) : 600-603.

CAS Registry No. 1907661-22-6, May 10, 2016.

CAS Registry No. 1902001-53-9, May 2, 2016.

CAS Registry No. 1645275-22-4, Feb. 6, 2015.

CAS Registry No. 1645275-17-7, Feb. 6, 2015.

CAS Registry No. 1645275-13-3, Feb. 6, 2015.

International Search Report in PCT/KR2021/000614 dated Apr. 16, 2021.

Caporuscio et al. "Structure-Based Design of Potent Aromatase Inhibitors by High Throughput Docking" Journal of Medicinal Chemistry 2011 54:4006-4017.

Chen et al. "Prolyl isomerase Pin1:a promoter of cancer and a target for therapy" Cell death and Disease 2018 8:883 pp. 1-17.

Cho et al. "PINI Inhibition Suppresses Osteoclast Differentiation and Inflammatory Responses" Journal of Dental Research 2015 94(2) : 371-380.

Lu et al. "Function of WW Domains as Phosphoserine—or Phosphothreonine-Binding Modules" Science 1999 283:1325-1328.

Nakatsu et al. "Pin1 Associates with and Induces Translocation of CRTC2 to the Cytosol, Thereby Suppressing cAMP-responsive Element Transcriptional Activity" Journal of Biological Chemistry 2010 285 (43) : 33018-33027.

Zhou, X.G. & Lu, K. P. "The isomerase PIN1 controls numerous cancer-driving pathways and is a unique drug target" Nature Reviews 2016 pp. 1-16.

CAS Registry No. 1022721-44-3, May 26, 2008 1 page.

* cited by examiner

COMPOUND, PREPARATION METHOD THEREOF, AND USE THEREOF

CROSS-REFERENCES TO RELATED APPLICATION

This patent application is the National Stage of International Application No. PCT/KR2021/000614 filed Jan. 15, 2021, which claims the benefit of priority under 35 U.S.C. § 119 from Korean Patent Application 10-2020-0174237 filed Dec. 14, 2020 and Korean Patent Application 10-2020-0006739 filed on Jan. 17, 2020, the contents of each of which are incorporated herein by reference in their entirety.

TECHNICAL FIELD

The present invention relates to a pharmaceutical composition for the prevention or treatment of cancer, inflammatory disease or metabolic disease, particularly to a pharmaceutical composition comprising a compound that inhibits Pin1 (Peptidyl-prolyl cis-trans isomerase NIMA-interacting 1) as an active ingredient for the prevention or treatment of cancer, inflammatory disease or metabolic disease.

BACKGROUND ART

Pin1 (Peptidyl-prolyl cis-trans isomerase NIMA-interacting 1), a proryl isomerase, is an enzyme that catalyzes the cis/trans isomerization of a proline residue amide by binding to the phosphorylated Ser/Thr-Pro site (Lu, et al. Science 1999, 283(5406):1325-8). During the intracellular signaling process, serine (Ser), threonine (Thr) and tyrosine (Tyr) residues of proteins are phosphorylated. After this phosphorylation, Pin1 changes the structure of various proteins through the cis/trans isomerization of a proline residue amide, allowing these proteins to start their functions in the cell.

According to studies to date, the Pin1 enzyme is known to be involved in the onset and progression of inflammatory disease, metabolic disease and cancer. In particular, it has been reported that the Pin1 enzyme activates 56 oncogenes involved in oncogenesis such as beta-catenin, AKT, AR, CyclinD1, Plk, NF-kB, Stat3, Myc, c-Jun, c-Fos, c-Myb, Raf-1, HIF-1, Nanog, Notch1, Oct4, etc., and inhibits the activity of 26 tumor suppressor genes such as ATR, Bax, Btk, FADD, Fbw7, PML, etc., thereby inducing cancer metastasis and cancer angiogenesis in the overall cancer development mechanism. Therefore, a lot of research is being conducted on Pin1 protein as a target for the development of cancer diagnostic reagents, prognostic factors, and useful new anticancer agents (Nature reviews Cancer 2016, 16:463-478; Cell Death and Disease 2018, 9:883).

As reported through the studies on surgically excised samples, Pin1 is known to be highly expressed in various types of cancer, such as colon cancer, cervical cancer, breast cancer, lung cancer, pancreatic cancer, stomach cancer, liver cancer, etc. In fact, it has been reported that transgenic mice overexpressing Pin1 exhibit a cancer-causing phenotype. In addition, it is known that mitotic arrest and apoptosis can be induced, and stem cell properties of cancer can be suppressed in cancer cells knocked down Pin1 using a specific inhibitor or siRNA. In particular, the Pin1 enzyme has a function of inducing self-renewal, metastasis and tumor formation of breast cancer stem cells.

When Pin1 is overexpressed, human breast epithelial cells differentiate into pseudo-stem cells, and epithelial to mesenchymal transition occurs. In other words, when cancer cells grow invasively and metastasize, in order to break the adhesion with surrounding cells and move through blood vessels or lymphatic vessels, the bond between cells is loosened, the skeleton of cells changes, and motility is acquired. Pin1 enzyme is known as an important factor in self-renewal of stem cells, which maintains the stability of Nanog, Oct4, and Myc proteins.

Although Pin1 is involved in many mechanisms in the living body as described above, it is known that Pin1 knockout mice grow well without major problems. Therefore, it is expected that the inhibition of Pin1 will not have a significant effect on the human body. However, while there are reports that Pin1 can help in the treatment of Alzheimer's disease in the brain, there are reports that it acts inversely in Parkinson's disease, and there are many parts that have not been identified yet. In conclusion, Pin1 plays a very important role in the occurrence of cancer as a whole, and inhibiting it in areas other than the brain is very useful for effective and safe treatment of cancer.

In addition, it has been reported that when Pin1 is inhibited or Pin1 gene expression is knocked down, the productions of prostaglandin E2 and nitric oxide stimulated by lipopolysaccharide (LPS) and nicotine are weakened, and the expressions of cyclooxygenase-2 (COX-2) and inducible nitric oxide synthase (iNOS) are also weakened, resulting in an anti-inflammatory effect (Journal of Dental Research, 2015, 94(2):371-380). It is well known that when Pin1 is attached to CRTC2, the production of CBP-CRTC2-CREB complex that promotes gluconeogenesis is inhibited, so that CRTC2 can be regulated according to the expression level of Pin1 and thus may be involved in the regulation of glucose metabolism (J. Biol. Chem., 2010, 285(43):33018-27). Therefore, drugs that affect Pin1 expression or activity can be used as a therapeutic agent for inflammatory disease or metabolic disease such as diabetes.

Thus, the present inventors performed pharmaceutical chemical synthesis and biological and pharmacological evaluation of the synthesized compounds to discover the compounds that inhibit the activity of Pint. Through this, the present inventors discovered the compounds showing excellent anticancer effect by strongly inhibiting Pint, and completed the present invention. In addition, it is believed that the compounds of the present invention can be used as therapeutic agents for the diseases based on the role of Pin1 in inflammatory and metabolic diseases.

DISCLOSURE OF INVENTION

Technical Problem

It is an object of the present invention to provide a novel compound that inhibits Pin1 (Peptidyl-prolyl cis-trans isomerase NIMA-interacting 1), an isomer thereof or a pharmaceutically acceptable salt thereof.

It is another object of the present invention to provide a preparation method of the compound.

It is another object of the present invention to provide a pharmaceutical composition comprising the compound, the isomer thereof or the pharmaceutically acceptable salt thereof as an active ingredient for the prevention or treatment of cancer, inflammatory disease or metabolic disease.

It is another object of the present invention to provide a health functional food composition comprising the compound, the isomer thereof or the pharmaceutically acceptable salt thereof as an active ingredient for the prevention or amelioration of cancer, inflammatory disease or metabolic disease.

Solution to Problem

To achieve the above objects, in one aspect of the present invention, the present invention provides a compound represented by formula 1, an isomer thereof or a pharmaceutically acceptable salt thereof:

[Formula 1]

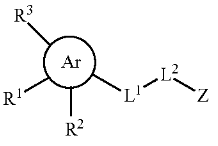

(In formula 1,

Ar is 6-10 membered aryl or 5-10 membered heteroaryl containing one or more heteroatoms selected from the group consisting of N, S and O;

$R^1$ and $R^2$ are independently hydrogen, halogen or 5-8 membered heterocycloalkyl $C_{1-5}$ alkoxy containing at least one N;

$R^3$ is hydrogen, halogen, nonsubstituted or substituted straight or branched $C_{1-8}$ alkoxy, nonsubstituted or substituted straight or branched $C_{1-8}$ alkyl, $NR^{a1}R^{a2}$, or $OR^{a3}$, wherein $R^{a1}$, $R^{a2}$ and $R^{a3}$ are independently hydrogen, nonsubstituted or substituted straight or branched $C_{1-8}$ alkyl, nonsubstituted or substituted phenyl or 5-8 membered nonsubstituted or substituted heteroaryl containing one or more heteroatoms selected from the group consisting of N, S and O, at this time, the substituted alkoxy, the substituted alkyl, the substituted phenyl and the substituted heteroaryl are independently substituted with one or more substituents selected from the group consisting of 4-8 membered nonsubstituted or substituted heterocycloalkyl containing one or more heteroatoms selected from the group consisting of N, S and O, 4-8 membered nonsubstituted or substituted heteroaryl containing one or more heteroatoms selected from the group consisting of N, S and O, $NR^{b1}R^{b2}$, 3-6 membered cycloalkyl, halogen, hydroxy and sulfonyl, or the substituted alkoxy and the substituted alkyl can be further substituted to form 3-6 membered cycloalkyl with each independently substituted carbon, the substituted heterocycloalkyl and the substituted heteroaryl are substituted with one or more substituents selected from the group consisting of straight or branched $C_{1-5}$ alkyl nonsubstituted or substituted with one or more halogens, straight or branched $C_{1-5}$ alkylcarbonyl, $NR^{b1}R^{b2}$, halogen, hydroxy and oxo, $R^{b1}$ and $R^{b2}$ are independently hydrogen, or straight or branched $C_{1-6}$alkyl;

$L^1$ is

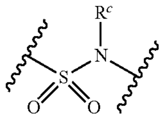
or
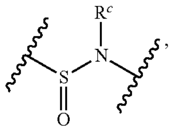
, wherein $R^c$ is hydrogen or $L^2$ and forms 5-8 membered heterocycloalkylene containing N along with nitrogen to which they are attached;

$L^2$ is a single bond, straight or branched $C_{1-8}$alkylene, $C_{3-8}$cycloalkylene or phenylene nonsubstituted or substituted with one of hydroxy and oxo;

Z is nonsubstituted or substituted $C_{6-10}$ aryl, $C_{3-8}$ cycloalkyl nonsubstituted or fused with 5-9 membered nonsubstituted or substituted heteroaryl containing one or more heteroatoms selected from the group consisting of N, S, and O, 4-8 membered nonsubstituted or substituted heterocycloalkyl containing one or more heteroatoms selected from the group consisting of N, S and O, 5-9 membered nonsubstituted or substituted heteroaryl containing one or more heteroatoms selected from the group consisting of N, S and O, or 5-9 membered nonsubstituted or substituted heteroaryl $C_{1-5}$ alkyl containing one or more heteroatoms selected from the group consisting of N, S and O, the substituted aryl is substituted with halogen, phenyl, carboxy, 4-8 membered nonsubstituted or substituted heterocycloalkyl containing one or more heteroatoms selected from the group consisting of N, S, and O, or straight or branched $C_{1-8}$ alkoxycarbonyl, at this time, the substituted heterocycloalkyl, the substituted heteroaryl and the substituted heteroarylalkyl are independently substituted with one or more substituents selected from the group consisting of straight or branched $C_{1-5}$alkyl, straight or branched $C_{1-8}$alkoxy, phenyl, benzyl, halogen, hydroxy or oxo.)

In another aspect of the present invention, a preparation method of a compound represented by formula 1 comprising a step of preparing a compound represented by formula 1 by reacting a compound represented by formula 2 with a compound represented by formula 3 as shown in reaction formula 1 below:

[Reaction Formula 1]

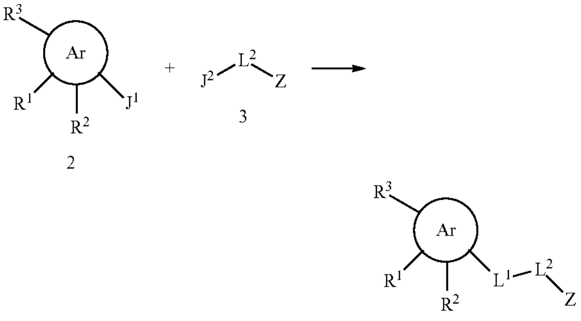
2
3
1

(In reaction formula 1, Ar, $R^1$, $R^2$, $R^3$, $L^1$, $L^2$ and Z are as defined in formula 1 of claim 1, $J^1$ is chlorosulfone or carboxy; and $J^2$ is amine or piperidine.)

In another aspect of the present invention, the present invention provides a pharmaceutical composition comprising the compound represented by formula 1, the isomer thereof or the pharmaceutically acceptable salt thereof as an active ingredient for the prevention or treatment of cancer, inflammatory disease or metabolic disease.

In another aspect of the present invention, the present invention provides a health functional food composition comprising the compound represented by formula 1, the isomer thereof or the pharmaceutically acceptable salt thereof as an active ingredient for the prevention or amelioration of cancer, inflammatory disease or metabolic disease.

In another aspect of the present invention, the present invention provides a method for preventing or treating cancer, inflammatory disease or metabolic disease comprising a step of administering the pharmaceutical composition or the health functional food composition comprising the compound represented by formula 1 or the pharmaceutically acceptable salt thereof as an active ingredient to a subject in need thereof.

In another aspect of the present invention, the present invention provides a use of the pharmaceutical composition or the health functional food composition comprising the compound represented by formula 1 or the pharmaceutically acceptable salt thereof as an active ingredient in the prevention or treatment of cancer, inflammatory disease or metabolic disease.

Advantageous Effects of Invention

Since the novel compound according to the present invention exhibits excellent inhibitory activity against Pint, a pharmaceutical composition comprising the compound as an active ingredient can be effectively used in the prevention or treatment of cancer, inflammatory disease or metabolic disease.

BEST MODE FOR CARRYING OUT THE INVENTION

Hereinafter, the present invention is described in detail.

In one aspect of the present invention, the present invention provides a compound represented by formula 1, an isomer thereof or a pharmaceutically acceptable salt thereof:

[Formula 1]

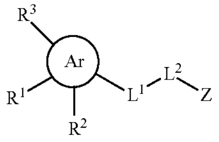

(In formula 1,

Ar is 6-10 membered aryl or 5-10 membered heteroaryl containing one or more heteroatoms selected from the group consisting of N, S and O;

$R^1$ and $R^2$ are independently hydrogen, halogen or 5-8 membered heterocycloalkyl $C_{1-5}$ alkoxy containing at least one N;

$R^3$ is hydrogen, halogen, nonsubstituted or substituted straight or branched $C_{1-8}$ alkoxy, nonsubstituted or substituted straight or branched $C_{1-8}$ alkyl, $NR^{a1}R^{a2}$, or $OR^{a3}$, wherein $R^{a1}$, $R^{a2}$ and $R^{a3}$ are independently hydrogen, nonsubstituted or substituted straight or branched $C_{1-8}$alkyl, nonsubstituted or substituted phenyl or 5-8 membered nonsubstituted or substituted heteroaryl containing one or more heteroatoms selected from the group consisting of N, S and O, at this time, the substituted alkoxy, the substituted alkyl, the substituted phenyl and the substituted heteroaryl are independently substituted with one or more substituents selected from the group consisting of 4-8 membered nonsubstituted or substituted heterocycloalkyl containing one or more heteroatoms selected from the group consisting of N, S and O, 4-8 membered nonsubstituted or substituted heteroaryl containing one or more heteroatoms selected from the group consisting of N, S and O, $NR^{b1}R^{b2}$, 3-6 membered cycloalkyl, halogen, hydroxy and sulfonyl, or the substituted alkoxy and the substituted alkyl can be further substituted to form 3-6 membered cycloalkyl with each independently substituted carbon, the substituted heterocycloalkyl and the substituted heteroaryl are substituted with one or more substituents selected from the group consisting of straight or branched $C_{1-5}$ alkyl nonsubstituted or substituted with one or more halogens, straight or branched $C_{1-5}$ alkylcarbonyl, $NR^{b1}R^{b2}$, halogen, hydroxy and oxo, $R^{b1}$ and $R^{b2}$ are independently hydrogen, or straight or branched $C_{1-6}$alkyl;

$L^1$ is

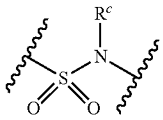 or 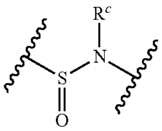, wherein $R^c$ is hydrogen or $L^2$ and forms 5-8 membered heterocycloalkylene containing N along with nitrogen to which they are attached;

$L^2$ is a single bond, straight or branched $C_{1-8}$alkylene, $C_{3-8}$cycloalkylene or phenylene nonsubstituted or substituted with one of hydroxy and oxo;

Z is nonsubstituted or substituted $C_{6-10}$ aryl, $C_{3-8}$ cycloalkyl nonsubstituted or fused with 5-9 membered nonsubstituted or substituted heteroaryl containing one or more heteroatoms selected from the group consisting of N, S, and O, 4-8 membered nonsubstituted or substituted heterocycloalkyl containing one or more heteroatoms selected from the group consisting of N, S and O, 5-9 membered nonsubstituted or substituted heteroaryl containing one or more heteroatoms selected from the group consisting of N, S and O, or 5-9 membered nonsubstituted or substituted heteroaryl $C_{1-5}$alkyl containing one or more heteroatoms selected from the group consisting of N, S and O, the substituted aryl is substituted with halogen, phenyl, carboxy, 4-8 membered nonsubstituted or substituted heterocycloalkyl containing one or more heteroatoms selected from the group consisting of N, S, and O, or straight or branched $C_{1-8}$ alkoxycarbonyl, at this time, the substituted heterocycloalkyl, the substituted heteroaryl and the substituted heteroarylalkyl are independently substituted with one or more substituents selected from the group consisting of straight or branched $C_{1-5}$alkyl, straight or branched $C_{1-8}$alkoxy, phenyl, benzyl, halogen, hydroxy or oxo.)

The compound, the isomer thereof or the pharmaceutically acceptable salt thereof according to claim 1, wherein:

- Ar is 6-10 membered aryl or 5-6 membered heteroaryl containing one or more heteroatoms selected from the group consisting of N, S and O;
- $R^1$ and $R^2$ are independently hydrogen or fluorine;
- $R^3$ is hydrogen, bromine, nonsubstituted or substituted straight or branched $C_{1-6}$ alkoxy, nonsubstituted or substituted straight or branched $C_{1-6}$alkyl, $NR^{a1}R^{a2}$, or $OR^{a3}$, wherein $R^{a1}$, $R^{a2}$ and $R^{a3}$ are independently hydrogen, nonsubstituted or substituted straight or branched $C_{1-6}$alkyl, nonsubstituted or substituted phenyl or 5-7 membered nonsubstituted or substituted heteroaryl containing one or more heteroatoms selected from the group consisting of N, S and O, at this time, the substituted alkoxy, the substituted alkyl, the substituted phenyl and the substituted heteroaryl are independently substituted with one or more substituents selected from the group consisting of 4-7 membered nonsubstituted or substituted heterocycloalkyl containing one or more heteroatoms selected from the group consisting of N, S and O, 4-7 membered nonsubstituted or substituted heteroaryl containing one or more heteroatoms selected from the group consisting of N, S and O, $NR^{b1}R^{b2}$, 3-5 membered cycloalkyl, fluorine, bromine, hydroxy and sulfonyl, or the substituted alkoxy and the substituted alkyl can be further substituted to form 3-5 membered cycloalkyl with each independently substituted carbon, the substituted heterocycloalkyl and the substituted heteroaryl are substituted with one or more substituents selected from the group consisting of straight or branched $C_{1-4}$ alkyl nonsubstituted or substituted with one or more halogens, straight or branched $C_{1-4}$ alkylcarbonyl, $NR^{b1}R^{b2}$, chlorine, fluorine, bromine, hydroxy and oxo, $R^{b1}$ and $R^{b2}$ are independently hydrogen, or straight or branched $C_{1-3}$alkyl;

$L^1$ is

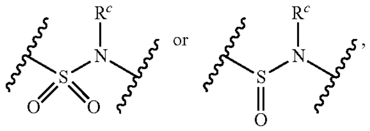

wherein $R^c$ hydrogen or $L^2$ and forms piperidinylene along with nitrogen to which they are attached;

$L^2$ is a single bond, straight or branched $C_{1-6}$alkylene, $C_{4-6}$cycloalkylene or phenylene nonsubstituted or substituted with one of hydroxy and oxo;

Z is nonsubstituted or substituted $C_{6-9}$ aryl, $C_{4-7}$ cycloalkyl nonsubstituted or fused with 5-9 membered nonsubstituted or substituted heteroaryl containing one or more heteroatoms selected from the group consisting of N, S, and O, 5-6 membered nonsubstituted or substituted heterocycloalkyl containing one or more heteroatoms selected from the group consisting of N, S and O, 6-9 membered nonsubstituted or substituted heteroaryl containing one or more heteroatoms selected from the group consisting of N, S and O, or 6-9 membered nonsubstituted or substituted heteroaryl $C_{1-4}$ alkyl containing one or more heteroatoms selected from the group consisting of N, S and O, the substituted aryl is substituted with chlorine, phenyl, carboxy, morpholinyl or straight or branched $C_{1-3}$alkoxycarbonyl, at this time, the substituted heterocycloalkyl, the substituted heteroaryl and the substituted heteroarylalkyl are independently substituted with one or more substituents selected from the group consisting of straight or branched $C_{1-4}$ alkyl, straight or branched $C_{1-4}$alkoxy, benzyl, phenyl, fluorine, chlorine, bromine, hydroxy or oxo.

The compound, the isomer thereof or the pharmaceutically acceptable salt thereof according to claim 1, wherein:

Ar is phenyl, naphthyl, pyridine or thiazole;

$R^1$ and $R^2$ are independently hydrogen or fluorine;

$R^3$ is hydrogen, bromine, nonsubstituted or substituted straight or branched $C_{1-5}$ alkoxy, nonsubstituted or substituted straight or branched $C_{1-5}$ alkyl, $NR^{a1}R^{a2}$, or $OR^{a3}$, wherein $R^{a1}$, $R^{a2}$ and $R^{a3}$ are independently hydrogen, nonsubstituted or substituted straight or branched $C_{1-5}$ alkyl, nonsubstituted or substituted phenyl or 5-6 membered nonsubstituted or substituted heteroaryl containing one or more heteroatoms selected from the group consisting of N, S and O, at this time, the substituted alkoxy, the substituted alkyl, the substituted phenyl and the substituted heteroaryl are independently substituted with one or more substituents selected from the group consisting of 4-7 membered nonsubstituted or substituted heterocycloalkyl containing one or more heteroatoms selected from the group consisting of N, S and O, 5-7 membered nonsubstituted or substituted heteroaryl containing one or more heteroatoms selected from the group consisting of N, S and O, $NR^{b1}R^{b2}$, 3-4 membered cycloalkyl, fluorine, bromine, hydroxy and sulfonyl, or the substituted alkoxy and the substituted alkyl can be further substituted to form cyclopropyl with each independently substituted carbon, the substituted heterocycloalkyl and the substituted heteroaryl are substituted with one or more substituents selected from the group consisting of straight or branched $C_{1-3}$ alkyl nonsubstituted or substituted with one or more fluorines, straight or branched $C_{1-4}$ alkylcarbonyl, $NR^{b1}R^{b2}$, chlorine, fluorine, bromine, hydroxy and oxo, $R^{b1}$ and $R^{b2}$ are independently hydrogen, methyl or ethyl;

$L^1$ is

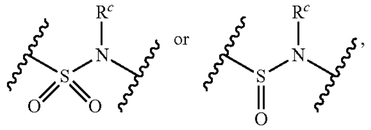

wherein $R^c$ is hydrogen or $L^2$ and forms piperidinylene along with nitrogen to which they are attached;

$L^2$ is a single bond, straight or branched $C_{1-4}$ alkylene, cyclohexylene or phenylene nonsubstituted or substituted with one of hydroxy and oxo;

Z is nonsubstituted or substituted phenyl, cyclohexyl, naphthyl, $C_{5-6}$ cycloalkyl fused with 5-9 membered nonsubstituted or substituted heteroaryl containing one or more heteroatoms selected from the group consisting of N, S, and O, 5-6 membered nonsubstituted or substituted heterocycloalkyl containing one or more heteroatoms selected from the group consisting of N, S and O, 6-9 membered nonsubstituted or substituted heteroaryl containing one or more heteroatoms selected from the group consisting of N, S and O, or 6-9 membered nonsubstituted or substituted heteroaryl $C_{1-3}$ alkyl containing one or more heteroatoms selected from the group consisting of N, S and O, the substituted phenyl is substituted with chlorine, phenyl, carboxy, morpholinyl or methoxycarbonyl, at this time, the substituted heterocycloalkyl, the substituted heteroaryl and the substituted heteroarylalkyl are independently substituted with one or more substituents selected from the group consisting of straight or branched $C_{1-3}$ alkyl, methoxy, benzyl, phenyl, fluorine, chlorine, bromine, hydroxy or oxo.
The compound, the isomer thereof or the pharmaceutically acceptable salt thereof according to claim 1, wherein:
Ar is phenyl, naphthyl, pyridine or thiazole;
$R^1$ and $R^2$ are independently hydrogen or fluorine;
$R^3$ is hydrogen, bromine,
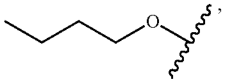
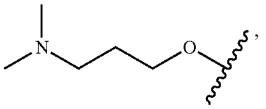
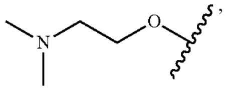
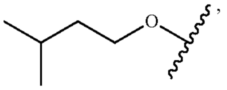
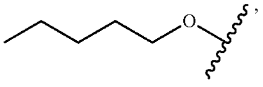
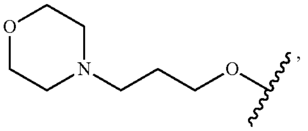
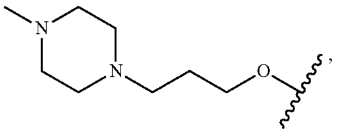
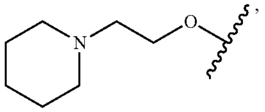
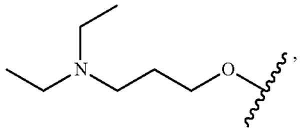
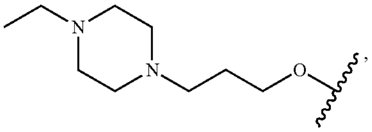
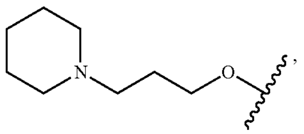
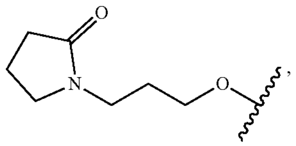
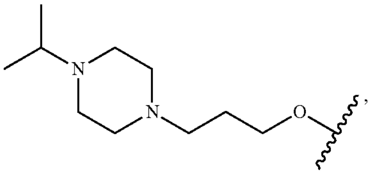
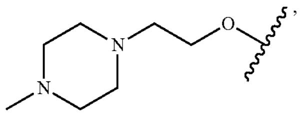
-continued
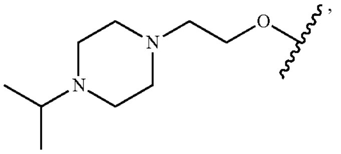
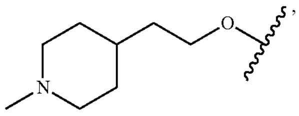
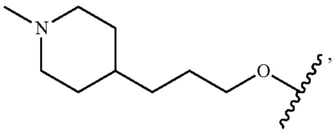
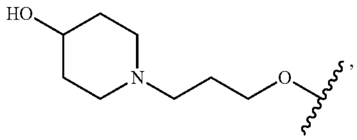
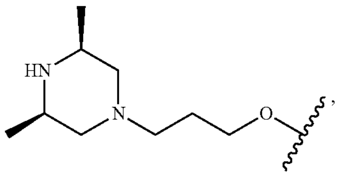
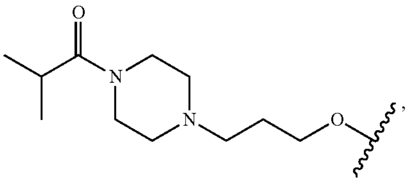
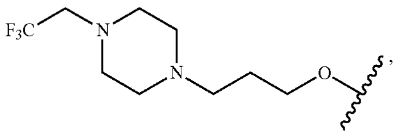
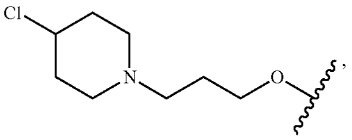
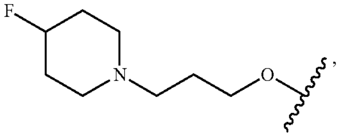
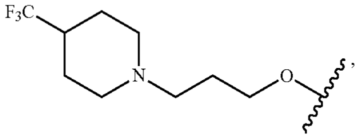
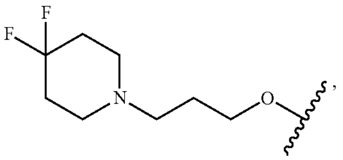

-continued
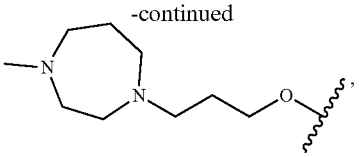,
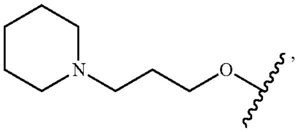,
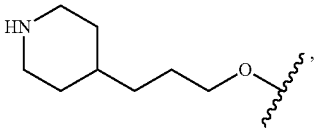,
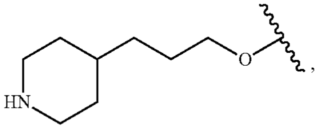,
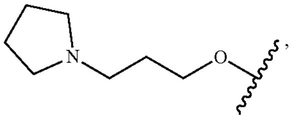,
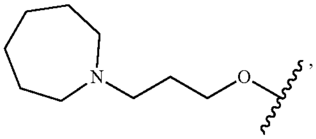,
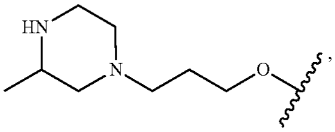,
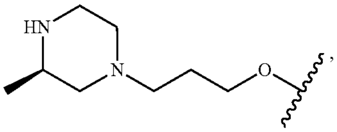,
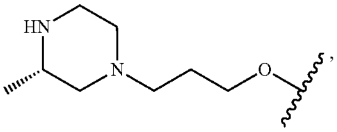,
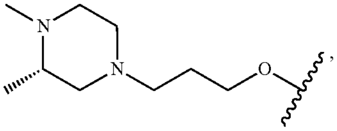,
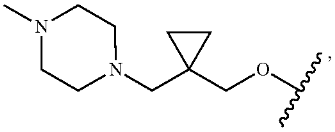,
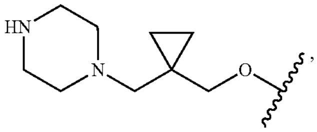,
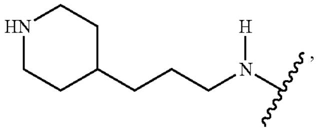,
-continued
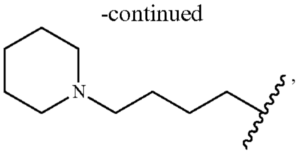,
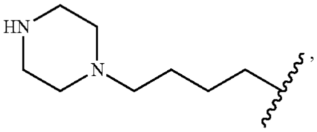,
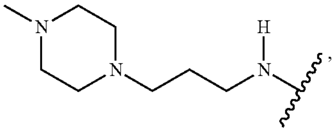,
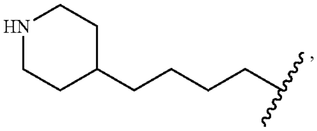,
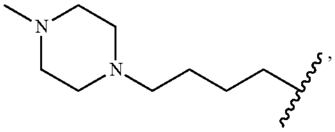,
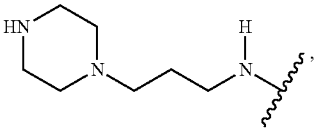,
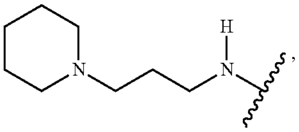,
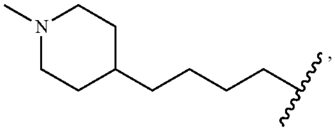,
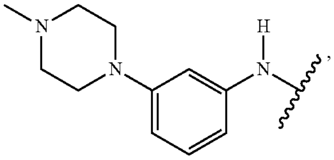,
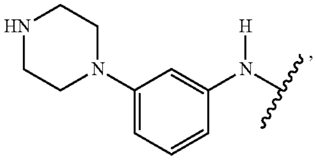,
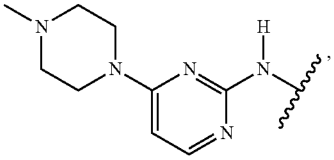,
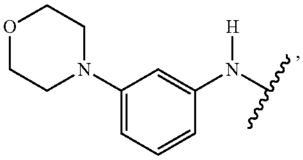, -continued
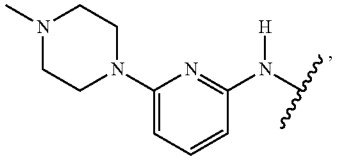
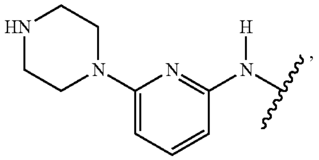
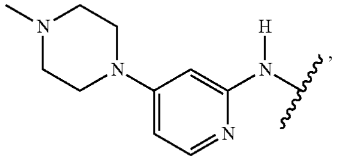
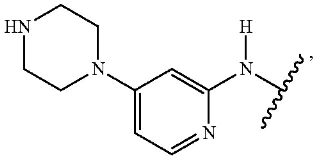
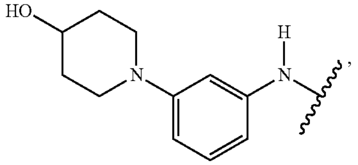
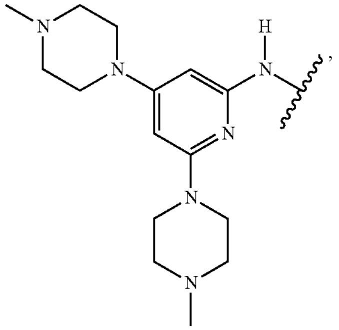
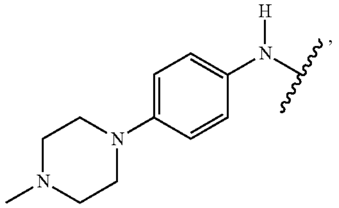
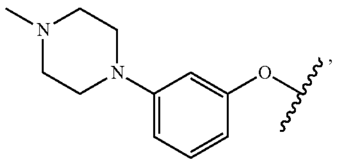
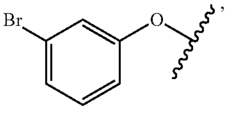
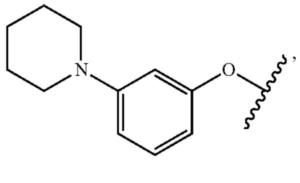
-continued
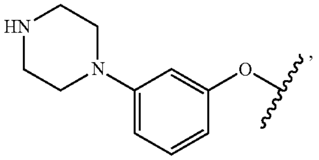
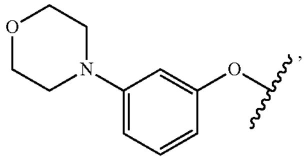
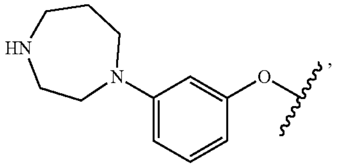
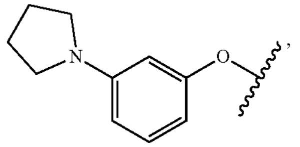
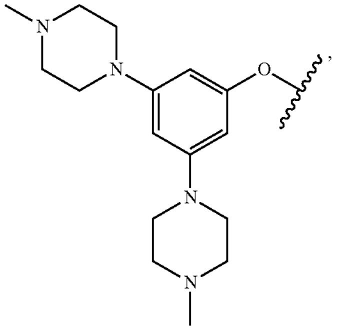
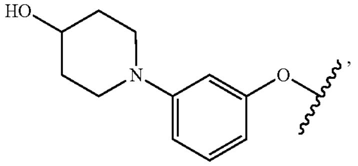
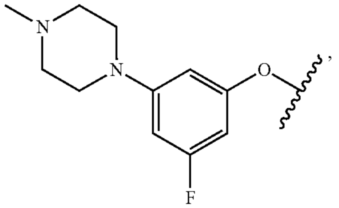
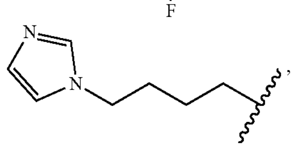
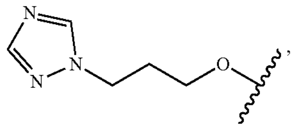
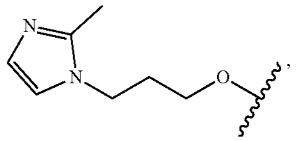

-continued
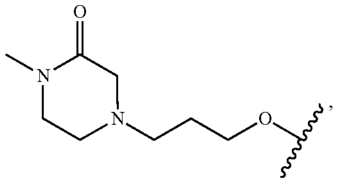
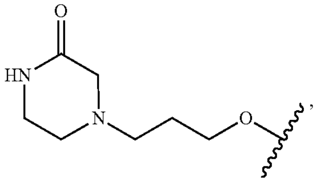
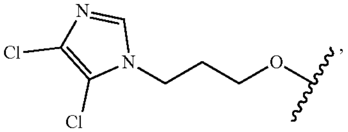
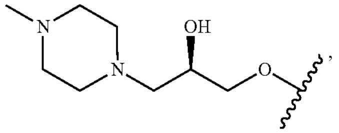
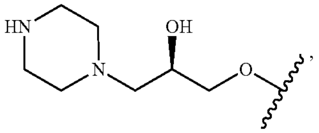
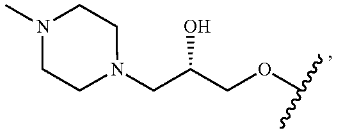
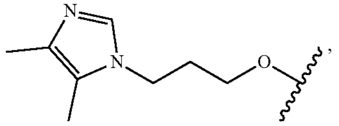
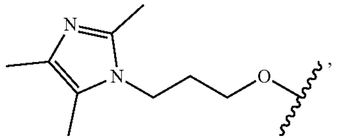
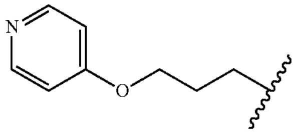
or
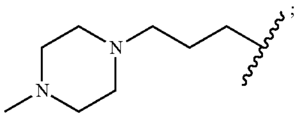
$L^1$ is
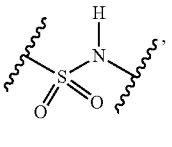
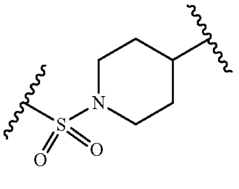
or
-continued
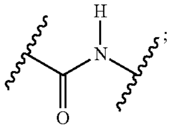
$L^2$ is a single bond,
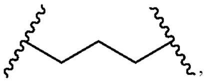
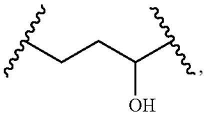
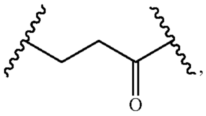
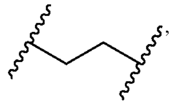
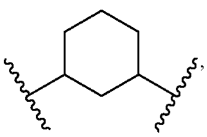
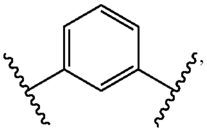
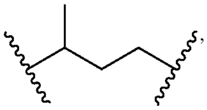
or
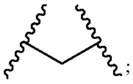
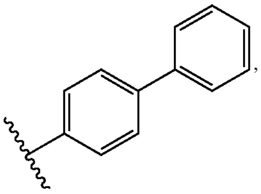
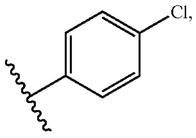
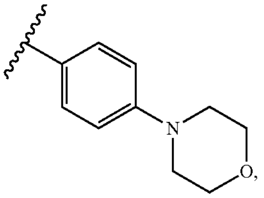
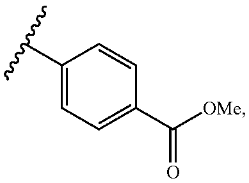
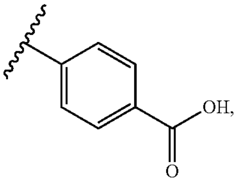
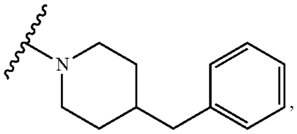
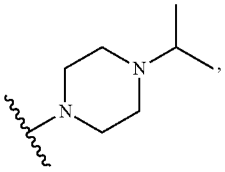
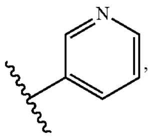

-continued

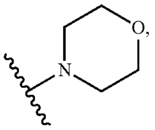,
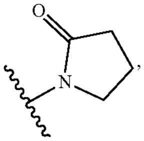,
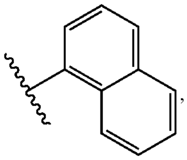,
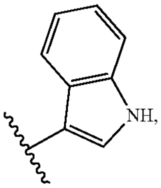,
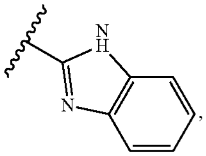,
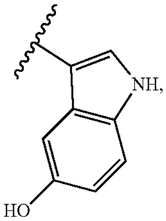,
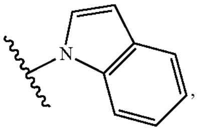,
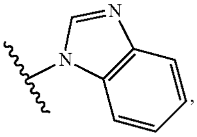,
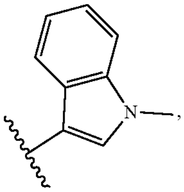,
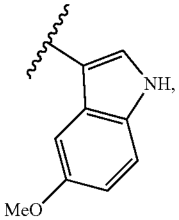,
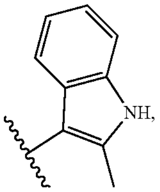,
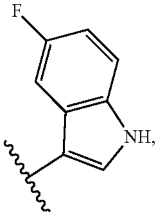,
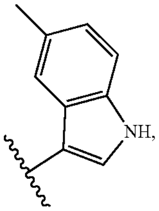,
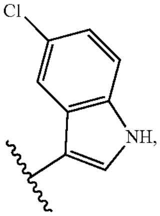,
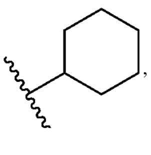,
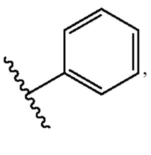,
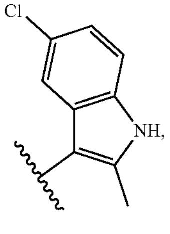,
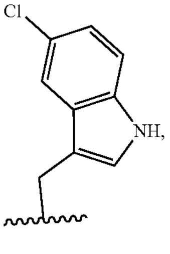, -continued

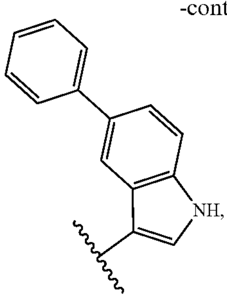,
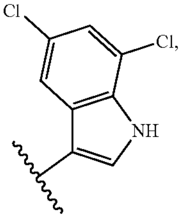,
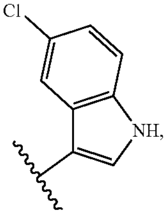,
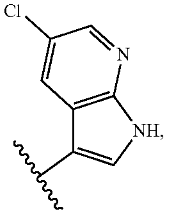,
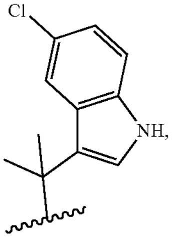,
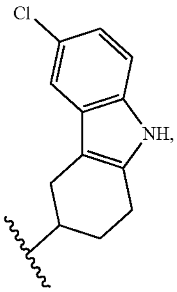,
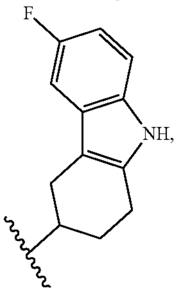,
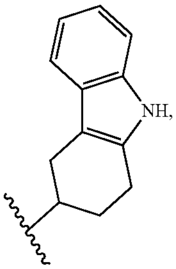,
or
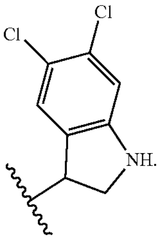.

The compound, the isomer thereof or the pharmaceutically acceptable salt thereof according to claim 1, wherein the compound represented by formula 1 is selected from the group consisting of the following compounds:

<1> N-(3-([1,1'-biphenyl]-4-yl)propyl)-4-butoxybenzenesulfonamide;

<2> 4-butoxy-N-(3-(4-isopropylpiperazin-1-yl)propyl)benzenesulfonamide;

<3> 4-butoxy-N-(3-(4-chlorophenyl)propyl)benzenesulfonamide;

<4> 4-butoxy-N-(3-cyclohexylpropyl)benzenesulfonamide;

<5> 4-butoxy-N-(3-(pyridin-3-yl)propyl)benzenesulfonamide;

<6> 4-butoxy-N-(3-morpholinopropyl)benzenesulfonamide;

<7> 4-butoxy-N-(4-morpholinophenethyl)benzenesulfonamide;

<8> 4-(2-(4-butoxyphenylsulfonamido)ethyl)benzoic acid;

<9> methyl 4-(2-(4-butoxyphenylsulfonamido)ethyl)benzoate;

<10> N-(2-(4-benzylpiperidin-1-yl)ethyl)-4-butoxybenzenesulfonamide;

<11> 4-butoxy-N-(3-hydroxy-3-phenylpropyl)benzenesulfonamide;

<12> 4-butoxy-N-(3-oxo-3-phenylpropyl)benzenesulfonamide;

<13> 4-butoxy-N-(3-(2-oxopyrrolidin-1-yl)propyl)benzenesulfonamide;

<14> 4-(3-(dimethylamino)propoxy)-N-phenethylbenzenesulfonamide;

<15> 4-(3-(dimethylamino)propoxy)-N-(3-phenylpropyl)benzenesulfonamide;

<16> methyl 4-(2-(4-(3-(dimethylamino)propoxy)phenylsulfonamido)ethyl)benzoate;

<17> 4-(2-(4-(3-(dimethylamino)propoxy)phenylsulfonamido)ethyl)benzoic acid;

<18> 4-(3-(dimethylamino)propoxy)-N-(3-(2-oxopyrrolidin-1-yl)propyl)benzenesulfonamide;

<19> 4-butoxy-N-(3-(naphthalen-1-yl)propyl)benzenesulfonamide;

<20> N-(3-(1H-indol-3-yl)propyl)-4-butoxybenzenesulfonamide;

<21> N-(3-(1H-indol-3-yl)propyl)-4-(2-(dimethylamino)ethoxy)benzenesulfonamide;

<22> N-(3-(1H-indol-3-yl)propyl)-4-(3-(dimethylamino)propoxy)benzenesulfonamide;

<23> N-(2-(1H-benzo[d]imidazol-2-yl)ethyl)-4-butoxybenzenesulfonamide;

<24> N-(2-(1H-indol-3-yl)ethyl)-4-butoxybenzenesulfonamide;

<25> N-(2-(1H-indol-2-yl)ethyl)-4-butoxybenzenesulfonamide;

<26> N-(3-(1H-indol-3-yl)propyl)-4-(isopentyloxy)benzenesulfonamide;

<27> N-(3-(1H-indol-3-yl)propyl)-4-(pentyloxy)benzenesulfonamide;

<28> N-(3-(1H-benzo[d]imidazol-2-yl)propyl)-4-butoxybenzenesulfonamide;

<29> 4-butoxy-N-(2-(5-hydroxy-1H-indol-3-yl)ethyl)benzenesulfonamide;

<30> N-(3-(1H-indol-3-yl)propyl)-4-(3-morpholinopropoxy)benzenesulfonamide;

<31> N-(3-(1H-indol-3-yl)propyl)-4-(3-(4-methylpiperazin-1-yl)propoxy)benzenesulfonamide;

<32> N-(3-(1H-indol-1-yl)propyl)-4-butoxybenzenesulfonamide;

<33> N-(3-(1H-benzo[d]imidazol-1-yl)propyl)-4-butoxybenzenesulfonamide;

<34> N-(3-(1H-benzo[d]imidazol-1-yl)propyl)-4-butoxybenzenesulfonamide;

<35> N-(3-(1H-indol-3-yl)propyl)-4-(3-(diethylamino)propoxy)benzenesulfonamide;

<36> N-(3-(1H-indol-3-yl)propyl)-4-(3-(4-ethylpiperazin-1-yl)propoxy)benzenesulfonamide;

<37> N-(2-(1H-benzo[d]imidazol-2-yl)ethyl)-4-(3-(dimethylamino)propoxy)benzenesulfonamide;

<38> N-(2-(1H-indol-2-yl)ethyl)-4-(3-(dimethylamino)propoxy)benzenesulfonamide;

<39> N-(3-(1H-indol-1-yl)propyl)-4-(3-(dimethylamino)propoxy)benzenesulfonamide;

<40> N-(3-(1H-benzo[d]imidazol-1-yl)propyl)-4-(3-(dimethylamino)propoxy)benzenesulfonamide;

<41> N-(3-(1H-indol-1-yl)propyl)-4-(3-(4-methylpiperazin-1-yl)propoxy)benzenesulfonamide;

<42> N-(3-(1H-benzo[d]imidazol-1-yl)propyl)-4-(3-(4-methylpiperazin-1-yl)propoxy)benzenesulfonamide;

<43> N-(3-(1H-indol-3-yl)propyl)-4-(3-(piperidin-1-yl)propoxy)benzenesulfonamide;

<44> N-(3-(1H-indol-3-yl)propyl)-4-(3-(2-oxopyrrolidin-1-yl)propoxy)benzenesulfonamide;

<45> N-(3-(1H-indol-3-yl)propyl)-4-(3-(piperazin-1-yl)propoxy)benzenesulfonamide;

<46> 4-(3-(dimethylamino)propoxy)-N-(3-(1-methyl-1H-indol-3-yl)propyl)benzenesulfonamide;

<47> N-(3-(1H-indol-3-yl)propyl)-4-bromobenzenesulfonamide;

<48> N-(3-(1H-indol-3-yl)propyl)-4-(3-(4-isopropylpiperazin-1-yl)propoxy)benzenesulfonamide;

<49> N-(2-(5-methoxy-1H-indol-3-yl)ethyl)-4-(3-(4-methylpiperazin-1-yl)propoxy)benzenesulfonamide;

<50> N-(2-(1H-indol-3-yl)ethyl)-4-(3-(4-methylpiperazin-1-yl)propoxy)benzenesulfonamide;

<51> N-(2-(1H-indol-3-yl)ethyl)-4-(3-(4-isopropylpiperazin-1-yl)propoxy)benzenesulfonamide <52> N-(3-(1H-indol-3-yl)propyl)-4-(2-(4-methylpiperazin-1-yl)ethoxy)benzenesulfonamide;

<53> N-(3-(1H-indol-3-yl)propyl)-4-(2-(4-isopropylpiperazin-1-yl)ethoxy)benzenesulfonamide <54> N-(2-(2-methyl-1H-indol-3-yl)ethyl)-4-(3-(4-methylpiperazin-1-yl)propoxy)benzenesulfonamide;

<55> N-(3-(1H-indol-3-yl)propyl)-4-(2-(1-methylpiperidin-4-yl)ethoxy)benzenesulfonamide;

<56> N-(3-(5-fluoro-1H-indol-3-yl)propyl)-4-(3-(4-methylpiperazin-1-yl)propoxy)benzenesulfonamide;

<57> 3-(1-((4-(3-(4-methylpiperazin-1-yl)propoxy)phenyl)sulfonyl)piperidin-4-yl)-1H-indole;

<58> N-(3-(2-methyl-1H-indol-3-yl)propyl)-4-(3-(4-methylpiperazin-1-yl)propoxy)benzenesulfonamide;

<59> N-(3-(5-fluoro-1H-indol-3-yl)propyl)-4-(3-(1-methylpiperidin-4-yl)propoxy)benzenesulfonamide;

<60> N-(3-(1H-indol-3-yl)propyl)-4-(3-(1-methylpiperidin-4-yl)propoxy)benzenesulfonamide;

<61> N-(3-(5-fluoro-1H-indol-3-yl)propyl)-4-(3-(piperazin-1-yl)propoxy)benzenesulfonamide;

<62> N-(3-(1H-indol-3-yl)propyl)-3-fluoro-4-(3-(4-methylpiperazin-1-yl)propoxy)benzenesulfonamide;

<63> 4-(3-(4-ethylpiperazin-1-yl)propoxy)-N-(3-(5-fluoro-1H-indol-3-yl)propyl)benzenesulfonamide;

<64> 5-methoxy-3-(1-((4-(3-(4-methylpiperazin-1-yl)propoxy)phenyl)sulfonyl)piperidin-4-yl)-1H-indole;

<65> 5-methyl-3-(1-((4-(3-(4-methylpiperazin-1-yl)propoxy)phenyl)sulfonyl)piperidin-4-yl)-1H-indole;

<66> N-(3-(5-chloro-1H-indol-3-yl)propyl)-4-(3-(4-methylpiperazin-1-yl)propoxy)benzenesulfonamide;

<67> N-(3-(5-methyl-1H-indol-3-yl)propyl)-4-(3-(4-methylpiperazin-1-yl)propoxy)benzenesulfonamide;

<68> N-(3-(5-methoxy-1H-indol-3-yl)propyl)-4-(3-(4-methylpiperazin-1-yl)propoxy)benzenesulfonamide;

<69> N-(3-(1H-indol-3-yl)propyl)-4-(3-(4-hydroxypiperidin-1-yl)propoxy)benzenesulfonamide <70> N-(3-(5-chloro-1H-indol-3-yl)propyl)-4-(3-(piperazin-1-yl)propoxy)benzenesulfonamide;

<71> 5-fluoro-3-(1-((4-(3-(4-methylpiperazin-1-yl)propoxy)phenyl)sulfonyl)piperidin-4-yl)-1H-indole;

<72> 4-(3-((3S,5R)-3,5-dimethylpiperazin-1-yl)propoxy)-N-(3-(5-fluoro-1H-indol-3-yl)propyl)benzenesulfonamide;

<73> N-(3-(5-fluoro-1H-indol-3-yl)propyl)-4-(3-(4-isobutyrylpiperazin-1-yl)propoxy)benzenesulfonamide;

<74> N-(3-(5-fluoro-1H-indol-3-yl)propyl)-4-(3-(4-(2,2,2-trifluoroethyl)piperazin-1-yl)propoxy)benzenesulfonamide;
<75> N-(3-(5-chloro-1H-indol-3-yl)propyl)-4-(3-(4-hydroxypiperidin-1-yl)propoxy)benzenesulfonamide;
<76> N-(3-(5-chloro-1H-indol-3-yl)propyl)-4-(3-(4-(2,2,2-trifluoroethyl)piperazin-1-yl)propoxy)benzenesulfonamide;
<77> N-(3-(5-chloro-1H-indol-3-yl)propyl)-4-(3-(3-(methylamino)azetidin-1-yl)propoxy)benzenesulfonamide;
<78> N-(3-(5-chloro-1H-indol-3-yl)propyl)-4-(3-(4-chloropiperidin-1-yl)propoxy)benzenesulfonamide;
<79> N-(3-(5-chloro-1H-indol-3-yl)propyl)-6-(3-(piperazin-1-yl)propoxy)pyridin-3-sulfonamide;
<80> N-(3-(5-chloro-1H-indol-3-yl)propyl)-4-(3-(4-fluoropiperidin-1-yl)propoxy)benzenesulfonamide;
<81> N-(3-(5-chloro-1H-indol-3-yl)propyl)-4-(3-(4-(trifluoromethyl)piperidin-1-yl)propoxy)benzenesulfonamide;
<82> N-(3-(5-chloro-1H-indol-3-yl)propyl)-4-(3-(4,4-difluoropiperidin-1-yl)propoxy)benzenesulfonamide;
<83> N-(3-(5-chloro-1H-indol-3-yl)propyl)-4-(3-(4-methyl-1,4-diazepan-1-yl)propoxy)benzenesulfonamide;
<84> N-(3-(5-fluoro-1H-indol-3-yl)propyl)-4-(3-(piperidin-1-yl)propoxy)benzenesulfonamide;
<85> N-(3-(1H-indol-3-yl)cyclohexyl)-4-(3-(4-methylpiperazin-1-yl)propoxy)benzenesulfonamide;
<86> N-(3-(5-chloro-1H-indol-3-yl)propyl)-4-(3-(4-methylpiperazin-1-yl)propoxy)naphthalene-1-sulfonamide;
<87> N-(3-(5-chloro-1H-indol-3-yl)propyl)-4-(3-(piperidin-1-yl)propoxy)benzenesulfonamide;
<88> N-(3-(5-chloro-1H-indol-3-yl)propyl)-4-((3-(piperidin-4-yl)propyl)amino)benzenesulfonamide;
<89> N-(3-(1H-indol-3-yl)phenyl)-4-(3-(4-methylpiperazin-1-yl)propoxy)benzenesulfonamide;
<90> N-(3-(5-chloro-1H-indol-3-yl)propyl)-4-(4-(piperidin-1-yl)butyl)benzenesulfonamide;
<91> N-(3-(5-chloro-1H-indol-3-yl)propyl)-4-(4-(piperazin-1-yl)butyl)benzenesulfonamide;
<92> N-(3-(5-chloro-1H-indol-3-yl)propyl)-4-(3-(1-methylpiperidin-4-yl)propoxy)benzenesulfonamide;
<93> N-(3-(5-chloro-1H-indol-3-yl)propyl)-4-(3-(piperidin-4-yl)propoxy)benzenesulfonamide;
<94> N-(3-(5-chloro-1H-indol-3-yl)propyl)-3-(3-(piperidin-4-yl)propoxy)benzenesulfonamide;
<95> N-(3-(5-chloro-1H-indol-3-yl)propyl)-3-(3-(piperidin-1-yl)propoxy)benzenesulfonamide;
<96> N-(3-(5-chloro-1H-indol-3-yl)propyl)-3-(3-(piperazin-1-yl)propoxy)benzenesulfonamide;
<97> N-(3-(5-fluoro-1H-indol-3-yl)propyl)-4-(3-(piperidin-4-yl)propoxy)benzenesulfonamide;
<98> N-(3-(5-chloro-1H-indol-3-yl)propyl)-4-((3-(4-methylpiperazin-1-yl)propyl)amino)benzenesulfonamide;
<99> N-(3-(5-chloro-1H-indol-3-yl)propyl)-4-(4-(piperidin-4-yl)butyl)benzenesulfonamide;
<100> N-(3-(5-chloro-1H-indol-3-yl)propyl)-4-(3-(pyrrolidin-1-yl)propoxy)benzenesulfonamide
<101> 4-(3-(azepan-1-yl)propoxy)-N-(3-(5-chloro-1H-indol-3-yl)propyl)benzenesulfonamide;
<102> 4-(3-(1,4-diazepan-1-yl)propoxy)-N-(3-(5-chloro-1H-indol-3-yl)propyl)benzenesulfonamide;
<103> N-(3-(5-chloro-1H-indol-3-yl)propyl)-3-fluoro-4-(3-(4-methylpiperazin-1-yl)propoxy)benzenesulfonamide;
<104> N-(3-(5-chloro-1H-indol-3-yl)propyl)-3-fluoro-4-(3-(piperazin-1-yl)propoxy)benzenesulfonamide;
<105> N-(3-(5-chloro-1H-indol-3-yl)propyl)-3-fluoro-4-(3-(4-hydroxypiperidin-1-yl)propoxy)benzenesulfonamide;
<106> 4-(3-(1,4-diazepan-1-yl)propoxy)-N-(3-(5-chloro-1H-indol-3-yl)propyl)-3-fluorobenzenesulfonamide;
<107> N-(3-(5-chloro-1H-indol-3-yl)propyl)-4-(3-(3-methylpiperazin-1-yl)propoxy)benzenesulfonamide;
<108> (R)—N-(3-(5-chloro-1H-indol-3-yl)propyl)-4-(3-(3-methylpiperazin-1-yl)propoxy)benzenesulfonamide;
<109> (S)—N-(3-(5-chloro-1H-indol-3-yl)propyl)-4-(3-(3-methylpiperazin-1-yl)propoxy)benzenesulfonamide;
<110> N-(3-(5-chloro-1H-indol-3-yl)propyl)-4-(3-((3S,5R)-3,5-dimethylpiperazin-1-yl)propoxy)benzenesulfonamide;
<111> (S)—N-(3-(5-chloro-1H-indol-3-yl)propyl)-4-(3-(3,4-dimethylpiperazin-1-yl)propoxy)benzenesulfonamide;
<112> N-(3-(5-chloro-1H-indol-3-yl)propyl)-4-(4-(4-methylpiperazin-1-yl)butyl)benzenesulfonamide;
<113> N-(3-(5-chloro-1H-indol-3-yl)propyl)-4-((3-(piperazin-1-yl)propyl)amino)benzenesulfonamide;
<114> N-(3-(5-chloro-1H-indol-3-yl)propyl)-4-((3-(piperidin-1-yl)propyl)amino)benzenesulfonamide;
<115> N-(3-(5-chloro-1H-indol-3-yl)propyl)-4-(4-(1-methylpiperidin-4-yl)butyl)benzenesulfonamide;
<116> N-(3-(5-chloro-1H-indol-3-yl)propyl)-4-((1-((4-methylpiperazin-1-yl)methyl)cyclopropyl)methoxy)benzenesulfonamide;
<117> N-(3-(5-chloro-1H-indol-3-yl)propyl)-4-((1-(piperazin-1-ylmethyl)cyclopropyl)methoxy)benzenesulfonamide;
<118> N-(3-(5-chloro-1H-indol-3-yl)propyl)-4-(3-(4-methylpiperazin-1-yl)phenoxy)benzenesulfonamide;
<119> 4-(3-bromophenoxy)-N-(3-(5-chloro-1H-indol-3-yl)propyl)benzenesulfonamide;
<120> N-(3-(5-chloro-1H-indol-3-yl)propyl)-4-(3-(piperidin-1-yl)phenoxy)benzenesulfonamide;
<121> N-(3-(5-chloro-1H-indol-3-yl)propyl)-4-(3-(piperazin-1-yl)phenoxy)benzenesulfonamide;
<122> N-(3-(5-chloro-1H-indol-3-yl)propyl)-4-(3-(4-methyl-1,4-diazepan-1-yl)phenoxy)benzenesulfonamide;
<123> N-(3-(5-chloro-1H-indol-3-yl)propyl)-4-((3-(4-methylpiperazin-1-yl)phenyl)amino)benzenesulfonamide;
<124> N-(3-(5-chloro-1H-indol-3-yl)propyl)-4-((3-(piperazin-1-yl)phenyl)amino)benzenesulfonamide;
<125> N-(3-(5-chloro-1H-indol-3-yl)propyl)-4-((4-(4-methylpiperazin-1-yl)pyrimidin-2-yl)amino)benzenesulfonamide;
<126> N-(3-(5-chloro-1H-indol-3-yl)propyl)-4-((3-morpholinophenyl)amino)benzenesulfonamide;
<127> N-(3-(5-chloro-1H-indol-3-yl)propyl)-4-((4-(piperazin-1-yl)pyrimidin-2-yl)amino)benzenesulfonamide;
<128> N-(3-(5-chloro-1H-indol-3-yl)propyl)-4-(3-morpholinophenoxy)benzenesulfonamide;
<129> 4-(3-(1,4-diazepan-1-yl)phenoxy)-N-(3-(5-chloro-1H-indol-3-yl)propyl)benzenesulfonamide;
<130> 4-(3,5-bis(4-methylpiperazin-1-yl)phenoxy)-N-(3-(5-chloro-1H-indol-3-yl)propyl)benzenesulfonamide;
<131> N-(3-(5-chloro-1H-indol-3-yl)propyl)-4-((6-(4-methylpiperazin-1-yl)pyridin-2-yl)amino)benzenesulfonamide;
<132> N-(3-(5-chloro-1H-indol-3-yl)propyl)-4-((6-(piperazin-1-yl)pyridin-2-yl)amino)benzenesulfonamide;
<133> N-(3-(5-chloro-1H-indol-3-yl)propyl)-4-((4-(4-methylpiperazin-1-yl)pyridin-2-yl)amino)benzenesulfonamide;
<134> N-(3-(5-chloro-1H-indol-3-yl)propyl)-4-((4-(piperazin-1-yl)pyridin-2-yl)amino)benzenesulfonamide;
<135> N-(3-(5-chloro-1H-indol-3-yl)propyl)-4-(3-(pyrrolidin-1-yl)phenoxy)benzenesulfonamide <136> N-(3-(5-chloro-1H-indol-3-yl)propyl)-4-(3-(4-hydroxypiperidin-1-yl)phenoxy)benzenesulfonamide;
<137> N-(3-(5-chloro-1H-indol-3-yl)propyl)-4-(3-fluoro-5-(4-methylpiperazin-1-yl)phenoxy)benzenesulfonamide;
<138> 4-(3-bromo-5-(4-methylpiperazin-1-yl)phenoxy)-N-(3-(5-chloro-1H-indol-3-yl)propyl)benzenesulfonamide;
<139> N-(3-(5-chloro-1H-indol-3-yl)propyl)-4-((3-(4-hydroxypiperidin-1-yl)phenyl)amino)benzenesulfonamide;
<140> N-(3-(5-chloro-1H-indol-3-yl)propyl)-4-((6-chloro-4-(4-methylpiperazin-1-yl)pyridin-2-yl)amino)benzenesulfonamide;
<141> 4-((4,6-bis(4-methylpiperazin-1-yl)pyridin-2-yl)amino)-N-(3-(5-chloro-1H-indol-3-yl) propyl)benzenesulfonamide;
<142> N-(3-(5-chloro-1H-indol-3-yl)propyl)-4-((4-(4-methylpiperazin-1-yl)phenyl)amino)benzenesulfonamide;
<143> N-(3-(5-chloro-1H-indol-3-yl)propyl)-4-(3-(4-methylpiperazin-1-yl)propoxy)benzamide;
<144> N-(3-(5-chloro-1H-indol-3-yl)propyl)-4-(3-(piperazin-1-yl)propoxy)benzamide;
<145> N-(3-(5-chloro-1H-indol-3-yl)propyl)-4-(3-(methylsulfonyl)propoxy)benzenesulfonamide
<146> N-(3-(5-chloro-1H-indol-3-yl)propyl)-2-((3-(piperazin-1-yl)propyl)amino)thiazole-5-sulfonamide;
<147> N-(3-(5-chloro-2-methyl-1H-indol-3-yl)propyl)-4-(3-(4-methylpiperazin-1-yl)propoxy)benzenesulfonamide;
<148> 4-(4-(1H-imidazol-1-yl)butyl)-N-(3-(5-chloro-1H-indol-3-yl)propyl)benzenesulfonamide;
<149> N-(2-((5-chloro-1H-indol-3-yl)methyl)phenyl)-4-(3-(4-methylpiperazin-1-yl)propoxy)benzenesulfonamide;
<150> N-(2-((5-chloro-1H-indol-3-yl)methyl)phenyl)-4-(3-(piperazin-1-yl)propoxy)benzenesulfonamide;
<151> N-(4-(5-chloro-1H-indol-3-yl)butan-2-yl)-4-(3-(4-methylpiperazin-1-yl)propoxy)benzenesulfonamide;
<152> N-(4-(5-chloro-1H-indol-3-yl)butan-2-yl)-4-(3-(piperazin-1-yl)propoxy)benzenesulfonamide;
<153> N-(3-(5-bromo-1H-indol-3-yl)propyl)-4-(3-(piperazin-1-yl)propoxy)benzenesulfonamide;
<154> N-(3-(5-bromo-1H-indol-3-yl)propyl)-4-(3-(4-methylpiperazin-1-yl)propoxy)benzenesulfonamide;
<155> N-(3-(5-phenyl-1H-indol-3-yl)propyl)-4-(3-(piperazin-1-yl)propoxy)benzenesulfonamide
<156> 4-(3-(4-methylpiperazin-1-yl)propoxy)-N-(3-(5-phenyl-1H-indol-3-yl)propyl)benzenesulfonamide;
<157> N-(3-(5-chloro-2-methyl-1H-indol-3-yl)propyl)-4-(3-(piperazin-1-yl)propoxy)benzenesulfonamide;
<158> N-(2-(5-chloro-1H-indol-3-yl)ethyl)-4-(3-(4-methylpiperazin-1-yl)propoxy)benzenesulfonamide;
<159> N-(2-(5-chloro-1H-indol-3-yl)ethyl)-4-(3-(piperazin-1-yl)propoxy)benzenesulfonamide;
<160> 4-(3-(1H-1,2,4-triazol-1-yl)propoxy)-N-(3-(5-chloro-1H-indol-3-yl)propyl)benzenesulfonamide;
<161> N-(3-(5-chloro-1H-indol-3-yl)propyl)-4-(3-(2-methyl-1H-imidazol-1-yl)propoxy)benzenesulfonamide;
<162> N-(3-(5-chloro-1H-indol-3-yl)propyl)-4-(3-(4-methyl-3-oxopiperazin-1-yl)propoxy)benzenesulfonamide;
<163> N-(3-(5-chloro-1H-indol-3-yl)propyl)-4-(3-(3-oxopiperazin-1-yl)propoxy)benzenesulfonamide;
<164> N-(3-(5,7-dichloro-1H-indol-3-yl)propyl)-4-(3-(piperazin-1-yl)propoxy)benzenesulfonamide;
<165> N-(3-(5,7-dichloro-1H-indol-3-yl)propyl)-4-(3-(4-methylpiperazin-1-yl)propoxy)benzenesulfonamide;
<166> N-(3-(5-chloro-1H-indol-3-yl)propyl)-4-(3-(4,5-dichloro-1H-imidazol-1-yl)propoxy)benzenesulfonamide;
<167> N-(3-(5-chloro-1H-indazol-3-yl)propyl)-4-(3-(4-methylpiperazin-1-yl)propoxy)benzenesulfonamide;
<168> N-(3-(5-chloro-1H-indazol-3-yl)propyl)-4-(3-(piperazin-1-yl)propoxy)benzenesulfonamide;
<169> N-(3-(5-chloro-1H-pyrrolo[2,3-b]pyridin-3-yl)propyl)-4-(3-(4-methylpiperazin-1-yl)propoxy)benzenesulfonamide;
<170> N-(3-(5-chloro-1H-pyrrolo[2,3-b]pyridin-3-yl)propyl)-4-(3-(piperazin-1-yl)propoxy)benzenesulfonamide;
<171> (R)—N-(3-(5-chloro-1H-indol-3-yl)propyl)-4-(2-hydroxy-3-(4-methylpiperazin-1-yl)propoxy)benzenesulfonamide;
<172> (R)—N-(3-(5-chloro-1H-indol-3-yl)propyl)-4-(2-hydroxy-3-(piperazin-1-yl)propoxy)benzenesulfonamide;
<173> (S)—N-(3-(5-chloro-1H-indol-3-yl)propyl)-4-(2-hydroxy-3-(4-methylpiperazin-1-yl)propoxy)benzenesulfonamide;
<174> (S)—N-(3-(5-chloro-1H-indol-3-yl)propyl)-4-(2-hydroxy-3-(piperazin-1-yl)propoxy)benzenesulfonamide;
<175> N-(3-(5-chloro-1H-indol-3-yl)propyl)-4-(3-(4,5-dimethyl-1H-imidazol-1-yl)propoxy)benzenesulfonamide;
<176> N-(3-(5-chloro-1H-indol-3-yl)propyl)-4-(3-(2,4,5-trimethyl-1H-imidazol-1-yl)propoxy)benzenesulfonamide;
<177> N-((6-chloro-2,3,4,9-tetrahydro-1H-carbazol-3-yl)methyl)-4-(3-(4-methylpiperazin-1-yl)propoxy)benzenesulfonamide;
<178> N-((6-chloro-2,3,4,9-tetrahydro-1H-carbazol-3-yl)methyl)-4-(3-(piperazin-1-yl)propoxy)benzenesulfonamide;
<179> N-(3-(5-chloro-1H-indol-3-yl)cyclohexyl)-4-(3-(4-methylpiperazin-1-yl)propoxy)benzenesulfonamide;
<180> N-(3-(5-chloro-1H-indol-3-yl)cyclohexyl)-4-(3-(piperazin-1-yl)propoxy)benzenesulfonamide;
<181> N-(2-(2-(5-chloro-1H-indol-3-yl)propan-2-yl)phenyl)-4-(3-(4-methylpiperazin-1-yl)propoxy)benzene sulfonamide;
<182> N-(2-(2-(5-chloro-1H-indol-3-yl)propan-2-yl)phenyl)-4-(3-(piperazin-1-yl)propoxy)benzenesulfonamide;
<183> N-(3-(5,6-dichloro-1H-indol-3-yl)propyl)-4-(3-(piperazin-1-yl)propoxy)benzenesulfonamide;
<184> N-(3-(5,6-dichloro-1H-indol-3-yl)propyl)-4-(3-(4-methylpiperazin-1-yl)propoxy)benzenesulfonamide;
<185> N-(3-(5-chloro-1H-indol-3-yl)propyl)-4-(3-(pyridin-4-yloxy)propyl)benzenesulfonamide;
<186> N-(3-(5-chloro-1H-indol-3-yl)propyl)-4-(3-(4-methylpiperazin-1-yl)propyl)benzenesulfonamide;
<187> N-((6-fluoro-2,3,4,9-tetrahydro-1H-carbazol-3-yl)methyl)-4-(3-(4-methylpiperazin-1-yl)propoxy)benzenesulfonamide;
<188> N-((6-fluoro-2,3,4,9-tetrahydro-1H-carbazol-3-yl)methyl)-4-(3-(piperazin-1-yl)propoxy)benzenesulfonamide;
<189> 4-(3-(4-methylpiperazin-1-yl)propoxy)-N-((2,3,4,9-tetrahydro-1H-carbazol-3-yl)methyl)benzenesulfonamide;
<190> 4-(3-(piperazin-1-yl)propoxy)-N-((2,3,4,9-tetrahydro-1H-carbazol-3-yl)methyl)benzenesulfonamide.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

Furthermore, the present invention includes not only the compound represented by formula 1 and the pharmaceutically acceptable salt thereof, but also solvates, isomers, hydrates, etc., which may be prepared therefrom.

The term "isomer" refers to a compound of the present invention or a salt thereof having the same chemical formula or molecular formula, but structurally or sterically different. Such isomer includes structural isomers such as tautomers, R or S isomers having asymmetric carbon center, stereoisomers such as geometric isomers (trans, cis), and optical isomers. All these isomers and mixtures thereof are also included within the scope of the present invention.

The compound represented by formula 1 of the present invention can be prepared according to the preparation method shown in the following example, but this is only an example, and is not limited thereto, and each preparation step can be performed using a method well known to those in the art.

In another aspect of the present invention, the present invention provides a preparation method of a compound represented by formula 1 comprising a step of preparing a compound represented by formula 1 by reacting a compound represented by formula 2 with a compound represented by formula 3 as shown in reaction formula 1 below.

[Reaction Formula 1]

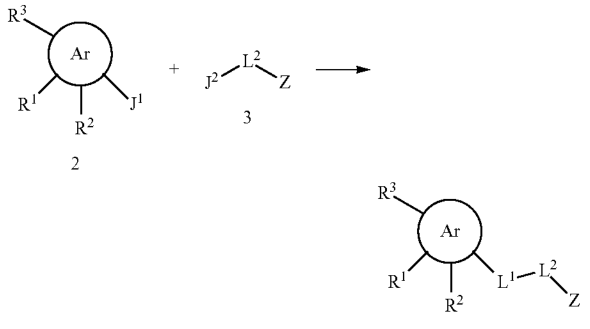

2 3 1

In reaction formula 1, Ar, $R^1$, $R^2$, $R^3$, $L^1$, $L^2$ and Z are as defined in formula 1 above, $J^1$ is chlorosulfone or carboxy; and $J^2$ is amine or piperidine.

Hereinafter, the preparation method shown in reaction formula 1 is described in detail.

In the preparation method of the compound represented by formula 1 of the present invention, the step of reaction formula 1 is a step of preparing a compound represented by formula 1 by reacting a compound represented by formula 2 with a compound represented by formula 3. Particularly, this is a step in which the compound represented by formula 1 is formed by reacting chlorosulfone or carboxy of the compound represented by formula 2 with amine of the compound represented by formula 3.

At this time, the step is not particularly limited as long as it is a method of preparing the compound represented by formula 1, and is included in the scope of the present invention. The compound represented by formula 2 can be understood as a compound having a group that is easy to accept electrons such as sulfone and a leaving group that is easy to react such as chloro, or a compound having carboxy that can react with amine to form amide, and the compound represented by formula 3 can be understood as amine capable of nucleophilic substitution or amide formation reaction, but not always limited thereto. The compound having a group that is easy to accept electrons and a leaving group and the amine having sufficient nucleophilicity to react therewith undergo nucleophilic substitution, or the carboxy and the amine undergo amide formation reaction, thereby preparing the final compound.

In more detail, it can be understood with reference to the preparation method of the example compound of the present invention, but each reaction condition (reaction condition that can be considered by a person skilled in the field of organic synthesis such as reaction temperature, time, atmospheric condition, pressure condition, etc.) can be changed. It can be understood that the invention is not limited thereto, and the compounds and derivatives thereof used in each step include the modified derivatives that can be modified by simply modifying, changing, or removing a substituent, in addition to the disclosed ones, which are included in the present invention.

As preferred embodiments of the preparation method, the preparation methods disclosed in Examples 1 to 190 below can be exemplified, but the present invention is not limited thereto.

In another aspect of the present invention, the present invention provides a pharmaceutical composition comprising a compound represented by formula 1, an isomer thereof or a pharmaceutically acceptable salt thereof as an active ingredient for the prevention or treatment of cancer, inflammatory disease or metabolic disease.

The compound represented by formula 1 according to the present invention, an isomer thereof or a pharmaceutically acceptable salt thereof can inhibit Pin1 (Peptidyl-prolyl cis-trans isomerase NIMA-interacting 1).

Pin1, a proryl isomerase, is an enzyme that catalyzes the cis/trans isomerization of a proline residue amide by binding to the phosphorylated Ser/Thr-Pro site. According to studies to date, Pin1 is known to be involved in the onset and progression of inflammatory disease, metabolic disease and cancer.

In particular, it has been reported that Pin1 activates 56 oncogenes involved in oncogenesis and inhibits the activity of 26 tumor suppressor genes, thereby inducing cancer metastasis and cancer angiogenesis in the overall cancer development mechanism.

In addition, it has been reported that when Pin1 is inhibited or Pin1 gene expression is knocked down, the productions of prostaglandin E2 and nitric oxide stimulated by lipopolysaccharide (LPS) and nicotine are weakened, and the expressions of cyclooxygenase-2 (COX-2) and inducible nitric oxide synthase (iNOS) are also weakened, resulting in an anti-inflammatory effect.

It is well known that when Pin1 is attached to CRTC2, the production of CBP-CRTC2-CREB complex that promotes gluconeogenesis is inhibited, so that CRTC2 can be regulated according to the expression level of Pin1 and thus may be involved in the regulation of glucose metabolism.

Therefore, drugs that affect Pin1 expression or activity can be used as a therapeutic agent for cancer, inflammatory disease or metabolic disease such as diabetes.

Thus, the compound represented by formula 1 according to the present invention, the isomer thereof or the pharmaceutically acceptable salt thereof can be effectively used as a pharmaceutical composition for preventing or treating cancer, inflammatory disease or metabolic disease, or a health functional food for preventing or ameliorating cancer, inflammatory disease or metabolic disease comprising the same as an active ingredient.

The cancer can be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell cancer, ovarian epithelial carcinoma, ovarian germ cell carcinoma, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal cancer, kidney cancer, heart Cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal interstitial cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, rectal cancer, rectal carcinoid tumor, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer and thymus cancer.

The inflammatory disease can be at least one selected from the group consisting of arthritis, encephalomyelitis, meningitis, peritonitis, osteomyelitis, encephalitis, ankylosing spondylitis, vasculitis, uveitis, ileitis, atherosclerosis, myositis, leukocyte damage, inflammatory bowel disease, ulcerative colitis, retinal detachment, retinitis pigmentosa, macular degeneration, pancreatitis, atopic dermatitis, gout, vasculitis, non-alcoholic steatohepatitis, primary sclerosing cholangitis, nephritis, intraperitoneal disease, sepsis, systemic inflammatory reaction syndrome, myocardial infarction, allergic disease, asthma, atopic dermatitis, Wegener's granulomatosis, pulmonary sarcoidosis, Behcet's disease, chronic obstructive pulmonary disease and periodontitis.

The metabolic disease can be at least one selected from the group consisting of obesity, diabetes, hypertension, hyperlipidemia, hypercholesterolosis, arteriosclerosis, fatty liver, gout, stroke and heart disease.

In another aspect of the present invention, the present invention provides a health functional food comprising a compound represented by formula 1, an isomer thereof or a pharmaceutically acceptable salt thereof as an active ingredient for the prevention or amelioration of cancer, inflammatory disease or metabolic disease.

The term "prevention" used in the present invention refers to any action that suppresses or delays the onset of a neurological disorder by administering the pharmaceutical composition according to the present invention to a subject.

The term "treatment" used in the present invention refers to any action to improve or benefit the symptoms of a neurological disorder by administering the pharmaceutical composition according to the present invention to a subject.

When the composition of the present invention is used as a medicament, the pharmaceutical composition comprising the compound represented by formula 1, the isomer thereof or the pharmaceutically acceptable salt thereof as an active ingredient can be formulated and administered in various oral or parenteral forms as follows upon clinical administration, but not always limited thereto.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

When the compound represented by formula 1, its isomer, or its pharmaceutically acceptable salt is used as a pharmaceutical composition for the prevention or treatment of cancer, inflammatory disease or metabolic disease, it can be administered as an individual therapeutic agent or can be used in combination with other therapeutic agents in use.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by formula 1, the isomer thereof or the pharmaceutically acceptable salt thereof as a formulation for parenteral administration, the compound represented by formula 1, the isomer thereof or the pharmaceutically acceptable salt thereof is mixed with a stabilizer or a buffering agent in water to produce a solution or a suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated according to the conventional methods such as dispersion and gelation.

The dosage of the pharmaceutical composition comprising the compound represented by formula 1 as an active ingredient to the human body can be determined according to formulation method, age, weight, gender, administration method, health condition, and severity of disease. The preferable dosage of the composition of the present invention is 0.001~1000 mg/kg per day, which can be administered orally or parenterally several times a day or preferably 1~3 times per day according to the judgment of a doctor or a pharmacist.

The pharmaceutical composition of the present invention can be used as a single formulation. The pharmaceutical composition of the present invention can also be prepared and used as a combined formulation further including one or more other therapeutic agents.

In another aspect of the present invention, the present invention provides a method for treating cancer, inflammatory disease or metabolic disease comprising a step of administering the pharmaceutical composition to a subject in need thereof. The pharmaceutical composition refers to a pharmaceutical composition for the prevention or treatment of cancer, inflammatory disease or metabolic disease, comprising the compound represented by formula 1, the isomer thereof or the pharmaceutically acceptable salt thereof as an active ingredient.

In another aspect of the present invention, the present invention provides a use of the pharmaceutical composition or the health functional food composition comprising the compound represented by formula 1, the isomer thereof or the pharmaceutically acceptable salt thereof as an active ingredient in the prevention or treatment of cancer, inflammatory disease or metabolic disease.

MODE FOR THE INVENTION

Hereinafter, the present invention will be described in detail by the following examples and experimental examples.

However, the following examples and experimental examples are only for illustrating the present invention, and the contents of the present invention are not limited thereto.

<Example 1> Preparation of N-(3-([1,1'-biphenyl]-4-yl)propyl)-4-butoxybenzenesulfonamide

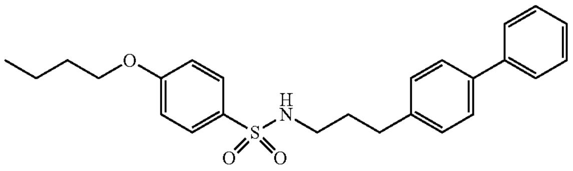 [SMILES: CCCCOc1ccc(S(=O)(=O)NCCCc2ccc(-c3ccccc3)cc2)cc1]

Step 1: Preparation of (E)-4-(2-isocyanovinyl)-1,1'-biphenyl

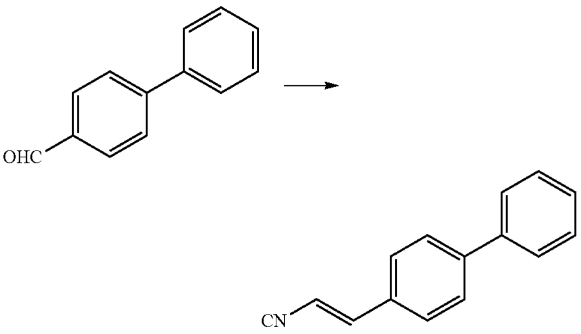

Sodium hydride (60% wt, 0.263 g, 6.59 mmol) was dissolved in anhydrous tetrahydrofuran (13 ml), to which diethyl(cyanomethyl)phosphonate (0.977 ml, 6.04 mmol) was added dropwise at 0° C. [1,1'-Biphenyl]-4-carbaaldehyde (1 g, 5.49 mmol) was added dropwise to the reaction mixture, followed by stirring at room temperature for 30 minutes. Upon completion of the reaction, the reaction mixture was extracted with dichloromethane, and the organic layer was sequentially washed with water and brine, dried over anhydrous sodium sulfate, and the solvent was removed under reduced pressure. As a result, (E)-4-(2-isocyanovinyl)-1,1'-biphenyl was obtained as a white solid without further purification.

Step 2: Preparation of 3-([1,1'-biphenyl]-4-yl)propanenitrile

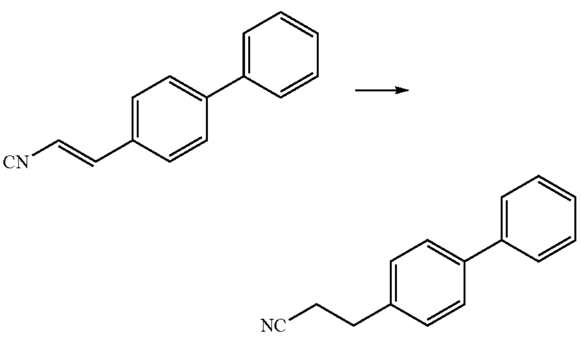

The compound (1.126 g, 5.49 mmol) prepared in step 1 above was dissolved in ethyl acetate:methanol (1:1) (24 ml), to which Pd/C (10% wt) was added dropwise at 0° C., followed by stirring at room temperature for 12 hours in hydrogen atmosphere. Upon completion of the reaction, the reaction mixture was filtered with celite and the solvent was removed under reduced pressure. As a result, 3-([1,1'-biphenyl]-4-yl)propanenitrile was obtained as a white solid without further purification.

Step 3: Preparation of 3-([1,1'-biphenyl]-4-yl)propan-1-amine

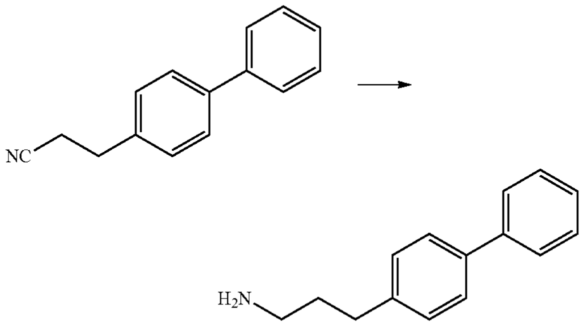

The compound 3-([1,1'-biphenyl]-4-yl)propanenitrile (1.137 g, 5.49 mmol) synthesized in step 2 above was dissolved in anhydrous tetrahydrofuran (10 ml), to which 1 M lithium aluminum hydride (10.97 ml, 10.97 mmol) was added dropwise at 0° C., followed by stirring at room temperature for 2 hours. The reaction was terminated by dropwise addition of water, and the reaction mixture was filtered with a filter, and the solvent was removed under reduced pressure. As a result, 3-([1,1'-biphenyl]-4-yl)propane-1-amine was obtained as a sticky yellow compound without further purification.

Step 4: Preparation of N-(3-([1,1'-biphenyl]-4-yl)propyl)-4-butoxybenzenesulfonamide

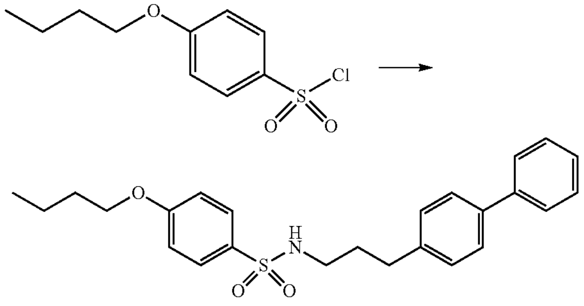

4-Butoxy benzenesulfonylchloride (40 μl, 0.200 mmol) was dissolved in dichloromethane (1 ml), to which 3-([1,1'-biphenyl]-4-yl)propane-1-amine (127 mg, 0.601 mmol) synthesized in step 3 above was added, followed by stirring at room temperature for 1 hour. Upon completion of the reaction, the reaction mixture was extracted with dichloromethane, and the organic layer was sequentially washed with water and brine, dried over anhydrous sodium sulfate, and the solvent was removed under reduced pressure. Then, the reaction mixture was separated and purified by MPLC to give a target compound (14.4 mg, 16%, white solid).

The compounds of Examples 2 to 7 were prepared in a similar manner to the method described in step 4 of Example 1.

<Example 8> Preparation of 4-(2-(4-butoxyphenylsulfonamido)ethyl)benzoic acid

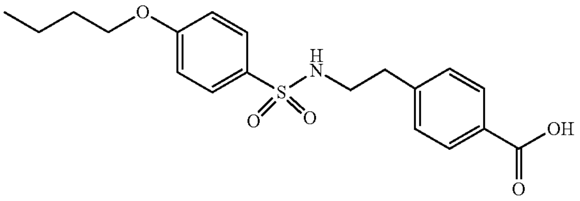 [SMILES: CCCCOc1ccc(S(=O)(=O)NCCc2ccc(C(=O)O)cc2)cc1]

Step 1: Preparation of methyl 4-(2-((4-butoxyphenyl)sulfonamido)ethyl)benzoate

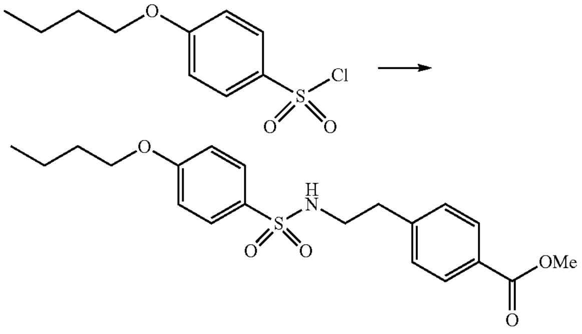

A target compound (6.7 mg, 28%, white solid) was obtained in a similar manner to the method described in step 4 of Example 1.

Step 2: Preparation of 4-(2-(4-butoxyphenylsulfonamido)ethyl)benzoic acid

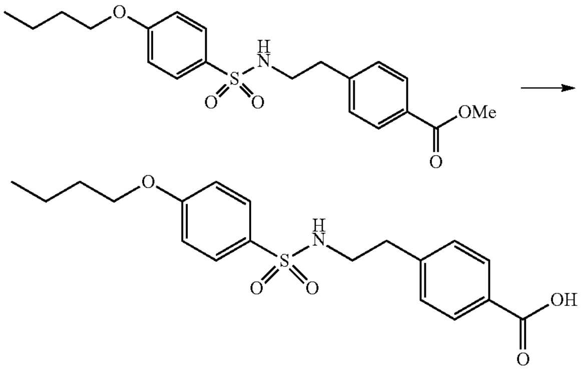

The compound methyl 4-(2-((4-butoxyphenyl)sulfonamido)ethyl)benzoate (23 mg, 0.059 mmol) prepared in step 1 above was dissolved in methanol (0.5 ml), to which 4 M potassium hydroxide aqueous solution (0.147 ml, 0.588 mmol) was added dropwise, followed by stirring at room temperature for 3 hours. Upon completion of the reaction, the reaction mixture was neutralized using 1 M HCl aqueous solution. The reaction mixture was extracted with dichloromethane, and the organic layer was sequentially washed with water and brine, dried over anhydrous sodium sulfate, and the solvent was removed under reduced pressure. Then, the reaction mixture was separated and purified by MPLC to give a target compound (3.4 g, 15%, white solid).

The compound of Example 9 was prepared by the same manner as described in step 1 of Example 8.

<Example 10> Preparation of N-(2-(4-benzylpiperidin-1-yl)ethyl)-4-butoxybenzenesulfonamide

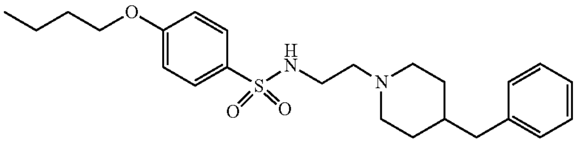 [SMILES: CCCCOc1ccc(S(=O)(=O)NCCN2CCC(Cc3ccccc3)CC2)cc1]

Step 1: Preparation of tert-butyl (2-(4-benzylpiperidin-1-yl)ethyl)carbamate

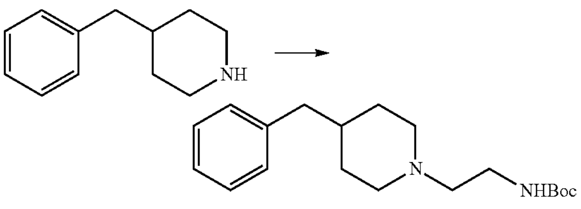

4-Benzylpiperidine (8 g, 45.6 mmol) and potassium carbonate ($K_2CO_3$) (9.46 g, 68.5 mmol) were dissolved in DMF (228 ml), followed by stirring at room temperature for 5 minutes. Tert-butyl(2-bromoethyl)carbamate (12.27 g, 54.8 mmol) was added dropwise to the reaction mixture, followed by stirring at 60° C. for 12 hours. Tertbutyl(2-bromoethyl)carbamate (12.27 g, 54.8 mmol) was added dropwise to the reaction product again, followed by stirring at 60° C. for 12 hours. Upon completion of the reaction, 1 M HCl aqueous solution was added dropwise thereto, followed by extraction with dichloromethane. The organic layer was sequentially washed with water and brine, dried over anhydrous sodium sulfate, and the solvent was removed under reduced pressure. Then, the reaction mixture was separated and purified by MPLC to give tert-butyl(2-(4-benzylpiperidin-1-yl)ethyl)carbamate (12.9 g, 89%, white solid).

Step 2: Preparation of 2-(4-benzylpiperidin-1-yl)ethanamine 2 HCl salt

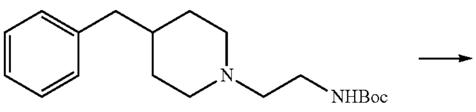

-continued

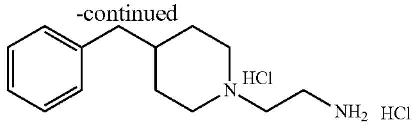

Tert-butyl (2-(4-benzylpiperidin-1-yl)ethyl)carbamate (12.9 g, 40.5 mmol) prepared in step 1 above was directly treated with 4 M HCl dioxane solution (10.13 ml, 40.5 mmol), followed by stirring at room temperature for 2 hours. Upon completion of the reaction, excess HCl was removed under reduced pressure. As a result, 2-(4-benzylpiperidin-1-yl)ethanamine 2HCl salt (8.9 g, 75%, white solid) was obtained.

Step 3: Preparation of N-(2-(4-benzylpiperidin-1-yl)ethyl)-4-butoxybenzenesulfonamide

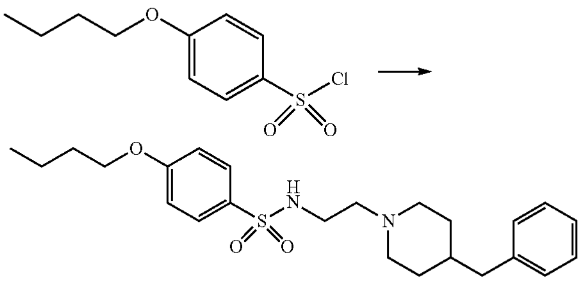

A target compound (7.6 mg, 14%, transparent oil) was obtained in a similar manner to the method described in step 4 of Example 1 using the compound prepared in step 2 above.

The compound of Example 11 was prepared in a similar manner to the method described in step 4 of Example 1.

<Example 12> Preparation of 4-butoxy-N-(3-oxo-3-phenylpropyl)benzenesulfonamide

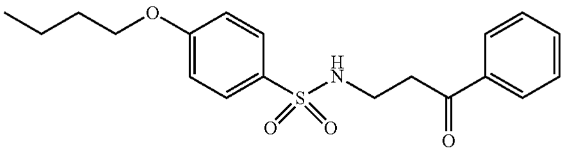 [SMILES: CCCCOc1ccc(S(=O)(=O)NCCC(=O)c2ccccc2)cc1]

Step 1: Preparation of (4-butoxy-N-(3-hydroxy-3-phenylpropyl)benzenesulfonamide

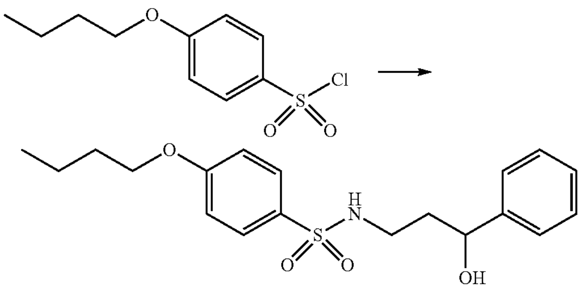

A target compound was obtained in a similar manner to the method described in step 4 of Example 1.

Step 2: Preparation of 4-butoxy-N-(3-oxo-3-phenylpropyl)benzenesulfonamide

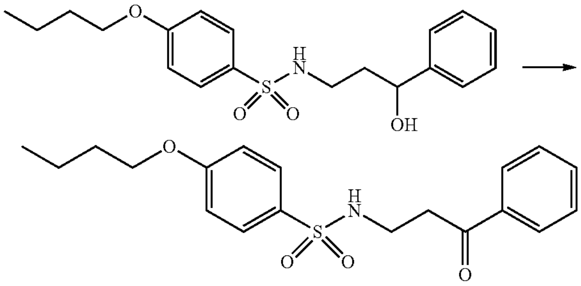

The compound (30 mg, 0.121 mmol) prepared in step 1 above was dissolved in dichloromethane (0.5 ml), to which manganese oxide (IV) (31.1 mg, 0.358 mmol) was added dropwise, followed by stirring at room temperature for 12 hours. Upon completion of the reaction, the reaction mixture was filtered with celite, and the solvent was removed under reduced pressure. Then, the reaction mixture was separated and purified by MPLC to give a target compound (9.2 mg, 71%, white solid).

The compound of Example 13 was prepared in a similar manner to the method described in step 4 of Example 1.

<Example 14> Preparation of 4-(3-(dimethylamino)propoxy)-N-phenethylbenzenesulfonamide

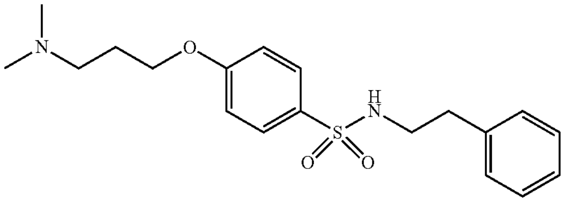 [SMILES: CN(C)CCCOc1ccc(S(=O)(=O)NCCc2ccccc2)cc1]

Step 1: Preparation of N,N-dimethyl-3-phenoxypropane-1-amine

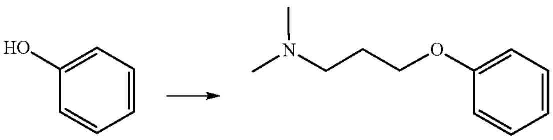

Phenol (600 mg, 6.38 mmol), 3-(dimethylamino)propane-1-ol (0.88 ml, 7.44 mmol) and triphenylphosphine (2.508 g, 9.56 mmol) were dissolved in tetrahydrofuran (12 ml) at 0° C., to which diethyl azodicarboxylate solution (DEAD) (4.34 ml, 9.56 mmol) was added dropwise, followed by stirring at room temperature for 12 hours in nitrogen atmosphere. Upon completion of the reaction, the solvent was removed under reduced pressure. The reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give N,N-dimethyl-3-phenoxypropane-1-amine (922 mg, 81%, yellow oil).

Step 2: Preparation of 4-(3-(dimethylamino)propoxy)benzene-1-sulfonyl chloride

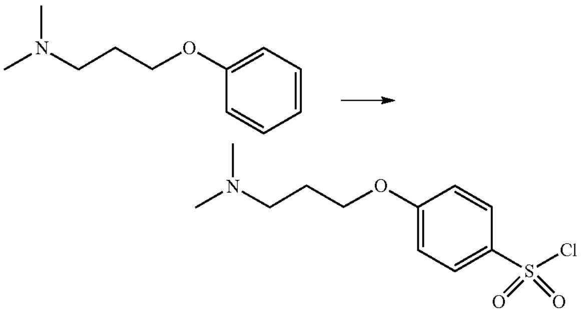

N,N-dimethyl-3-phenoxypropane-1-amine (922 mg, 5.14 mmol) prepared in step 1 above was dissolved in dichloromethane (6 ml), to which chlorosulfonic acid (1.37 ml, 20.57 mmol) was added dropwise, followed by stirring at room temperature for 3 hours. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and then the solvent was removed under reduced pressure. As a result, 4-(3-(dimethylamino)propoxy)benzene-1-sulfonyl chloride (451 mg, 32%, yellow solid) was obtained without further purification.

Step 3: Preparation of 4-(3-(dimethylamino)propoxy)-N-phenethylbenzenesulfonamide

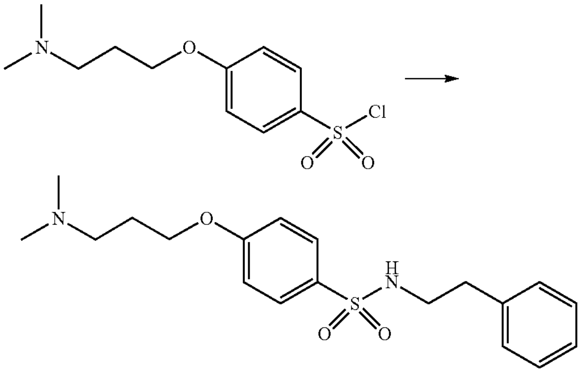

4-(3-(Dimethylamino)propoxy)benzene-1-sulfonyl chloride (100 mg, 0.318 mmol) prepared in step 2 above was dissolved in dichloromethane (2 ml), to which 2-phenylethanamine (116 mg, 0.955 mmol) and potassium carbonate ($K_2CO_3$) (48.4 mg, 0.35 mmol) were added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (88 mg, 75%, transparent oil).

The compounds of Examples 15 and 16 were prepared in a similar manner to the method described in step 3 of Example 14.

<Example 17> Preparation of 4-(2-(4-(3-(dimethylamino)propoxy)phenylsulfonamido)ethyl)benzoic acid

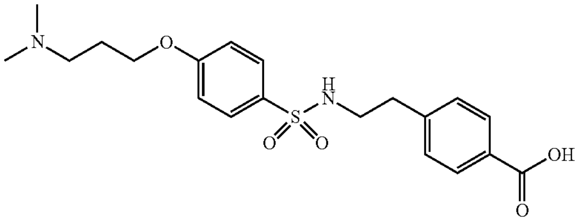 [SMILES: CN(C)CCCOc1ccc(S(=O)(=O)NCCc2ccc(C(=O)O)cc2)cc1]

Step 1: Preparation of methyl 4-(2-(4-(3-(dimethylamino)propoxy)phenylsulfonamido)ethyl)benzoate

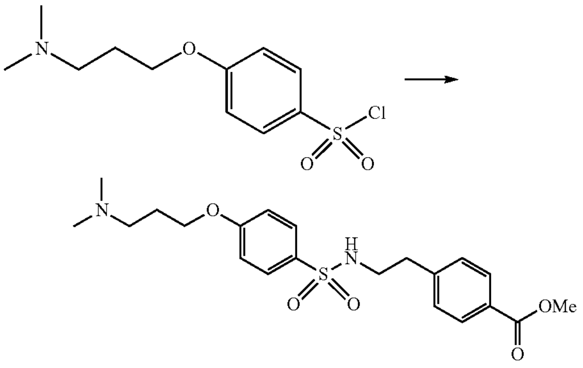

A target compound was prepared in a similar manner to the method described in step 3 of Example 14.

Step 2: Preparation of 4-(2-(4-(3-(dimethylamino)propoxyphenylsulfonamido)ethyl)benzoic acid

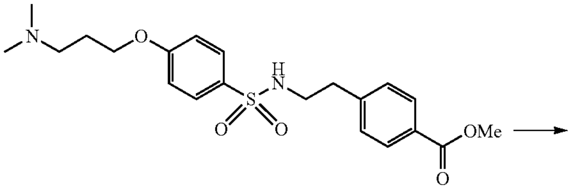

-continued

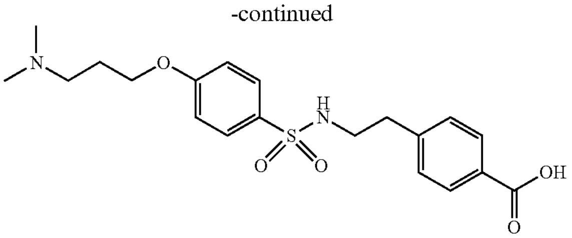

The compound (58 mg, 0.138 mmol) prepared in step 1 above was dissolved in methanol (1 ml), to which 4 M potassium hydroxide aqueous solution (0.69 ml, 2.76 mmol) was added dropwise, followed by stirring at room temperature for 1 hour. Upon completion of the reaction, the reaction mixture was neutralized with 1 M HCl aqueous solution, extracted with dichloromethane, dried over anhydrous sodium sulfate, and then the solvent was removed under reduced pressure. Then, the reaction mixture was separated and purified by prep TLC to give a target compound (1.7 mg, 3%, white solid).

The compound of Example 18 was prepared in a similar manner to the method described in step 3 of Example 14.

<Example 19> Preparation of 4-butoxy-N-(3-(naphthalene-1-yl)propyl)benzenesulfonamide

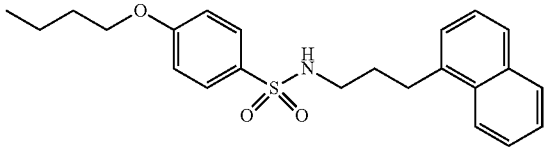 [SMILES: CCCCOc1ccc(S(=O)(=O)NCCCc2cccc3ccccc23)cc1]

Step 1: Preparation of tert-butyl(3-(naphthalene-1-yl)propyl)carbamate

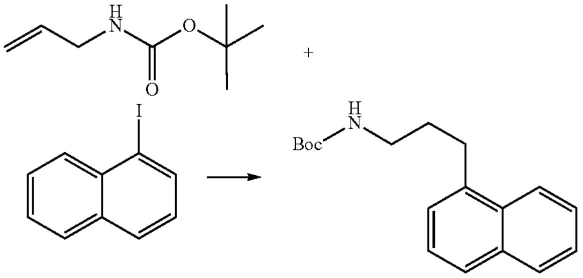

Tert-butylallylcarbamate (1 g, 6.36 mmol) was dissolved in tetrahydrofuran (6 ml), to which 9-BBN (10 mmol) dissolved in 0.5 M tetrahydrofuran was added dropwise, followed by stirring at room temperature for 2.5 hours. 1-Iodonaphthalene (0.925 ml, 6.36 mmol), $PdCl_2(dppf)-CH_2Cl_2$ (308 mg, 0.377 mmol) and 1 M sodium hydroxide aqueous solution (10 ml) were added dropwise to the reaction mixture, followed by stirring at room temperature for 3 hours. $PdCl_2(dppf)-CH_2Cl_2$ (55 mg, 0.07 mmol) was added dropwise thereto, followed by stirring at room temperature for 14 hours. Upon completion of the reaction, saturated ammonium chloride aqueous solution was added dropwise thereto, and the reaction mixture was extracted with ethyl acetate, dried over magnesium sulfate, and the solvent was removed under reduced pressure. Then, the compound (1.6 g) obtained by separating and purifying the reaction mixture by MPLC was added dropwise to a mixture of tetrahydrofuran (20 ml), 15% sodium hydroxide aqueous solution (5 ml) and 30% hydrogen peroxide (10 ml) at 0° C., followed by stirring at the same temperature for 2 hours. Upon completion of the reaction, ethyl acetate was added dropwise thereto, and the reaction mixture was washed with a supersaturated sodium hydrogen carbonate aqueous solution and brine, dried over anhydrous magnesium sulfate, and then the solvent was removed under reduced pressure. Then, the reaction mixture was separated and purified by MPLC to give tertbutyl(3-(naphthalene-1-yl)propyl)carbamate (1.4 g, 77%).

Step 2: Preparation of 3-(naphthalene-1-yl)propane-1-amine

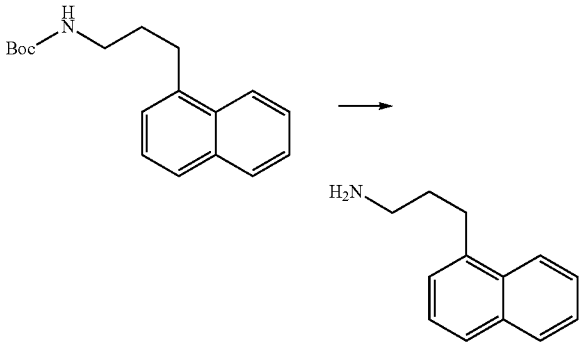

Tert-butyl(3-(naphthalene-1-yl)propyl)carbamate (1.4 g, 4.9 mmol) prepared in step 1 above was dissolved in dichloromethane (20 ml), to which trifluoroacetic acid (10 ml, 130 mmol) was added dropwise, followed by stirring at room temperature for 3 hours. Upon completion of the reaction, the reaction mixture was neutralized by adding 10% sodium hydroxide aqueous solution dropwise. The reaction mixture was extracted with dichloromethane, and the organic layer was sequentially washed with water and brine, dried over anhydrous sodium sulfate, and the solvent was removed under reduced pressure to give 3-(naphthalene-1-yl)propane-1-amine (925 mg, 100%).

Step 3: Preparation of 4-butoxy-N-(3-(naphthalene-1-yl)propyl)benzenesulfonamide

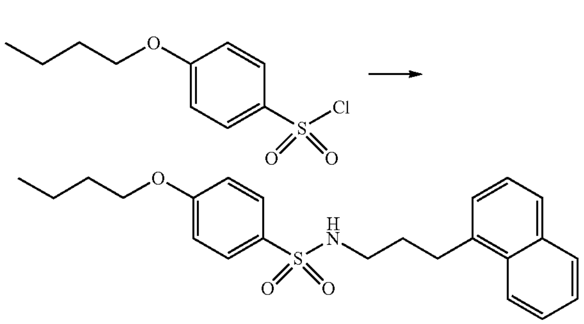

A target compound (66 mg, 82%, transparent solid) was obtained in a similar manner to the method described in step 4 of Example 1 using the compound prepared in step 2 above.

The compound of Example 20 was prepared in a similar manner to the method described in step 4 of Example 1.

<Example 21> Preparation of N-(3-(1H-indole-3-yl)propyl)-4-(2-(dimethylamino)ethoxy)benzene-sulfonamide

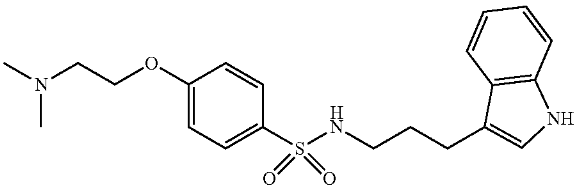 [SMILES: CN(C)CCOc1ccc(S(=O)(=O)NCCCc2c[nH]c3ccccc23)cc1]

Step 1: Preparation of N,N-dimethyl-2-phenoxyethane-1-amine

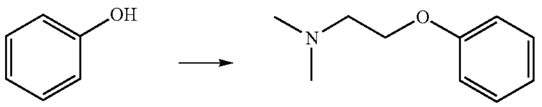

Phenol (500 mg, 5.31 mmol), 2-(dimethylamino)ethane-1-ol (521 mg, 5.84 mmol) and triphenylphosphine (2.089 g, 797 mmol) were dissolved in tetrahydrofuran (20 ml) at 0° C., to which diethyl azodicarboxylate solution (DEAD) (3.61 ml, 7.97 mmol) was added dropwise, followed by stirring at room temperature for 12 hours in nitrogen atmosphere. Upon completion of the reaction, the solvent was removed under reduced pressure. The reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give N,N-dimethyl-2-phenoxyethane-1-amine (870 mg, 99%, yellow solid).

Step 2: Preparation of 4-(2-(dimethylamino)ethoxy)benzenesulfonyl chloride

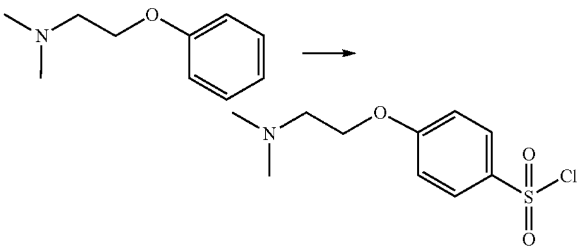

N,N-dimethyl-3-phenoxyethane-1-amine (533 mg, 3.23 mmol) prepared in step 1 above was dissolved in dichloromethane (3 ml), to which chlorosulfonic acid (0.858 ml, 12.90 mmol) was added dropwise at 0° C., followed by stirring at room temperature for 3 hours. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and then the solvent was removed under reduced pressure. As a result, 4-(2-(dimethylamino)ethoxy)benzenesulfonyl chloride (622 mg, 73%, yellow oil) was obtained without further purification.

Step 3: Preparation of N-(3-(1H-indole-3-yl)propyl)-4-(2-(dimethylamino)ethoxy)benzenesulfonamide

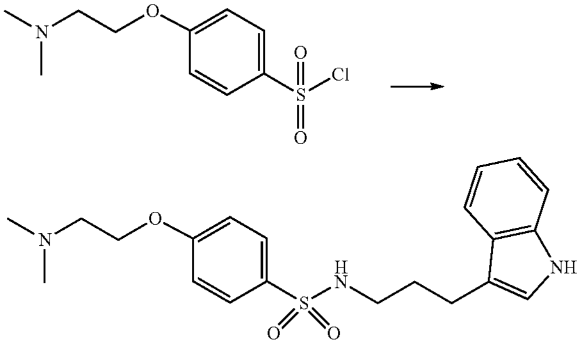

4-(2-(Dimethylamino)ethoxy)benzenesulfonyl chloride (45 mg, 0.171 mmol) prepared in step 2 above was dissolved in dichloromethane, to which 3-(1H-indole-3-yl)propanee-1-amine (131 mg, 0.751 mmol) was added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (11 mg, 17%, yellow solid).

The compound of Example 22 was prepared in a similar manner to the method described in Example 14.

The compounds of Examples 23 to 25 were prepared in a similar manner to the method described in step 4 of Example 1.

<Example 26> Preparation of N-(3-(1H-indole-3-yl)propyl)-4-(isopentyloxy)benzenesulfonamide

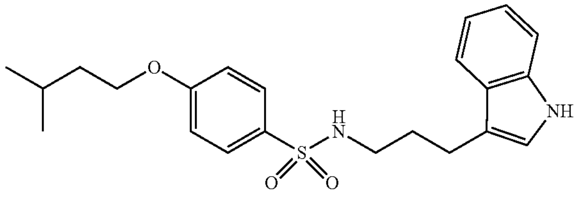 [SMILES: CC(C)CCOc1ccc(S(=O)(=O)NCCCc2c[nH]c3ccccc23)cc1]

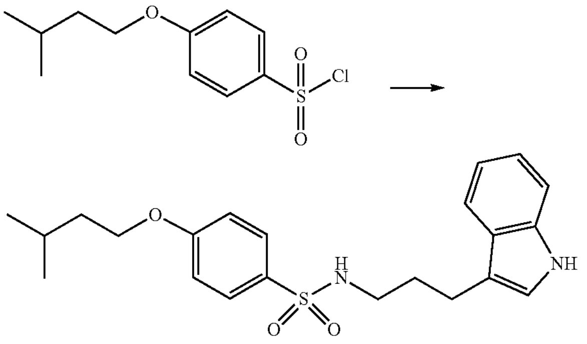

4-(Isopentyloxy)benzenesulfonyl chloride (20 mg, 0.076 mmol) was dissolved in dichloromethane (1.5 ml), to which 3-(1H-indole-3-yl)propane-1-amine (30 mg, 0.172 mmol) was added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (26 mg, 85%, yellow solid).

<Example 27> Preparation of N-(3-(1H-indole-3-yl)propyl)-4-(pentyloxy)benzenesulfonamide

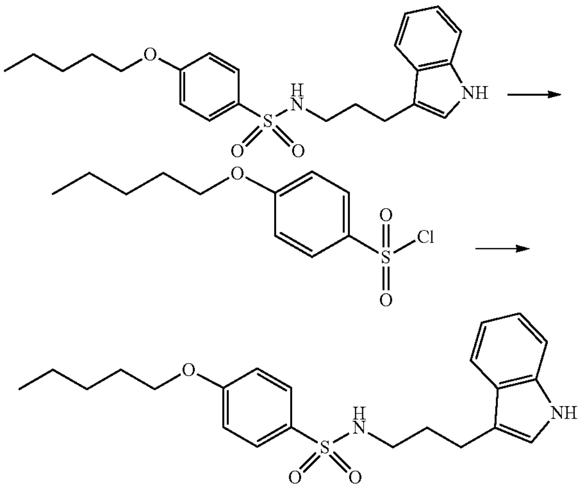

4-(Pentyloxy)benzenesulfonyl chloride (20 mg, 0.076 mmol) was dissolved in dichloromethane, to which 3-(1H-indole-3-yl)propane-1-amine (30 mg, 0.172 mmol) was added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (25 mg, 81%, white solid).

The compound of Example 28 was prepared in a similar manner to the method described in step 4 of Example 1.

<Example 29> Preparation of 4-butoxy-N-(2-(5-hydroxy-1H-indole-3-yl)ethyl)benzenesulfonamide

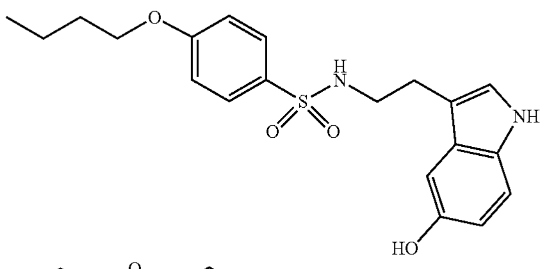

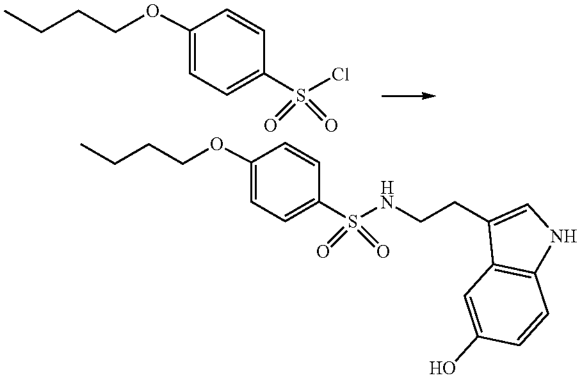

4-Butoxy benzenesulfonyl chloride (50 mg, 0.201 mmol) was dissolved in dichloromethane (1 ml), to which 3-(2-aminoethyl)-1H-indole-5-olhydrochloride (128 mg, 0.603 mmol) and triethylamine (0.084 ml, 0.603 mmol) were added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (10.2 mg, 13%, white solid).

<Example 30> Preparation of N-(3-(1H-indole-3-yl)propyl)-4-(3-morpholinopropoxy)benzenesulfonamide

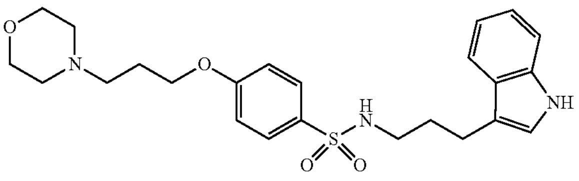 [SMILES: O=S(=O)(NCCCc1c[nH]c2ccccc12)c1ccc(OCCCN2CCOCC2)cc1]

Step 1: Preparation of 4-(3-phenoxypropyl)morpholine

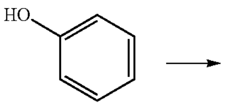

-continued

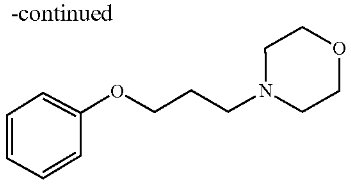

Phenol (600 mg, 6.38 mmol), 4-(3-hydroxypropyl) morpholine (1.11 g, 7.65 mmol) and triphenylphosphine (2.5 g, 9.56 mmol) were dissolved in tetrahydrofuran (16 ml) at 0° C., to which diethyl azodicarboxylate solution (DEAD) (4.34 ml, 9.56 mmol) was added dropwise, followed by stirring at room temperature for 12 hours in nitrogen atmosphere. Upon completion of the reaction, the solvent was removed under reduced pressure. The reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give 4-(3-phenoxypropyl)morpholine (1.41 g, 100%, transparent oil).

Step 2: Preparation of 4-(3-morpholinopropoxy)benzene-1-sulfonyl chloride

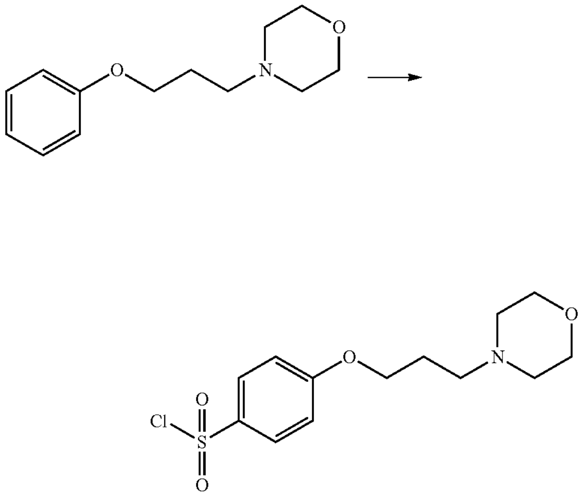

4-(3-Phenoxypropyl)morpholine (1.41 g, 6.38 mmol) prepared in step 1 above was dissolved in dichloromethane (12 ml), to which chlorosulfonic acid (1.69 ml, 25.5 mmol) was added at 0° C., followed by stirring at room temperature for 3 hours. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and then the solvent was removed under reduced pressure. As a result, 4-(3-morpholinopropoxy) benzene-1-sulfonyl chloride (2.22 g, 67%, yellow solid) was obtained without further purification.

Step 3: Preparation of N-(3-(1H-indole-3-yl)propyl)-4-(3-morpholinopropoxy)benzenesulfonamide

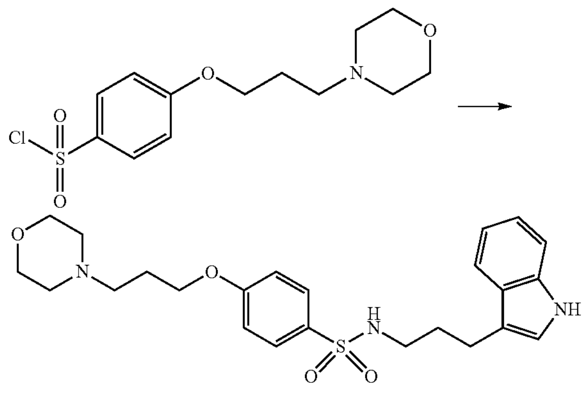

4-(3-Morpholinopropoxy)benzene-1-sulfonyl chloride (150 mg, 0.469 mmol) prepared in step 2 above was dissolved in dichloromethane (1.5 ml), to which 3-(1H-indole-3-yl)propane-1-amine (245 mg, 1.407 mmol) and potassium carbonate (194 mg, 1.407 mmol) were added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (10.6 mg, 5%, yellow solid).

<Example 31> Preparation of N-(3-(1H-indole-3-yl)propyl)-4-(3-(4-methylpiperazine-1-yl)propoxy) benzenesulfonamide

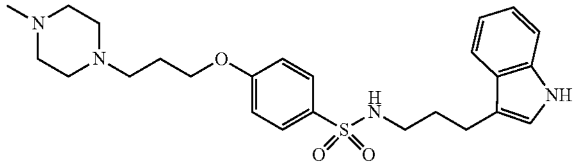 [SMILES: CN1CCN(CCCOc2ccc(S(=O)(=O)NCCCc3c[nH]c4ccccc34)cc2)CC1]

Step 1: Preparation of 4-(3-bromopropoxy)benzene-1-sulfonyl chloride

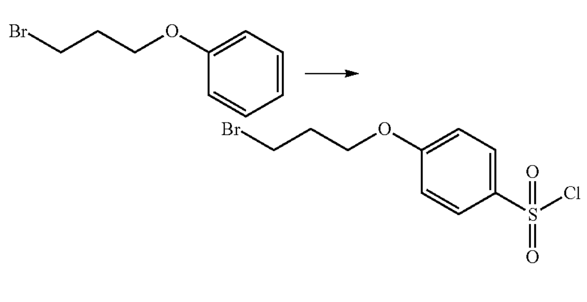

(3-Bromopropoxy)benzene (1 g, 4.65 mmol) was dissolved in dichloromethane (15 ml), to which chlorosulfonic acid (1.236 ml, 18.60 mmol) was added dropwise at 0° C., followed by stirring at room temperature for 1 hour. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and then the solvent was removed under reduced pressure. As a result, 4-(3-bromopropoxy)benzene-1-sulfonyl chloride (1.1 g, 38%, yellow solid) was obtained without further purification.

Step 2: Preparation of N-(3-(1H-indole-3-yl)propyl)-4-(3-bromopropoxy)benzenesulfonamide

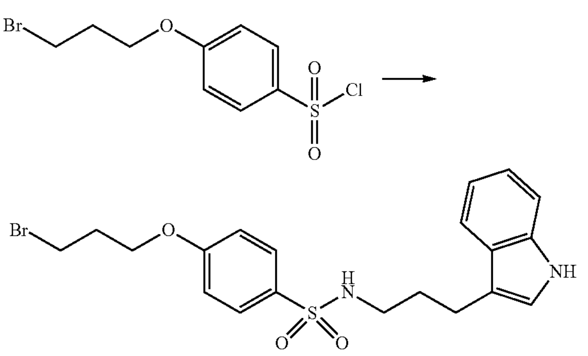

4-(3-Bromopropoxy)benzene-1-sulfonyl chloride (538 mg, 1.716 mmol) prepared in step 1 above was dissolved in dichloromethane (5 ml), to which 3-(1H-indole-3-yl)propane-1-amine (897 mg, 5.15 mmol) and potassium carbonate ($K_2$ $CO_3$) (711 mg, 5.15 mmol) were added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give N-(3-(1H-indole-3-yl)propyl)-4-(3-bromopropoxy)benzenesulfonamide (230 mg, 29%, white solid).

Step 3: Preparation of N-(3-(1H-indole-3-yl)propyl)-4-(3-(4-methylpiperazine-1-yl)propoxy)benzenesulfonamide

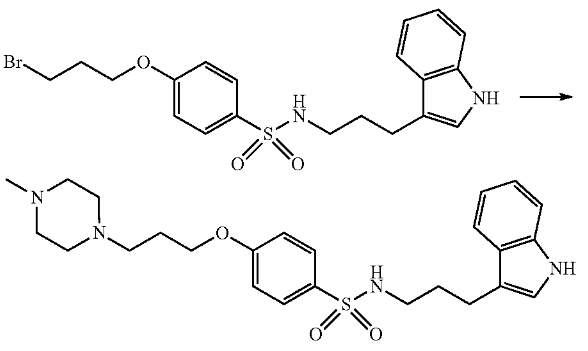

N-(3-(1H-indole-3-yl)propyl)-4-(3-bromopropoxy)benzenesulfonamide (175 mg, 0.388 mmol) prepared in step 2 above was dissolved in ethanol (1.5 ml), to which 1-methylpiperazine (0.172 ml, 1.551 mmol) and potassium carbonate ($K_2CO_3$) (80 mg, 0.582 mmol) were added dropwise, followed by stirring at 70° C. for 12 hours. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (66 mg, 36%, white solid).

The compounds of Examples 23 to 25 were prepared in a similar manner to the method described in step 4 of Example 1.

The compounds of Examples 34 and 35 were prepared in a similar manner to the method described in Example 30.

The compound of Example 36 was prepared in a similar manner to the method described in Example 31.

The compounds of Examples 37 to 40 were prepared in a similar manner to the method described in Example 14.

The compounds of Examples 41 and 42 were prepared in a similar manner to the method described in Example 30.

The compounds of Examples 43 to 45 were prepared in a similar manner to the method described in Example 31.

<Example 46> Preparation of 4-(3-(dimethylamino)propoxy)-N-(3-(1-methyl-1H-indole-3-yl)propyl)benzenesulfonamide

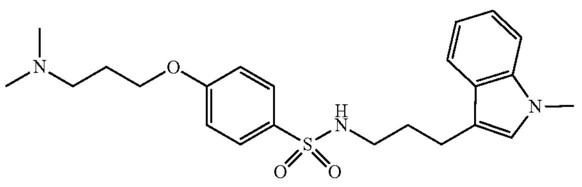

Step 1: Preparation of N-(3-(1H-indole-3-yl)propyl)-4-(3-(dimethylamino)propoxy)benzenesulfonamide N-(3-(1H-indole-3-yl)propyl)-4-(3-(dimethylamino)propoxy)benzenesulfonamide was prepared in a similar manner to the method described in Example 14.

Step 2: Preparation of 4-(3-(dimethylamino)propoxy)-N-(3-(1-methyl-1H-indole-3-yl)propyl)benzenesulfonamide

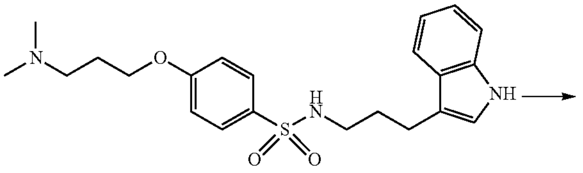

-continued

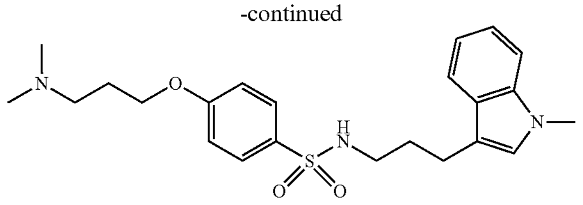

N-(3-(1H-indole-3-yl)propyl)-4-(3-(dimethylamino)propoxy)benzenesulfonamide (150 mg, 0.981 mmol) prepared in step 1 above was dissolved in DMF (1 ml), to which sodium hydride (60%) (51.5 mg, 1.287 mmol) was added dropwise at −20° C., followed by stirring for 30 minutes. Iodomethane (23 μl, 0.368 mmol) dissolved in DMF (0.1 ml) at the same temperature was slowly added dropwise thereto, followed by stirring at room temperature for 12 hours. Upon completion of the reaction, the reaction mixture was extracted with ethyl acetate, and neutralized using a supersaturated ammonium chloride aqueous solution. The organic layer was washed sequentially with water and brine, dried over anhydrous sodium sulfate, and then the solvent was removed under reduced pressure. Then, the reaction mixture was separated and purified by MPLC to give a target compound (13.7 mg, 8%, transparent oil).

<Example 47> Preparation of N-(3-(1H-indole-3-yl)propyl)-4-bromobenzenesulfonamide

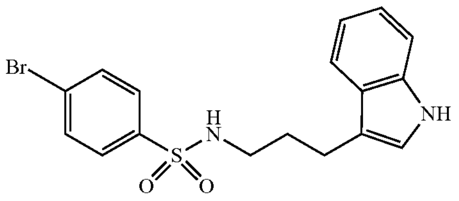 [SMILES: O=S(=O)(NCCCc1c[nH]c2ccccc12)c1ccc(Br)cc1]

Step 1: Preparation of 4-bromobenzene-1-sulfonyl chloride

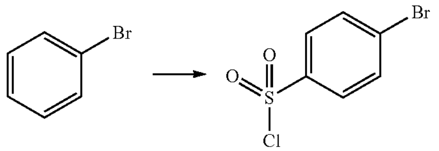 [SMILES: Brc1ccccc1 ; O=S(=O)(Cl)c1ccc(Br)cc1]

Bromobenzene (0.067 ml, 0.637 mmol) was dissolved in dichloromethane (2 ml), to which chlorosulfonic acid (0.169 ml, 2.55 mmol) was added dropwise at 0° C., followed by stirring at room temperature for 3 hours. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and then the solvent was removed under reduced pressure. As a result, 4-bromobenzene-1-sulfonyl chloride (74 mg, 45%, white solid) was obtained without further purification.

Step 2: Preparation of N-(3-(1H-indole-3-yl)propyl)-4-bromobenzenesulfonamide

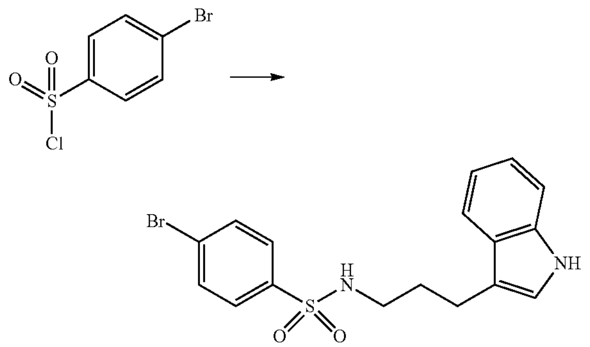

4-Bromobenzene-1-sulfonyl chloride (74 mg, 0.29 mmol) prepared in step 1 above in dichloromethane (1 ml), to which 3-(1H-indole-3-yl)propane-1-amine (151 mg, 0.869 mmol) and potassium carbonate ($K_2CO_3$) (120 mg, 0.869 mmol) were added dropwise, followed by stirring at room temperature for 1 hour. Upon completion of the reaction, the reaction mixture was extracted with dichloromethane, and the organic layer was washed sequentially with water and brine, dried over anhydrous sodium sulfate, and then the solvent was removed under reduced pressure. Then, the reaction mixture was separated and purified by MPLC to give a target compound (71 mg, 62%, white solid).

The compounds of Examples 48 to 54 were prepared in a similar manner to the method described in Example 31.

The compound of Example 55 was prepared in a similar manner to the method described in Example 30.

The compounds of Examples 56 to 58 were prepared in a similar manner to the method described in Example 31.

The compounds of Examples 59 and 60 were prepared in a similar manner to the method described in Example 30.

The compound of Example 61 was prepared in a similar manner to the method described in Example 31.

The compound of Example 62 was prepared in a similar manner to the method described in Example 30.

The compounds of Examples 63 to 71 were prepared in a similar manner to the method described in Example 31.

<Example 72> Preparation of 4-(3-((3S,5R)-3,5-dimethylpiperazine-1-yl)propoxy)-N-(3-(5-fluoro-1H-indole-3-yl)propyl)benzenesulfonamide

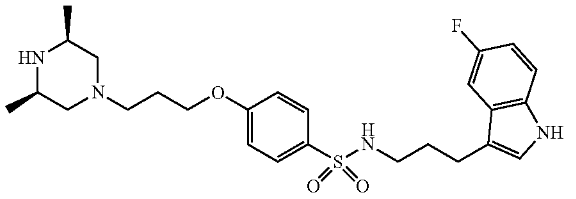 [SMILES: C[C@@H]1CN(CCCOc2ccc(S(=O)(=O)NCCCc3c[nH]c4ccc(F)cc34)cc2)C[C@H](C)N1]

Step 1: Preparation of (2S,6R)-tert-butyl 4-(3-(4-(N-(3-(5-fluoro-1H-indole-3-yl)propyl)sulfamoyl)phenoxy)propyl)-2,6-dimethylpiperazine-1-carboxylate (2S,6R)-tert-butyl 4-(3-(4-(N-(3-(5-fluoro-1H-indole-3-yl)propyl)sulfamoyl)phenoxy)propyl)-2,6-dimethylpiperazine-1-carboxylate was prepared in a similar manner to the method described in Example 31.

Step 2: Preparation of 4-(3-((3S,5R)-3,5-dimethylpiperazine-1-yl)propoxy)-N-(3-(5-fluoro-1H-indole-3-yl)propyl)benzenesulfonamide

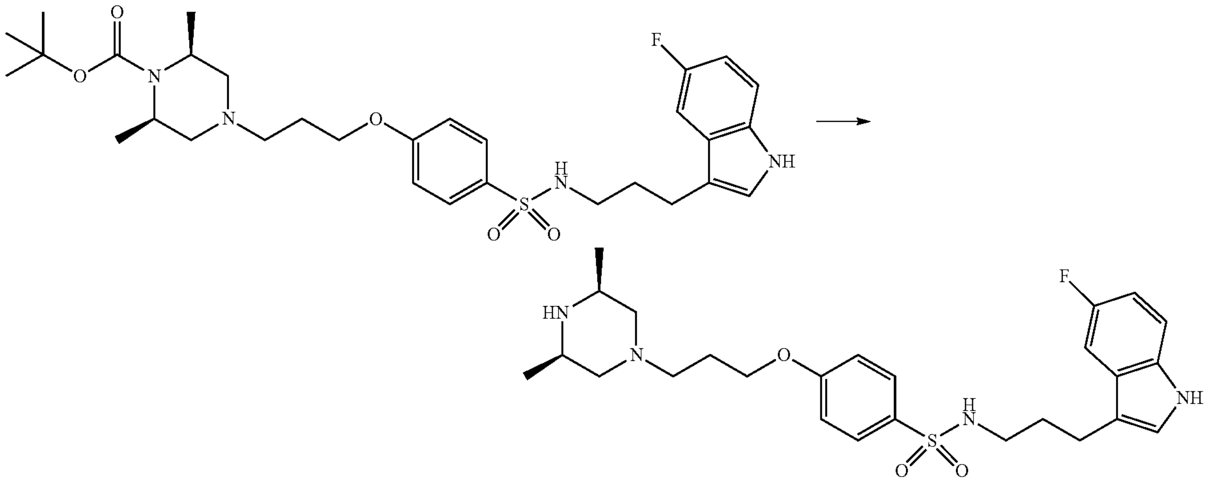

(2S,6R)-tert-butyl 4-(3-(4-(N-(3-(5-fluoro-1H-indole-3-yl)propyl)sulfamoyl)phenoxy)propyl)-2,6-dimeth ylpiperazine-1-carboxylate (80 mg, 0.133 mmol) prepared in step 1 above was dissolved in dichloromethane (1 ml), to which trifluoroacetic acid (0.2 ml, 2.65 mmol) was added at room temperature, followed by stirring at room temperature for 3 hours. Upon completion of the reaction, ice was added thereto. The reaction mixture was extracted with ethyl acetate, and neutralized using a supersaturated sodium carbonate aqueous solution. The organic layer was washed sequentially with water and brine, dried over anhydrous sodium sulfate, and the solvent was removed under reduced pressure. Then, the reaction mixture was separated and purified by MPLC to give a target compound (5.2 mg, 7%, white solid).

The compounds of Examples 73 to 76 were prepared in a similar manner to the method described in Example 31.

<Example 77> Preparation of N-(3-(5-chloro-1H-indole-3-yl)propyl)-4-(3-(3-(methylamino)azetidine-1-yl)propoxy)benzenesulfonamide

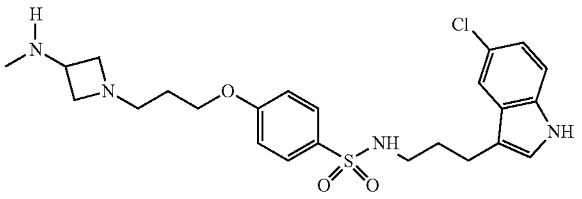 [SMILES: CNC1CN(CCCOc2ccc(S(=O)(=O)NCCCc3c[nH]c4ccc(Cl)cc34)cc2)C1]

Step 1: Preparation of tertbutyl(1-(3-(4-(N-(3-(5-chloro-1H-indole-3-yl)propyl)sulfamoyl)phenoxy)propyl)azetidine-3-yl)(methyl)carbamate Tert-butyl(1-(3-(4-(N-(3-(5-chloro-1H-indole-3-yl) propyl)sulfamoyl)phenoxy)propyl)azetidine-3-yl(methyl)carbamate was prepared in a similar manner to the method described in Example 31.

Step 2: Preparation of N-(3-(5-chloro-1H-indole-3-yl)propyl)-4-(3-(3-(methylamino)azetidine-1-yl)propoxy)benzenesulfonamide

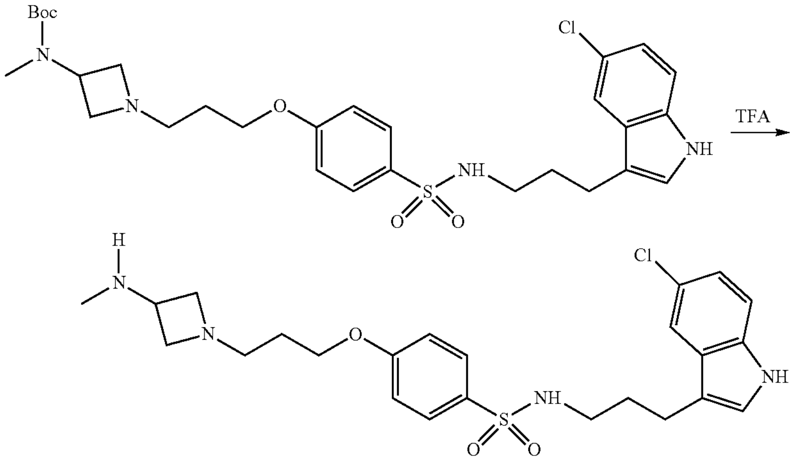

Tert-butyl(1-(3-(4-(N-(3-(5-chloro-1H-indole-3-yl)propyl)sulfamoyl)phenoxy)propyl) azetidine-3-yl)(methyl)carbamate (38 mg, 0.064 mmol) was dissolved in dichloromethane (0.5 ml) using tert-butylazetidine-3-yl(methyl) carbamate prepared in step 1 above, to which trifluoroacetic acid (0.2 ml, 2.61 mmol) was added dropwise at room temperature, followed by stirring at room temperature for 2 hours. Upon completion of the reaction, ice was added thereto. The reaction mixture was extracted with ethyl acetate, and neutralized using a supersaturated sodium carbonate aqueous solution. The organic layer was washed sequentially with water and brine, dried over anhydrous sodium sulfate, and the solvent was removed under reduced pressure. Then, the reaction mixture was separated and purified by MPLC to give a target compound (7 mg, 22%, yellow solid).

The compound of Example 78 was prepared in a similar manner to the method described in Example 31.

<Example 79> Preparation of N-(3-(5-chloro-1H-indole-3-yl)propyl)-6-(3-(piperazine-1-yl)propoxy) pyridine-3-sulfonamide

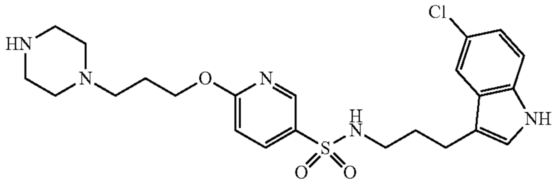 [SMILES: O=S(=O)(NCCCc1c[nH]c2ccc(Cl)cc12)c1ccc(OCCCN2CCNCC2)nc1]

Step 1: Preparation of tertbutyl-4-(3-((5-bromopyridine-2-yl)oxy)propylpiperazine-1-carboxylate

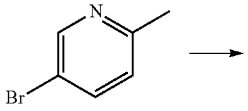

-continued

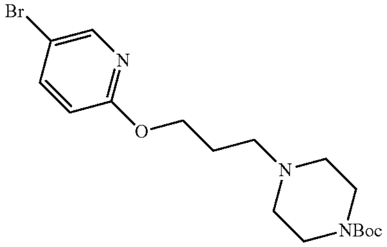

5-Bromo-2-fluoropyridine (0.326 ml, 2.84 mmol) was dissolved in DMF (12 ml), to which sodium hydride 60% wt (0.159 g, 3.98 mmol) was added dropwise at 0° C., followed by stirring for 5 minutes. Tertbutyl-4-(3-hydroxypropyl) piperazine-1-carboxylate was added dropwise thereto, followed by stirring at 70° C. for 6 hours. Upon completion of the reaction, ice was added thereto. The reaction mixture was extracted with dichloromethane, and neutralized using a supersaturated sodium carbonate aqueous solution. The organic layer was washed sequentially with water and brine, dried over anhydrous sodium sulfate, and the solvent was removed under reduced pressure. As a result, tertbutyl-4-(3-((5-bromopyridine-2-yl)oxy)propylpiperazine-1-carboxylate (1.35 g, 110%) was obtained without further purification.

Step 2: Preparation of tert-butyl 4-(3-((5-((4-methoxybenzyl)thio)pyridine-2-yl)oxy)propyl)piperazine-1-carboxylate

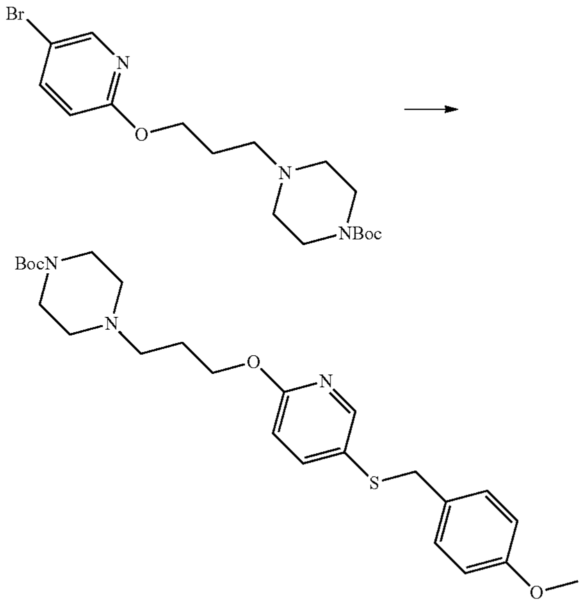

Tert-butyl-4-(3-((5-bromopyridine-2-yl)oxy)propyl piperazine-1-carboxylate (0.52 g, 1.3 mmol) prepared in step 1 above was dissolved in 1.4-dioxane (12 ml), to which (4-methoxyphenyl)methanethiol (0.199 ml, 1.23 mmol) and N-ethyl-N-isopropylpropane-2-amine (0.681 ml, 3.90 mmol) were added dropwise, followed by reaction for 5 minutes in nitrogen atmosphere. $Pd_2(dba)_3$ (9.91 mg, 0.032 mmol), Xantphos (0.038 g, 0.065 mmol) and tertbutyl-4-(3-hydroxypropyl)piperazine-1-carboxylate were added dropwise thereto, followed by reaction at 150° C. for 30 minutes in a Biotage microwave. Upon completion of the reaction, the reaction mixture was extracted with dichloromethane, and neutralized using a supersaturated sodium carbonate aqueous solution. The organic layer was washed sequentially with water and brine, dried over anhydrous sodium sulfate, and the solvent was removed under reduced pressure. As a result, tert-butyl 4-(3-((5-((4-methoxybenzyl)thio) pyridine-2-yl)oxy)propyl)piperazine-1-carboxylate (0.51 g, 51.8%) was obtained without further purification.

Step 3: Preparation of tert-butyl 4-(3-((5-(chlorosulfonyl)pyridine-2-yl)oxy)propyl)piperazine-1-carboxylate

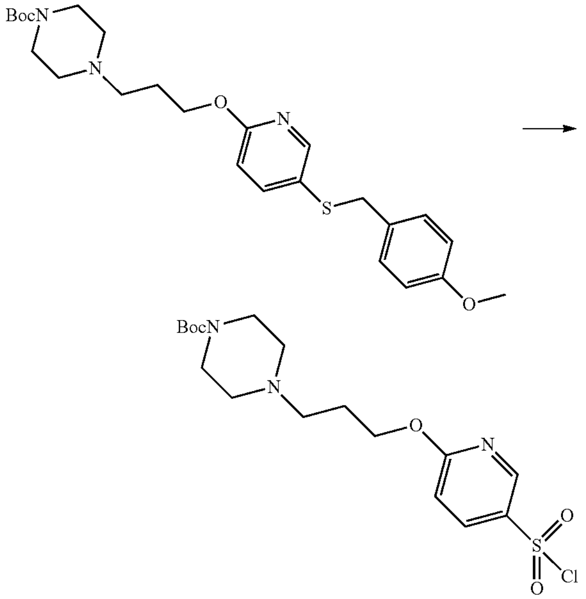

Tert-butyl 4-(3-((5-((4-methoxybenzyl)thio)pyridin-2-yl) oxy)propyl)piperazine-1-carboxylate (0.469 g, 0.99 mmol) prepared in step 2 above was dissolved in acetic acid (8 ml) and water (2 ml), to which N-chlorosuccinimide (0.529 g, 3.96 mmol) was added dropwise, followed by reaction at room temperature for 1 hour. Upon completion of the reaction, the reaction mixture was extracted with dichloromethane, and neutralized using a supersaturated sodium carbonate aqueous solution. The organic layer was washed sequentially with water and brine, dried over anhydrous sodium sulfate, and the solvent was removed under reduced pressure. As a result, tert-butyl 4-(3-((5-(chlorosulfonyl) pyridine-2-yl)oxy)propyl)piperazine-1-carboxylate (0.25 g, 60%) was obtained without further purification.

Step 4: Preparation of tert-butyl 4-(3-((5-(N-(3-(5-chloro-1H-indole-3-yl)propyl)sulfamoyl)pyridine-2-yl)oxy)propyl)piperazine-1-carboxylate

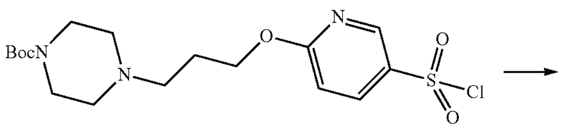

-continued

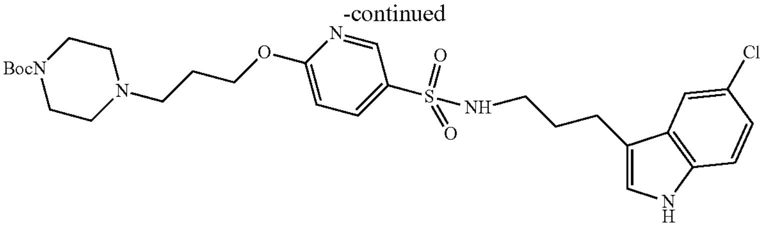

Tert-butyl 4-(3-((5-(chlorosulfonyl)pyridine-2-yl)oxy)propyl)piperazine-1-carboxylate (0.1 g, 0.238 mmol) prepared in step 3 above was dissolved in DMF (2 ml), to which 3-(5-chloro-1H-indole-3-yl)propane-1-amine (0.055 g, 0.262 mmol) and potassium carbonate (0.066 g, 0.476 mmol) were added dropwise, followed by stirring at room temperature for 2 hours. Upon completion of the reaction, the reaction mixture was extracted with dichloromethane, and neutralized using a supersaturated sodium carbonate aqueous solution. The organic layer was washed sequentially with water and brine, dried over anhydrous sodium sulfate, and the solvent was removed under reduced pressure. Then, the reaction mixture was separated and purified by Prep TLC to give tert-butyl 4-(3-((5-(N-(3-(5-chloro-1H-indole-3-yl)propyl)sulfamoyl)pyridine-2-yl)oxy)propyl)piperazine-1-carboxylate (18 mg, 12.8%).

Step 5: Preparation of N-(3-(5-chloro-1H-indole-3-yl)propyl)-6-(3-(piperazine-1-yl)propoxy)pyridine-3-sulfonamide

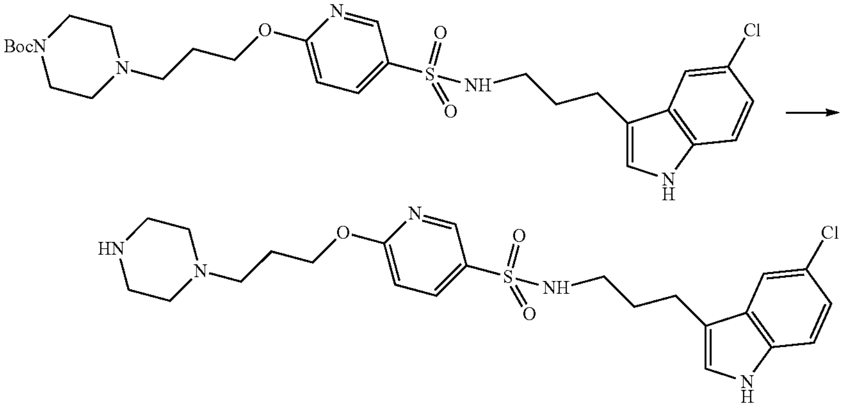

4-(3-((5-(N-(3-(5-chloro-1H-indole-3-yl)propyl) sulfamoyl)pyridine-2-yl)oxy)propyl)piperazine-1-carboxylate (18 mg, 0.034 mmol) prepared in step 4 above was dissolved in tetrahydrofuran (1 ml), to which trifluoroacetic acid (0.5 ml, 6.49 mmol) was added dropwise at room temperature, followed by stirring at room temperature for 2 hours. Upon completion of the reaction, ice was added thereto. The reaction mixture was extracted with ethyl acetate, and neutralized using a supersaturated sodium carbonate aqueous solution. The organic layer was washed sequentially with water and brine, dried over anhydrous sodium sulfate, and then the solvent was removed under reduced pressure. Then, the reaction mixture was separated and purified by Prep TLC to give a target compound (4.5 mg, 30%).

The compounds of Examples 80 to 84 were prepared in a similar manner to the method described in Example 31.

<Example 85> Preparation of N-(3-(1H-indole-3-yl)cyclohexyl)-4-(3-(4-methylpiperazine-1-yl)propoxy)benzenesulfonamide

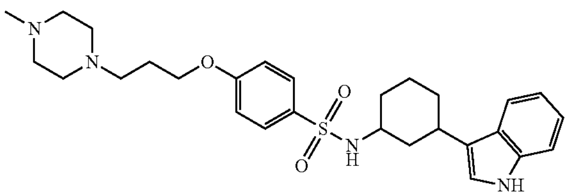 [SMILES: CN1CCN(CCCOc2ccc(S(=O)(=O)NC3CCCC(c4c[nH]c5ccccc45)C3)cc2)CC1]

Step 1: Preparation of 3-(1H-indole-3-yl)cyclohexane-1-one

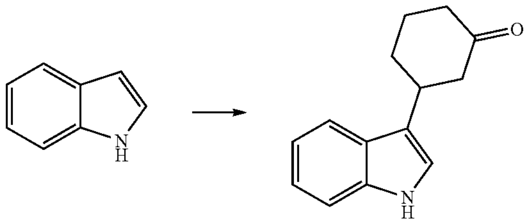 [SMILES: c1ccc2[nH]ccc2c1 ; O=C1CCCC(c2c[nH]c3ccccc23)C1]

1H-indole (1 g, 8.54 mmol) and cyclohex-2-enone (1.64 g, 17.1 mmol) were dissolved in $CH_3CN$ (30 ml), to which $Sc(OTf)_3$ (0.42 g, 0.854 mmol) was added, followed by stirring at 30° C. for 3 hours in $N_2$ atmosphere. Upon completion of the reaction, the reaction solution was concentrated under reduced pressure and purified by Prep HPLC to give a target compound (805 mg, 44%).

Step 2: Preparation of 3-(1H-indole-3-yl)cyclohexane-1-amine

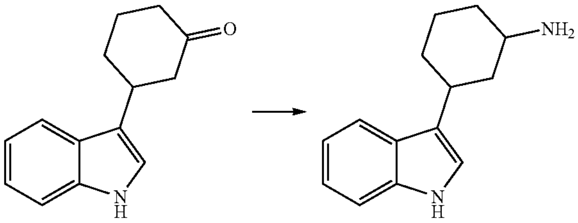 [SMILES: O=C1CCCC(c2c[nH]c3ccccc23)C1 ; NC1CCCC(c2c[nH]c3ccccc23)C1]

3-(1H-indole-3-yl)cyclohexane-1-one (800 mg, 3.75 mmol) prepared in step 1 above was dissolved in dichloroethane (10 ml) and acetic acid (0.5 ml), to which ammonium acetate (8.67 g, 113 mmol) was added at room temperature, followed by stirring for 2 hours. Then, sodium triacetoxyborohydride (3.18 g, 15.0 mmol) was added thereto at room temperature, followed by stirring for 5 hours. Upon completion of the reaction, the reaction mixture obtained by concentrating the mixture under reduced pressure was separated and purified by MPLC to give a target compound (250 mg, 31%, yellow solid).

Step 3: Preparation of N-(3-(1H-indole-3-yl)cyclohexyl)-4-(3-bromopropoxy)benzenesulfonamide

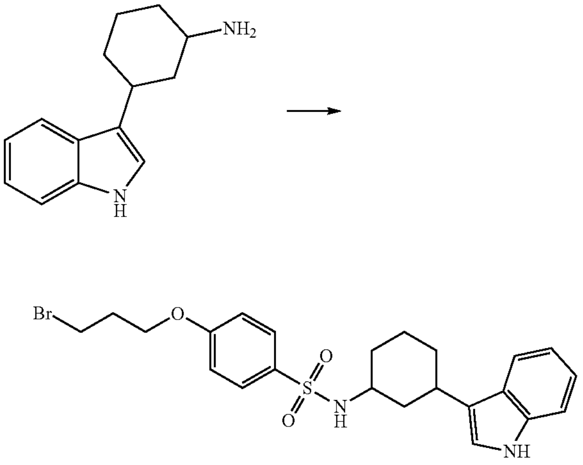

A target compound (100 mg, 46%, white solid) was obtained in a similar manner to the method described in step 2 of Example 31 using 3-(1H-indole-3-yl)cyclohexane-1-amine (105 mg, 0.491 mmol) prepared in step 2 above and 4-(3-bromopropoxy)benzenesulfonyl chloride (140 mg, 0.446 mmol) obtained in a similar manner to the method described in step 2 of Example 31.

Step 4: Preparation of N-(3-(1H-indole-3-yl)cyclohexyl)-4-(3-(4-methylpiperazine-1-yl)propoxy)benzenesulfonamide

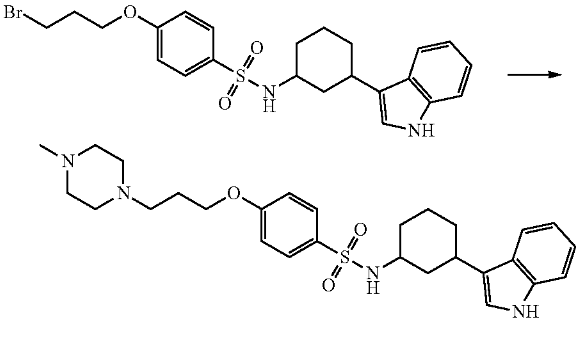

A target compound (21.6 mg, 69% yield) was obtained as a white solid in a similar manner to the method described in step 3 of Example 31 using N-(3-(1H-indole-3-yl)cyclohexyl)-4-(3-bromopropoxy)benzenesulfonamide (30 mg, 0.061 mmol) prepared in step 3 above and 1-methylpiperazine (24.5 mg, 0.244 mmol).

<Example 86> Preparation of N-(3-(5-chloro-1H-indole-3-yl)propyl)-4-(3-(4-methylpiperazine-1-yl)propoxy)naphthalene-1-sulfonamide

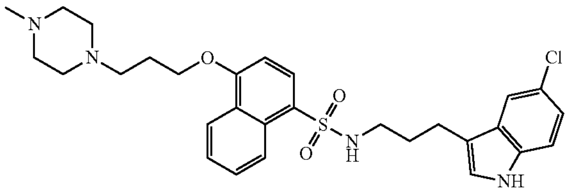 [SMILES: CN1CCN(CCCOc2ccc(S(=O)(=O)NCCCc3c[nH]c4ccc(Cl)cc34)c3ccccc23)CC1]

Step 1: Preparation of 4-(3-bromopropoxy)naphthalene-1-sulfonate, sodium (I) salt

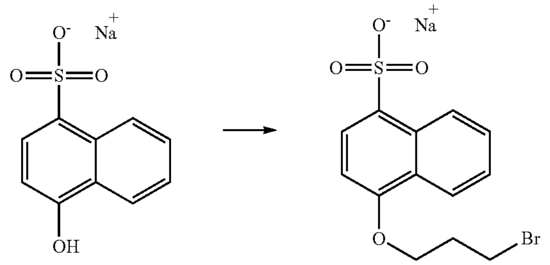

4-Hydroxynaphthalene-1-sulfonate, sodium (I) salt (0.3 g, 1.218 mmol) was dissolved in ethanol (2.5 ml), to which 1,3-dibromopropane (0.211 ml, 2.071 mmol), tetrabutyl ammonium sulfate (0.033 g, 0.097 mmol) and potassium hydroxide aqueous solution (1.56 ml, 1.218 mmol) were added, followed by heating to reflux for 3 hours. Upon completion of the reaction, the reaction solution was concentrated under reduced pressure, dissolved in ethanol again, and concentrated again. After hot methanol was added to the reaction solution, the insoluble material was filtered, and the filtrate was concentrated. The resulting solid was washed with dichloromethane and filtered to give a target compound (0.4 g, 99%, white solid).

Step 2: Preparation of 4-(3-bromopropoxy)naphthalene-1-sulfonylchloride

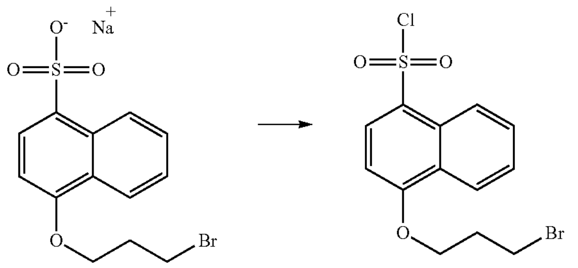

Thionyl chloride (0.286 ml, 3.92 mmol) and dimethylformamide (1.91 μl) were added to the compound (0.2 g, 0.545 mmol) prepared in step 1 above, followed by heating to reflux for 4 hours. Upon completion of the reaction, the temperature was lowered to room temperature, and the reaction mixture was diluted with ethyl acetate, and washed with water and brine. The organic layer residue was dried over anhydrous sodium sulfate, filtered and concentrated, and used in the next step without further purification.

Step 3: Preparation of 4-(3-bromopropoxy)-N-(3-(5-chloro-1H-indole-3-yl)propyl)naphthalene-1-sulfonamide

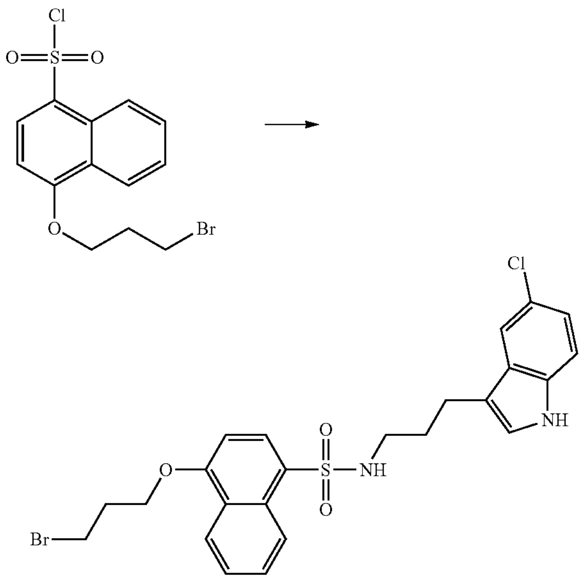

A target compound was prepared in a similar manner to the method described in step 2 of Example 31.

Step 4: Preparation of N-(3-(5-chloro-1H-indole-3-yl)propyl)-4-(3-(4-methylpiperazine-1-yl)propoxy) naphthalene-1-sulfonamide

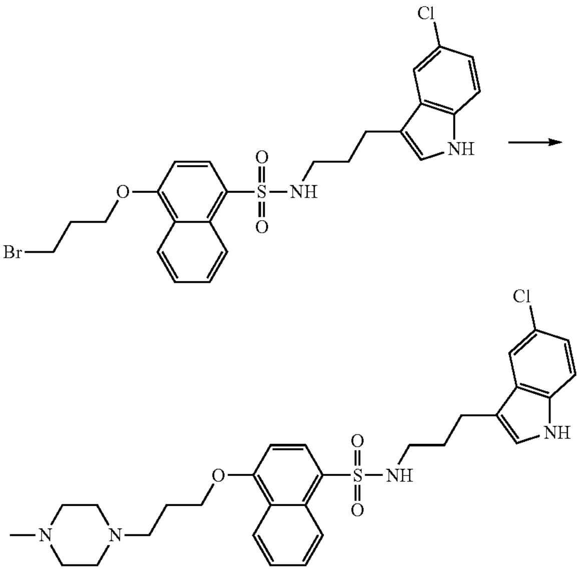

A target compound was prepared in a similar manner to the method described in step 3 of Example 31.

The compound of Example 87 was prepared in a similar manner to the method described in Example 31.

<Example 88> Preparation of N-(3-(5-chloro-1H-indole-3-yl)propyl)-4-((3-(piperidine-4-yl)propyl) amino)benzenesulfonamide

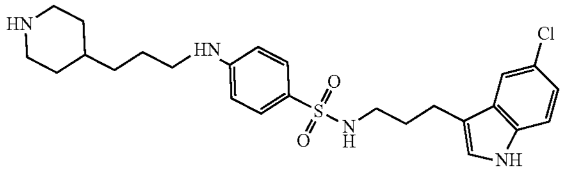 [SMILES: O=S(=O)(NCCCc1c[nH]c2ccc(Cl)cc12)c1ccc(NCCCC2CCNCC2)cc1]

Step 1: Preparation of tert-butyl-4-(3-oxopropyl)piperidine-1-carboxylate

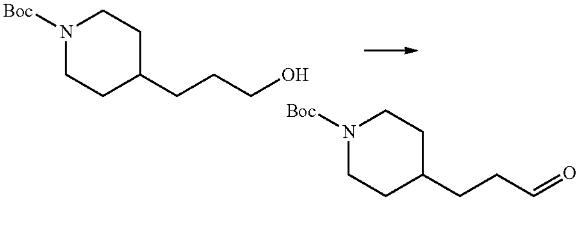

Tert-butyl-4-(3-hydroxypropyl)piperidine-1-carboxylate (0.3 g, 1.233 mmol) was dissolved in dichloromethane (6 ml), to which Dess-Martin Periodinane (0.680 g, 1.603 mmol) was added at 0° C., followed by stirring at room temperature for 4 hours. Upon completion of the reaction, the reaction solution was filtered, and the filtrate was washed with a sodium hydrogen carbonate aqueous solution and brine. The organic layer residue was dried over anhydrous sodium sulfate, filtered and concentrated. The concentrate was purified by MPLC to give a target compound (0.24 g, 79%, transparent oil).

Step 2: Preparation of N-(3-(5-chloro-1H-indole-3-yl)propyl)-4-nitrobenzenesulfonamide

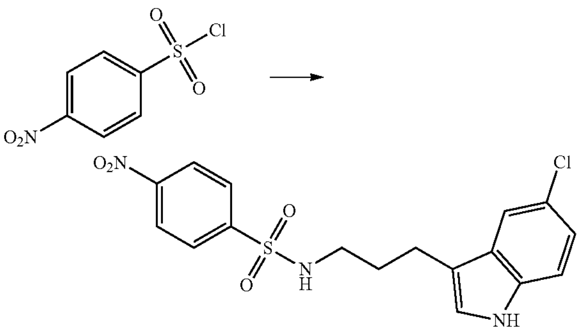

A target compound was prepared in a similar manner to the method described in step 2 of Example 31.

Step 3: Preparation of 4-amino-N-(3-(5-chloro-1H-indole-3-yl)propyl)benzenesulfonamide

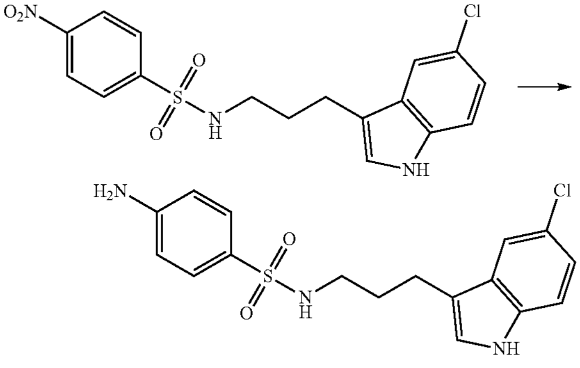

The compound (0.72 g, 1.840 mmol) prepared in step 2 above was dissolved in ethyl acetate (12 ml), to which tin (II) chloride and dihydrate (4.15 g, 18.40 mmol) were added, followed by heating at 60° C. for 5 hours. Upon completion of the reaction, ammonia water was added to the reaction solution to make the pH 5, and sodium carbonate was added to make the pH 7. The reaction solution was filtered with celite, and the filtrate was concentrated under reduced pressure, which was used in the next step without further purification.

Step 4: Preparation of tert-butyl 4-(3-((4-(N-(3-(5-chloro-1H-indole-3-yl)propyl)sulfamoyl)phenyl)amino)propyl)piperidine-1-carboxylate

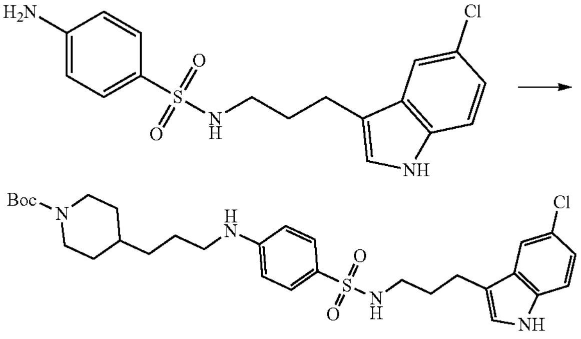

The compound (0.05 g, 0.137 mmol) prepared in step 3 above was dissolved in dichloroethane (1 ml), to which the compound (0.046 g, 0.192 mmol) prepared in step 1 above and acetic acid (0.024 ml, 0.412 mmol) were added, followed by stirring at room temperature for 1 hour. Sodium triacetoxyborohydride (0.087 g, 0.412 mmol) was added thereto, followed by stirring at room temperature for 1 hour. Upon completion of the reaction, the reaction mixture was diluted with dichloromethane and washed with water and brine. The residue of the organic layer was dried over anhydrous sodium sulfate, filtered and concentrated, purified by Prep HPLC, and neutralized by adding a sodium hydrogen carbonate aqueous solution to give a target compound (0.017 g, 5%, yellow solid).

Step 5: Preparation of N-(3-(5-chloro-1H-indole-3-yl)propyl)-4-((3-(piperidine-4-yl)propyl)amino)benzenesulfonamide

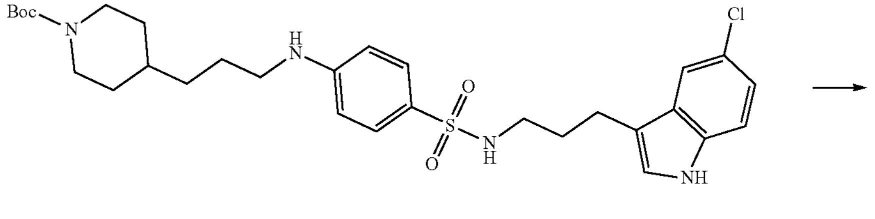

-continued

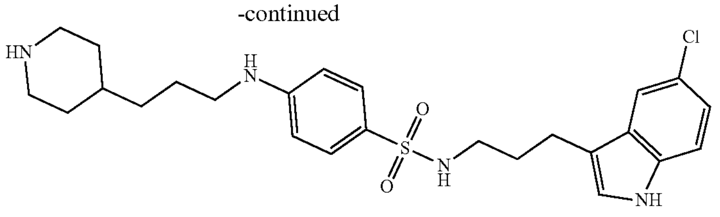

A target compound was prepared in a similar manner to the method described in step 5 of Example 79.

<Example 89> Preparation of N-(3-(1H-indole-3-yl)phenyl)-4-(3-(4-methylpiperazine-1-yl)propoxy) benzenesulfonamide

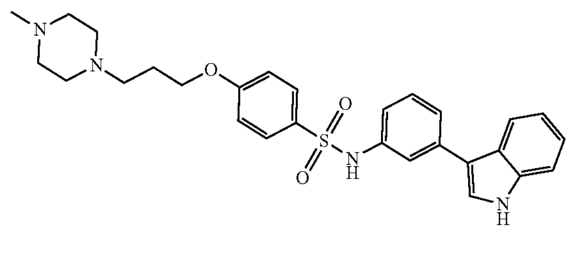 [SMILES: CN1CCN(CCCOc2ccc(S(=O)(=O)Nc3cccc(-c4c[nH]c5ccccc45)c3)cc2)CC1]

Step 1: Preparation of 3-(3-nitrophenyl)-1H-indole

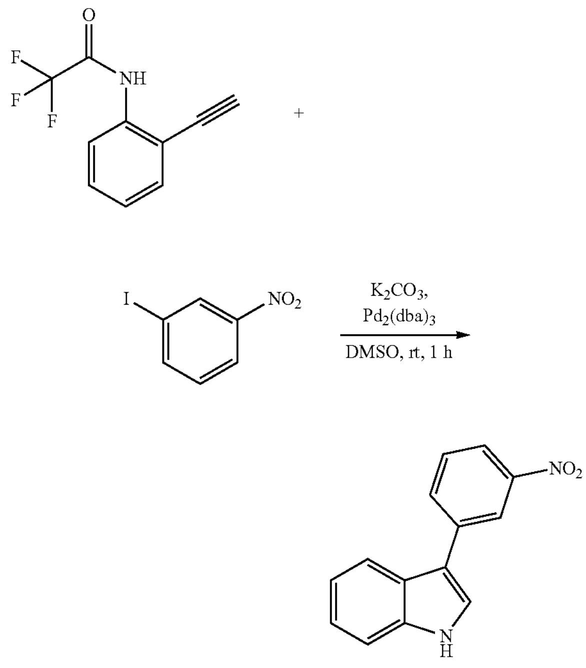

N-(2-ethynylphenyl)-2,2,2-trifluoroacetamide and 1-iodo-3-nitrobenzene were dissolved in DMSO, to which an excessive amount of $K_2CO_3$ was treated in the presence of a catalytic amount of $Pd_2(dba)_3$ to give the target compound 3-(3-nitrophenyl-1H-indole).

Step 2: Preparation of 3-(1H-indole-3-yl)aniline

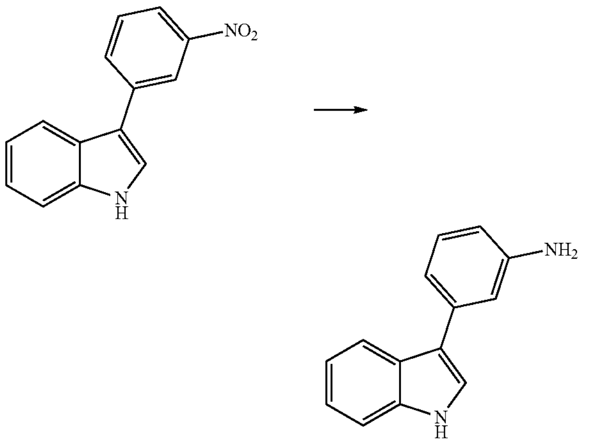

The compound (0.047 g, 0.197 mmol) prepared in step 1 above was dissolved in methanol (2 ml), to which Pd/C (0.004 g, 3.76 μmol) was added, followed by stirring at room temperature for 3 hours under hydrogen gas. Upon completion of the reaction, the reaction solution was filtered with celite and washed with methanol. The filtrate was concentrated under reduced pressure and used in the next step without further purification.

Step 3: Preparation of N-(3-(1H-indole-3-yl)phenyl)-4-(3-bromopropoxy)benzenesulfonamide

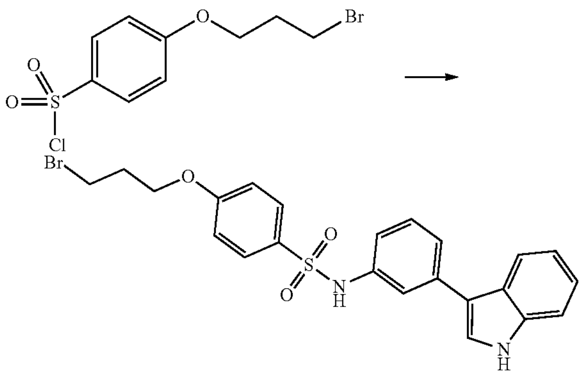

The compound (0.041 g, 0.197 mmol) prepared in step 2 above was dissolved in pyridine (1 ml), to which the compound (0.068 g, 0.217 mmol) prepared in step 1 of Example 31 was added at 0° C., followed by stirring at room temperature for 3 hours. Upon completion of the reaction, the reaction mixture was diluted with ethyl acetate and washed with water and brine. The residue of the organic layer was dried over anhydrous sodium sulfate, filtered and concentrated, and purified by MPLC to give a target compound (0.047 g, 49%, yellow solid).

Step 4: Preparation of N-(3-(1H-indole-3-yl)phenyl)-4-(3-(4-methylpiperazine-1-yl)propoxy)benzenesulfonamide

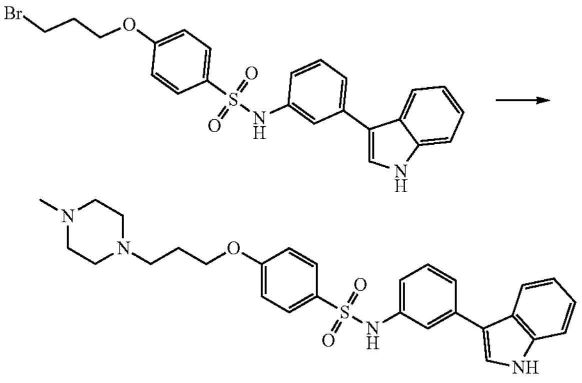

A target compound was prepared in a similar manner to the method described in step 3 of Example 31.

<Example 90> Preparation of N-(3-(5-chloro-1H-indole-3-yl)propyl)-4-(4-(piperidine-1-yl)butyl)benzenesulfonamide

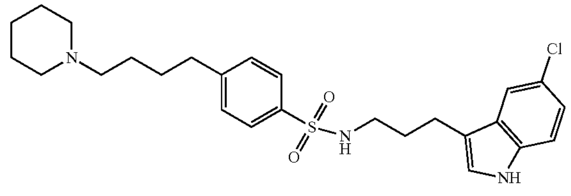 [SMILES: O=S(=O)(NCCCc1c[nH]c2ccc(Cl)cc12)c1ccc(CCCCN2CCCCC2)cc1]

Step 1: Preparation of 4-(4-bromobutyl)benzene-1-sulfonyl chloride

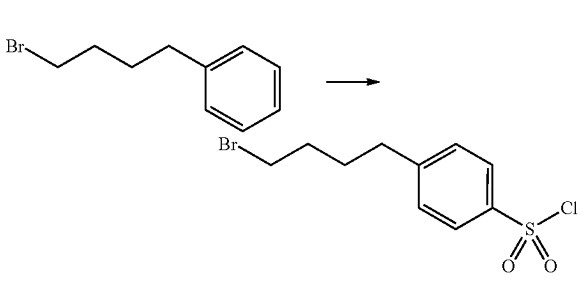

A target compound (1.4 g, 96%, white solid) was obtained in a similar manner to the method described in step 1 of Example 31 using (4-bromobutyl)benzene (1.0 g, 4.69 mmol) and chlorosulfonic acid (0.936 ml, 14.1 mmol).

Step 2: Preparation of 4-(4-bromobutyl)-N-(3-(5-chloro-1H-indole-3-yl)propyl)benzenesulfonylamide

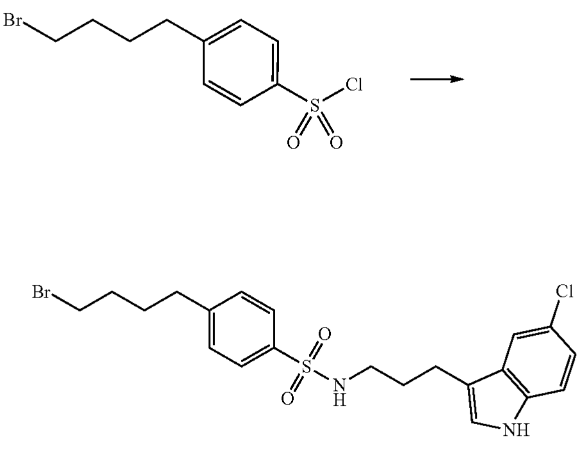

4-(4-Bromobutyl)benzene-1-sulfonyl chloride (300 mg, 0.963 mmol) prepared in step 1 above was dissolved in dichloromethane (5 ml), to which 3-(5-chloro-1H-indole-3-yl)propane-1-amine (211 mg, 1.01 mmol) and triethylamine (0.268 ml, 1.93 mmol) were added at room temperature, followed by stirring for 3 hours. Upon completion of the reaction, the mixture was concentrated under reduced pressure and purified by MPLC to give a target compound (330 mg, 71%, white solid).

Step 3: Preparation of N-(3-(5-chloro-1H-indole-3-yl)propyl)-4-(4-(piperidine-1-yl)butyl)benzenesulfonamide

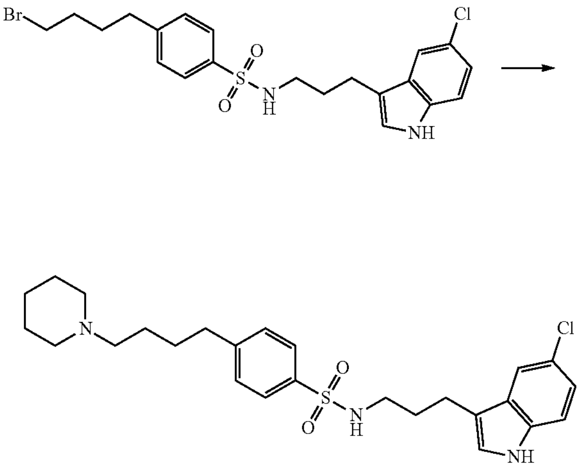 [SMILES: O=S(=O)(NCCCc1c[nH]c2ccc(Cl)cc12)c1ccc(CCCCBr)cc1 ; O=S(=O)(NCCCc1c[nH]c2ccc(Cl)cc12)c1ccc(CCCCN2CCCCC2)cc1]

A target compound (16 mg, 53%, white solid) was obtained in a similar manner to the method described in step 3 of Example 31 using 4-(4-bromobutyl)-N-(3-(5-chloro-1H-indole-3-yl)propyl)benzenesulfonylamide (30 mg, 0.062 mmol) prepared in step 2 above, piperidine (15.9 mg, 0.186 mmol) and potassium carbonate (12.9 mg, 0.093 mmol).

The compound of Example 91 was prepared in a similar manner to the method described in Example 90.

<Example 92> Preparation of N-(3-(5-chloro-1H-indole-3-yl)propyl)-4-(3-(1-methylpiperidine-4-yl)propoxy)benzenesulfonamide

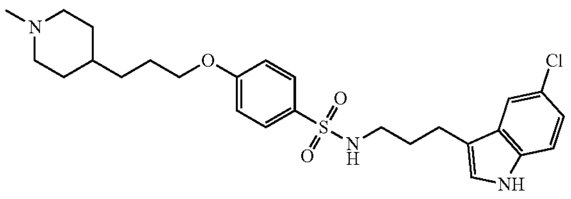 [SMILES: CN1CCC(CCCOc2ccc(S(=O)(=O)NCCCc3c[nH]c4ccc(Cl)cc34)cc2)CC1]

Step 1: Preparation of N-(3-(5-chloro-1H-indole-3-yl)propyl)-4-hydroxybenzenesulfonamide

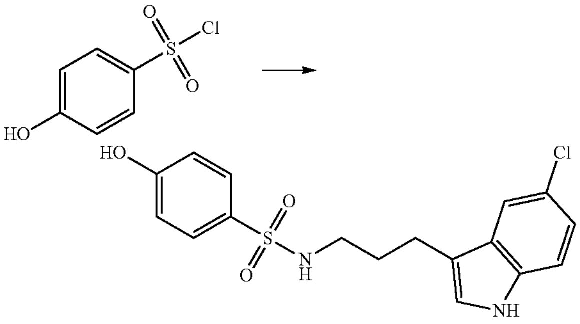

4-Hydroxybenzene-1-sulfonyl chloride (0.5 g, 2.60 mmol) was dissolved in dichloromethane (8.7 ml), to which 3-(5-chloro-1H-indole-3-yl)propane-1-amine (0.596 g, 2.86 mmol) and triethylamine (0.724 ml, 5.19 mmol) were added, followed by stirring at room temperature for 3 hours. Upon completion of the reaction, the reaction mixture was diluted with ethyl acetate and washed with water and brine. The residue of the organic layer was dried over anhydrous sodium sulfate, filtered and concentrated, and then purified by MPLC to give a target compound (0.19 g, 21%, white solid).

Step 2: Preparation of N-(3-(5-chloro-1H-indole-3-yl)propyl)-4-(3-(1-methylpiperidine-4-yl)propoxy)benzenesulfonamide

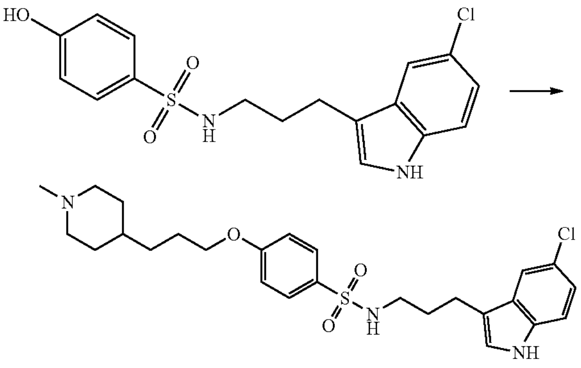

The compound (0.05 g, 0.137 mmol) prepared in step 1 above was dissolved in tetrahydrofuran (1.5 ml) under nitrogen gas at 0° C., to which 3-(1-methylpiperidine-4-yl)propane-1-ol (0.026 g, 0.164 mmol), $PPh_3$ (0.054 g, 0.206 mmol) and DEAD (0.093 ml, 0.206 mmol) were added, followed by stirring for 1 hour. Upon completion of the reaction, the reaction mixture was diluted with dichloromethane, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (0.004 g, 7%, white solid).

<Example 93> Preparation of N-(3-(5-chloro-1H-indole-3-yl)propyl)-4-(3-(piperidine-4-yl)propoxy)benzenesulfonamide

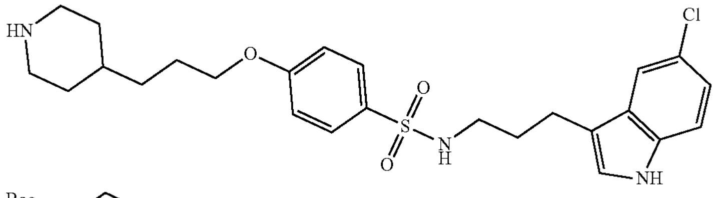

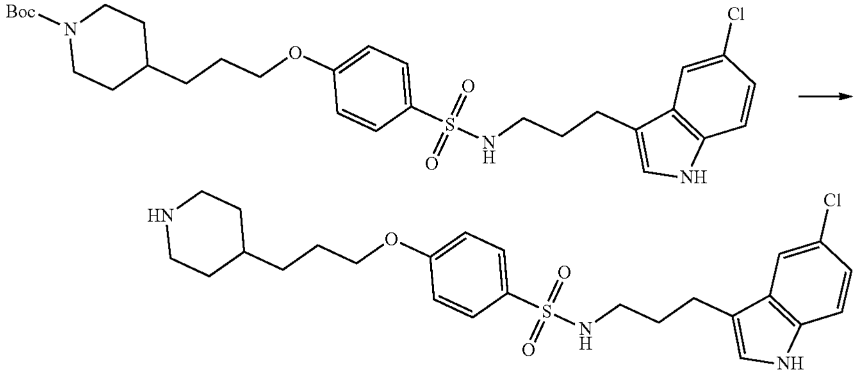

The compound (0.035 g, 0.061 mmol) prepared in a similar manner to the method described in Example 92 was dissolved in dichloromethane (2 ml), to which trifluoroacetic acid (1 ml, 12.98 mmol) was added, followed by stirring at room temperature for 1 hour. Upon completion of the reaction, the reaction solution was concentrated under reduced pressure, purified by Prep HPLC, and neutralized by adding a sodium hydrogen carbonate aqueous solution to give a target compound (0.01 g, 37%, white solid).

The compound of Example 94 was prepared in a similar manner to the method described in Example 93.

The compounds of Examples 95 and 96 were prepared in a similar manner to the method described in Example 94.

The compound of Example 97 was prepared in a similar manner to the method described in Example 31.

<Example 98> Preparation of N-(3-(5-chloro-1H-indole-3-yl)propyl)-4-((3-(4-methylpiperazine-1-yl)propyl)amino)benzenesulfonamide

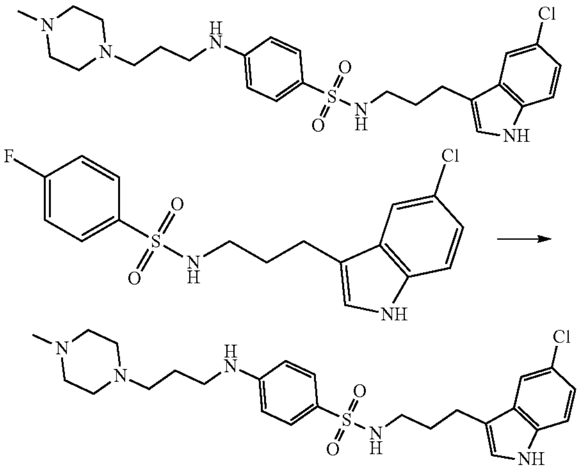

The compound (0.05 g, 0.136 mmol) prepared in a similar manner to the method described in step 2 of Example 47 was dissolved in dimethylformamide (1 ml), to which 3-(4-methylpiperazine-1-yl)propane-1-amine (0.043 g, 0.273 mmol) and potassium carbonate (0.021 g, 0.150 mmol) were added, followed by stirring at 100° C. for 3 days. Upon completion of the reaction, the reaction solution was concentrated under reduced pressure, purified by Prep HPLC, and neutralized by adding a sodium hydrogen carbonate aqueous solution to give a target compound (0.01 g, 16%, white solid).

<Example 99> Preparation of N-(3-(5-chloro-1H-indole-3-yl)propyl)-4-(4-(piperidine-4-yl)butyl)benzenesulfonamide

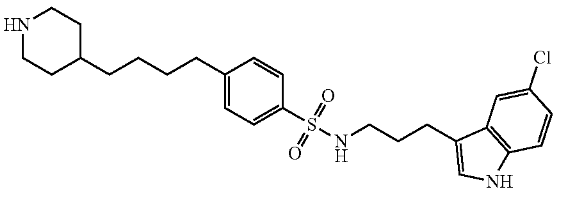 [SMILES: O=S(=O)(NCCCc1c[nH]c2ccc(Cl)cc12)c1ccc(CCCCC2CCNCC2)cc1]

Step 1: Preparation of tert-Butyl 4-(but-3-en-1-yl)piperidine-1-carboxylate

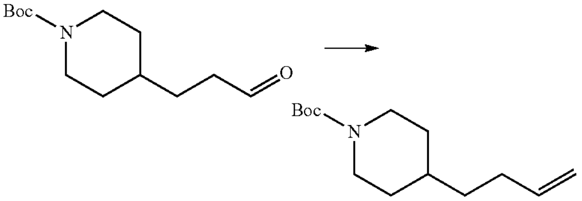

Methyltriphenylphosphonium bromide (1.184 g, 3.32 mmol) was dissolved in anhydrous tetrahydrofuran (2 ml), to which lithium bistrimethylsilylamide (3.32 ml, 3.32 mmol) was slowly added at 0° C. After dissolving tert-butyl 4-(3-oxopropyl)piperidine-1-carboxylate (0.4 g, 1.66 mmol) prepared in step 1 of Example 88 in anhydrous tetrahydrofuran (2 ml), which was slowly added dropwise thereto at 0° C. The mixture was stirred at 0° C. for 30 minutes, and then stirred at room temperature for 20 hours. Upon completion of the reaction, the reaction mixture was concentrated under reduced pressure, washed with brine, and extracted with ethyl acetate. The extracted organic layer was dried over anhydrous sodium sulfate, filtered, concentrated under reduced pressure, and purified by MPLC to give a target compound (0.2 g, 50%, transparent oil).

Step 2: Preparation of tert-butyl 4-(4-(4-(N-(3-(5-chloro-1H-indole-3-yl)propyl)sulfamoyl)phenyl)butyl)piperidine-1-carboxylate

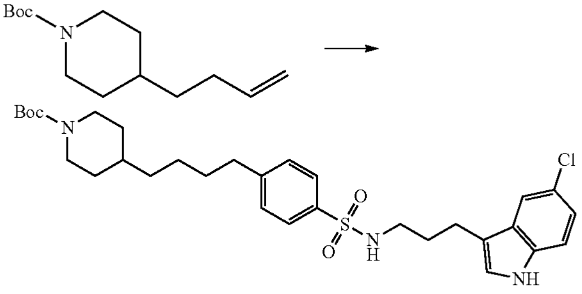

Tert-butyl 4-(but-3-en-1-yl)piperidine-1-carboxylate (50 mg, 0.209 mmol) prepared in step 2 above was dissolved in anhydrous tetrahydrofuran (1.5 ml), to which 9-borabicyclo [3.3.1]nonane (0.796 ml, 0.398 mmol) was added at room temperature. The reaction mixture was gradually heated and stirred under reflux for 1 hour. Upon completion of the reaction, the reaction mixture was cooled down to room temperature and concentrated under reduced pressure. The obtained residue was dissolved in 1,4-dioxane (1.5 ml), to which 4-bromo-N-(3-(5-chloro-1H-indole-3)-yl)propyl) benzenesulfonamide (85 mg, 0.199 mmol) prepared in a similar manner to the method described in step 2 of Example 90 and 1 M sodium carbonate aqueous solution (0.597 ml, 0.597 mmol) were added. $Pd(PPh_3)_4$ (23 mg, 0.02 mmol) was added to the reaction mixture, and the mixture was gradually heated and stirred at 90° C. for 3 hours. Upon completion of the reaction, the reaction mixture was cooled down to room temperature, filtered with celite, concentrated under reduced pressure, and purified by prep HPLC to give a target compound (15 mg, 13%, yellow solid).

Step 3: Preparation of N-(3-(5-chloro-1H-indole-3-yl)propyl)-4-(4-(piperidine-4-yl)butyl)benzenesulfonamide

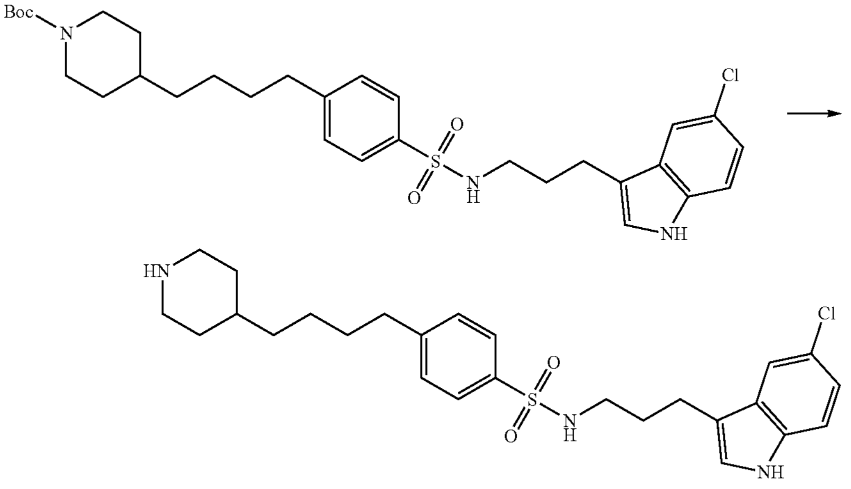

Tert-butyl 4-(4-(4-(N-(3-(5-chloro-1H-indole-3-yl)propyl)sulfamoyl)phenyl)butyl)piperidine-1-carboxylate (15 mg, 0.013 mmol) prepared in step 2 above was dissolved in dichloromethane (2 ml), to which trifluoroacetic acid (1 ml, 13.1 mmol) was added at room temperature, followed by stirring for 1 hour. Upon completion of the reaction, the residue obtained by concentrating the mixture was neutralized with a supersaturated sodium hydrogen carbonate aqueous solution, and then extracted with ethyl acetate. The extracted organic layer was washed with distilled water, dried over anhydrous sodium sulfate, filtered, and then concentrated under reduced pressure to give a target compound (5 mg, 56%, white solid).

The compounds of Examples 100 to 102 were prepared in a similar manner to the method described in Example 31.

<Example 103> Preparation of N-(3-(5-chloro-1H-indole-3-yl)propyl)-3-fluoro-4-(3-(4-methylpiperazine-1-yl)propoxy)benzenesulfonamide

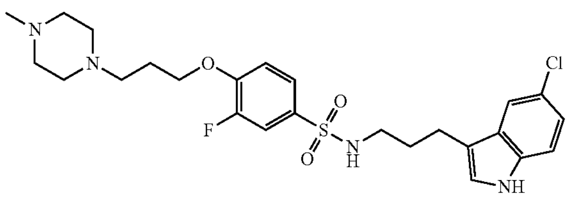 [SMILES: CN1CCN(CCCOc2ccc(S(=O)(=O)NCCCc3c[nH]c4ccc(Cl)cc34)cc2F)CC1]

Step 1: Preparation of 1-(3-bromopropoxy)-2-fluorobenzene

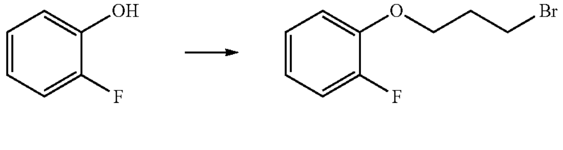 [SMILES: Oc1ccccc1F ; Fc1ccccc1OCCCBr]

2-Fluorophenol (5 g, 44.6 mmol) was dissolved in acetonitrile (74 ml), to which 1,3-dibromopropane (90 g, 446 mmol) and potassium carbonate (6.16 g, 44.6 mmol) were added, followed by stirring at 80° C. for 16 hours. Upon completion of the reaction, the reaction solution was filtered, concentrated under reduced pressure, which was used in the next step without further purification.

Step 2: Preparation of 4-(3-bromopropoxy)-3-fluorobenzenesulfonyl chloride

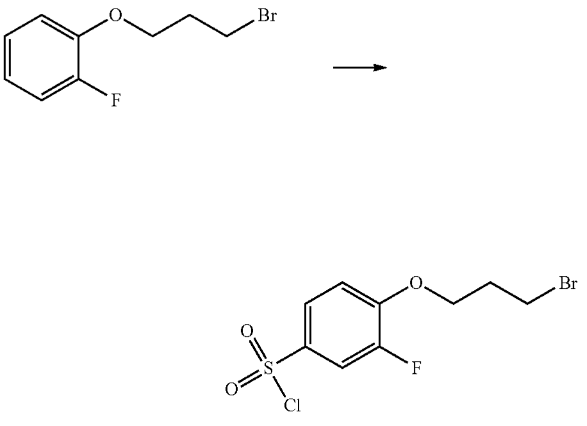

The compound (5 g, 19.31 mmol) prepared in step 1 above was dissolved in dichloromethane (38 ml), to which chlorosulfonic acid (5.13 ml, 77 mmol) was added, followed by stirring at room temperature for 1 hour. Upon completion of the reaction, the reaction mixture was diluted with dichloromethane and neutralized with a sodium carbonate aqueous solution at 0° C. The residue of the organic layer was dried over anhydrous sodium sulfate, filtered and concentrated, which was used in the next step without further purification.

Step 3: Preparation of 4-(3-bromopropoxy)-N-(3-(5-chloro-1H-indole-3-yl)propyl)-3-fluorobenzene-sulfonamide

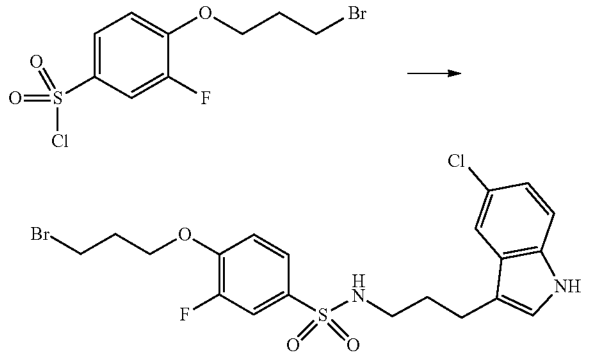

The compound (1 g, 3.02 mmol) prepared in step 2 above was dissolved in dichloromethane (6 ml), to which 3-(5-chloro-1H-indole-3-yl)propane-1-amine (0.818 g, 3.92 mmol) and potassium carbonate (0.542 g, 3.92 mmol) were added, followed by stirring at room temperature for 3 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (1.1 g, 77%, white solid).

Step 4: Preparation of N-(3-(5-chloro-1H-indole-3-yl)propyl)-3-fluoro-4-(3-(4-methylpiperazine-1-yl)propoxy)benzenesulfonamide

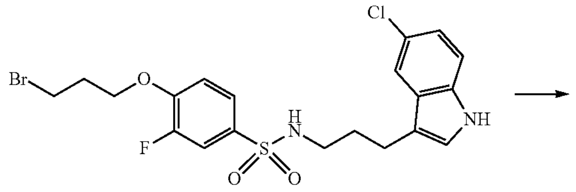

-continued

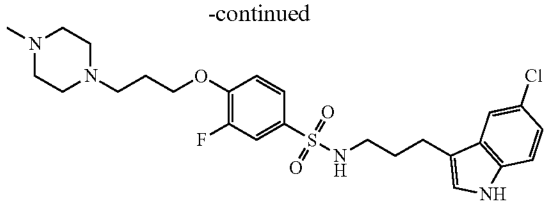

The compound (0.05 g, 0.099 mmol) prepared in step 3 above was dissolved in ethanol (1 ml), to which potassium carbonate (0.021 g, 0.149 mmol) and 1-methylpiperazine (0.020 g, 0.198 mmol) were added, followed by stirring at 70° C. for 16 hours. Upon completion of the reaction, the reaction mixture was diluted with dichloromethane, and washed with water and brine. The residue of the organic layer was dried over anhydrous sodium sulfate, filtered and concentrated, purified by Prep HPLC, and then neutralized by adding a sodium hydrogen carbonate aqueous solution to give a target compound (0.011 g, 22%, white solid).

The compounds of Examples 104 to 106 were prepared in a similar manner to the method described in Example 103.

<Example 107> Preparation of N-(3-(5-chloro-1H-indole-3-yl)propyl)-4-(3-(3-methylpiperazine-1-yl)propoxy)benzenesulfonamide

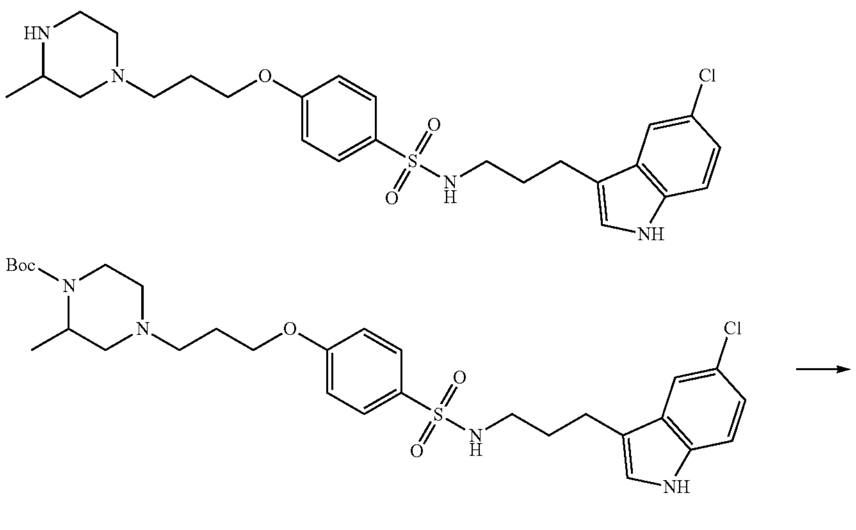

-continued

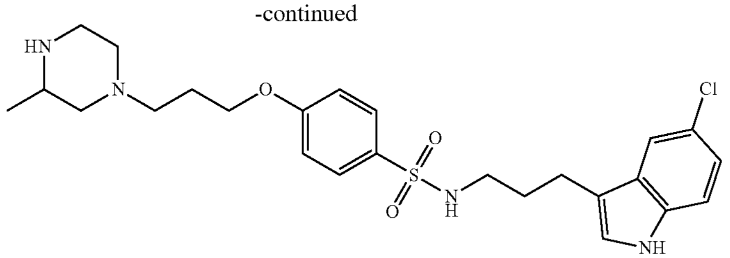

A target compound (15 mg, 72%) was obtained as a pale yellow solid in a similar manner to the method described in step 4 of Example 99 using tert-butyl 4-(3-(4-(N-(3-(5-chloro-1H-indole-3-yl)propyl)sulfamoyl)phenoxy)propyl)-2-methylpiperazine-1-carboxylate (25 mg, 0.041 mmol) obtained in a similar manner to the method described in Example 31 and trifluoroacetic acid (1 ml, 13.1 mmol).

The compounds of Examples 108 to 111 were prepared in a similar manner to the method described in Example 107.

The compound of Example 112 was prepared in a similar manner to the method described in Example 90.

<Example 113> Preparation of N-(3-(5-chloro-1H-indole-3-yl)propyl)-4-((3-(piperazine-1-yl)propyl)amino)benzenesulfonamide

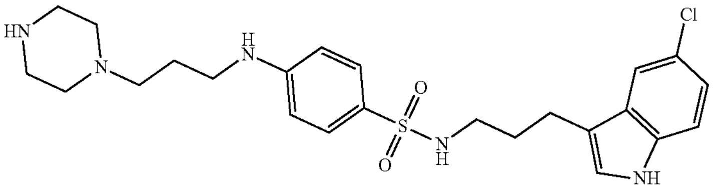

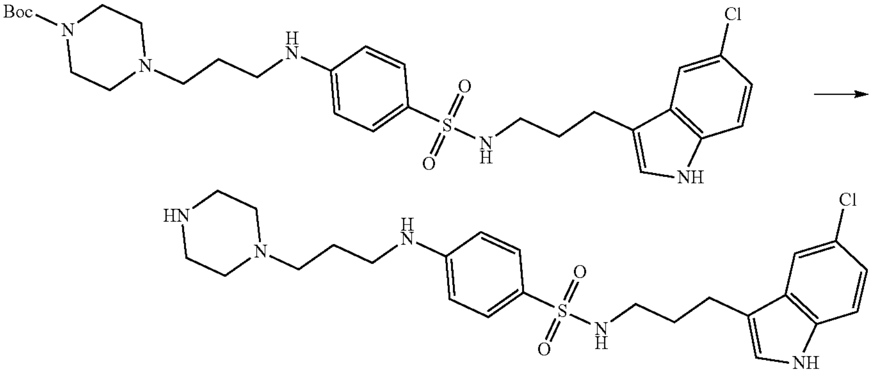

The compound (0.0142 g, 0.024 mmol) prepared in a similar manner to the method described in Example 98 was dissolved in dichloromethane (2 ml), to which trifluoroacetic acid (1 ml, 12.98 mmol) was added, followed by stirring at room temperature for 1 hour. Upon completion of the reaction, the reaction solution was concentrated under reduced pressure, purified by Prep HPLC, and neutralized by adding a sodium hydrogen carbonate aqueous solution to give a target compound (0.005 g, 50%, white solid).

The compound of Example 114 was prepared in a similar manner to the method described in Example 98.

The compound of Example 115 was prepared in a similar manner to the method described in steps 1 to 3 of Example 99.

<Example 116> Preparation of N-(3-(5-chloro-1H-indole-3-yl)propyl)-4-((1-((4-methylpiperazine-1-yl)methyl)cyclopropyl)methoxy)benzenesulfonamide

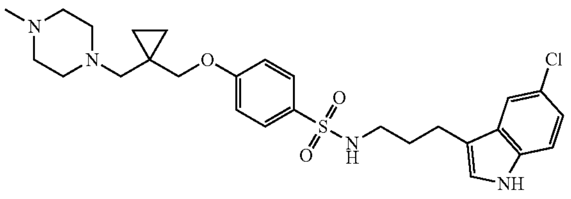 [SMILES: CN1CCN(CC2(COc3ccc(S(=O)(=O)NCCCc4c[nH]c5ccc(Cl)cc45)cc3)CC2)CC1]

Step 1: Preparation of (1-(((tert-butyldimethylsilyl)oxy)methyl)cyclopropyl)methanol

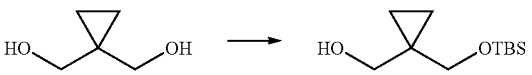 [SMILES: OCC1(CO)CC1 ; CC(C)(C)[Si](C)(C)OCC1(CO)CC1]

Cyclopropane-1,1-diyldimethanol (5 g, 49.0 mmol) was dissolved in dichloromethane (130 mL), to which imidazole (5 g, 73.4 mmol) and tert-butyldimethylsilyl chloride (7.75 g, 51.4 mmol) was added. The reaction mixture was stirred at 0° C. for 30 minutes, and then stirred at room temperature for 16 hours. Upon completion of the reaction, the reaction mixture was neutralized with a supersaturated sodium hydrogen carbonate aqueous solution, and extracted with ethyl acetate. The extracted organic layer was washed with distilled water, dried over anhydrous sodium sulfate, filtered, and then concentrated under reduced pressure. The reaction mixture was purified by MPLC to give a target compound (4.7 g, 44%, transparent oil).

Step 2: Preparation of ((1-(bromomethyl)cyclopropyl)methoxy)(tert-butyl)dimethylsilane

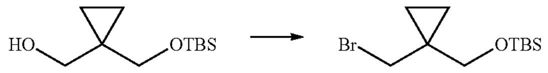 [SMILES: CC(C)(C)[Si](C)(C)OCC1(CO)CC1 ; CC(C)(C)[Si](C)(C)OCC1(CBr)CC1]

(1-(((Tert-butyldimethylsilyl)oxy)methyl)cyclopropyl) methanol (1.1 g, 5.08 mmol) prepared in step 1 above was dissolved in dichloromethane (10 ml), to which carbon tetrabromide (1.85 g, 5.59 mmol) and triphenylphosphine (1.47 g, 5.59 mmol) were added. The reaction mixture was stirred at 0° C. for 30 minutes, and then stirred at room temperature for 16 hours. Upon completion of the reaction, the reaction mixture was concentrated under reduced pressure, and purified by MPLC to give a target compound (1 g, 70%, transparent oil).

Step 3: Preparation of (1-(bromomethyl)cyclopropyl)methanol

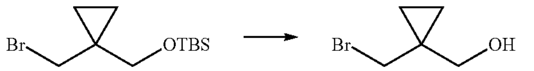 [SMILES: CC(C)(C)[Si](C)(C)OCC1(CBr)CC1 ; OCC1(CBr)CC1]

((1-(Bromomethyl)cyclopropyl)methoxy)(tert-butyl)dimethylsilane (1 g, 3.58 mmol) prepared in step 2 above was dissolved in acetic acid/tetrahydrofuran/distilled water (12 ml/4 ml/4 ml), followed by stirring at room temperature for 3 hours. Upon completion of the reaction, the reaction mixture was neutralized with a supersaturated sodium hydrogen carbonate aqueous solution and extracted with ethyl acetate. The extracted organic layer was washed with distilled water, dried over anhydrous sodium sulfate, filtered, and then concentrated under reduced pressure. The obtained reaction mixture was purified by MPLC to give a target compound (0.3 g, 51%, yellow oil).

Step 4: Preparation of 4-((1-(bromomethyl)cyclopropyl)methoxy)-N-(3-(5-chloro-1H-indole-3-yl)propyl)benzenesulfonamide

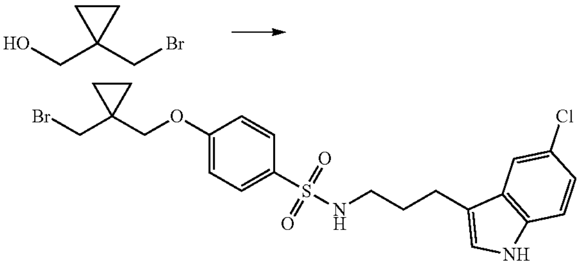

A target compound (45 mg, 48%, yellow solid) was obtained in a similar manner to the method described in step 2 of Example 92 using (1-(bromomethyl)cyclopropyl) methanol (30 mg, 0.182 mmol) prepared in step 3 above, N-(3-(5-chloro-1H-indole-3-yl)propyl)-4-hydroxybenzenesulfonamide (66 mg, 0.182 mmol), triphenylphosphine (72 mg, 0.273 mmol), and diethyl azodicarboxylate (0.124 ml, 0.273 mmol).

Step 5: Preparation of N-(3-(5-chloro-1H-indole-3-yl)propyl)-4-((1-((4-methylpiperazine-1-yl)methyl)cyclopropyl)methoxy)benzenesulfonamide

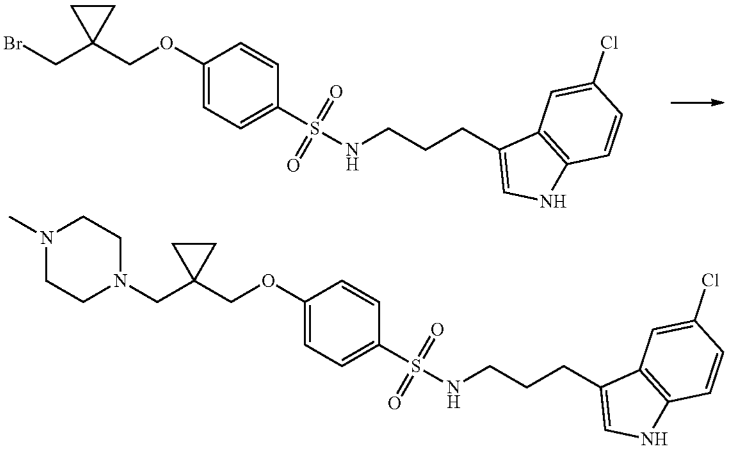

A target compound (12.3 mg, 59%, yellow solid) was obtained in a similar manner to the method described in step 3 of Example 31 using 4-((1-(bromomethyl)cyclopropyl)methoxy)-N-(3-(5-chloro-1H-indole-3-yl)propyl)benzenesulfonamide (20 mg, 0.039 mmol) prepared in step 4 above, 1-methylpiperazine (0.013 ml, 0.117 mmol), and potassium carbonate (8.1 mg, 0.059 mmol).

The compound of Example 117 was prepared in a similar manner to the method described in Example 116.

<Example 118> Preparation of N-(3-(5-chloro-1H-indole-3-yl)propyl)-4-(3-(4-methylpiperazine-1-yl)phenoxy)benzenesulfonamide

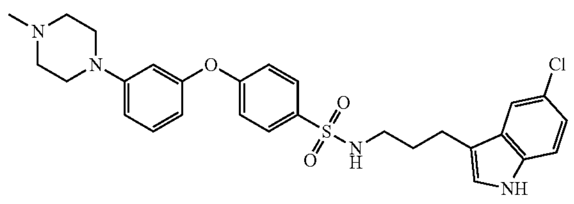 [SMILES: CN1CCN(c2cccc(Oc3ccc(S(=O)(=O)NCCCc4c[nH]c5ccc(Cl)cc45)cc3)c2)CC1]

Step 1: Preparation of 4-(3-bromophenoxy)benzenesulfonic acid

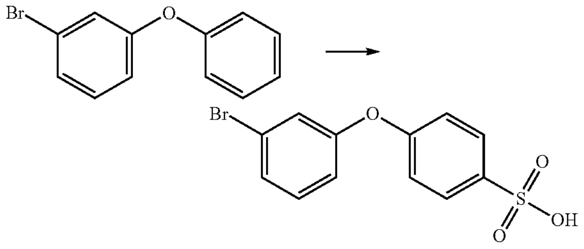

1-Bromo-3-phenoxybenzene (300 mg, 1.20 mmol) was dissolved in dichloromethane, to which chlorosulfonic acid (0.088 ml, 1.33 mmol) was slowly added at 0° C. The reaction mixture was stirred at 0° C. for 30 minutes, and then stirred at room temperature for 3 hours. Upon completion of the reaction, the reaction mixture was concentrated under reduced pressure to give a target compound (395 mg, 100%, yellow oil).

Step 2: Preparation of 4-(3-bromophenoxy)benzenesulfonyl chloride

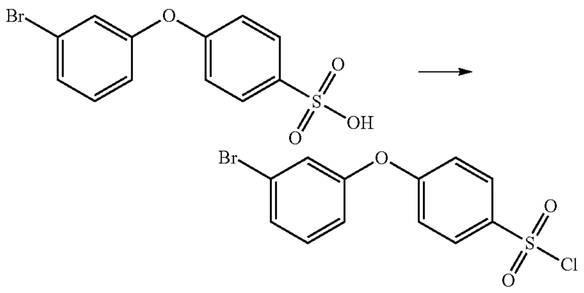

4-(3-Bromophenoxy)benzenesulfonic acid (395 mg, 1.20 mmol) prepared in step 1 above was dissolved in $SnCl_2 \cdot H_2O$ (3 ml, 41.4 mmol) at 0° C., followed by stirring. Then, two drops of diformamide were added thereto at 0° C., and the reaction mixture was gradually heated and stirred under reflux for 2 hours. Upon completion of the reaction, the reaction mixture was cooled down to room temperature, concentrated under reduced pressure, and purified by MPLC to give a target compound (380 mg, 91%, yellow oil).

Step 3: Preparation of 4-(3-bromophenoxy)-N-(3-(5-chloro-1H-indole-3-yl)propyl)benzenesulfonamide

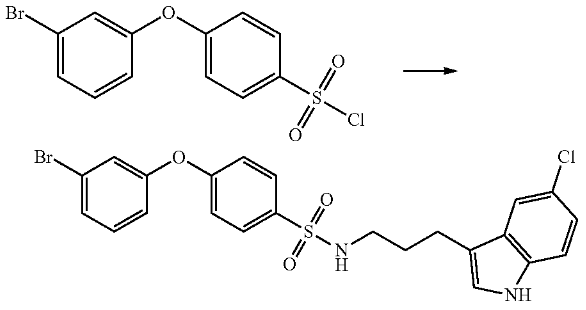

A target compound (170 mg, 76%, yellow solid) was obtained in a similar manner to the method described in step 2 of Example 90 using 4-(3-bromophenoxy)benzenesulfonyl chloride (150 mg, 0.432 mmol) prepared in step 2 above, 3-(5-chloro-1H-indole-3-yl)propane-1-amine (90 mg, 0.432 mmol), and triethylamine (0.090 ml, 0.647 mmol).

Step 4: Preparation of N-(3-(5-chloro-1H-indole-3-yl)propyl)-4-(3-(4-methylpiperazine-1-yl)phenoxy)benzenesulfonamide

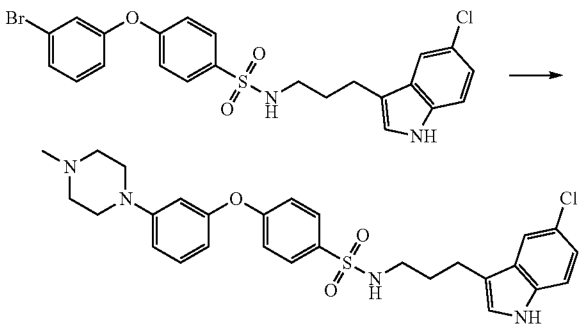

4-(3-Bromophenoxy)-N-(3-(5-chloro-1H-indole-3-yl)propyl)benzenesulfonamide (90 mg, 0.173 mmol) prepared in step 3 above was dissolved in 1,4-dioxane (1.5 ml), to which t-BuOK (29.1 mg, 0.260 mmol) and 1-methylpiperazine (0.03 ml, 0.260 mmol) were added at room temperature. The reaction mixture was heated at 70° C. and stirred, and degassed for 5 minutes using a nitrogen balloon, to which $Pd(t\text{-}Bu_3P)_2$ (8 mg, 0.016 mmol) was added, followed by reflux stirring for 3 hours. Upon completion of the reaction, the reaction mixture was cooled down to room temperature, filtered and concentrated with celite, and purified by prep HPLC. The obtained trifluoroacetate compound was neutralized by adding a supersaturated sodium hydrogencarbonate aqueous solution, and extracted with a 10% methanol/dichloromethane solution. The organic layer was dried over anhydrous sodium sulfate, filtered, and then concentrated under reduced pressure to give a target compound (6.5 mg, 53%, white solid).

The compound of Example 119 was prepared in a similar manner to the method described in steps 1 to 3 of Example 118.

The compounds of Examples 120 to 122 were prepared in a similar manner to the method described in Example 118.

<Example 123> Preparation of N-(3-(5-chloro-1H-indole-3-yl)propyl)-4-((3-(4-methylpiperazine-1-yl)phenyl)amino)benzenesulfonamide

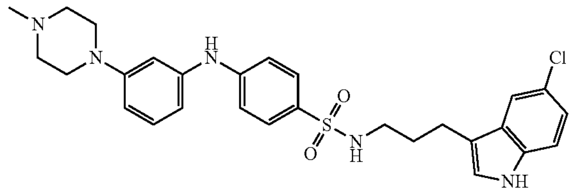

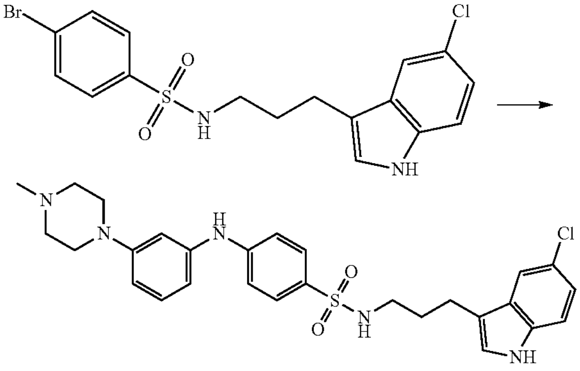

The compound (0.05 g, 0.117 mmol) prepared in a similar manner to the method described in step 2 of Example 47 was dissolved in 2-butanol (1.5 ml), to which 3-(4-methylpiperazine-1-yl)aniline (0.02 g, 0.117 mmol) and potassium carbonate (0.08 g, 0.584 mmol) were added, followed by degassing for 1 minute. Then, $Pd_2(dba)_3$ (0.01 g, 0.012 mmol) and Xphos (0.005 g, 0.012 mmol) were added thereto at 80° C., followed by stirring at 100° C. for 1 hour. Upon completion of the reaction, the reaction solution was filtered with celite, and washed with ethyl acetate and dichloromethane. The filtrate was concentrated under reduced pressure, purified by Prep HPLC, and neutralized by adding a sodium hydrogen carbonate aqueous solution to give a target compound (0.023 g, 37%, yellow solid).

The compounds of Examples 124 to 127 were prepared in a similar manner to the method described in Example 123.

The compounds of Examples 128 and 129 were prepared in a similar manner to the method described in Example 119.

<Example 130> Preparation of 4-(3,5-bis(4-methylpiperazine-1-yl)phenoxy)-N-(3-(5-chloro-1H-indole-3-yl)propyl)benzenesulfonamide

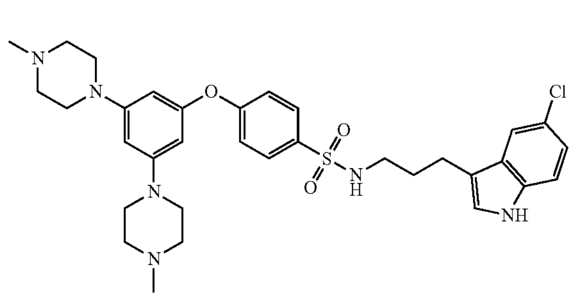 [SMILES: CN1CCN(c2cc(Oc3ccc(S(=O)(=O)NCCCc4c[nH]c5ccc(Cl)cc45)cc3)cc(N3CCN(C)CC3)c2)CC1]

Step 1: Preparation of 1,3-dibromo-5-phenoxybenzene

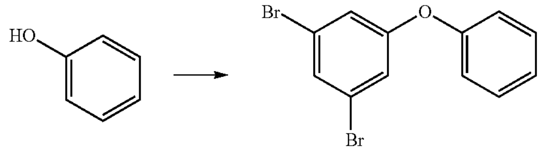 [SMILES: Oc1ccccc1 ; Brc1cc(Br)cc(Oc2ccccc2)c1]

Phenol (100 mg, 1.06 mmol) was dissolved in N-methyl-2-pyrrolidinone (2 ml), to which cesium carbonate (173 mg, 0.531 mmol), 1,3-dibromo-5-fluorobenzene (0.201 ml, 1.59 mmol), TMHDA (0.057 ml, 0.266 mmol) and CuCl (52.6 mg, 0.531 mmol) were added at room temperature. The reaction mixture was degassed at room temperature using a nitrogen balloon, followed by stirring for 20 minutes. The reaction mixture was gradually heated and stirred at 120° C. for 16 hours. Upon completion of the reaction, the reaction mixture was cooled down to room temperature, filtered with celite, extracted with ethyl acetate, and concentrated under reduced pressure. The obtained reaction mixture was purified by MPLC to give a target compound (220 mg, 63%, yellow solid).

Step 2: Preparation of 4-(3,5-dibromophenoxy)benzenesulfonic acid

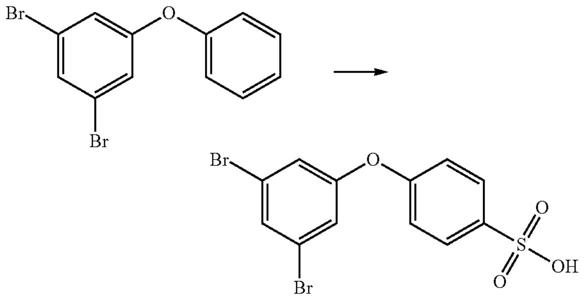

A target compound (274 mg, 100%, yellow solid) was obtained in a similar manner to the method described in step 1 of Example 118 using 1,3-dibromo-5-phenoxybenzene (220 mg, 0.671 mmol) prepared in step 1 above, and chlorosulfonic acid (0.049 ml, 0.738 mmol).

Step 3: Preparation of 4-(3,5-dibromophenoxy)benzenesulfonyl chloride

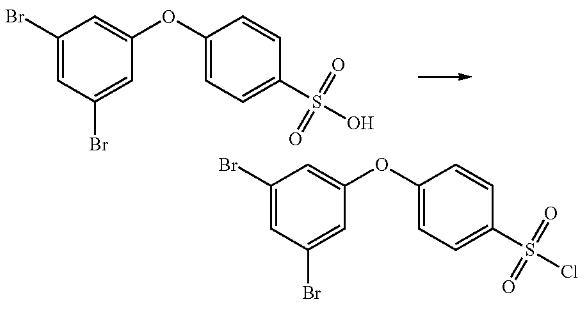

A target compound (230 mg, 80%, yellow solid) was obtained in a similar manner to the method described in step 2 of Example 118 using 4-(3,5-dibromophenoxy)benzenesulfonic acid (274 mg, 0.671 mmol) prepared in step 2 above, and thionyl chloride (4 ml, 55.1 mmol).

Step 4: Preparation of N-(3-(5-chloro-1H-indole-3-yl)propyl)-4-(3,5-dibromophenoxy)benzenesulfonamide

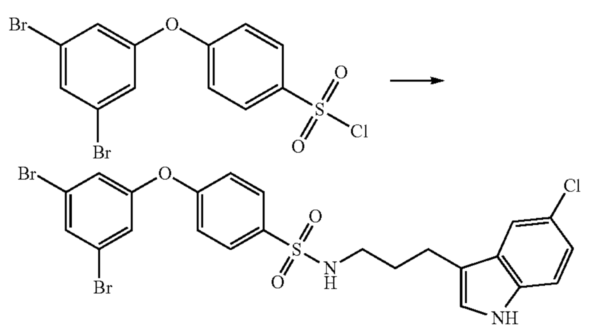

A target compound (300 mg, 93%, white solid) was obtained in a similar manner to the method described in step 2 of Example 90 using 4-(3,5-dibromophenoxy)benzenesulfonyl chloride (230 mg, 0.539 mmol) prepared in step 3 above, 3-(5-chloro-1H-indole-3-yl)propane-1-amine (118 mg, 0.566 mmol), and triethylamine (0.113 ml, 0.809 mmol).

Step 5: Preparation of 4-(3,5-bis(4-methylpiperazine-1-yl)phenoxy)-N-(3-(5-chloro-1H-indole-3-yl)propyl)benzenesulfonamide

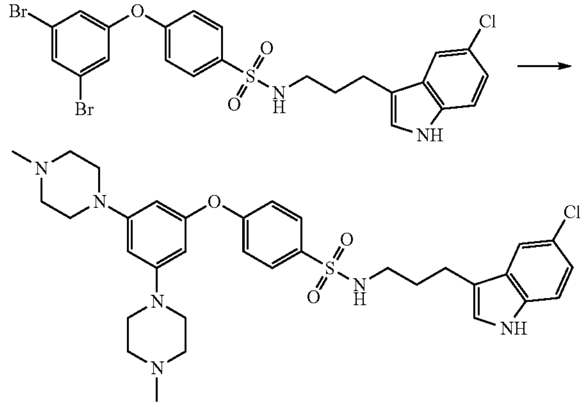

A target compound (5 mg, 9%, yellow solid) was obtained in a similar manner to the method described in step 4 of Example 118 using N-(3-(5-chloro-1H-indole-3-yl)propyl)-4-(3,5-dibromophenoxy)benzenesulfonamide (50 mg, 0.084 mmol) prepared in step 4 above, 1-methylpiperazine (0.037 ml, 0.334 mmol), potassium tert-butoxide (37.5 mg, 0.334 mmol), and $Pd(t-Bu_3P)_2$ (8.54 mg, 0.017 mmol).

The compounds of Examples 131 to 134 were prepared in a similar manner to the method described in Example 123.

The compounds of Examples 135 and 136 were prepared in a similar manner to the method described in Example 118.

The compound of Example 137 was prepared in a similar manner to the method described in Example 138.

<Example 138> Preparation of N-(3-(5-chloro-1H-indole-3-yl)propyl)-4-(3-bromo-5-(4-methylpiperazine-1-yl)phenoxy)benzenesulfonamide

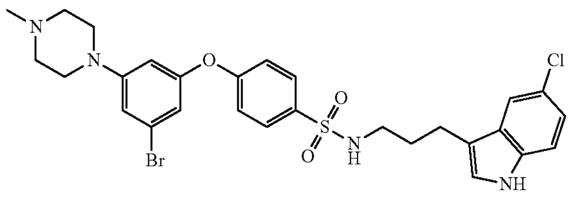 [SMILES: CN1CCN(c2cc(Br)cc(Oc3ccc(S(=O)(=O)NCCCc4c[nH]c5ccc(Cl)cc45)cc3)c2)CC1]

Step 1: Preparation of 1-bromo-3-fluoro-5-phenoxybenzene

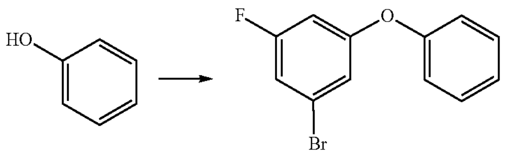 [SMILES: Oc1ccccc1 ; Fc1cc(Br)cc(Oc2ccccc2)c1]

A target compound (0.45 g, 32%, transparent oil) was obtained in a similar manner to the method described in step 1 of Example 130 using phenol (0.5 g, 5.31 mmol), cesium carbonate (0.866 g, 2.66 mmol), 1-bromo-3,5-difluorobenzene (1.54 g, 7.97 mmol), TMHDA (0.284 ml, 1.33 mmol) and CuCl (0.263 mg, 2.66 mmol).

Step 2: Preparation of 4-(3-bromo-5-fluorophenoxy)benzene-1-sulfonyl chloride

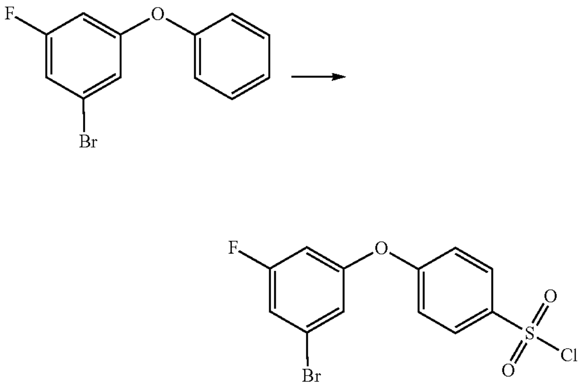

A target compound (0.44 g, 71%, yellow oil) was obtained in a similar manner to the method described in step 1 of Example 31 using 1-bromo-3-fluoro-5-phenoxybenzene (0.45 g, 1.685 mmol) prepared in step 1 above and chlorosulfonic acid (0.123 ml, 1.853 mmol).

Step 3: Preparation of 4-(3-bromo5-fluorophenoxy)-N-(3-(5-chloro-1H-indole-3-yl)propyl)benzenesulfonamide

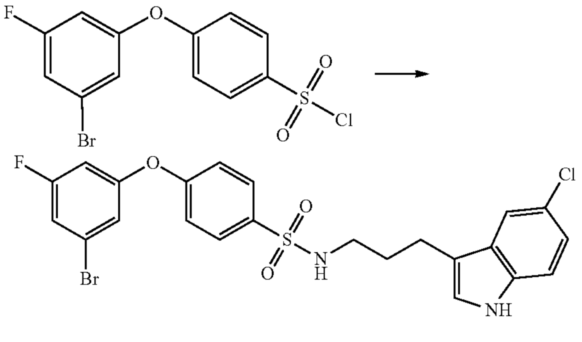

A target compound (300 mg, 93%, yellow solid) was obtained in a similar manner to the method described in step 2 of Example 90 using 4-(3-bromo-5-fluorophenoxy)benzene-1-sulfonyl chloride (200 mg, 0.547 mmol) prepared in step 2 above, 3-(5-chloro-1H-indole-3-yl))propane-1-amine (115 mg, 0.553 mmol) and triethylamine (0.114 ml, 0.821 mmol).

Step 4: Preparation of 4-(3-bromo-5-(4-methylpiperazine-1-yl)phenoxy)-N-(3-(5-chloro-1H-indole-3-yl)propyl)benzenesulfonamide

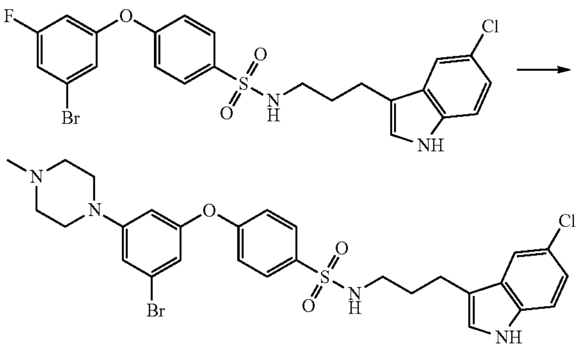

4-(3-Bromo-5-fluorophenoxy)-N-(3-(5-chloro-1H-indole-3-yl)propyl)benzenesulfonamide (30 mg, 0.056 mmol) prepared in step 3 above was dissolved in dimethyl sulfoxide (1 ml), to which 1-methylpiperazine (0.025 ml, 0.223 mmol) and potassium carbonate (30.8 mg, 0.223 mmol) were added at room temperature. Then, the reaction mixture was heated at 120° C., and stirred for 16 hours. Upon completion of the reaction, the mixture was cooled down to room temperature, washed with distilled water and brine, and extracted with ethyl acetate. The extracted organic layer was dried over anhydrous sodium sulfate, filtered, concentrated under reduced pressure, and purified by prep HPLC. The obtained trifluoroacetate compound was neutralized by adding a supersaturated sodium hydrogen carbonate aqueous solution, followed by extraction with a 10% methanol/dichloromethane solution. The extracted organic layer was dried over anhydrous sodium sulfate, filtered, and then concentrated under reduced pressure to give a target compound (6.2 mg, 22%, ivory solid).

The compounds of Examples 139 to 142 were prepared in a similar manner to the method described in Example 123.

<Example 143> Preparation of N-(3-(5-chloro-1H-indole-3-yl)propyl)-4-(3-(4-methylpiperazine-1-yl)propoxy)benzamide

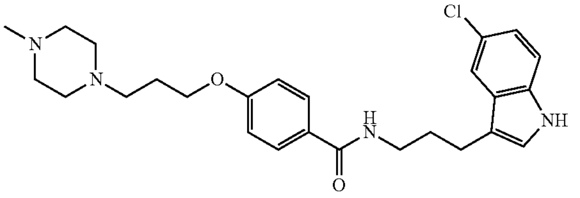 [SMILES: CN1CCN(CCCOc2ccc(C(=O)NCCCc3c[nH]c4ccc(Cl)cc34)cc2)CC1]

Step 1: Preparation of methyl 4-(3-bromopropoxy)benzoate

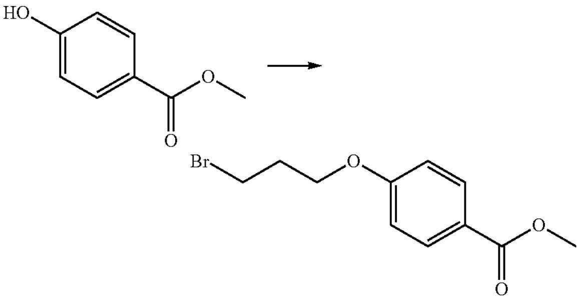

Methyl 4-hydroxybenzoate (0.5 g, 3.29 mmol) was dissolved in acetonitrile (10 ml), to which 1,3-dibromopropane (0.995 g, 4.93 mmol) and potassium carbonate (0.681 g, 4.93 mmol) were added. The reaction mixture was heated at 80° C., and stirred for 5 hours. Upon completion of the reaction, the mixture was cooled down to room temperature, filtered with celite, and concentrated under reduced pressure. The obtained residue was purified by MPLC to give a target compound (0.7 g, 78%, transparent oil).

Step 2: Preparation of 4-(3-bromopropoxy)benzoic acid

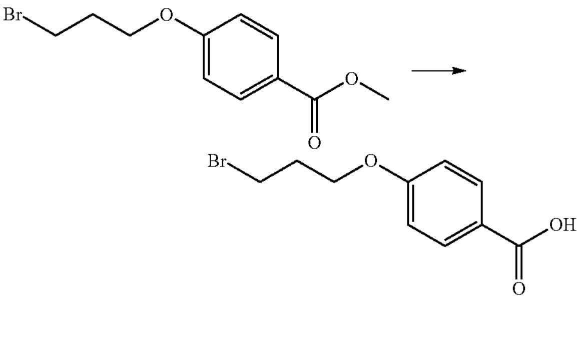

Methyl 4-(3-bromopropoxy)benzoate (0.7 g, 2.56 mmol) prepared in step 1 above was dissolved in tetrahydrofuran/methanol/distilled water (6.0 ml/3 ml/3 ml), to which $LiOH.H_2O$ (0.323 g, 7.69 mmol) was added at room temperature. Then, the reaction mixture was heated at 50° C., and stirred for 2 hours. Upon completion of the reaction, the mixture was cooled down to room temperature, and a 1 N hydrochloric acid aqueous solution was slowly added dropwise to adjust the pH to 2. The resulting solid was washed with distilled water and then dried in vacuo to give a target compound (0.35 g, 53%, white solid).

Step 3: Preparation of 4-(3-bromopropoxy)-N-(3-(5-chloro-1H-indole-3-yl)propyl)benzamide

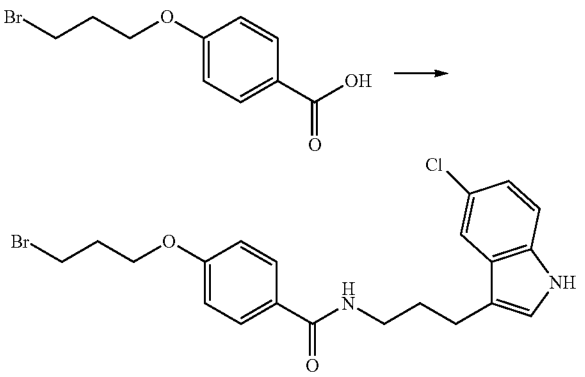

4-(3-Bromopropoxy)benzoic acid (0.1 g, 0.386 mmol) prepared in step 2 above was dissolved in dichloromethane (2 ml), to which 3-(5-chloro-1H-indole-3-yl)propane-1-amine (0.081 g, 0.390 mmol), HATU (0.294 g, 0.772 mmol) and N,N-diisopropylethylamine (0.15 g, 1.158 mmol) were added at room temperature, followed by stirring at room temperature for 16 hours. Upon completion of the reaction, the mixture was washed with distilled water and extracted with dichloromethane. The extracted organic layer was dried over anhydrous sodium sulfate, filtered, concentrated under reduced pressure, and purified by MPLC to give a target compound (0.1 g, 58%, ivory solid).

Step 4: Preparation of N-(3-(5-chloro-1H-indole-3-yl)propyl)-4-(3-(4-methylpiperazine-1-yl)propoxy)benzamide

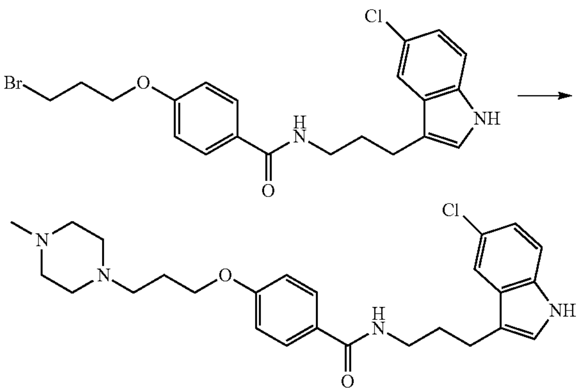

A target compound (8 mg, 38%, ivory solid) was obtained in a similar manner to the method described in step 3 of Example 31 using 4-(3-bromopropoxy)-N-(3-(5-chloro-1H-indole-3-yl)propyl)benzamide (20 mg, 0.044 mmol) prepared in step 3 above, 1-methylpiperazine (0.02 ml, 0.178 mmol) and potassium carbonate (12.3 mg, 0.089 mmol).

The compound of Example 144 was prepared in a similar manner to the method described in Example 143.

The compound of Example 145 was prepared in a similar manner to the method described in Example 92.

<Example 146> Preparation of N-(3-(5-chloro-1H-indole-3-yl)propyl)-2-((3-(piperazine-1-yl)propyl)amino)thiazole-5-sulfonamide

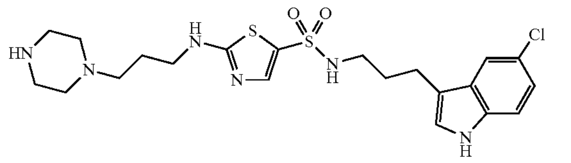 [SMILES: O=S(=O)(NCCCc1c[nH]c2ccc(Cl)cc12)c1cnc(NCCCN2CCNCC2)s1]

Step 1: Preparation of 2-chloro-N-(3-(5-chloro-1H-indole-3-yl)propyl)thiazole-5-sulfonamide

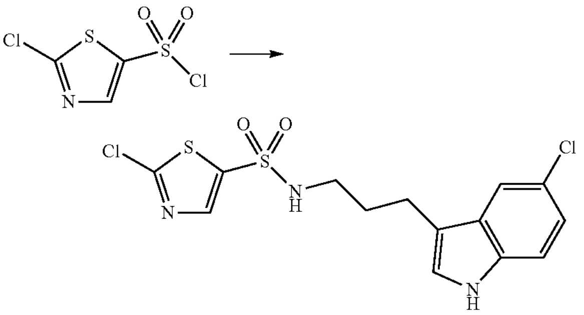

A target compound was prepared in a similar manner to the method described in step 2 of Example 31.

Step 2: Preparation of tert-butyl 4-(3-((5-(N-(3-(5-chloro-1H-indole-3-yl)propyl)sulfamoyl)thiazol-2-yl)amino)propyl)piperazine-1-carboxylate

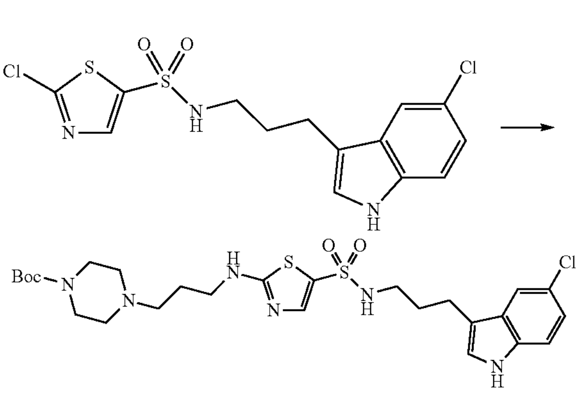

2-Chloro-N-(3-(5-chloro-1H-indole-3-yl)propyl) thiazole-5-sulfonamide (30 mg, 0.077 mmol) prepared in step 1 above was dissolved in dimethylformamide, to which tertbutyl 4-(3-aminopropyl)piperazine-1-carboxylate (28 mg, 0.115 mmol) and DIPEA (0.022 mL, 0.154 mmol) were added. The reaction mixture was stirred at room temperature for 2 hours. Upon completion of the reaction, the solvent was removed under reduced pressure, and then the reaction mixture was separated and purified by MPLC to give a target compound (37 mg, 81%, yellow solid).

Step 3: Preparation of N-(3-(5-chloro-1H-indole-3-yl)propyl)-2-((3-(piperazine-1-yl)propyl)amino)thiazole-5-sulfonamide

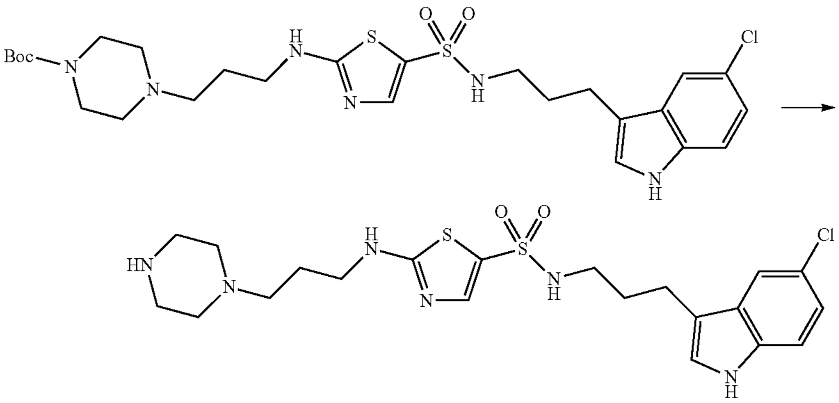

A target compound (30 mg, 97%, pale yellow solid) was obtained in a similar manner to the method described in step 3 of Example 99.

<Example 147> Preparation of N-(3-(5-chloro-2-methyl-1H-indole-3-yl)propyl)-4-(3-(4-methylpiperazine-1-yl)propoxy)benzenesulfonamide

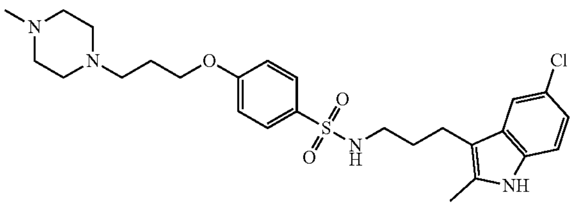 [SMILES: Cc1[nH]c2ccc(Cl)cc2c1CCCNS(=O)(=O)c1ccc(OCCCN2CCN(C)CC2)cc1]

Step 1: Preparation of 3-(5-chloro-2-methyl-1H-indole-3-yl)propane-1-amine hydrochloride

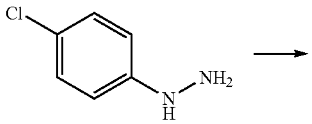

-continued

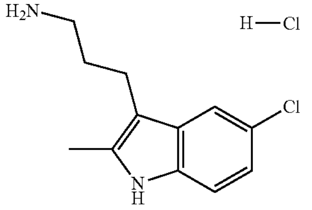

Chlorophenyl hydrazine (1.40 g, 9.81 mmol) and 6-chlorohexene-2-one (1.10 g, 8.17 mmol) were dissolved in ethanol (30 ml), followed by reflux stirring for 20 hours. Upon completion of the reaction, the mixture was cooled down to room temperature, and the solvent was removed under reduced pressure to give 3-(5-chloro-2-methyl-1H-indole-3-yl)propane-1-amine hydrochloride (2.114 g, quantitative, pale yellow solid).

Step 2: Preparation of 4-(3-bromopropoxy)-N-(3-(5-chloro-2-methyl-1H-indole-3-yl)propyl)benzenesulfonamide

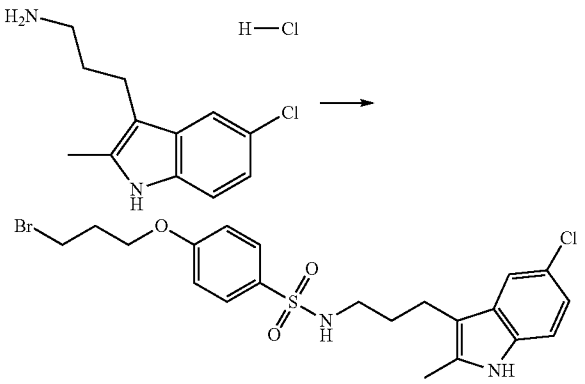

3-(5-Chloro-2-methyl-1H-indole-3-yl)propane-1-amine hydrochloride (0.413 g, 1.59 mmol) prepared in step 1 above was dissolved in ethylenechloride (6 ml), to which triethylamine (0.444 ml, 3.19 mmol) was added dropwise, followed by stirring for 5 minutes. 4-(3-Bromopropoxy)benzene-1- sulfonyl chloride (0.200 g, 0.638 mmol) was added dropwise thereto, followed by stirring at room temperature for 1 hour. Water was added dropwise thereto to terminate the reaction, followed by extraction with dichloromethane. The extracted organic layer was dried over anhydrous sodium sulfate and filtered, and the solvent was removed under reduced pressure. Then, the mixture was separated and purified by MPLC to give a target compound (177 mg, 56%, brown solid).

Step 3: Preparation of N-(3-(5-chloro-2-methyl-1H-indole-3-yl)propyl)-4-(3-(4-methylpiperazine-1-yl)propoxy)benzenesulfonamide

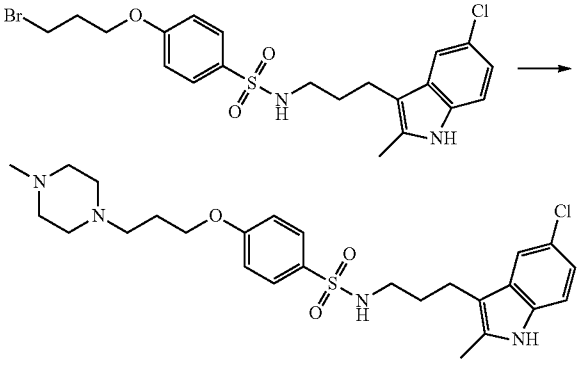

A target compound (19.8 mg, 64%, pale yellow solid) was obtained in a similar manner to the method described in step 3 of Example 31.

<Example 148> Preparation of N-(3-(5-chloro-2-methyl-1H-indole-3-yl)propyl)-4-(3-(4-methylpiperazine-1-yl)propoxy)benzenesulfonamide

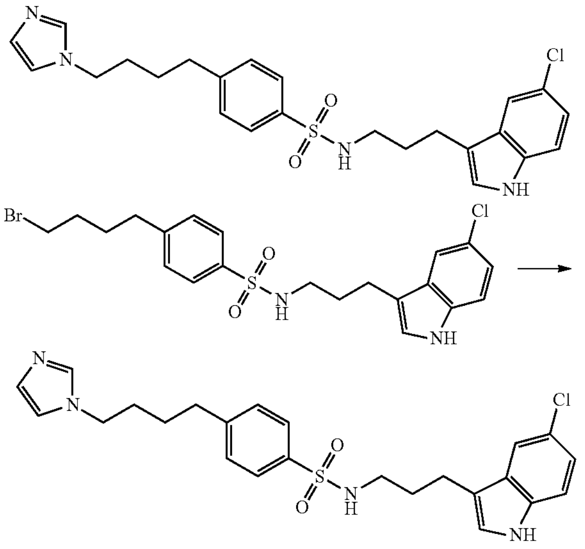

4-(4-Bromobutyl)-N-(3-(5-chloro-1H-indole-3-yl)propyl)benzenesulfonylamide (30 mg, 0.062 mmol) prepared in step 2 of Example 90 was dissolved in acetonitrile, to which potassium carbonate (25.7 mg, 0.186 mmol) and 1H-imidazole (8.44 mg, 0.124 mmol) were added at room temperature, followed by stirring at 60° C. for 4 hours. Upon completion of the reaction, the mixture was filtered with celite. The filtrate was concentrated under reduced pressure, and then separated and purified by MPLC to give a target compound (13 mg, 45%, white solid).

<Example 149> Preparation of N-(2-((5-chloro-1H-indole-3-yl)methyl)phenyl)-4-(3-(4-methylpiperazine-1-yl)propoxy)benzenesulfonamide

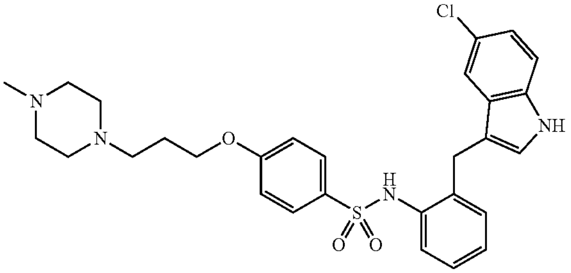 [SMILES: CN1CCN(CCCOc2ccc(S(=O)(=O)Nc3ccccc3Cc3c[nH]c4ccc(Cl)cc34)cc2)CC1]

Step 1: Preparation of 2-((5-chloro-1H-indole-3-yl)methyl)aniline

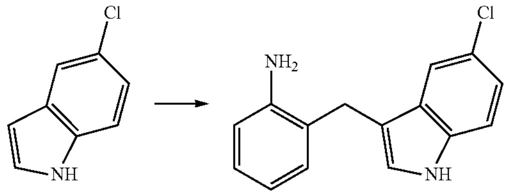 [SMILES: Clc1ccc2[nH]ccc2c1 ; Nc1ccccc1Cc1c[nH]c2ccc(Cl)cc12]

5-Chloro-1H-indole (1 g, 6.60 mmol) and (2-aminophenyl)methanol (0.812 g, 6.60 mmol) were dissolved in 1,2-dichloroethane (20 mL), to which trifluoroacetic acid (0.151 mL, 1.979 mmol) was added at room temperature, followed by stirring at 50° C. for 16 hours. After cooling the mixture to room temperature, a supersaturated sodium carbonate aqueous solution was added dropwise to terminate the reaction, followed by extraction with ethyl acetate. The extracted organic layer was dried over anhydrous sodium sulfate, filtered, and then separated and purified by MPLC to give a target compound (0.55 g, 33%, yellow solid).

Step 2: Preparation of 4-(3-bromopropoxy)-N-(2-((5-chloro-1H-indole-3-yl)methyl)phenyl)benzenesulfonamide

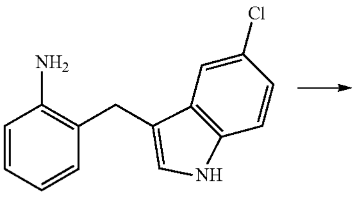

-continued

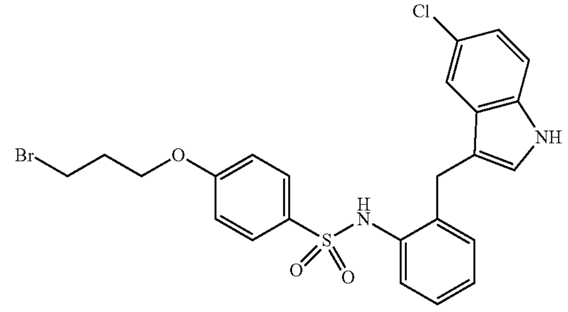

A target compound was prepared in a similar manner to the method described in step 2 of Example 31.

Step 3: Preparation of N-(2-((5-chloro-1H-indole-3-yl)methyl)phenyl)-4-(3-(4-methylpiperazine-1-yl)propoxy)benzenesulfonamide

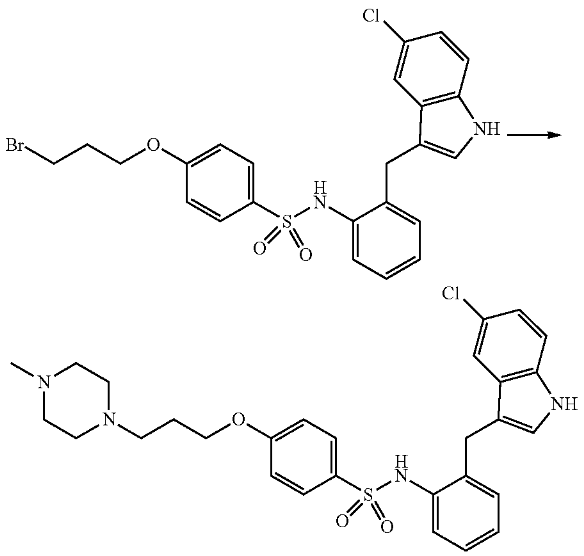

A target compound (13.2 mg, 64%, pale yellow solid) was obtained in a similar manner to the method described in Example 148.

The compound of Example 150 was prepared in a similar manner to the method described in Example 149.

<Example 151> Preparation of N-(2-((5-chloro-1H-indole-3-yl)methyl)phenyl)-4-(3-(4-methylpiperazine-1-yl)propoxy)benzenesulfonamide

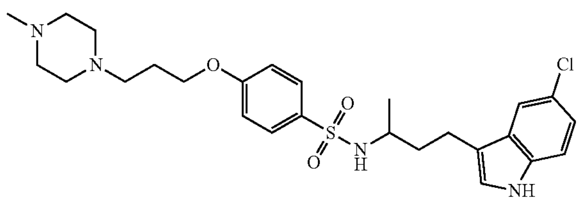 [SMILES: CC(CCc1c[nH]c2ccc(Cl)cc12)NS(=O)(=O)c1ccc(OCCCN2CCN(C)CC2)cc1]

Step 1: Preparation of 4-((5-chloro-1H-indole-3-yl)butan-2-one

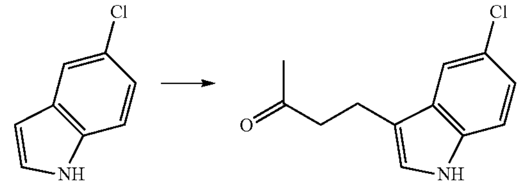

5-Chloro-1H-indole (1 g, 6.60 mmol) was dissolved in distilled water (20 mL), to which 3-butene-2-one (1.387 g, 19.79 mmol) and trifluoromethanesulfonic acid (10 mg, 0.066 mmol) were added at room temperature. The reaction mixture was stirred at room temperature for 16 hours. Upon completion of the reaction, the mixture was washed with a supersaturated sodium carbonate aqueous solution, and then extracted with ethyl acetate. The extracted organic layer was dried over anhydrous sodium sulfate, filtered, and then separated and purified by MPLC to give a target compound (0.64 g, 44%, pale yellow solid).

Step 2: Preparation of 4-(5-chloro-1H-indole-3-yl)butane-2-amine

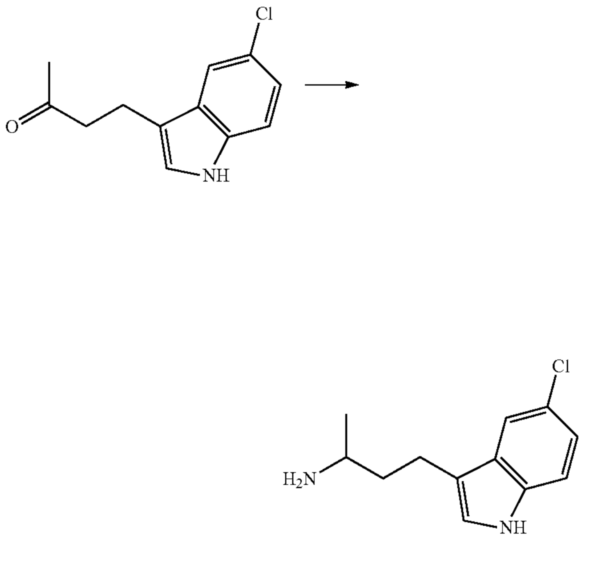

4-((5-Chloro-1H-indole-3-yl)butane-2-one (200 mg, 0.902 mmol) prepared in step 1 above was dissolved in methanol (8 mL), to which ammonium acetate (695 mg, 9.02 mmol) and sodium cyanoborohydride (283 mg, 4.51 mmol) were added at room temperature. The reaction mixture was stirred at room temperature for 16 hours. Upon completion of the reaction, the mixture was washed with a supersaturated sodium carbonate aqueous solution, and then extracted with ethyl acetate. The extracted organic layer was dried over anhydrous sodium sulfate, filtered, and separated and purified by MPLC to give a target compound (0.2 g, 100%, pale yellow oil).

Step 3: Preparation of 4-(3-bromopropoxy)-N-(4-(5-chloro-1H-indole-3-yl)butane-2-yl)benzenesulfonamide

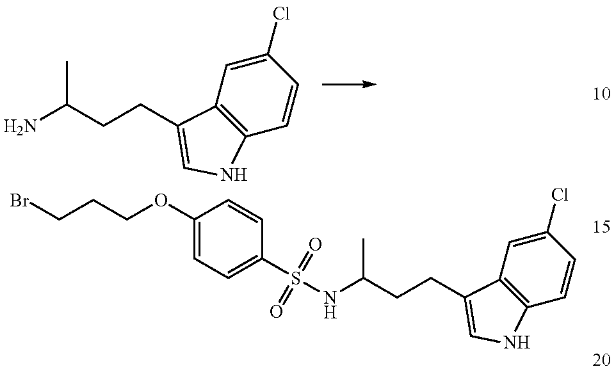

A target compound was prepared in a similar manner to the method described in step 2 of Example 31.

Step 4: Preparation of N-(2-((5-chloro-1H-indole-3-yl)methyl)phenyl)-4-(3-(4-methylpiperazine-1-yl)propoxy)benzenesulfonamide

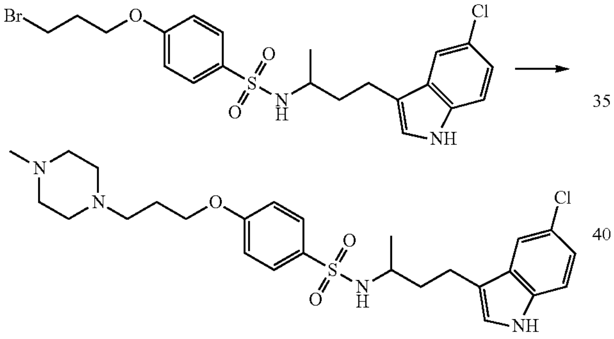

A target compound (16 mg, 77%, white solid) was prepared in a similar manner to the method described in Example 149.

The compound of Example 152 was prepared in a similar manner to the method described in Example 151.

<Example 153> Preparation of N-(3-(5-bromo-1H-indole-3-yl)propyl)-4-(3-(piperazine-1-yl)propoxy)benzenesulfonamide

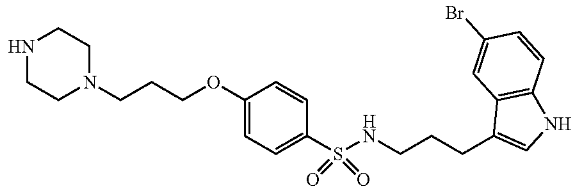

Step 1: Preparation of 3-(5-bromo-1H-indole-3-yl)propane-1-ol

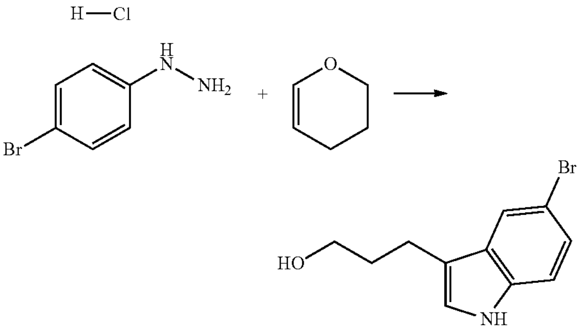

(4-Bromophenyl)hydrazine hydrochloride (1 g, 4.47 mmol) was dissolved in acetonitrile (10 ml), to which 4% sulfuric acid aqueous solution (10 ml) was added. 3,4-Dihydro-2H-pyran (0.40 ml, 4.47 mmol) was slowly added thereto at 100° C. for 2 minutes, followed by stirring at 100° C. for 2 hours. Upon completion of the reaction, the reaction mixture was diluted with ethyl acetate and washed with water and brine. The residue of the organic layer was dried over anhydrous sodium sulfate, filtered and concentrated, and then purified by MPLC to give a target compound (0.61 g, 54%).

Step 2: Preparation of 5-bromo-3-(3-bromopropyl)-1H-indole

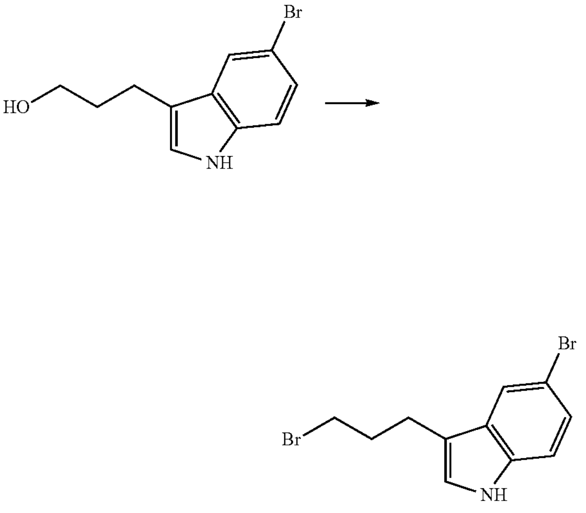

The compound (0.31 g, 1.231 mmol) prepared in step 1 above was dissolved in dichloromethane (2 ml), to which carbon tetrabromide (0.49 g, 1.477 mmol) and triphenylphosphine (0.38 g, 1.477 mmol) were added at 0° C. The reaction mixture was stirred for 30 minutes and then stirred at room temperature for 4 hours. Upon completion of the reaction, the reaction solution was concentrated under reduced pressure, and then purified by MPLC to give a target compound (0.29 g, 77%).

Step 3: Preparation of 3-(3-azidopropyl)-5-bromo-1H-indole

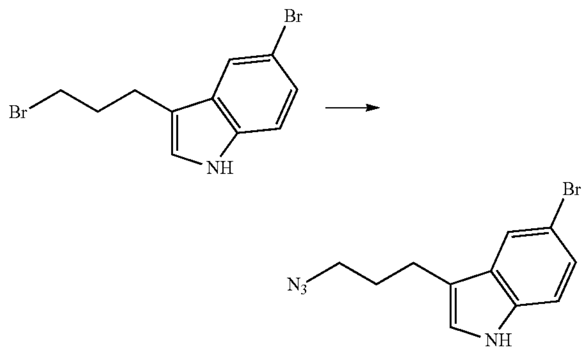

The compound (0.99 g, 3.25 mmol) prepared in step 2 above was dissolved in dimethylformamide (11 ml), to which sodium azide (1.05 g, 16.24 mmol) was added, followed by stirring at room temperature for 4 hours. Upon completion of the reaction, the reaction mixture was diluted with ethyl acetate and washed with water and brine. The residue of the organic layer was dried over anhydrous sodium sulfate, filtered and concentrated, and then purified by MPLC to give a target compound (0.54 g, 62%).

Step 4: Preparation of 3-(5-bromo-1H-indole-3-yl)propane-1-amine

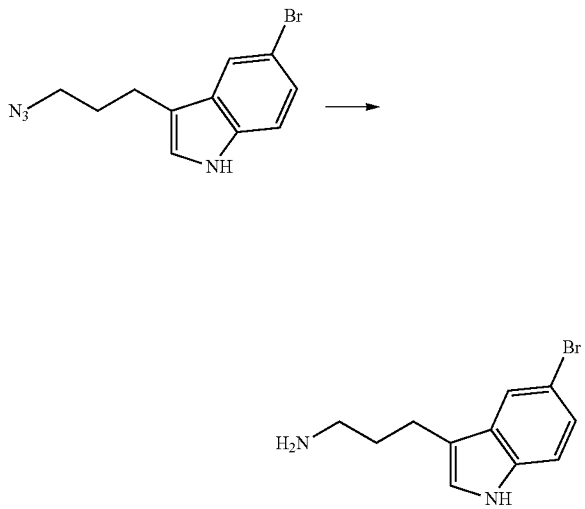

The compound (0.1 g, 0.358 mmol) prepared in step 3 above was dissolved in tetrahydrofuran (3 ml) and water (0.2 ml), to which triphenylphosphine (0.47 g, 1.791 mmol) was added, followed by stirring at room temperature for 16 hours. Upon completion of the reaction, the reaction mixture was diluted with dichloromethane and washed with water and brine. The residue of the organic layer was dried over anhydrous sodium sulfate, filtered and concentrated, and then purified by MPLC to give a target compound (0.075 g, 83%).

Step 5: Preparation of N-(3-(5-bromo-1H-indole-3-yl)propyl)-4-(3-bromopropoxy)benzenesulfonamide

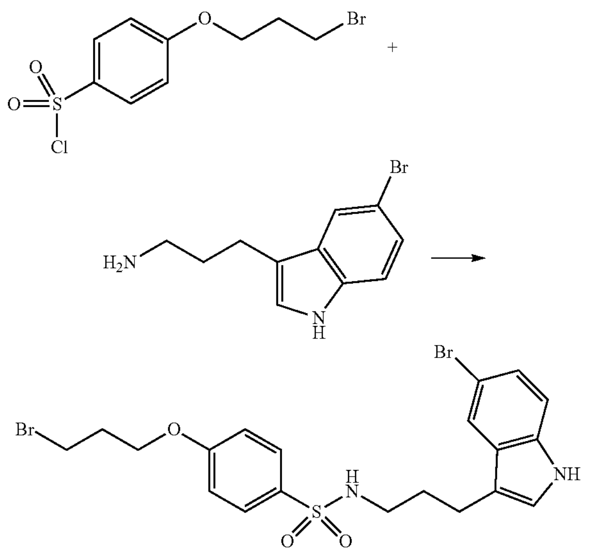

The compound (0.094 g, 0.299) prepared in step 1 of Example 31 was dissolved in dichloromethane (1 ml), to which the compound (0.075 g, 0.299 mmol) prepared in step 4 above and potassium carbonate (0.124 g, 0.896 mmol) were added, followed by stirring at room temperature for 1 hour. Upon completion of the reaction, the reaction mixture was diluted with dichloromethane and washed with water and brine. The residue of the organic layer was dried over anhydrous sodium sulfate, filtered and concentrated, and then purified by MPLC to give a target compound (0.12 g, 80%).

Step 6: Preparation of N-(3-(5-bromo-1H-indole-3-yl)propyl)-4-(3-(piperazine-1-yl)propoxy)benzene-sulfonamide

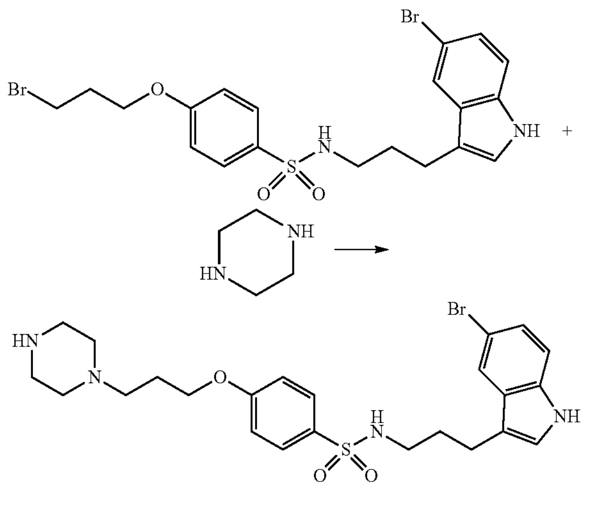

The compound (0.06 g, 0.113 mmol) prepared in step 5 above was dissolved in ethanol (1.5 ml), to which potassium carbonate (0.031 g, 0.226 mmol) and piperazine (0.02 g, 0.339 mmol) were added, followed by stirring at 70° C. for 16 hours. Upon completion of the reaction, the reaction solution was concentrated under reduced pressure, diluted with dichloromethane, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (0.032 g, 53%, yellow solid).

The compounds of Examples 154 to 156 were prepared in a similar manner to the method described in Example 153.

The compound of Example 147 was prepared in a similar manner to the method described in Example 147.

The compounds of Examples 158 and 159 were prepared in a similar manner to the method described in Example 31.

The compounds of Examples 160 and 161 were prepared in a similar manner to the method described in Example 148.

The compounds of Examples 162 and 163 were prepared in a similar manner to the method described in Example 31.

The compounds of Examples 164 and 165 were prepared in a similar manner to the method described in Example 153.

The compound of Example 148 was prepared in a similar manner to the method described in Example 148.

<Example 167> Preparation of N-(3-(5-chloro-1H-indazole-3-yl)propyl)-4-(3-(4-methylpiperazine-1-yl)propoxy)benzenesulfonamide

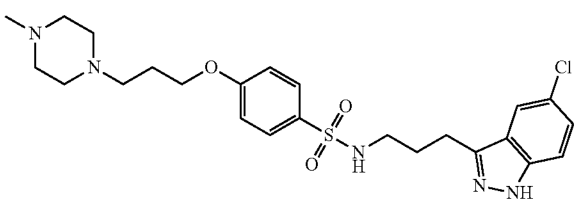 [SMILES: CN1CCN(CCCOc2ccc(S(=O)(=O)NCCCc3n[nH]c4ccc(Cl)cc34)cc2)CC1]

Step 1: Preparation of (cyanomethyl)triphenylphosphonium

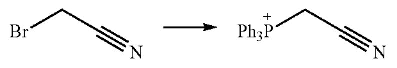

2-Bromoacetonitrile (1.328 mL, 19.06 mmol) was dissolved in dichloromethane (80 mL), to which triphenylphosphine (5 g, 19.06 mmol) was added at room temperature, followed by stirring for 6 hours. Upon completion of the reaction, the mixture was washed with diethyl ether without further purification to give a target compound (7 g, 96%, white solid).

Step 2: Preparation of (E)-3-(5-chloro-1H-indazole-3-yl)acrylonitrile

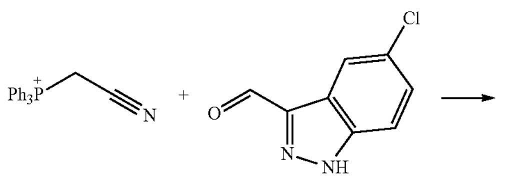

-continued

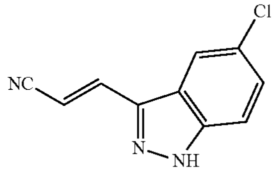

(Cyanomethyl)triphenylphosphonium (3.17 g, 8.31 mmol) prepared in step 1 above was dissolved in anhydrous tetrahydrofuran (10 mL), to which sodium tert-butoxide (0.8 g, 8.31 mmol) was added at −78° C., followed by stirring for 30 minutes. 5-Chloro-1H-indazole-3-carbaldehyde (1.0 g, 5.44 mmol) was dissolved in anhydrous tetrahydrofuran at −78° C., which was added thereto. The temperature of the reaction mixture was slowly raised to room temperature, followed by stirring for 1 hour. Upon completion of the reaction, the mixture was washed with a supersaturated ammonium chloride aqueous solution and extracted with ethyl acetate. The extracted organic layer was dried over anhydrous sodium sulfate, filtered, and then separated and purified by MPLC to give a target compound (0.3 g, 27%, pale yellow solid).

Step 3: Preparation of 3-(5-chloro-1H-indazole-3-yl)propane-1-amine

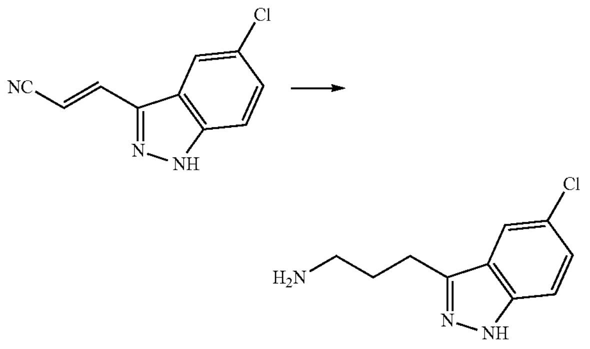

(E)-3-(5-chloro-1H-indazole-3-yl)acrylonitrile (300 mg, 1.473 mmol) prepared in step 2 above was dissolved in ether (5 mL), to which LAH (168 mg, 4.42 mmol) was added at −78° C. The temperature of the reaction mixture was slowly raised to room temperature, followed by stirring for 2 hours. The reaction was terminated by additional addition of LAH (112 mg, 2.95 mmol). Upon completion of the reaction, the mixture was filtered with celite. The filtrate was concentrated under reduced pressure, and then separated and purified by MPLC to give a target compound (200 mg, 65%, yellow oil).

Step 4: Preparation of 4-(-bromopropoxy)-N-(3-(5-chloro-1H-indazole-3-yl)propyl)benzenesulfonamide

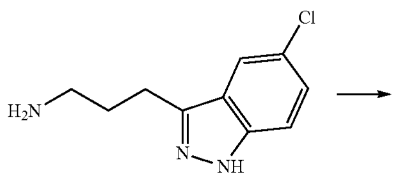

-continued

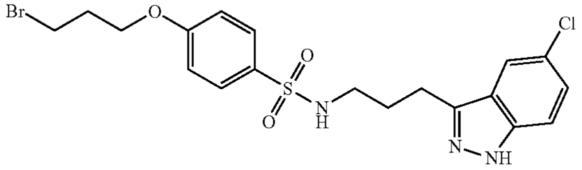

A target compound (75 mg, 18%, white solid) was prepared in a similar manner to the method described in step 2 of Example 31.

Step 5: Preparation of N-(3-(5-chloro-1H-indazole-3-yl)propyl)-4-(3-(4-methylpiperazine-1-yl)propoxy) benzenesulfonamide

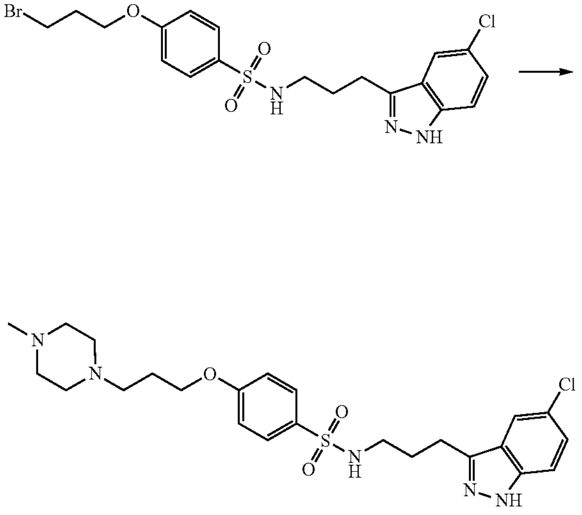

A target compound (13.3 mg, 85%, pale yellow solid) was prepared in a similar manner to the method described in Example 148.

The compounds of Examples 168 to 170 were prepared in a similar manner to the method described in Example 167.

<Example 171> Preparation of (R)—N-(3-(5-chloro-1H-indole-3-yl)propyl)-4-(2-hydroxy-3-(4-methylpiperazine-1-yl)propoxy)benzenesulfonamide

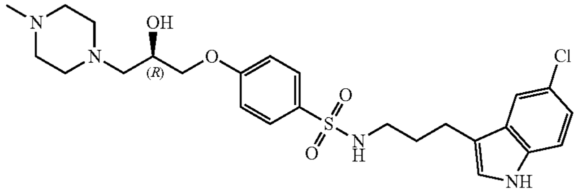

Step 1: Preparation of (R)—N-(3-(5-chloro-1H-indole-3-yl)propyl)-4-(oxirane-2-ylmethoxy)benzenesulfonamide

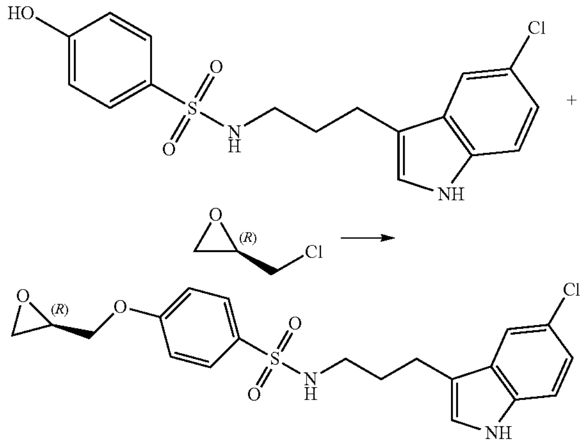

The compound (0.41 g, 1.026 mmol) prepared in step 1 of Example 92 was dissolved in dimethylformamide (3.4 ml), to which (R)-2-(chloromethyl)oxirane (0.095 g, 1.026 mmol) and potassium carbonate (0.21 g, 1.539 mmol) were added, followed by stirring at 60° C. for 16 hours. Upon completion of the reaction, the reaction mixture was diluted with dichloromethane and washed with water and brine. The residue of the organic layer was dried over anhydrous sodium sulfate, filtered and concentrated, and then purified by MPLC to give a target compound (0.16 g, 37%).

Step 2: Preparation of (R)—N-(3-(5-chloro-1H-indole-3-yl)propyl)-4-(2-hydroxy-3-(4-methylpiperazine-1-yl)propoxy)benzenesulfonamide

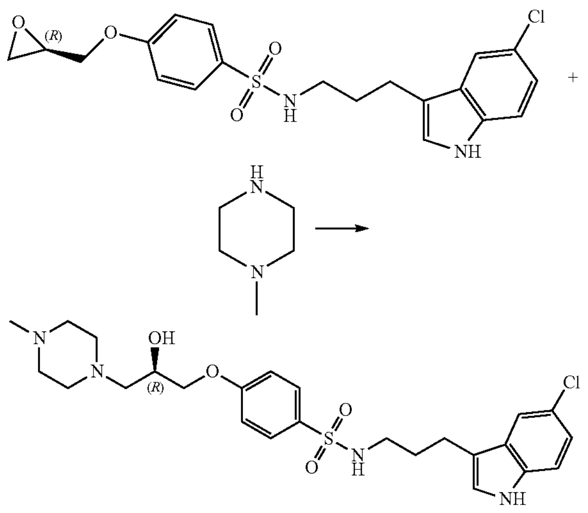

The compound (0.083 g, 0.198 mmol) prepared in step 1 above was dissolved in acetone (1 ml), to which 1-methylpiperazine (0.19 g, 1.981 mmol) and potassium carbonate (0.274 g, 1.981 mmol) were added, followed by stirring at 80° C. for 16 hours. Upon completion of the reaction, the reaction mixture was diluted with dichloromethane and washed with water and brine. The residue of the organic layer was dried over anhydrous sodium sulfate, filtered and concentrated, purified by Prep HPLC, and neutralized by adding a sodium hydrogen carbonate aqueous solution to give a target compound (0.030 g, 30%, yellow solid).

The compounds of Examples 172 to 174 were prepared in a similar manner to the method described in Example 171.

The compounds of Examples 175 and 176 were prepared in a similar manner to the method described in Example 148.

<Example 177> Preparation of N-((6-chloro-2,3,4,9-tetrahydro-1H-carbazole-3-yl)methyl) 4-(3-(4-methylpiperazine-1-yl)propoxy)benzenesulfonamide

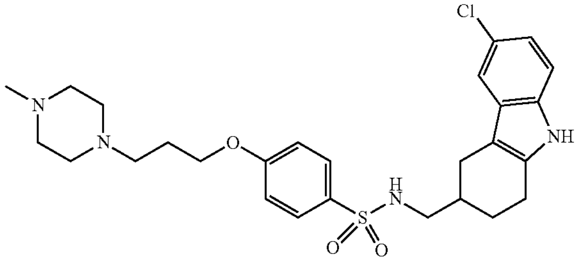 [SMILES: CN1CCN(CCCOc2ccc(S(=O)(=O)NCC3CCc4[nH]c5ccc(Cl)cc5c4C3)cc2)CC1]

Step 1: Preparation of 4-(3-bromopropoxy)-N-(3-(5-chloro-1H-indazole-3-yl)propyl)benzenesulfonamide

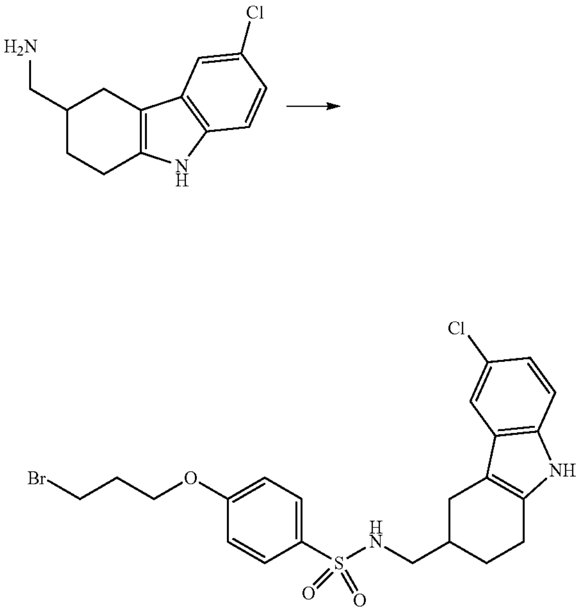

A target compound was obtained in a similar manner to the method described in step 2 of Example 31 using (6-chloro-2,3,4,9-tetrahydro-1H-carbazole-3-yl)methanamine prepared in a similar manner to the method described in the reference literature [WO2006/89053].

Step 2: Preparation of N-((6-chloro-2,3,4,9-tetrahydro-1H-carbazole-3-yl)methyl) 4-(3-(4-methylpiperazine-1-yl)propoxy)benzenesulfonamide

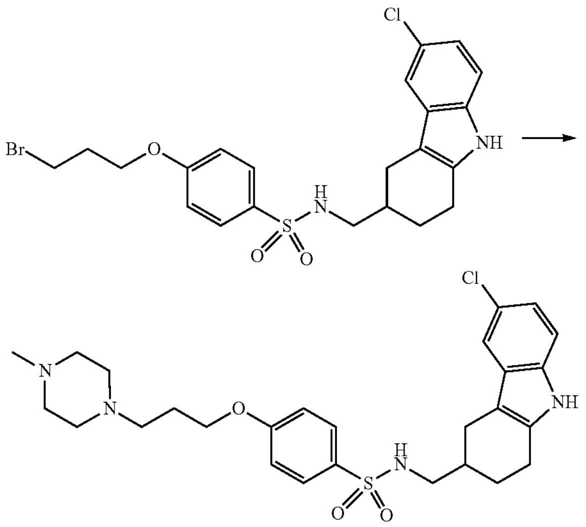

A target compound (6.3 mg, 20%, pale yellow solid) was obtained in a similar manner to the method described in Example 148.

The compound of Example 178 was prepared in a similar manner to the method described in Example 177.

The compounds of Examples 179 and 180 were prepared in a similar manner to the method described in Example 85.

<Example 181> Preparation of N-(2-(2-(5-chloro-1H-indole-3-yl)propane-2-yl)phenyl)-4-(3-(4-methylpiperazine-1-yl) propoxy)benzenesulfonamide

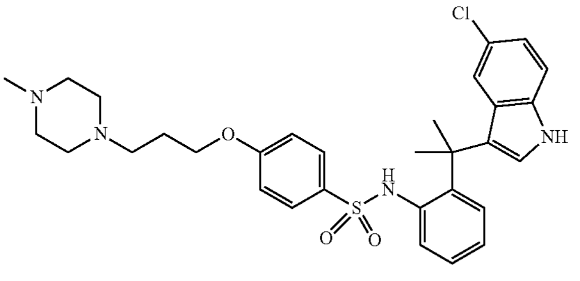 [SMILES: CN1CCN(CCCOc2ccc(S(=O)(=O)Nc3ccccc3C(C)(C)c3c[nH]c4ccc(Cl)cc34)cc2)CC1]

Step 1: Preparation of N-(2-(2-(5-chloro-1H-indole-3-yl)propane-2-yl)phenyl)-4-methylbenzenesulfonamide

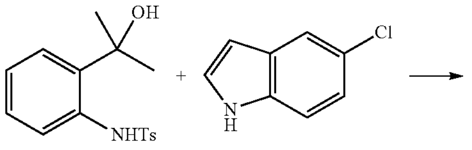

-continued

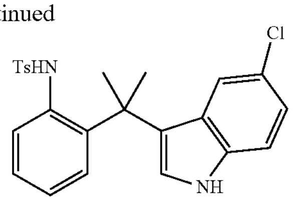

5-Chloro-1H-indole (0.400 g, 5.28 mmol) and N-(2-(2-hydroxypropane-2-yl)phenyl)-4-methylbenzenesulfonamide (0.967 g, 3.17 mmol) were dissolved in 1,2-dichloroethane (40 ml), to which $PdCl_2 \cdot (CH_3CN)_2$ (0.0340 g, 0.132 mmol) was added, followed by stirring for 3 hours in nitrogen atmosphere. Upon completion of the reaction, the reaction mixture was cooled down to room temperature, the solvent was removed under reduced pressure, and separated and purified by MPLC to give a target compound (1.02 g, 88%, white solid).

Step 2: Preparation of 2-(2-(5-chloro-1H-indole-3-yl)propane-2-yl)aniline

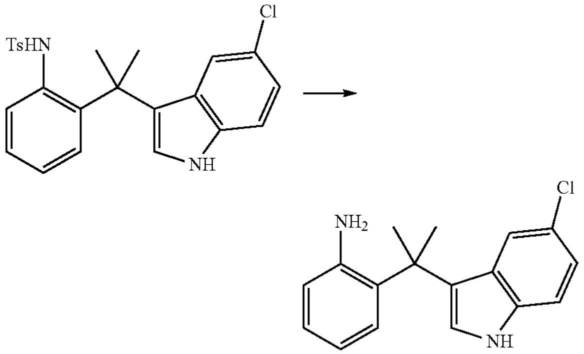

N-(2-(2-(5-chloro-1H-indole-3-yl)propane-2-yl)phenyl)-4-methylbenzenesulfonamide (0.540 g, 1.23 mmol) prepared in step 1 above was dissolved in sulfuric acid (6 mL), followed by stirring at room temperature for 40 minutes. After the reaction was terminated by adding ice to the reaction product, 2 N sodium hydroxide aqueous solution was added dropwise to neutralize. The reaction mixture was extracted with ethyl acetate, dried over anhydrous magnesium sulfate, and filtered. The filtrate was concentrated under reduced pressure, and then separated and purified by MPLC to give a target compound (0.175 g, 50%, pale yellow solid).

Step 3: Preparation of 4-(3-bromopropoxy)-N-(2-(2-(5-chloro-1H-indole-3-yl)propane-2-yl)phenyl)benzenesulfonamide

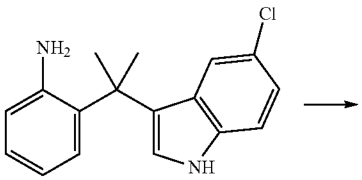

-continued

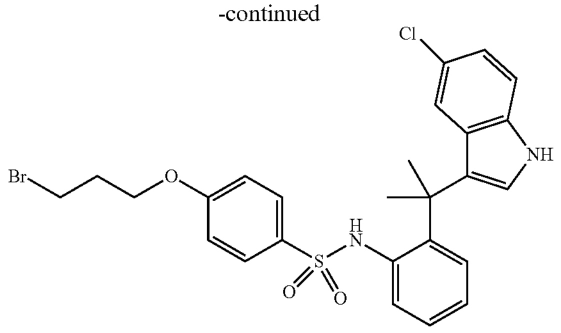

A target compound was obtained in a similar manner to the method described in step 2 of Example 31.

Step 4: Preparation of N-(2-(2-(5-chloro-1H-indole-3-yl)propane-2-yl)phenyl)-4-(3-(4-methylpiperazine-1-yl)propoxy)benzenesulfonamide

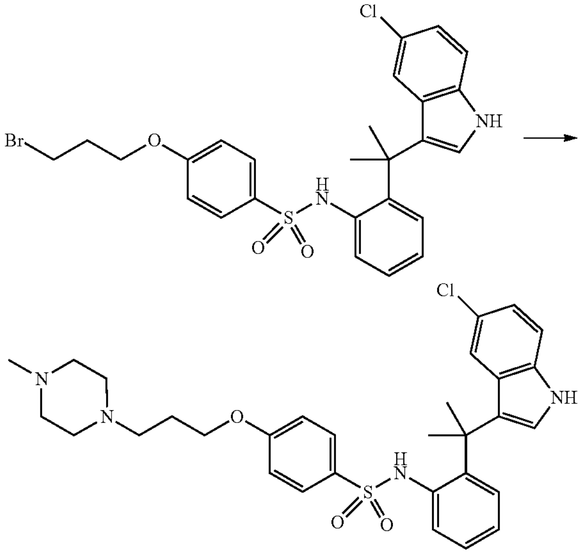

A target compound (17.2 mg, 33%, pale yellow solid) was obtained in a similar manner to the method described in Example 148.

The compound of Example 182 was prepared in a similar manner to the method described in Example 181.

The compounds of Examples 183 and 184 were prepared in a similar manner to the method described in Example 153.

<Example 185> Preparation of N-(3-(5-chloro-1H-indole-3-yl)propyl)-4-(3-(pyridine-4-yloxy)propyl)benzenesulfonamide

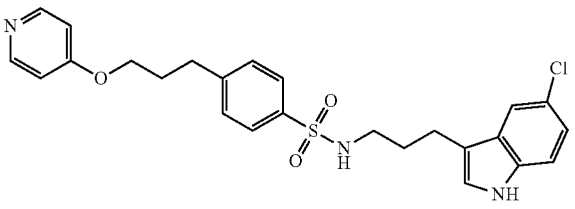

-continued

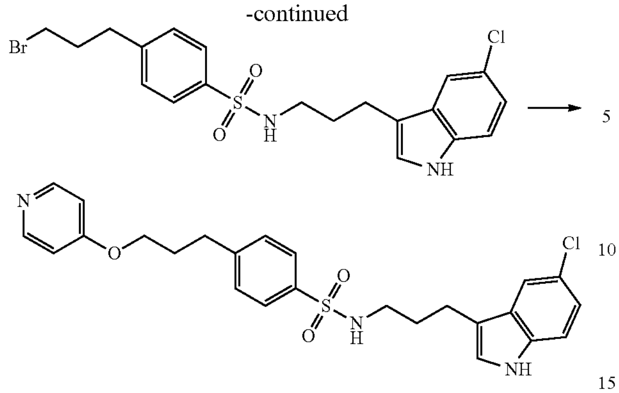

A target compound (18.5 mg, 60%, white solid) was obtained in a similar manner to the method described in Example 148 using 4-(3-bromopropyl)-N-(3-(5-chloro-1H-indole-3-yl)propyl)benzenesulfonamide prepared in a similar manner to the method described in steps 1 and 2 of Example 90.

The compound of Example 186 was prepared in a similar manner to the method described in Example 185.

The compounds of Examples 187 to 190 were prepared in a similar manner to the method described in Example 177.

Compound names, structural formulas and analysis results of $^{1}H$ NMR and MS of the compounds of Examples 1 to 190 are summarized in Table 1 below.

TABLE 1

| Example | Structure | Name | $^{1}H$ NMR, MS |
|---|---|---|---|
| 1 | 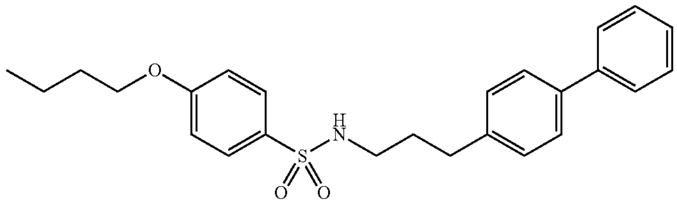 [SMILES: CCCCOc1ccc(S(=O)(=O)NCCCc2ccc(-c3ccccc3)cc2)cc1] | N-(3-([1,1'-biphenyl]-4-yl)propyl)-4-butoxybenzenesulfonamide | $^{1}H$ NMR (400 MHz, $CDCl_3$) δ 7.78-7.74 (m, 2H), 7.59-7.54 (m, 2H), 7.50-7.46 (m, 2H), 7.46-7.39 (m, 2H), 7.36-7.30 (m, 1H), 7.16 (d, J = 8.2 Hz, 2H), 6.98-6.92 (m, 2H), 4.24 (t, J = 6.3 Hz, 1H), 4.00 (t, J = 6.5 Hz, 2H), 2.99 (dd, J = 13.4, 6.8 Hz, 2H), 2.69-2.62 (m, 2H), 1.80 (ddt, J = 14.4, 12.7, 6.8 Hz, 4H), 1.47 (dd, J = 14.8, 7.5 Hz, 2H), 0.98 (t, J = 7.4 Hz, 3H); 424 $[M + H]^+$ |
| 2 | 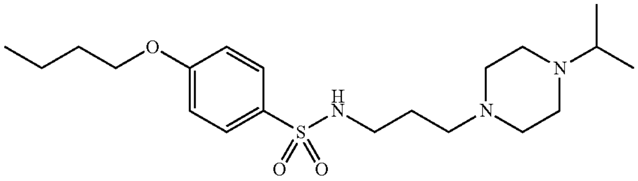 [SMILES: CCCCOc1ccc(S(=O)(=O)NCCCN2CCN(C(C)C)CC2)cc1] | 4-butoxy-N-(3-(4-isopropylpiperazin-1-yl)propyl)benzenesulfonamide | $^{1}H$ NMR (400 MHz, $CDCl_3$) δ 7.77 (d, J = 8.9 Hz, 2H), 6.95 (d, J = 8.9 Hz, 2H), 4.02 (t, J = 6.5 Hz, 2H), 3.04 (t, J = 5.6 Hz, 2H), 2.65-2.40 (m, 9H), 2.39 (t, J = 5.8 Hz, 2H), 1.81-1.77 (m, 2H), 1.63-1.61 (m, 2H), 1.51-1.48 (m, 2H), 1.06 (d, J = 6.5 Hz, 6H), 0.99 (t, J = 7.4 Hz, 3H); 398.3 $[M + H]^+$ |
| 3 | 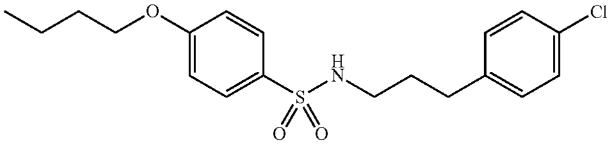 [SMILES: CCCCOc1ccc(S(=O)(=O)NCCCc2ccc(Cl)cc2)cc1] | 4-butoxy-N-(3-(4-chlorophenyl)propyl)benzenesulfonamide | $^{1}H$ NMR (400 MHz, $CDCl_3$) δ 7.75 (d, J = 8.9 Hz, 2H), 7.21 (d, J = 8.4 Hz, 2H), 7.01 (d, J = 8.4 Hz, 2H), 6.95 (d, J = 8.9 Hz, 2H), 4.02 (t, J = 6.5 Hz, 2H), 2.93 (t, J = 6.8 Hz, 2H), 2.58 (t, J = 7.4 Hz, 2H), 1.82-1.74 (m, 4H), 1.53-1.48 (m, 2H), 0.99 (t, J = 7.4 Hz, 3H); 382.2 $[M + H]^+$ |

TABLE 1-continued

| Example | Structure | Name | $^1H$ NMR, MS |
|---|---|---|---|
| 4 | 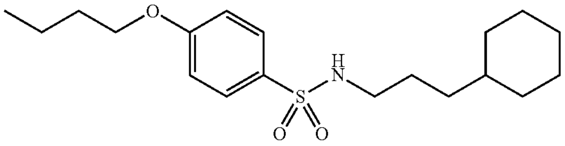 [SMILES: CCCCOc1ccc(S(=O)(=O)NCCCC2CCCCC2)cc1] | 4-butoxy-N-(3-cyclohexylpropyl) benzenesulfonamide | $^1H$ NMR (400 MHz, $CDCl_3$) δ 7.77 (d, J = 9.0 Hz, 2H), 6.96 (d, J = 9.0 Hz, 2H), 4.18 (t, J = 6.2 Hz, 1H, NH), 4.02 (t, J = 6.5 Hz, 2H), 2.93-2.88 (m, 2H), 1.79-1.77 (m, 2H), 1.64-1.46 (m, 11H), 1.13-1.10 (m, 6H), 0.99 (t, J = 7.4 Hz, 3H); 354.3 $[M + H]^+$ |
| 5 | 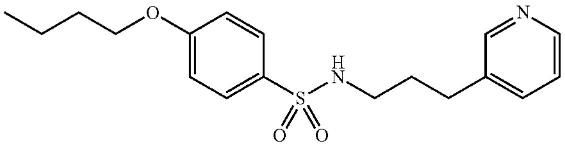 [SMILES: CCCCOc1ccc(S(=O)(=O)NCCCc2cccnc2)cc1] | 4-butoxy-N-(3-(pyridin-3-yl)propyl) benzensulfonamide | $^1H$ NMR (400 MHz, $CDCl_3$) δ 8.44 (d, J = 3.7 Hz, 1H), 8.38 (s, 1H), 7.76 (d, J = 8.8 Hz, 2H), 7.44 (d, J = 7.8 Hz, 1H), 7.20 (dd, J = 7.6, 4.8 Hz, 1H), 6.96 (d, J = 8.8 Hz, 2H), 4.41 (t, J = 6.2 Hz, 1H, NH), 4.02 (t, J = 6.5 Hz, 2H), 2.96 (dd, J = 13.4, 6.8 Hz, 2H), 2.63 (t, J = 7.5 Hz, 2H), 1.82-1.77 (m, 4H), 1.53-1.47 (m, 2H), 0.98 (t, J = 7.4 Hz, 3H); 349 $[M + H]^+$ |
| 6 | 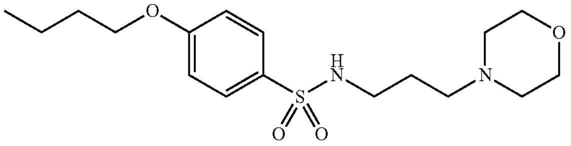 [SMILES: CCCCOc1ccc(S(=O)(=O)NCCCN2CCOCC2)cc1] | 4-butoxy-N-(3-morpholinopropyl) benzenesulfonamide | $^1H$ NMR (400 MHz, $CDCl_3$) δ 7.76 (d, J = 8.9 Hz, 2H), 6.95 (d, J = 8.9 Hz, 2H), 4.01 (t, J = 6.5 Hz, 2H), 3.71 (t, J = 4.6 Hz, 4H), 3.06 (t, J = 5.8 Hz, 2H), 2.41 (t, J = 5.7 Hz, 4H), 1.81-1.77 (m, 2H), 1.66-1.61 (m, 2H), 1.56-1.47 (m, 4H), 0.99 (t, J = 7.4 Hz, 3H); 357 $[M + H]^+$ |
| 7 | 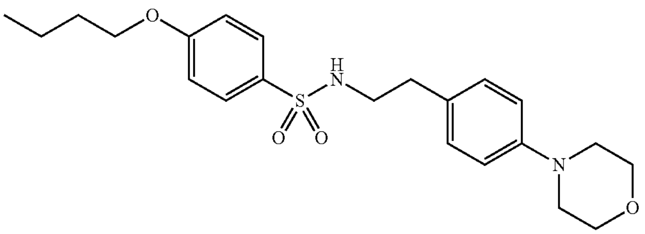 [SMILES: CCCCOc1ccc(S(=O)(=O)NCCc2ccc(N3CCOCC3)cc2)cc1] | 4-butoxy-N-(4-morpholinophenethyl) benzenesulfonamide | $^1H$ NMR (400 MHz, $CDCl_3$) δ 7.74-7.69 (m, 2H), 7.02-6.96 (m, 2H), 6.96-6.91 (m, 2H), 6.84-6.80 (m, 2H), 4.24-4.14 (m, 1H), 4.01 (t, J = 6.5 Hz, 2H), 3.92-3.80 (m, 4H), 3.16-(dd, J = 13.4, 6.9 Hz, 2H), 3.14-3.09 (m, 4H), 2.68 (t, J = 6.8 Hz, 2H), 1.84-1.74 m, 2H), 1.48 (dd, J = 15.0, 7.5 Hz, 2H), 0.99 (t, J = 7.4 Hz, 3H); 419.16 $[M + H]^+$ |

TABLE 1-continued

| Example | Structure | Name | $^1$H NMR, MS |
|---|---|---|---|
| 8 | 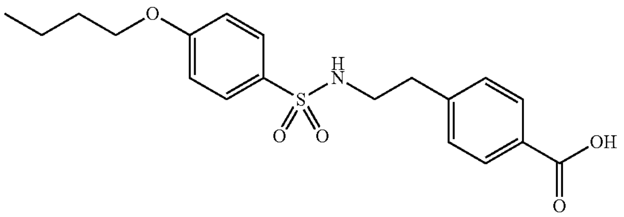 [SMILES: CCCCOc1ccc(S(=O)(=O)NCCc2ccc(C(=O)O)cc2)cc1] | 4-(2-(4-butoxyphenylsulfonamido)ethyl)benzoic acid | $^1$H NMR (400 MHz, $CDCl_3$) δ 7.95 (d, J = 7.9 Hz, 2H), 7.73 (d, J = 8.6 Hz, 2H), 7.20 (d, J = 7.5 Hz, 2H), 6.94 (d, J = 8.8 Hz, 2H), 4.61 (s, 1H), 4.01 (t, J = 6.5 Hz, 2H), 3.25 (dd, J = 12.4, 5.9 Hz, 2H), 2.86 (t, J = 6.4 Hz, 2H), 1.78 (dd, J = 14.5, 6.7 Hz, 2H), 1.50 (dt, J = 22.4, 7.6 Hz, 2H), 0.98 (t, J = 7.3 Hz, 3H); 378 $[M + H]^+$ |
| 9 | 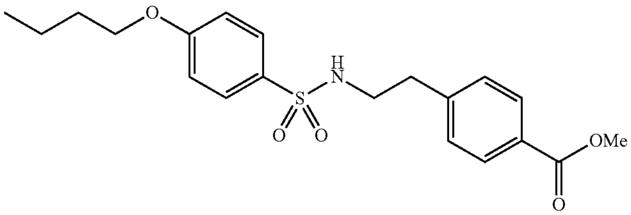 [SMILES: CCCCOc1ccc(S(=O)(=O)NCCc2ccc(C(=O)OC)cc2)cc1] | methyl 4-(2-(4-butoxyphenylsulfonamido)ethyl)benzoate | $^1$H NMR (400 MHz, $CDCl_3$) δ 7.94 (d, J = 8.2 Hz, 2H), 7.77-7.66 (m, 2H), 7.16 (d, J = 8.2 Hz, 2H), 6.97-6.88 (m, 2H), 4.22 (t, J = 6.3 Hz, 1H), 4.01 (t, J = 6.5 Hz, 2H), 3.91 (s, 3H), 3.24 (dd, J = 13.4, 6.8 Hz, 2H), 2.83 (t, J = 6.9 Hz, 2H), 1.84-1.75 (m, 2H), 1.48 (dd, J = 14.8, 7.4 Hz, 2H), 0.99 (t, J = 7.4 Hz, 3H); 392 $[M + H]^+$ |
| 10 | 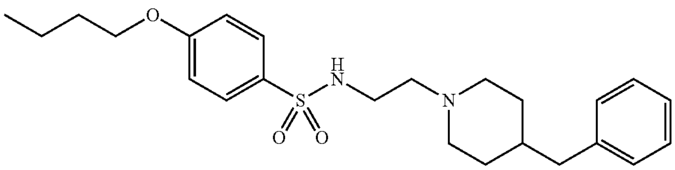 [SMILES: CCCCOc1ccc(S(=O)(=O)NCCN2CCC(Cc3ccccc3)CC2)cc1] | N-(2-(4-benzylpiperidin-1-yl)ethyl)-4-butoxybenzenesulfonamide | $^1$H NMR (400 MHz, $CDCl_3$) δ 7.77 (d, J = 8.9 Hz, 2H), 7.28 (d, J = 7.1 Hz, 2H), 7.19 (t, J = 7.3 Hz, 1H), 7.12 (d, J = 7.0 Hz, 2H), 6.95 (d, J = 8.9 Hz, 2H), 5.20 (s, 1H), 4.00 (t, J = 6.5 Hz, 2H), 2.94 (d, J = 5.6 Hz, 2H), 2.53 (dd, J = 16.1, 9.2 Hz, 4H), 2.33 (t, J = 5.7 Hz, 2H), 1.88-1.74 (m, 4H), 1.57-1.44 (m, 5H), 1.21-1.08 (m, 2H), 0.98 (t, J = 7.4 Hz, 3H); 431 $[M + H]^+$ |
| 11 | 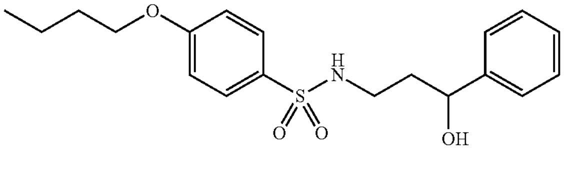 [SMILES: CCCCOc1ccc(S(=O)(=O)NCCC(O)c2ccccc2)cc1] | 4-butoxy-N-(3-hydroxy-3-phenylpropyl)benzenesulfonamide | $^1$H NMR (400 MHz, $CDCl_3$) δ 7.83-7.75 (m, 2H), 7.32 (dt, J = 12.9, 4.4 Hz, 2H), 7.28-7.23 (m, 3H), 7.00-6.91 (m, 2H), 5.05-4.99 (m, 2H), 4.81 (td, J = 6.3, 3.2 Hz, 2H), 4.02 (t, J = 6.5 Hz, 2H), 3.27-2.98 (m, 2H), 1.86 (dt, J = 9.5, 4.7 Hz, 2H), 1.83-1.73 (m, 2H), 1.54-1.46 (m, 3H), 0.99 (t, J = 7.4 Hz, 3H); 364 $[M + H]^+$ |

TABLE 1-continued

| Example | Structure | Name | $^1$H NMR, MS |
|---|---|---|---|
| 12 | 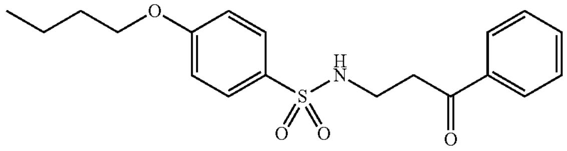 [SMILES: CCCCOc1ccc(S(=O)(=O)NCCC(=O)c2ccccc2)cc1] | 4-butoxy-N-(3-oxo-3-phenylpropyl)benzenesulfonamide | $^1$H NMR (400 MHz, $CDCl_3$) δ 7.88 (d, J = 7.2 Hz, 2H), 7.80 (d, J = 8.9 Hz, 2H), 7.59 (t, J = 7.4 Hz, 1H), 7.46 (t, J = 7.7 Hz, 2H), 6.95 (d, J = 8.9 Hz, 2H), 5.15 (t, J = 6.8 Hz, 1H), 4.00 (t, J = 6.5 Hz, 2H), 3.34 (dd, J = 11.9, 5.8 Hz, 2H), 3.25-3.16 (m, 2H), 1.85-1.72 (m, 2H), 1.53-1.45 (m, 2H), 0.99 (t, J = 7.4 Hz, 3H; 362 $[M + H]^+$ |
| 13 | 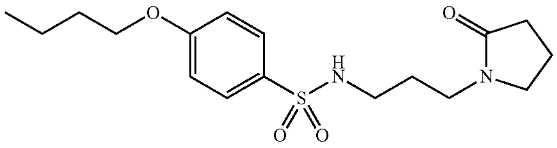 [SMILES: CCCCOc1ccc(S(=O)(=O)NCCCN2CCCC2=O)cc1] | 4-butoxy-N-(3-(2-oxopyrrolidin-1-yl)propyl)benzenesulfonamide | $^1$H NMR (400 MHz, $CDCl_3$) δ 7.81-7.72 (m, 2H), 6.97-6.89 (m, 2H), 5.75 (t, J = 6.8 Hz, 1H), 4.01 (t, J = 6.5 Hz, 2H), 3.33 (dd, J = 9.1, 5.1 Hz, 4H), 2.86 (dd, J = 12.4, 6.6 Hz, 2H), 2.34 (t, J = 8.1 Hz, 2H), 2.05-1.95 (m, 2H), 1.83-1.75 (m, 2H), 1.69 (dt, J = 12.2, 6.2 Hz, 2H), 1.49 (dt, J = 14.7, 7.5 Hz, 2H), 0.98 (t, J = 7.4 Hz, 3H); 355 $[M + H]^+$ |
| 14 | 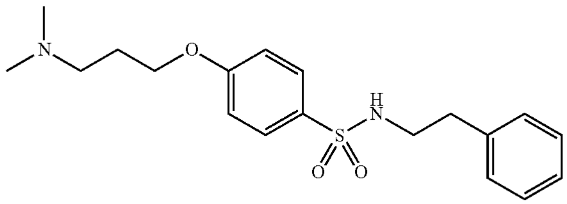 [SMILES: CN(C)CCCOc1ccc(S(=O)(=O)NCCc2ccccc2)cc1] | 4-(3-(dimethylamino)propoxy)-N-phenethylbenzenesulfonamide | $^1$H NMR (400 MHz, $CDCl_3$) δ 7.76-7.67 (m, 2H), 7.31-7.19 (m, 3H), 7.10-7.01 (m, 2H), 6.99-6.90 (m, 2H), 4.27 (t, J = 6.3 Hz, 1H), 4.08 (t, J = 6.4 Hz, 2H), 3.21 (q, J = 6.8 Hz, 2H), 2.76 (t, J = 6.9 Hz, 2H), 2.48 (t, J = 7.1 Hz, 2H), 2.28 (s, 6H), 2.05-1.92 (m, 2H); 363 $[M + H]^+$ |
| 15 | 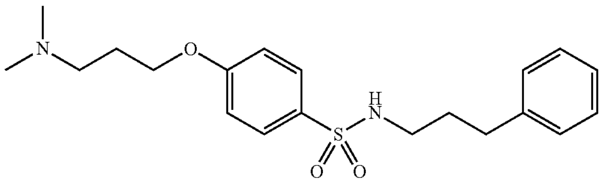 [SMILES: CN(C)CCCOc1ccc(S(=O)(=O)NCCCc2ccccc2)cc1] | 4-(3-(dimethylamino)propoxy)-N-(3-phenylpropyl)benzenesulfonamide | $^1$H NMR (400 MHz, $CDCl_3$) δ 7.78-7.73 (m, 2H), 7.29-7.21 (m, 2H), 7.21-7.15 (m, 1H), 7.11-7.05 (m, 2H), 6.99-6.93 (m, 2H), 4.31 (t, J = 6.2 Hz, 1H), 4.08 (t, J = 6.4 Hz, 2H), 2.96 (dd, J = 13.4, 6.8 Hz, 2H), 2.65-2.57 (m, 2H), 2.49 (t, J = 7.1 Hz, 2H), 2.28 (s, 6H), 2.04-1.95 (m, 2H), 1.79 (dt, J = 14.2, 7.0 Hz, 2H); 377 $[M + H]^+$ |

TABLE 1-continued

| Example | Structure | Name | $^1H$ NMR, MS |
| --- | --- | --- | --- |
| 16 | 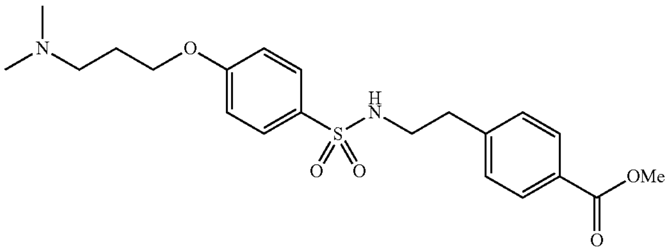 [SMILES: COC(=O)c1ccc(CCNS(=O)(=O)c2ccc(OCCCN(C)C)cc2)cc1] | methyl 4-(2-(4-(3-(dimethylamino)propoxy)phenylsulfonamido)ethyl) benzoate | $^1H$ NMR (400 MHz, $CDCl_3$) δ 7.96-7.92 (m, 2H), 7.75-7.67 (m, 2H), 7.16 (d, J = 8.3 Hz, 2H), 6.99-6.89 (m, 2H), 4.27 (t, J = 6.2 Hz, 1H), 4.08 (t, J = 6.4 Hz, 2H), 3.91 (s, 3H), 3.23 (q, J = 6.8 Hz, 2H), 2.83 (t, J = 6.9 Hz, 2H), 2.48 (t, J = 7.1 Hz, 2H), 2.28 (s, 6H), 2.03-1.94 (m, 2H); 421 $[M + H]^+$ |
| 17 | 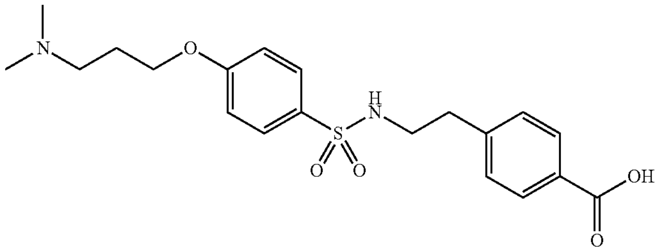 [SMILES: CN(C)CCCOc1ccc(S(=O)(=O)NCCc2ccc(C(=O)O)cc2)cc1] | 4-(2-(4-(3-(dimethylamino)propoxy)phenylsulfonamido) ethyl) benzoic acid | $^1H$ NMR (400 MHz, $CDCl_3$) δ 7.56 (d, J = 8.1 Hz, 2H), 7.21 (d, J = 8.9 Hz, 2H), 6.87 (d, J = 8.1 Hz, 2H), 6.58 (d, J = 8.9 Hz, 2H), 4.28 (dd, J = 12.3, 4.9 Hz, 1H), 4.11-4.00 (m, 2H), 3.56-3.49 (m, 2H), 3.06-2.97 (m, 2H), 2.68 (s, 2H), 2.66 (s, 6H), 2.13-2.07 (m, 2H); 407 $[M + H]^+$ |
| 18 | 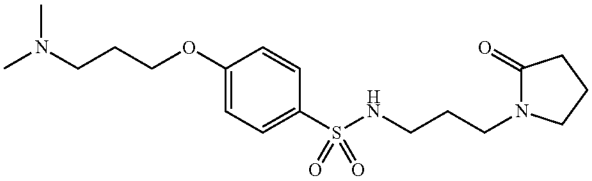 [SMILES: CN(C)CCCOc1ccc(S(=O)(=O)NCCCN2CCCC2=O)cc1] | 4-(3-(dimethylamino)propoxy)-N-(3-(2-oxopyrrolidin-1-yl)propyl)benzenesulfonamide | $^1H$ NMR (400 MHz, $CDCl_3$) δ 7.82-7.73 (m, 2 H), 6.98-6.93 (m, 2 H), 5.77 (t, J = 6.8 Hz, 1H), 4.07 (t, J = 6.4 Hz, 2H), 3.33 (dd, J = 9.4, 4.9 Hz, 4H), 2.85 (dd, J = 12.4, 6.6 Hz, 2H), 2.45 (t, J = 7.1 Hz, 2H), 2.35 (d, J = 7.9 Hz, 2H), 2.25 (s, 6H), 2.05-1.91 (m, 4H), 1.69 (dt, J = 12.3, 6.1 Hz, 2H); 384 $[M + H]^+$ |
| 19 | 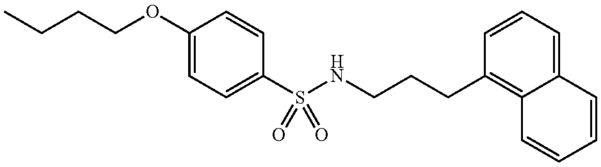 [SMILES: CCCCOc1ccc(S(=O)(=O)NCCCc2cccc3ccccc23)cc1] | 4-butoxy-N-(3-(naphthalen-1-yl) propyl) benzenesulfonamide | $^1H$ NMR (400 MHz, $CDCl_3$) δ 7.92-7.83 (m, 2H), 7.74 (d, J = 3.89 Hz, 2H), 7.71-(d, J = 8.5 Hz, 1H), 7.50-7.46 (m, 2H), 7.35 (dd, J = 8.1, 7.0 Hz, 1H), 7.22 (d, J = 6.8 Hz, 1H), 6.93 (d, J = 8.9 Hz, 2H), 4.27 (t, J = 6.1 Hz, 1H, NH), 4.01 (t, J = 6.5 Hz, 2H), 3.09-3.02 (m, 4H), 1.95-1.88 (m, 2H), 1.83-1.76 (m, 2H), 1.52-1.48 (m, 2H), 0.99 (t, J = 7.4 Hz, 3H); 398 $[M + H]^+$ |

TABLE 1-continued

| Example | Structure | Name | $^1$H NMR, MS |
|---|---|---|---|
| 20 | 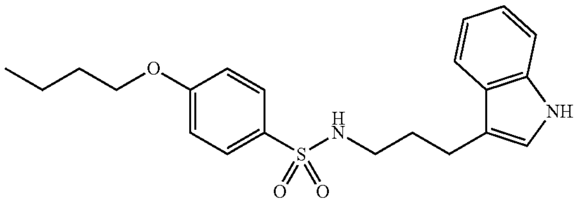 [SMILES: CCCCOc1ccc(S(=O)(=O)NCCCc2c[nH]c3ccccc23)cc1] | N-(3-(1H-indol-3-yl)propyl)-4-butoxybenzenesulfonamide | $^1$H NMR (400 MHz, $CDCl_3$) δ 7.92 (s, 1H), 7.75-7.69 (m, 2H), 7.49 (d, J = 7.9 Hz, 1H), 7.35 (d, J = 8.1 Hz, 1H), 7.22-7.15 (m, 1H), 7.12-7.05 (m, 1H), 6.95-6.90 (m, 3H), 4.25-4.18 (m, 1H), 4.00 (t, J = 6.5 Hz, 2H), 3.01 (dd, J = 13.3, 6.8 Hz, 2H), 2.77 (t, J = 7.2 Hz, 2H), 1.91-1.83 (m, 2H), 1.83-1.72 (m, 2H), 1.48 (dd, J = 14.8, 7.5 Hz, 2H), 0.99 (t, J = 7.4 Hz, 3H); 387.01 $[M + H]^+$ |
| 21 | 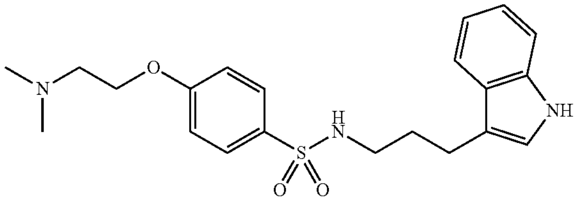 | N-(3-(1H-indol-3-yl)propyl)-4-(2-(dimethylamino)ethoxy)-benzenesulfonamide | $^1$H NMR (400 MHz, $CDCl_3$) δ 8.08 (s, 1H), 7.75-7.69 (m, 2H), 7.49 (d, J = 7.9 Hz, 1H), 7.35 (d, J = 8.1 Hz, 1H), 7.22-7.15 (m, 1H), 7.12-7.05 (m, 1H), 6.95-6.90 (m, 3H), 4.25-4.18 (m, 1H), 4.00 (t, J = 6.5 Hz, 2H), 3.01 (dd, J = 13.3, 6.8 Hz, 2H), 2.77 (t, J = 7.2 Hz, 2H), 1.91-1.83 (m, 2H), 1.83-1.72 (m, 2H), 1.48 (dd, J = 14.8, 7.5 Hz, 2H), 0.99 (t, J = 7.4 Hz, 3H); 387.01 $[M + H]^+$ |
| 22 | 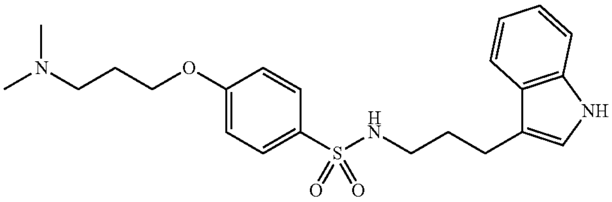 [SMILES: CN(C)CCCOc1ccc(S(=O)(=O)NCCCc2c[nH]c3ccccc23)cc1] | N-(3-(1H-indol-3-yl)propyl)-4-(3-(dimethylamino)propoxy)benzenesulfonamide | $^1$H NMR (400 MHz, $CDCl_3$) δ 8.37 (s, 1H), 7.74-7.69 (m, 2H), 7.49 (d, J = 7.6 Hz, 1H), 7.34 (d, J = 8.1 Hz, 1H), 7.21-7.16 (m, 1H), 7.11-7.06 (m, 1H), 6.95-6.90 (m, 2H), 6.80 (d, J = 2.3 Hz, 1H), 4.25-4.18 (m, 1H), 4.09 (t, J = 6.3 Hz, 2H), 2.99 (dd, J = 13.1, 6.7 Hz, 2H), 2.74 (t, J = 7.1 Hz, 2H), 2.48 (t, J = 7.0 Hz, 2H), 2.28 (s, 6H), 1.99 (dt, J = 13.4, 6.7 Hz, 2H), 1.85 (dt, J = 14.1, 7.0 Hz, 2H); 416 $[M + H]^+$ |
| 23 | 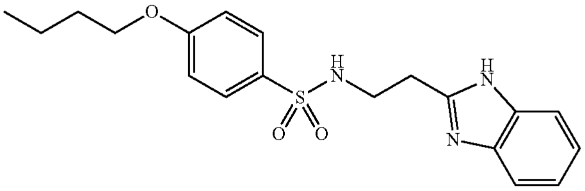 [SMILES: CCCCOc1ccc(S(=O)(=O)NCCc2nc3ccccc3[nH]2)cc1] | N-(2-(1H-benzo[[d]imidazol-2-yl)ethyl)-4-butoxybenzenesulfonamide | $^1$H NMR (400 MHz, MeOD) δ 7.74-7.68 (m, 2H), 7.48 (s, 2H), 7.24-7.18 (m, 2H), 6.97-6.90 (m, 2H), 4.03 (t, J = 6.4 Hz, 2H), 3.38-3.34 (m, 2H), 3.05 (d, J = 7.1 Hz, 2H), 1.78 (dd, J = 14.8, 6.7 Hz, 2H), 1.54 (dq, J = |

TABLE 1-continued

| Example | Structure | Name | $^1H$ NMR, MS |
|---|---|---|---|
| | | | 14.8, 7.4 Hz, 2H), 1.02 (t, J = 7.4 Hz, 3H); 374 $[M + H]^+$ |
| 24 | 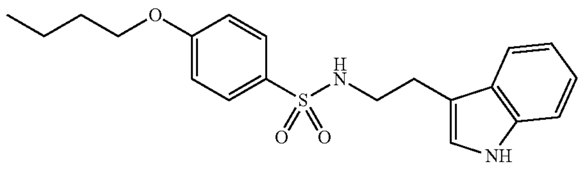 [SMILES: CCCCOc1ccc(S(=O)(=O)NCCc2c[nH]c3ccccc23)cc1] | N-(2-(1H-indol-3-yl)ethyl)-4-butoxybenzenesulfonamide | $^1H$ NMR (400 MHz, $CDCl_3$) δ 8.00 (s, 1H), 7.69-7.64 (m, 2H), 7.42 (d, J = 7.9 Hz, 1H), 7.36 (d, J = 8.2 Hz, 1H), 7.19 (t, J = 7.2 Hz, 1H), 7.07 (t, J = 7.5 Hz, 1H), 6.99 (d, J = 2.3 Hz, 1H), 6.90-6.84 (m, 2H), 4.28 (t, J = 6.1 Hz, 1H), 3.99 (t, J = 6.5 Hz, 2H), 3.28 (q, J = 6.5 Hz, 2H), 2.94 (t, J = 6.6 Hz, 2H), 1.84-1.73 (m, 2H), 1.48 (dd, J = 14.8, 7.4 Hz, 2H), 0.99 (t, J = 7.4 Hz, 3H); 373 $[M + H]^+$ |
| 25 | 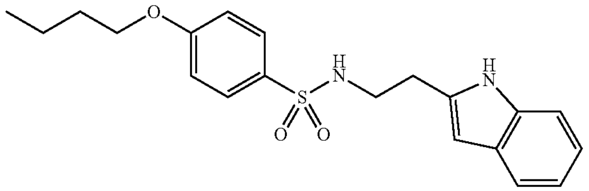 [SMILES: CCCCOc1ccc(S(=O)(=O)NCCc2cc3ccccc3[nH]2)cc1] | N-(2-(1H-indol-2-yl)ethyl)-4-butoxybenzenesulfonamide | $^1H$ NMR (400 MHz, $CDCl_3$) δ 8.00 (s, 1H), 7.75-7.67 (m, 2H), 7.51 (d, J = 7.7 Hz, 1H), 7.29 (d, J = 8.2 Hz, 1H), 7.14 (dd, J = 11.0, 4.1 Hz, 1H), 7.09 (dd, J = 10.9, 4.0 Hz, 1H), 6.96-6.88 (m, 2H), 6.21 (s, 1H), 4.43 (t, J = 6.3 Hz, 1H), 4.01 (t, J = 6.5 Hz, 2H), 3.28 (q, J = 6.4 Hz, 2H), 2.96 (t, J = 6.4 Hz, 2H), 1.84-1.75 (m, 2H), 1.57-1.44 (m, 2H), 0.99 (t, J = 7.4 Hz, 3H); 373 $[M + H]^+$ |
| 26 | 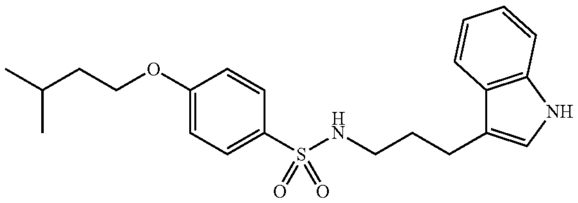 | N-(3-(1H-indol-3-yl)propyl)-4-(isopentyloxy)benzenesulfonamide | $^1H$ NMR (400 MHz, $CDCl_3$) δ 7.92 (s, 1H), 7.72 (d, J = 8.9 Hz, 2H), 7.49 (d, J = 7.6 Hz, 1H), 7.35 (d, J = 8.2 Hz, 1H), 7.19 (t, J = 7.1 Hz, 1H), 7.09 (t, J = 7.2 Hz, 1H), 6.95 (d, J = 2.1 Hz, 1H), 6.92 (d, J = 8.9 Hz, 2H), 4.22 (t, J = 6.2 Hz, 1H), 4.03 (t, J = 6.6 Hz, 2H), 3.01 (dd, J = 13.3, 6.7 Hz, 2H), 2.77 (t, J = 7.2 Hz, 2H), 1.91-1.79 (m, 3H), 1.70 (q, J = 6.7 Hz, 2H), 0.98 (s, 3H), 0.97 (s, 3H); 401 $[M + H]^+$ |

TABLE 1-continued

| Example | Structure | Name | $^1H$ NMR, MS |
|---|---|---|---|
| 27 | 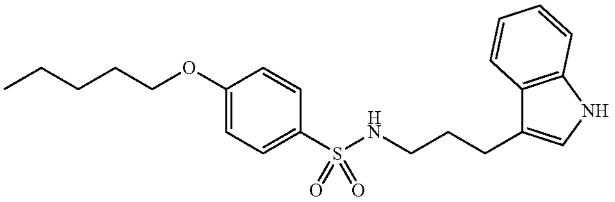 [SMILES: CCCCCOc1ccc(S(=O)(=O)NCCCc2c[nH]c3ccccc23)cc1] | N-(3-(1H-indol-3-yl)propyl)-4-(pentyloxy)benzenesulfonamide | $^1H$ NMR (400 MHz, $CDCl_3$) δ 7.92 (s, 1H), 7.72 (d, J = 8.9 Hz, 2H), 7.49 (d, J = 7.6 Hz, 1H), 7.35 (d, J = 8.1 Hz, 1H), 7.19 (t, J = 7.5 Hz, 1H), 7.09 (t, J = 7.4 Hz, 1H), 6.95 (s, 1H), 6.92 (d, J = 8.9 Hz, 2H), 4.21 (t, J = 6.2 Hz, 1H), 3.99 (t, J = 6.5 Hz, 2H), 3.01 (dd, J = 13.3, 6.8 Hz, 2H), 2.77 (t, J = 7.1 Hz, 2H), 1.88 (dd, J = 14.2, 7.1 Hz, 2H), 1.80 (dd, J = 14.6, 6.7 Hz, 2H), 1.49-1.34 (m, 4H), 0.94 (t, J = 7.1 Hz, 3H); 401 $[M + H]^+$ |
| 28 | 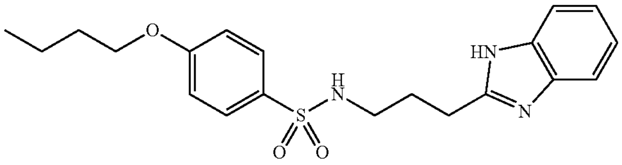 [SMILES: CCCCOc1ccc(S(=O)(=O)NCCCc2nc3ccccc3[nH]2)cc1] | N-(3-(1H-benzo[d]imidazol-2-yl)propyl)-4-butoxybenzenesulfonamide | $^1H$ NMR (400 MHz, MeOD) δ 7.75-7.66 (m, 2H), 7.50 (s, 2H), 7.27-7.17 (m, 2H), 7.00 (d, J = 8.9 Hz, 2H), 4.03 (t, J = 6.4 Hz, 2H), 2.92 (t, J = 7.0 Hz, 4H), 2.06-1.96 (m, 2H), 1.83-1.69 (m, 2H), 1.52 (dt, J = 14.7, 7.5 Hz, 2H), 1.01 (t, J = 7.4 Hz, 3H); 388 $[M + H]^+$ |
| 29 | 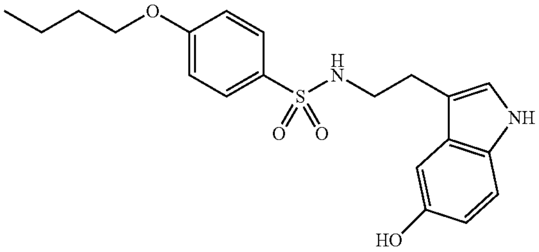 [SMILES: CCCCOc1ccc(S(=O)(=O)NCCc2c[nH]c3ccc(O)cc23)cc1] | 4-butoxy-N-(2-(5-hydroxy-1H-indol-3-yl)ethyl)benzenesulfonamide | $^1H$ NMR (400 MHz, $CDCl_3$) δ 7.88 (s, 1H), 7.70-7.63 (m, 2H), 7.23-7.18 (m, 1H), 6.97 (d, J = 2.4 Hz, 1H), 6.91-6.86 (m, 1H), 6.80-6.71 (m, 2H), 4.45 (s, 1H), 4.27 (t, J = 6.3 Hz, 1H), 4.00 (t, J = 6.5 Hz, 2H), 3.24 (dd, J = 12.9, 6.5 Hz, 2H), 2.87 (t, J = 6.6 Hz, 2H), 1.80 (dd, J = 14.4, 7.2 Hz, 2H), 1.48 (dd, J = 14.8, 7.5 Hz, 2H), 0.99 (t, J = 7.4 Hz, 3H); 389 $[M + H]^+$ |
| 30 | 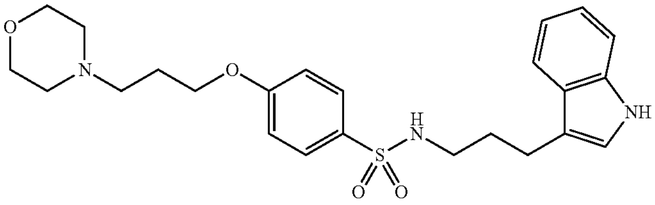 [SMILES: O=S(=O)(NCCCc1c[nH]c2ccccc12)c1ccc(OCCCN2CCOCC2)cc1] | N-(3-(1H-indol-3-yl)propyl)-4-(3-morpholinopropoxy)benzenesulfonamide | $^1H$ NMR (400 MHz, $CDCl_3$) δ 8.02 (s, 1H), 7.75-7.69 (m, 2H), 7.49 (d, J = 7.1 Hz, 1H), 7.35 (d, J = 8.1 Hz, 1H), 7.19 (t, J = 7.0 Hz, 1H), 7.12-7.06 (m, 1H), 6.96-6.88 (m, 3H), 4.23 (t, J = 6.3 Hz, 1H), 4.08 (t, J = 6.3 Hz, 2H), 3.79-3.66 (m, 4H), 3.01 (dd, J = 13.3, 6.8 Hz, 2H), 2.77 (t, J = 7.1 Hz, 2H), 2.58-2.50 (m, 2H), 2.48-2.46 (m, |

TABLE 1-continued

| Example | Structure | Name | $^1$H NMR, MS |
|---|---|---|---|
| | | | 4H), 2.00 (dd, J = 13.6, 6.6 Hz, 2H), 1.87 (dt, J = 14.2, 7.0 Hz, 2H); 458 $[M + H]^+$ |
| 31 | 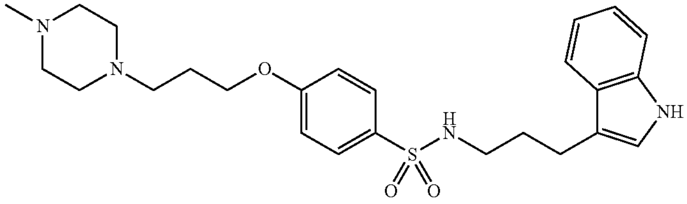 [SMILES: CN1CCN(CCCOc2ccc(S(=O)(=O)NCCCc3c[nH]c4ccccc34)cc2)CC1] | N-(3-(1H-indol-3-yl)propyl)-4-(3-(4-methylpiperazin-1-yl)propoxy)benzenesulfonamide | $^1$H NMR (400 MHz, $CDCl_3$) δ 8.10 (s, 1H), 7.71 (d, J = 8.9 Hz, 2H), 7.49 (d, J = 7.9 Hz, 1H), 7.35 (d, J = 8.1 Hz, 1H), 7.19 (t, J = 7.2 Hz, 1H), 7.09 (t, J = 7.4 Hz, 1H), 6.92 (d, J = 8.8 Hz, 3H), 4.24 (t, J = 6.3 Hz, 1H), 4.07 (t, J = 6.3 Hz, 2H), 3.01 (dd, J = 13.3, 6.7 Hz, 2H), 2.76 (t, J = 7.3 Hz, 2H), 2.69-2.36 (m, 10H), 2.31 (s, 3H), 2.05-1.93 (m, 2H), 1.90-1.80 (m, 2H); 471 $[M + H]^+$ |
| 32 | 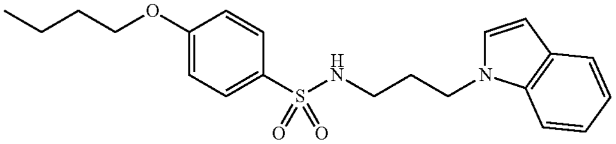 [SMILES: CCCCOc1ccc(S(=O)(=O)NCCCn2ccc3ccccc32)cc1] | N-(3-(1H-indol-1-yl)propyl)-4-butoxybenzenesulfonamide | $^1$H NMR (400 MHz, $CDCl_3$) δ 7.72-7.64 (m, 2H), 7.62 (d, J = 7.9 Hz, 1H), 7.28-7.26 (m, 1H), 7.23-7.15 (m, 1H), 7.13-7.07 (m, 1H), 7.05 (d, J = 3.1 Hz, 1H), 6.95-6.86 (m, 2H), 6.53-6.47 (m, 1H), 4.24-4.13 (m, 3H), 4.00 (t, J = 6.5 Hz, 2H), 2.88 (dd, J = 12.9, 6.4 Hz, 2H), 2.10-1.95 (m, 2H), 1.84-1.74 (m, 2H), 1.54-1.40 (m, 2H), 0.99 (t, J = 7.4 Hz, 3H); 387 $[M + H]^+$ |
| 33 | 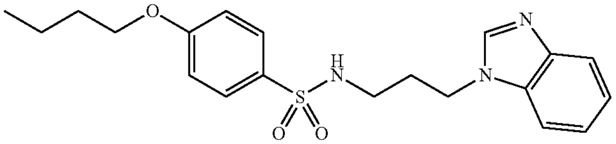 [SMILES: CCCCOc1ccc(S(=O)(=O)NCCCn2cnc3ccccc32)cc1] | N-(3-(1H-benzo[d]imidazol-1-yl)propyl)-4-butoxybenzenesulfonamide | $^1$H NMR (400 MHz, $CDCl_3$) δ 7.92 (s, 1H), 7.83-7.78 (m, 1H), 7.75-7.71 (m, 2H), 7.39-7.34 (m, 1H), 7.29 (dt, J = 5.3, 3.5 Hz, 2H), 6.96-6.90 (m, 2H), 4.44 (dd, J = 8.1, 7.2 Hz, 1H), 4.31 (t, J = 6.7 Hz, 2H), 4.00 (t, J = 6.5 Hz, 2H), 2.91 (dd, J = 12.8, 6.4 Hz, 2H), 2.13-2.04 (m, 2H), 1.79 (dt, J = 14.3, 6.4 Hz, 2H), 1.49 (dt, J = 14.7, 7.5 Hz, 2H), 0.98 (t, J = 7.4 Hz, 3H); 388 $[M + H]^+$ |

TABLE 1-continued

| Example | Structure | Name | $^1$H NMR, MS |
|---|---|---|---|
| 34 | 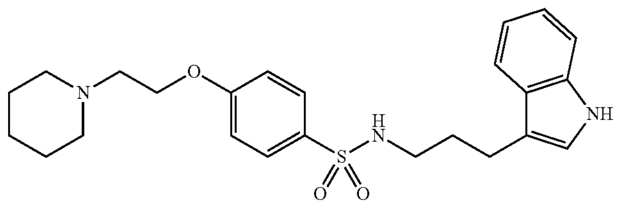 [SMILES: O=S(=O)(NCCCc1c[nH]c2ccccc12)c1ccc(OCCN2CCCCC2)cc1] | N-(3-(1H-benzo[d]imidazol-1-yl)propyl)-4-butoxy-benzensulfonamide | $^1$H NMR (400 MHz, $CDCl_3$) δ 8.05 (s, 1H), 7.71 (d, J = 8.9 Hz, 2H), 7.49 (d, J = 8.5 Hz, 1H), 7.35 (d, J = 8.2 Hz, 1H), 7.21-7.15 (m, 1H), 7.12-7.07 (m, 1H), 6.92 (d, J = 8.9 Hz, 3H), 4.22 (d, J = 6.4 Hz, 1H), 4.17-4.08 (m, 2H), 3.00 (dd, J = 13.3, 6.8 Hz, 2H), 2.83-2.72 (m, 4H), 2.53-2.50 (m, 4H), 1.86 (dt, J = 14.4, 7.1 Hz, 2H), 1.61 (d, J = 5.4 Hz, 4H), 1.45 (s, 2H); 442 $[M + H]^+$ |
| 35 | 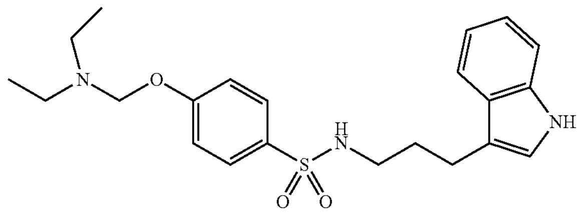 | N-(3-(1H-indol-3-yl)propyl)-4-(3-(diethylamino)propoxy)benzene-sulfonamide | $^1$H NMR (400 MHz, $CDCl_3$) δ 8.22 (s, 1H), 7.76-7.68 (m, 2H), 7.49 (d, J = 7.7 Hz, 1H), 7.35 (d, J = 8.1 Hz, 1H), 7.21-7.15 (m, 1H), 7.11-7.06 (m, 1H), 6.96-6.89 (m, 2H), 6.87 (d, J = 2.2 Hz, 1H), 4.28 (t, J = 6.2 Hz, 1H), 4.08 (t, J = 6.2 Hz, 2H), 3.00 (q, J = 6.7 Hz, 2H), 2.75 (t, J = 7.2 Hz, 2H), 2.71-2.46 (m, 6H), 2.05-1.94 (m, 2H), 1.89-1.80 (m, 2H), 1.08 (t, J = 7.1 Hz, 6H); 444 $[M + H]^+$ |
| 36 | 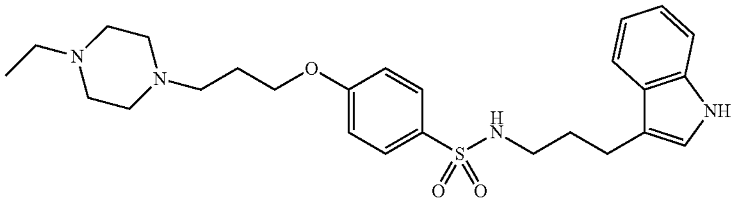 [SMILES: CCN1CCN(CCCOc2ccc(S(=O)(=O)NCCCc3c[nH]c4ccccc34)cc2)CC1] | N-(3-(1H-indol-3-yl)propyl)-4-(3-(4-ethyl-piperazin-1-yl)propoxy)benzene-sulfonamide | $^1$H NMR (400 MHz, $CDCl_3$) δ 8.12 (s, 1H), 7.71 (d, J = 8.9 Hz, 2H), 7.49 (d, J = 7.7 Hz, 1H), 7.35 (d, J = 8.1 Hz, 1H), 7.19 (t, J = 7.1 Hz, 1H), 7.09 (t, J = 7.0 Hz, 1H), 6.92 (d, J = 8.8 Hz, 3H), 4.24 (t, J = 6.4 Hz, 1H), 4.07 (t, J = 6.3 Hz, 2H), 3.00 (dd, J = 13.3, 6.7 Hz, 2H), 2.76 (t, J = 7.2 Hz, 2H), 2.53-2.44 (m, 12H), 2.00 (dt, J = 13.3, 6.5 Hz, 2H), 1.90-1.78 (m, 2H), 1.11 (t, J = 7.0 Hz, 3H); 485 $[M + H]^+$ |
| 37 | 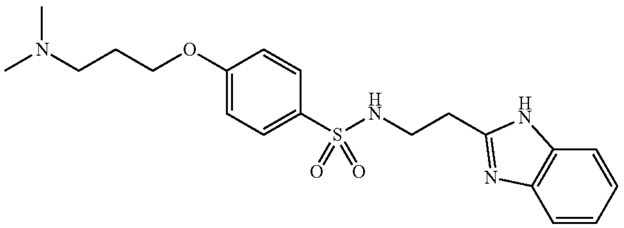 [SMILES: CN(C)CCCOc1ccc(S(=O)(=O)NCCc2nc3ccccc3[nH]2)cc1] | N-(2-(1H-benzo[d]imidazol-2-yl)ethyl)-4-(3-(dimethylamino)propoxy)benzene-sulfonamide | $^1$H NMR (400 MHz, $CDCl_3$) δ 7.77 (d, J = 8.9 Hz, 2H), 7.26-7.22 (m, 4H), 6.93 (d, J = 8.9 Hz, 2H), 5.73-5.67 (m, 1H), 4.08 (t, J = 6.4 Hz, 2H), 3.47 (dd, J = 11.9, 6.0 Hz, 2H), 3.07-3.01 (m, 2H), 2.50-2.44 (m, 2H), 2.27 (s, 6H), 1.99 |

TABLE 1-continued

| Example | Structure | Name | $^1$H NMR, MS |
|---|---|---|---|
| | | | (dd, J = 13.7, 6.7 Hz, 2H); 403 [M + H]$^+$ |
| 38 | 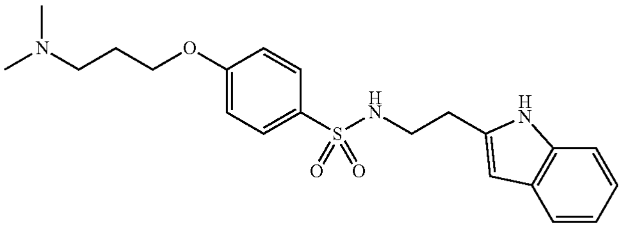 | N-(2-(1H-indol-2-yl)ethyl)-4-(3-(dimethyl-amino)propoxy)benzenesulfonamide | $^1$H NMR (400 MHz, $CDCl_3$) δ 8.06 (s, 1H), 7.75-7.68 (m, 2H), 7.51 (d, J = 7.7 Hz, 1H), 7.29 (d, J = 8.1 Hz, 1H), 7.17-7.11 (m, 1H), 7.11-7.05 (m, 1H), 6.97-6.90 (m, 2H), 6.20 (d, J = 1.2 Hz, 1H), 4.48 (s, 1H), 4.07 (t, J = 6.4 Hz, 2H), 3.27 (dd, J = 12.6, 6.3 Hz, 2H), 2.95 (t, J = 6.4 Hz, 2H), 2.47 (t, J = 7.1 Hz, 2H), 2.27 (s, 6H), 2.05-1.94 (m, 2H); 204 [M + H]$^+$ |
| 39 | 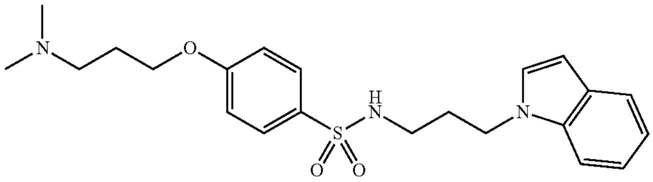 [SMILES: CN(C)CCCOc1ccc(S(=O)(=O)NCCCn2ccc3ccccc32)cc1] | N-(3-(1H-indol-1-yl)propyl)-4-(3-(dimethyl)-amino)propoxy)benzenesulfonamide | $^1$H NMR (400 MHz, $CDCl_3$) δ 7.70-7.64 (m, 2H), 7.62 (d, J = 7.9 Hz, 1H), 7.28-7.26 (m, 1H), 7.21-7.15 (m, 1H), 7.13-7.06 (m, 1H), 7.05 (d, J = 3.2 Hz, 1H), 6.96-6.88 (m, 2H), 6.50-6.45 (m, 1H), 4.27-4.15 (m, 3H), 4.06 (t, J = 6.4 Hz, 2H), 2.88 (dd, J = 13.0, 6.5 Hz, 2H), 2.46 (t, J = 6.9 Hz, 2H), 2.26 (s, 6H), 2.00 (td, J = 13.4, 6.8 Hz, 4H); 416 [M + H]$^+$ |
| 40 | 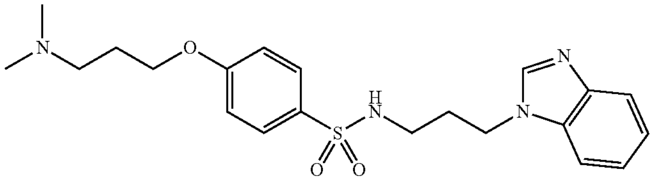 [SMILES: CN(C)CCCOc1ccc(S(=O)(=O)NCCCn2cnc3ccccc32)cc1] | N-(3-(1H-benzo[d]imidazol-1-yl)propyl)-4-(3-(dimethyl-amino)propoxy)benzenesulfonamide | $^1$H NMR (400 MHz, $CDCl_3$) δ 7.92 (s, 1H), 7.84-7.79 (m, 1H), 7.76-7.71 (m, 2H), 7.39-7.34 (m, 1H), 7.30 (dt, J = 5.4, 3.5 Hz, 2H), 6.97-6.92 (m, 2H), 4.55 (d, J = 6.1 Hz, 1H), 4.31 (t, J = 6.7 Hz, 2H), 4.07 (t, J = 6.4 Hz, 2H), 2.90 (dd, J = 12.7, 6.4 Hz, 2H), 2.46 (t, J = 7.0 Hz, 2H), 2.27 (s, 6H), 2.13-2.03 (m, 2H), 1.98 (dt, J = 13.5, 6.7 Hz, 2H); 417 [M + H]$^+$ |
| 41 | 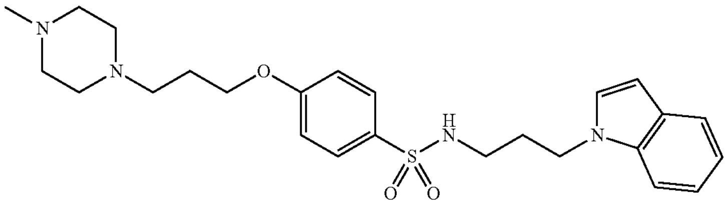 [SMILES: CN1CCN(CCCOc2ccc(S(=O)(=O)NCCCn3ccc4ccccc43)cc2)CC1] | N-(3-(1H-indol-1-yl)propyl)-4-(3-(4-methylpiperazin-1-yl)propoxy)benzenesulfonamide | $^1$H NMR (400 MHz, $CDCl_3$) δ 7.71-7.65 (m, 2H), 7.62 (d, J = 7.9 Hz, 1H), 7.30-7.27 (m, 1H), 7.19 (dd, J = 8.1, 7.1 Hz, 1H), 7.11 (dd, J = 10.9, 4.0 Hz, 1H), 7.05 (d, J = 3.1 Hz, 1H), 6.94-6.89 (m, 2H), 6.48 (d, J = 3.1 Hz, 1H), 4.20 (t, J = |

TABLE 1-continued

| Example | Structure | Name | $^1$H NMR, MS |
| --- | --- | --- | --- |
| | | | 6.6 Hz, 2H), 4.16 (t, J = 6.5 Hz, 1H), 4.06 (t, J = 6.3 Hz, 2H), 2.88 (dd, J = 12.9, 6.5 Hz, 2H), 2.69-2.35 (m, 10H), 2.29 (s, 3H), 2.00 (tt, J = 9.9, 6.5 Hz, 4H); 471 [M + H]$^+$ |
| 42 | 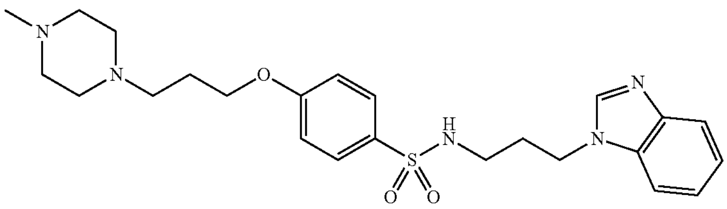 [SMILES: CN1CCN(CCCOc2ccc(S(=O)(=O)NCCCn3cnc4ccccc43)cc2)CC1] | N-(3-(1H-benzo[d]imidazol-1-yl)propyl)-4-(3-(4-methylpiperazin-1-yl)propoxy) benzensulfonamide | $^1$H NMR (400 MHz, $CDCl_3$) δ 7.92 (s, 1H), 7.83-7.78 (m, 1H), 7.73 (d, J = 8.9 Hz, 2H), 7.38-7.34 (m, 1H), 7.32-7.28 (m, 2H), 6.95 (d, J = 8.9 Hz, 2H), 4.36-4.28 (m, 3H), 4.06 (t, J = 6.3 Hz, 2H), 2.91 (dd, J = 12.8, 6.4 Hz, 2H), 2.59-2.35 (m, 10H), 2.29 (s, 3H), 2.07 (dd, J = 13.1, 6.6 Hz, 2H), 2.02-1.94 (m, 2H); 472 [M + H]$^+$ |
| 43 | 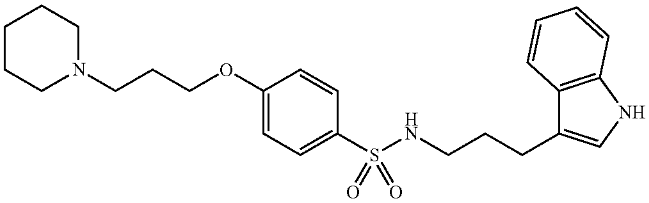 [SMILES: O=S(=O)(NCCCc1c[nH]c2ccccc12)c1ccc(OCCCN2CCCCC2)cc1] | N-(3-(1H-indol-3-yl)propyl)-4-(3-(piperidin-1-yl)propoxy)benzenesulfonamide | $^1$H NMR (400 MHz, CDCl3) δ 8.23 (s, 1H), 7.73-7.66 (m, 2H), 7.49 (d, J = 7.7 Hz, 1H), 7.35 (d, J = 8.1 Hz, 1H), 7.19 (t, J = 7.0 Hz, 1H), 7.09 (t, J = 7.0 Hz, 1H), 6.94-6.89 (m, 2H), 6.88 (t, J = 2.6 Hz, 1H), 4.23 (t, J = 6.1 Hz, 1H), 4.08 (t, J = 6.3 Hz, 2H), 3.00 (dd, J = 13.3, 6.7 Hz, 2H), 2.75 (t, J = 7.1 Hz, 2H), 2.62-2.32 (m, 6H), 2.07-1.94 (m, 2H), 1.90-1.79 (m, 2H), 1.69-1.60 (m, 4H), 1.47 (dd, J = 16.1, 10.0 Hz, 2H); 456 [M + H]$^+$ |
| 44 | 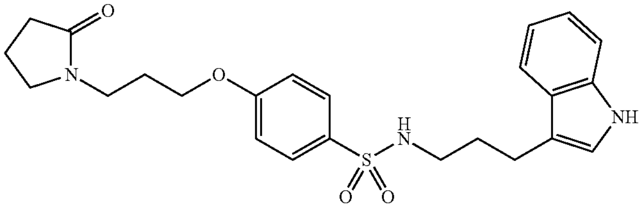 [SMILES: O=C1CCCN1CCCOc1ccc(S(=O)(=O)NCCCc2c[nH]c3ccccc23)cc1] | N-(3-(1H-indol-3-yl)propyl)-4-(3-(2-oxopyrrolidin-1-yl)propoxy)benzenesulfonamide | $^1$H NMR (400 MHz, $CDCl_3$) δ 8.70 (s, 1H), 7.74-7.67 (m, 2H), 7.49 (d, J = 7.5 Hz, 1H), 7.35 (d, J = 8.2 Hz, 1H), 7.19-7.13 (m, 1H), 7.11-7.05 (m, 1H), 6.91 (d, J = 7.1 Hz, 2H), 6.64 (s, 1H), 4.25-4.18 (m, 1H), 4.04 (t, J = 5.1 Hz, 2H), 3.54 (t, J = 6.4 Hz, 2H), 3.46 (t, J = 6.9 Hz, 2H), 2.98 (dd, J = 12.2, 5.8 Hz, 2H), 2.74 (t, J = 6.9 Hz, 2H), 2.40 (t, J = 8.0 Hz, 2H), 2.12-1.98 (m, 4H), 1.91-1.82 (m, 2H); 456 [M + H]$^+$ |

TABLE 1-continued

| Example | Structure | Name | $^1$H NMR, MS |
|---|---|---|---|
| 45 | 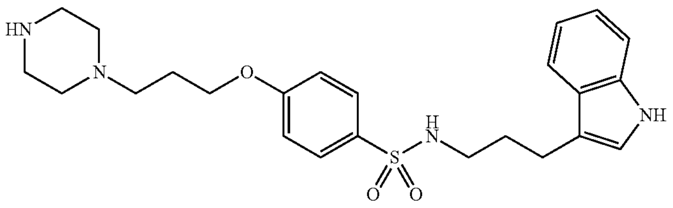 [SMILES: O=S(=O)(NCCCc1c[nH]c2ccccc12)c1ccc(OCCCN2CCNCC2)cc1] | N-(3-(1H-indol-3-yl)propyl)-4-(3-(piperazin-1-yl)propoxy)benzenesulfonamide | $^1$H NMR (400 MHz, $CDCl_3$) δ 8.13 (s, 1H), 7.71 (d, J = 8.9 Hz, 2H), 7.49 (d, J = 7.7 Hz, 1H), 7.35 (d, J = 8.1 Hz, 1H), 7.19 (t, J = 7.1 Hz, 1H), 7.09 (t, J = 7.1 Hz, 1H), 6.92 (d, J = 8.9 Hz, 2H), 4.26 (t, J = 6.4 Hz, 1H), 4.07 (t, J = 6.3 Hz, 2H), 3.00 (dd, J = 13.2, 6.7 Hz, 2H), 2.90 (t, J = 4.9 Hz, 4H), 2.76 (t, J = 7.2 Hz, 2H), 2.55-2.48 (m, 2H), 2.45 (br, 4H), 2.07-1.93 (m, 2H), 1.91-1.79 (m, 2H); 457 $[M + H]^+$ |
| 46 | 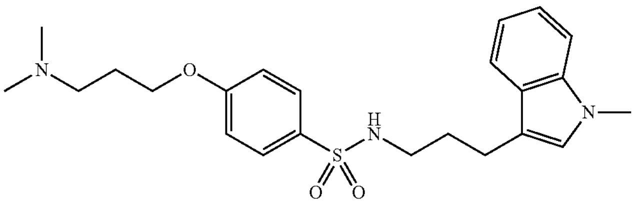 | 4-(3-(dimethylamino)propoxy)-N-(3-(1-methyl-1H-indol-3-yl)propyl)benzenesulfonamide | $^1$H NMR (400 MHz, $CDCl_3$) δ 7.75-7.69 (m, 2H), 7.47 (d, J = 7.9 Hz, 1H), 7.28-7.26 (m, 1H), 7.21 (t, J = 7.6 Hz, 1H), 7.08 (dd, J = 10.9, 4.0 Hz, 1H), 6.97-6.90 (m, 2H), 6.77 (s, 1H), 4.22 (t, J = 6.2 Hz, 1H), 4.07 (t, J = 6.4 Hz, 2H), 3.72 (s, 3H), 3.00 (dd, J = 13.3, 6.7 Hz, 2H), 2.75 (t, J = 7.3 Hz, 2H), 2.46 (t, J = 7.2 Hz, 2H), 2.26 (s, 6H), 1.98 (dt, J = 13.4, 6.7 Hz, 2H), 1.89-1.81 (m, 2H); 430 $[M + H]^+$ |
| 47 | 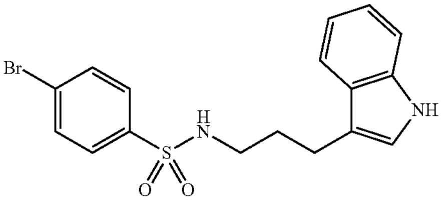 [SMILES: O=S(=O)(NCCCc1c[nH]c2ccccc12)c1ccc(Br)cc1] | N-(3-(1H-indol-3-yl)propyl)-4-bromobenzenesulfonamide | $^1$H NMR (400 MHz, $CDCl_3$) δ 7.95 (s, 1H), 7.66-7.56 (m, 4H), 7.48 (d, J = 7.8 Hz, 1H), 7.37 (d, J = 8.1 Hz, 1H), 7.21 (t, J = 7.6 Hz, 1H), 7.11 (t, J = 7.1 Hz, 1H), 6.95 (d, J = 2.2 Hz, 1H), 4.32 (t, J = 5.9 Hz, 1H), 3.04 (dd, J = 13.3, 6.7 Hz, 2H), 2.78 (d, J = 7.1 Hz, 2H), 1.88 (p, J = 7.1 Hz, 2H); 394 $[M + H]^+$ |
| 48 | 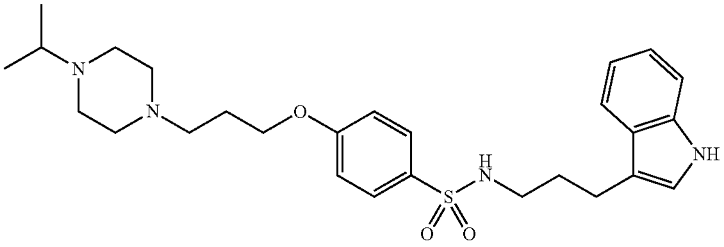 [SMILES: CC(C)N1CCN(CCCOc2ccc(S(=O)(=O)NCCCc3c[nH]c4ccccc34)cc2)CC1] | N-(3-(1H-indol-3-yl)propyl)-4-(3-(4-isopropylpiperazin-1-yl)propoxy)benzenesulfonamide | $^1$H NMR (400 MHz, $CDCl_3$) δ 8.10 (s, 1H), 7.71 (d, J = 8.9 Hz, 2H), 7.49 (d, J = 7.8 Hz, 1H), 7.35 (d, J = 8.2 Hz, 1H), 7.20-7.16 (m, 1H), 7.11-7.06 (m, 1H), 6.94-6.88 (m, 3H), 4.26-4.21 (m, 1H), 4.07 (t, J = 6.3 Hz, 2H), 3.01 (dd, J = 13.4, 6.8 Hz, 2H), 2.76 (t, J = 7.4 Hz, 2H), 2.71-2.46 (m, |

TABLE 1-continued

| Example | Structure | Name | $^1$H NMR, MS |
|---|---|---|---|
| | | | 10H), 2.26-2.17 (m, 1H), 1.99 (dd, J = 12.5, 5.8 Hz, 2H), 1.87 (dd, J = 14.2, 7.2 Hz, 2H), 1.06 (d, J = 5.5 Hz, 6H); 499 [M + H]$^+$ |
| 49 | 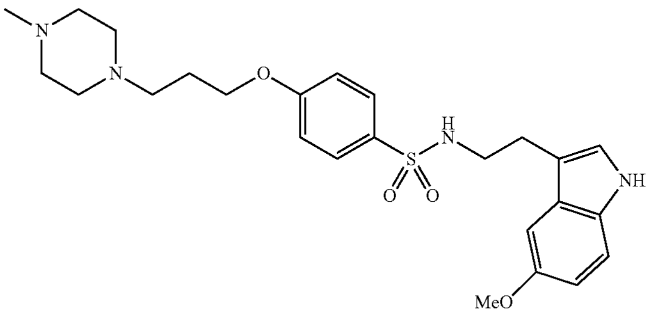 [SMILES: COc1ccc2[nH]cc(CCNS(=O)(=O)c3ccc(OCCCN4CCN(C)CC4)cc3)c2c1] | N-(2-(5-methoxy)-1H-indol-3-yl)ethyl)-4-(3-(4-methyl-piperazin-1-yl)propoxy)benzene-sulfonamide | $^1$H NMR (400 MHz, $CDCl_3$) δ 7.96 (s, 1H), 7.64 (d, J = 8.9 Hz, 2H), 7.29-7.21 (m, 1H), 6.94 (d, J = 2.1 Hz, 1H), 6.86 (dd, J = 7.6, 5.4 Hz, 3H), 4.32-4.24 (m, 1H), 4.05 (t, J = 6.2 Hz, 2H), 3.80 (s, 3H), 3.26 (dd, J = 12.8, 6.5 Hz, 2H), 2.91 (t, J = 6.5 Hz, 2H), 2.73-2.34 (m, 10H), 2.29 (s, 3H), 2.04-1.93 (m, 2H); 487 [M + H]$^+$ |
| 50 | 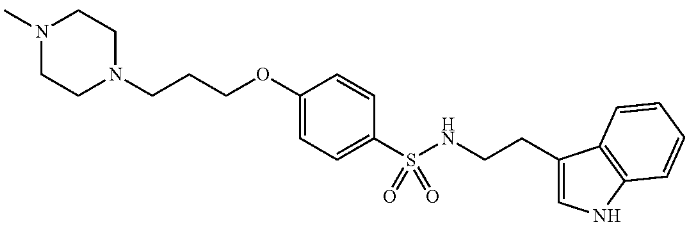 [SMILES: CN1CCN(CCCOc2ccc(S(=O)(=O)NCCc3c[nH]c4ccccc34)cc2)CC1] | N-(2-(1H-indol-3-yl)ethyl)-4-(3-(4-methylpiperazin-1-yl)propoxy)benzene-sulfonamide | $^1$H NMR (400 MHz, $CDCl_3$) δ 8.10 (s, 1H), 7.65 (d, J = 8.9 Hz, 2H), 7.43 (d, J = 8.1 Hz, 1H), 7.36 (d, J = 8.1 Hz, 1H), 7.19 (t, J = 7.2 Hz, 1H), 7.07 (t, J = 7.5 Hz, 1H), 6.97 (d, J = 2.2 Hz, 1H), 6.88 (d, J = 8.9 Hz, 2H), 4.29 (t, J = 6.1 Hz, 1H), 4.06 (t, J = 6.3 Hz, 2H), 3.28 (dd, J = 12.8, 6.4 Hz, 2H), 2.94 (t, J = 6.6 Hz, 2H), 2.67-2.33 (m, 10H), 2.30 (s, 3H), 2.04-1.95 (m, 2H); 457 [M + H]$^+$ |
| 51 | 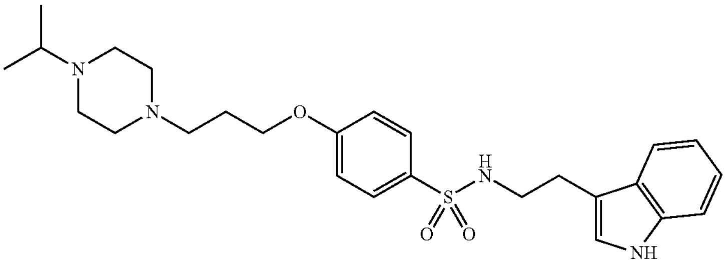 [SMILES: CC(C)N1CCN(CCCOc2ccc(S(=O)(=O)NCCc3c[nH]c4ccccc34)cc2)CC1] | N-(2-(1H-indol-3-yl)ethyl)-4-(3-(4-isopropyl-piperazin-1-yl)propoxy)benzene-sulfonamide | $^1$H NMR (400 MHz, $CDCl_3$) δ 8.10 (s, 1H), 7.65 (d, J = 8.9 Hz 2H), 7.43 (d, J = 7.9 Hz, 1H), 7.36 (d, J = 8.2 Hz, 1H), 7.23-7.16 (m, 1H), 7.07 (t, J = 7.6 Hz, 1H), 6.97 (s, 1H), 6.88 (d, J = 8.9 Hz, 2H), 4.29 (t, J = 6.2 Hz, 1H), 4.06 (t, J = 6.3 Hz, 2H), 3.28 (dd, J = 12.9, 6.5 Hz, 2H), 2.94 (t, J = 6.5 Hz, 2H), 2.78-2.37 (m, 10H), 2.07-1.95 (m, 2H), 1.16-0.97 (m, 6H); 485 [M + H]$^+$ |

TABLE 1-continued

| Example | Structure | Name | $^1$H NMR, MS |
|---|---|---|---|
| 52 | 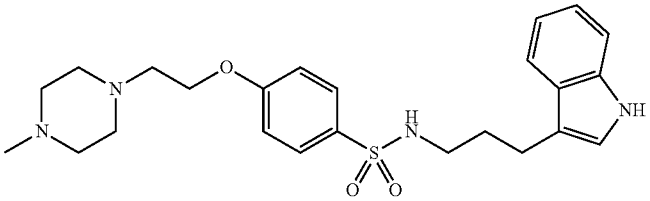 | N-(3-(1H-indol-3-yl)propyl)-4-(2-(4-methylpiperazin-1-yl)ethoxy)benzenesulfonamide | $^1$H NMR (400 MHz, $CDCl_3$) δ 8.31 (s, 1H), 7.73 (d, J = 8.9 Hz, 2H), 7.49 (d, J = 8.1 Hz, 1H), 7.34 (d, J = 8.1 Hz, 1H), 7.18 (t, J = 7.1 Hz, 1H), 7.09 (t, J = 7.0 Hz, 1H), 6.93 (d, J = 8.9 Hz, 2H), 6.87 (d, J = 2.3 Hz, 1H), 4.26 (t, J = 6.2 Hz, 1H), 4.15 (t, J = 5.6 Hz, 2H), 3.02 (dd, J = 13.3, 6.8 Hz, 2H), 2.88 (t, J = 5.6 Hz, 2H), 2.74 (t, J = 7.2 Hz, 2H), 2.69-2.39 (m, 8H), 2.32 (s, 2H), 1.83 (dd, J = 14.2, 7.1 Hz, 2H); 457 $[M + H]^+$ |
| 53 | 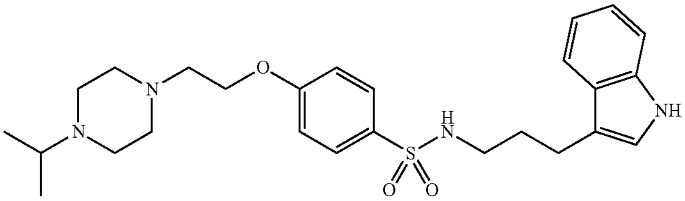 [SMILES: CC(C)N1CCN(CCOc2ccc(S(=O)(=O)NCCCc3c[nH]c4ccccc34)cc2)CC1] | N-(3-(1H-indol-3-yl)propyl)-4-(2-(4-isopropylpiperazin-1-yl)ethoxy)benzenesulfonamide | $^1$H NMR (400 MHz, $CDCl_3$) δ 8.20 (s, 1H), 7.72 (d, J = 8.9 Hz, 2H), 7.49 (d, J = 7.9 Hz, 1H), 7.35 (d, J = 8.0 Hz, 1H), 7.22-7.15 (m, 1H), 7.12-7.06 (m, 1H), 6.92 (d, J = 8.9 Hz, 2H), 6.89 (d, J = 2.2 Hz, 1H), 4.27-4.20 (m, 1H), 4.15 (t, J = 5.7 Hz, 2H), 3.01 (dd, J = 13.2, 6.6 Hz, 2H), 2.86 (t, J = 5.7 Hz, 2H), 2.75 (t, J = 7.3 Hz, 2H), 2.72-2.39 (m, 8H), 2.25-2.19 (m, 1H), 1.84 (dt, J = 14.3, 7.2 Hz, 2H), 1.06 (d, J = 5.9 Hz, 6H); 485 $[M + H]^+$ |
| 54 | 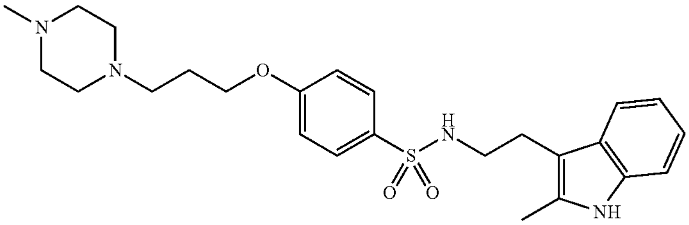 [SMILES: Cc1[nH]c2ccccc2c1CCNS(=O)(=O)c1ccc(OCCCN2CCN(C)CC2)cc1] | N-(2-(2-methyl-1H-indol-3-yl)ethyl)-4-(3-(4-methylpiperazin-1-yl)propoxy)benzenesulfonamide | $^1$H NMR (400 MHz, $CDCl_3$) δ 7.96 (s, 1H), 7.61 (d, J = 8.9 Hz, 2H), 7.31 (d, J = 7.9 Hz, 1H), 7.25 (d, J = 7.5 Hz, 1H), 7.11 (t, J = 7.0 Hz, 1H), 7.02 (t, J = 7.9 Hz, 1H), 6.85 (d, J = 8.9 Hz, 2H), 4.24 (t, J = 6.2 Hz, 1H), 4.06 (t, J = 6.3 Hz, 2H), 3.21 (q, J = 6.5 Hz, 2H), 2.89 (t, J = 6.6 Hz, 2H), 2.73-2.37 (m, 10H), 2.34 (s, 3H), 2.29 (s, 3H), 1.99 (dt, J = 13.4, 6.5 Hz, 2H); 471 $[M + H]^+$ |

TABLE 1-continued

| Example | Structure | Name | $^1$H NMR, MS |
|---|---|---|---|
| 55 | 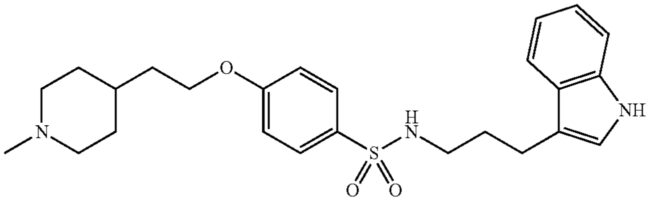 [SMILES: CN1CCC(CCOc2ccc(S(=O)(=O)NCCCc3c[nH]c4ccccc34)cc2)CC1] | N-(3-(1H-indol-3-yl)propyl)-4-(2-(1-methylpiperidin-4-yl)ethoxy)benzene-sulfonamide | $^1$H NMR (400 MHz, $CDCl_3$) δ 8.22 (s, 1H), 7.72 (d, J = 8.9 Hz, 2H), 7.49 (d, J = 8.0 Hz, 1H), 7.34 (d, J = 8.1 Hz, 1H), 7.18 (t, J = 7.2 Hz, 1H), 7.09 (t, J = 7.5 Hz, 1H), 6.91 (d, J = 8.8 Hz, 2H), 4.27 (t, J = 6.2 Hz, 1H), 4.05 (t, J = 6.4 Hz, 2H), 3.02 (q, J = 6.7 Hz, 2H), 2.89 (d, J = 11.7 Hz, 2H), 2.75 (t, J = 7.3 Hz, 2H), 2.30 (s, 3H), 1.97 (t, J = 11.6 Hz, 2H), 1.85 (dd, J = 14.3, 7.1 Hz, 2H), 1.76 (dt, J = 13.4, 6.7 Hz, 4H), 1.45-1.34 (m, 2H); 456 [M + H]$^+$ |
| 56 | 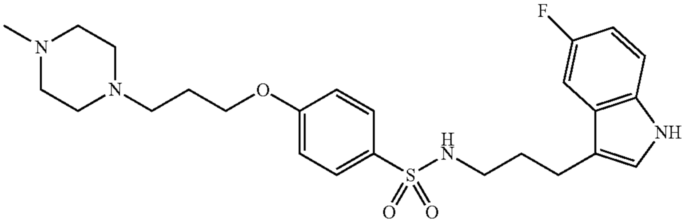 [SMILES: CN1CCN(CCCOc2ccc(S(=O)(=O)NCCCc3c[nH]c4ccc(F)cc34)cc2)CC1] | N-(3-(5-fluoro-1H-indol-3-yl)propyl)-4-(3-(4-methylpiperazin-1-yl)propoxy)benzene-sulfonamide | $^1$H NMR (400 MHz, $CDCl_3$) δ 8.10 (s, 1H), 7.71 (d, J = 8.9 Hz, 2H), 7.28-7.23 (m, 2H), 7.10 (dd, J = 9.6, 2.4 Hz, 1H), 6.99-6.88 (m, 4H), 4.25 (t, J = 6.2 Hz, 1H), 4.07 (t, J = 6.3 Hz, 2H), 3.00 (dd, J = 13.3, 6.8 Hz, 2H), 2.70 (t, J = 7.3 Hz, 2H), 2.65-2.35 (m, 10H), 2.30 (s, 3H), 2.04-1.95 (m, 2H), 1.90-1.77 (m, 2H); 489 [M + H]$^+$ |
| 57 | 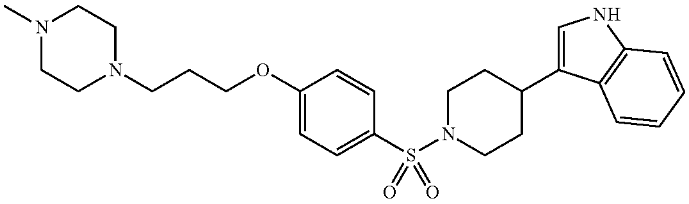 [SMILES: CN1CCN(CCCOc2ccc(S(=O)(=O)N3CCC(c4c[nH]c5ccccc45)CC3)cc2)CC1] | 3-(1-((4-(3-(4-methyl-piperazin-1-yl)propoxy)phenyl)sulfonyl)piperidin-4-yl)-1H-indole | $^1$H NMR (400 MHz, $CDCl_3$) δ 8.03 (s, 1H), 7.74 (d, J = 8.9 Hz, 2H), 7.51 (d, J = 8.0 Hz, 1H), 7.36 (d, J = 8.1 Hz, 1H), 7.18 (t, J = 7.2 Hz, 1H), 7.08 (t, J = 7.1 Hz, 1H), 7.01 (t, J = 7.1 Hz, 2H), 6.94 (d, J = 2.2 Hz, 1H), 4.11 (t, J = 6.3 Hz, 2H), 3.91 (d, J = 11.3 Hz, 2H), 2.82-2.72 (m, 1H), 2.68-2.32 (m, 12H), 2.31 (s, 3H), 2.09 (dd, J = 18.5, 7.0 Hz, 2H), 2.01 (dd, J = 13.8, 6.9 Hz, 2H), 1.88 (ddd, J = 25.3, 12.5, 3.8 Hz, 2H); 497 [M + H]$^+$ |
| 58 | 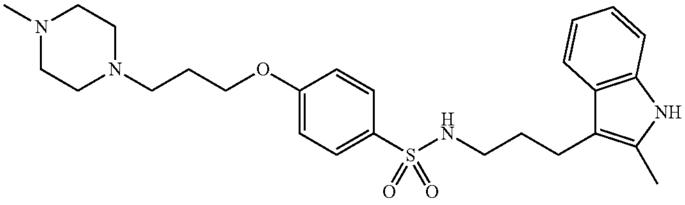 [SMILES: Cc1[nH]c2ccccc2c1CCCNS(=O)(=O)c1ccc(OCCCN2CCN(C)CC2)cc1] | N-(3-(2-methyl-1H-indol-3-yl)propyl)-4-(3-(4-methyl-piperazin-1-yl)propoxy)benzene-sulfonamide | $^1$H NMR (400 MHz, $CDCl_3$) δ 7.87 (s, 1H), 7.66 (d, J = 8.9 Hz, 2H), 7.36 (d, J = 7.8 Hz, 1H), 7.24 (d, J = 1.1 Hz, 1H), 7.10 (t, J = 6.9 Hz, 1H), 7.04 (dd, J = 10.8, 4.0 Hz, 1H), 6.90 (d, J = 8.9 Hz, |

TABLE 1-continued

| Example | Structure | Name | $^1$H NMR, MS |
|---|---|---|---|
| | | | 2H), 4.17 (t, J = 6.1 Hz, 1H), 4.07 (t, J = 6.3 Hz, 2H), 2.95 (dd, J = 13.3, 6.8 Hz, 2H), 2.69 (t, J = 7.2 Hz, 2H), 2.55-2.37 (m, 10H), 2.32 (s, 3H), 2.29 (s, 3H), 1.99 (dt, J = 13.4, 6.6 Hz, 2H), 1.78 (p, J = 7.0 Hz, 2H); 485 [M + H]$^+$ |
| 59 | 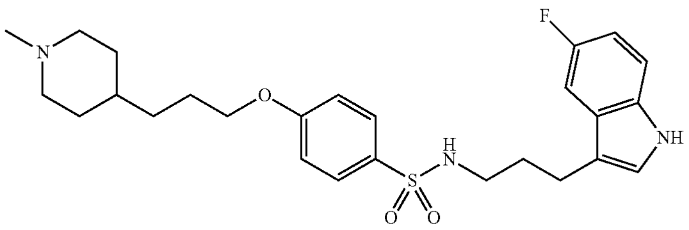 [SMILES: CN1CCC(CCCOc2ccc(S(=O)(=O)NCCCc3c[nH]c4ccc(F)cc34)cc2)CC1] | N-(3-(5-fluoro-1H-indol-3-yl)propyl)-4-(3-(1-methylpiperidin-4-yl)propoxy)benzene-sulfonamide | $^1$H NMR (400 MHz, $CDCl_3$) δ 8.06 (s, 1H), 7.72 (d, J = 8.9 Hz, 2H), 7.28-7.23 (m, 1H), 7.10 (dd, J = 9.6, 2.4 Hz, 1H), 7.00 (s, 1H), 6.92 (d, J = 8.9 Hz, 2H), 4.25 (t, J = 6.1 Hz, 1H), 3.99 (t, J = 6.5 Hz, 2H), 3.01 (dd, J = 13.3, 6.7 Hz, 2H), 2.88 (d, J = 11.0 Hz, 2H), 2.71 (t, J = 7.2 Hz, 2H), 2.28 (s, 3H), 1.93 (t, J = 10.4 Hz, 2H), 1.88-1.78 (m, 4H), 1.72 (d, J = 9.8 Hz, 2H), 1.44-1.36 (m, 2H), 1.36-1.24 (m, 3H); 488 [M + H]$^+$ |
| 60 | 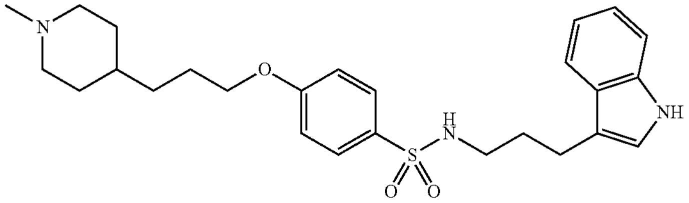 [SMILES: CN1CCC(CCCOc2ccc(S(=O)(=O)NCCCc3c[nH]c4ccccc34)cc2)CC1] | N-(3-(1H-indol-3-yl)propyl)-4-(3-(1-methyl-piperidin-4-yl)propoxy)benzene-sulfonamide | $^1$H NMR (400 MHz, $CDCl_3$) δ 8.04 (s, 1H), 7.72 (d, J = 8.9 Hz, 2H), 7.49 (d, J = 7.8 Hz, 1H), 7.35 (d, J = 8.1 Hz, 1H), 7.18 (t, J = 7.2 Hz, 1H), 7.09 (t, J = 7.1 Hz, 1H), 6.94 (d, J = 2.1 Hz, 1H), 6.91 (d, J = 8.9 Hz, 2H), 4.27 (t, J = 6.1 Hz, 1H), 3.99 (t, J = 6.5 Hz, 2H), 3.01 (dd, J = 13.3, 6.7 Hz, 2H), 2.87 (d, J = 11.3 Hz, 2H), 2.77 (t, J = 7.3 Hz, 2H), 2.27 (s, 3H), 1.98-1.88 (m, 2H), 1.88-1.84 (m, 2H), 1.84-1.77 (m, 2H), 1.71 (d, J = 9.3 Hz, 2H), 1.45-1.35 (m, 2H), 1.31-1.20 (m, 2H); 470 [M + H]$^+$ |
| 61 | 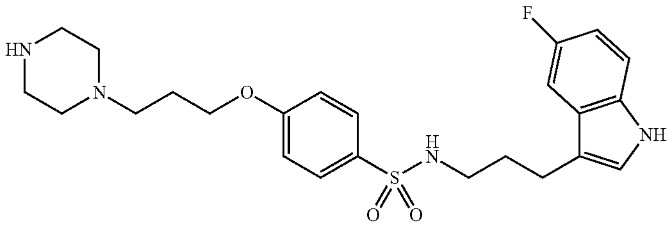 [SMILES: O=S(=O)(NCCCc1c[nH]c2ccc(F)cc12)c1ccc(OCCCN2CCNCC2)cc1] | N-(3-(5-fluoro-1H-indol-3-yl)propyl)-4-(3-(piperazin-1-yl)propoxy)benzene-sulfonamide | $^1$H NMR (400 MHz, $CDCl_3$) δ 8.13 (s, 1H), 7.71 (d, J = 8.9 Hz, 2H), 7.24 (s, 1H), 7.10 (dd, J = 9.6, 2.4 Hz, 1H), 6.97 (s, 1H), 6.96-6.89 (m, 3H), 4.26 (s, 1H), 4.08 (t, J = 6.3 Hz, 2H), 3.00 (dd, J = 12.7, 6.5 Hz, 2H), 2.91 (t, J = 4.9 Hz, 4H), 2.70 (t, |

TABLE 1-continued

| Example | Structure | Name | $^1$H NMR, MS |
|---|---|---|---|
| | | | J = 7.3 Hz, 2H), 2.56-2.49 (m, 2H), 2.46 (s, 4H), 2.05-1.92 (m, 2H), 1.87-1.76 (m, 2H); 475 $[M + H]^+$ |
| 62 | 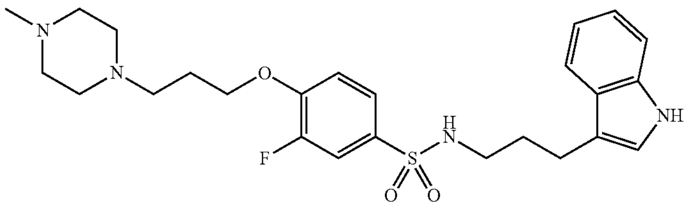 [SMILES: CN1CCN(CCCOc2ccc(S(=O)(=O)NCCCc3c[nH]c4ccccc34)cc2F)CC1] | N-(3-(1H-indol-3-yl)propyl)-3-fluoro-4-(3-(4-methylpiperazin-1-yl)propoxy)benzenesulfonamide | $^1$H NMR (400 MHz, $CDCl_3$) δ 8.11 (s, 1H), 7.53-7.47 (m, 2H), 7.36 (d, J = 8.1 Hz, 1H), 7.28 (s,1H), 7.22-7.15 (m, 1H), 7.12-7.05 (m, 1H), 7.00-6.91 (m, 2H), 4.29-4.21 (m, 1H), 4.15 (t, J = 6.3 Hz, 2H), 3.02 (dd, J = 13.3, 6.8 Hz, 2H), 2.77 (t, J = 7.1 Hz, 2H), 2.69-2.39 (m, 8H), 2.31 (s, 3H), 2.25-2.17 (m, 2H), 2.06-1.95 (m, 2H), 1.88 (dt, J = 14.1, 6.9 Hz, 2H); 489 $[M + H]^+$ |
| 63 | 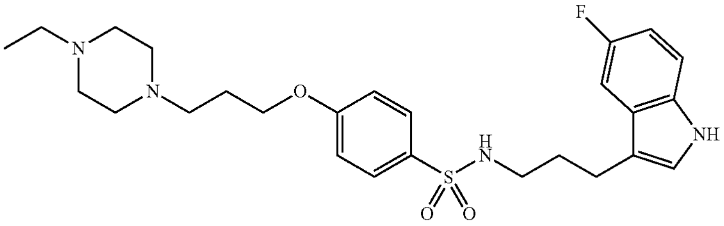 [SMILES: CCN1CCN(CCCOc2ccc(S(=O)(=O)NCCCc3c[nH]c4ccc(F)cc34)cc2)CC1] | 4-(3-(4-ethyl piperazin-1-yl)propoxy)-N-(3-(5-fluoro-1H-indol-3-yl)propyl)benzenesulfonamide | $^1$H NMR (400 MHz, $CDCl_3$) δ 8.11 (s, 1H), 7.71 (d, J = 8.9 Hz, 2H), 7.24 (s, 1H), 7.10 (dd, J = 9.6, 2.3 Hz, 1H), 6.98-6.88 (m, 4H), 4.22 (t, J = 6.2 Hz, 1H), 4.08 (t, J = 6.3 Hz, 2H), 3.00 (dd, J = 13.3, 6.8 Hz, 2H), 2.70 (t, J = 7.2 Hz, 2H), 2.56-2.39 (m, 10H), 2.03-1.96 (m, 2H), 1.86-1.77 (m, 2H), 1.10 (t, J = 6.9 Hz, 3H); 503 $[M + H]^+$ |
| 64 | 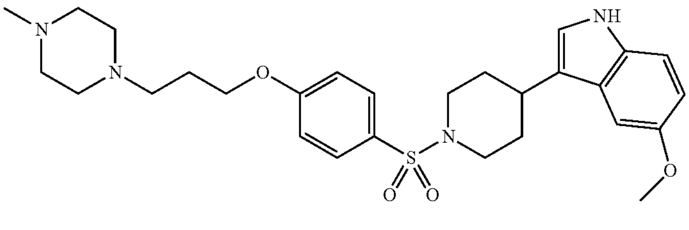 [SMILES: COc1ccc2[nH]cc(C3CCN(S(=O)(=O)c4ccc(OCCCN5CCN(C)CC5)cc4)CC3)c2c1] | 5-methoxy-3-(1-((4-(3-(4-methyl-piperazin-1-yl)propoxy)phenyl)sulfonyl)piperidin-4-yl)-1H-indole | $^1$H NMR (400 MHz, $CDCl_3$) δ 7.91 (s, 1H), 7.74 (d, J = 8.9 Hz, 2H), 7.24 (s, 1H), 7.01 (t, J = 6.8 Hz, 2H), 6.93 (dd, J = 7.2, 2.3 Hz, 2H), 6.85 (dd, J = 8.8, 2.3 Hz, 1H), 4.10 (t, J = 6.3 Hz, 2H), 3.91 (d, J = 11.8 Hz, 2H), 3.83 (s, 3H), 2.71 (t, J = 11.7 Hz, 1H), 2.66-2.37 (m, 12H), 2.31 (s, 3H), 2.07 (t, J = 11.1 Hz, 2H), 2.04-1.95 (m, 2H), 1.86 (ddd, J = 25.6, 12.6, 3.8 Hz, 2H); 527 $[M + H]^+$ |

TABLE 1-continued

| Example | Structure | Name | $^1$H NMR, MS |
|---|---|---|---|
| 65 | 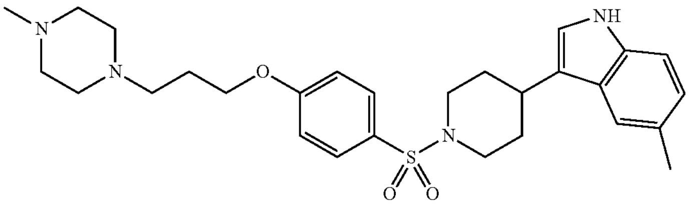 [SMILES: Cc1ccc2[nH]cc(C3CCN(S(=O)(=O)c4ccc(OCCCN5CCN(C)CC5)cc4)CC3)c2c1] | 5-methyl-3-(1-((4-(3-(4-methylpiperazin-1-yl)propoxy)phenyl)sulfonyl)piperidin-4-yl)-1H-indole | $^1$H NMR (400 MHz, $CDCl_3$) δ 7.91 (s, 1H), 7.74 (d, J = 8.9 Hz, 2H), 7.32-7.21 (m, 3H), 7.01 (dd, J = 7.6, 5.5 Hz, 2H), 6.90 (d, J = 2.2 Hz, 1H), 4.10 (t, J = 6.3 Hz, 2H), 3.91 (d, J = 11.9 Hz, 2H), 2.78-2.67 (m, 1H), 2.65-2.44 (m, 10H), 2.47-2.39 (m, 5H), 2.32 (s, 3H), 2.08 (dd, J = 15.6, 4.1 Hz, 2H), 2.01 (dd, J = 13.8, 6.9 Hz, 2H), 1.88 (ddd, J = 25.2, 12.5, 3.7 Hz, 2H); 511 $[M + H]^+$ |
| 66 | 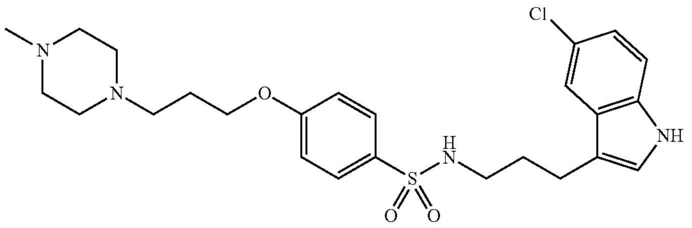 | N-(3-(5-chloro-1H-indol-3-yl)propyl)-4-(3-(4-methylpiperazin-1-yl)propoxy)benzenesulfonamide | $^1$H NMR (400 MHz, $CDCl_3$) δ 8.16 (s, 1H), 7.71 (d, J = 8.8 Hz, 2H), 7.44 (d, J = 1.6 Hz, 1H), 7.28 (s, 1H), 7.13 (dd, J = 8.7, 1.7 Hz, 1H), 6.97-6.89 (m, 3H), 4.22 (t, J = 6.1 Hz, 1H), 4.08 (t, J = 6.3 Hz, 2H), 3.00 (dd, J = 13.4, 6.8 Hz, 2H), 2.71 (t, J = 7.2 Hz, 2H), 2.63-2.40 (m, 10H), 2.30 (s, 3H), 1.99 (dt, J = 13.3, 6.5 Hz, 2H), 1.83 (dt, J = 14.0, 7.0 Hz, 2H); 505 $[M + H]^+$ |
| 67 | 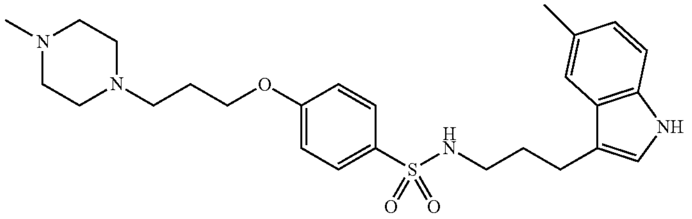 [SMILES: Cc1ccc2[nH]cc(CCCNS(=O)(=O)c3ccc(OCCCN4CCN(C)CC4)cc3)c2c1] | N-(3-(5-methyl-1H-indol-3-yl)propyl)-4-(3-(4-methylpiperazin-1-yl)propoxy)benzenesulfonamide | $^1$H NMR (400 MHz, $CDCl_3$) δ 7.99 (s, 1H), 7.71 (d, J = 8.9 Hz, 2H), 7.32-7.22 (m, 2H), 7.01 (d, J = 8.1 Hz, 1H), 6.92 (d, J = 8.8 Hz, 2H), 6.87 (d, J = 1.8 Hz, 1H), 4.23 (t, J = 6.1 Hz, 1H), 4.07 (t, J = 6.3 Hz, 2H), 3.00 (dd, J = 13.1, 6.6 Hz, 2H), 2.73 (t, J = 7.2 Hz, 2H), 2.50 (ddd, J = 14.0, 10.9, 5.9 Hz, 10H), 2.45 (s, 3H), 2.30 (s, 3H), 2.00 (dd, J = 13.8, 6.8 Hz, 2H), 1.84 (dd, J = 14.2, 7.0 Hz, 2H); 485 $[M + H]^+$ |
| 68 | 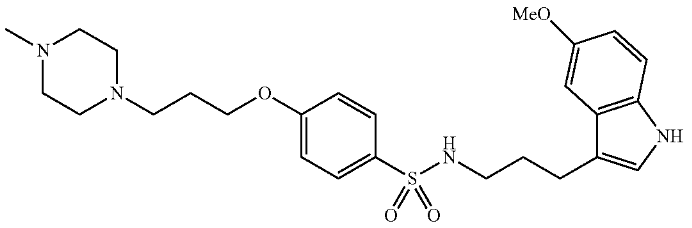 [SMILES: COc1ccc2[nH]cc(CCCNS(=O)(=O)c3ccc(OCCCN4CCN(C)CC4)cc3)c2c1] | N-(3-(5-methoxy-1H-indol-3-yl)propyl)-4-(3-(4-methylpiperazin-1-yl)propoxybenzenesulfonamide | $^1$H NMR (400 MHz, $CDCl_3$) δ 7.99 (s, 1H), 7.70 (d, J = 8.8 Hz, 2H), 7.23 (s, 1H), 6.97-6.88 (m, 4H), 6.85 (dd, J = 8.8, 2.3 Hz, 1H), 4.23 (t, J = 6.2 Hz, 1H), 4.07 (t, J = 6.3 Hz, 2H), 3.85 (s, 3H), 3.01 (dd, J = 13.2, 6.8 Hz, 2H), |

TABLE 1-continued

| Example | Structure | Name | $^1$H NMR, MS |
|---|---|---|---|
| | | | 2.73 (t, J = 7.2 Hz, 2H), 2.68-2.36 (m, 10H), 2.30 (s, 3H), 1.99 (dt, J = 13.4, 6.7 Hz, 2H), 1.86 (dt, J = 14.0, 7.1 Hz, 2H); 501 $[M + H]^+$ |
| 69 | 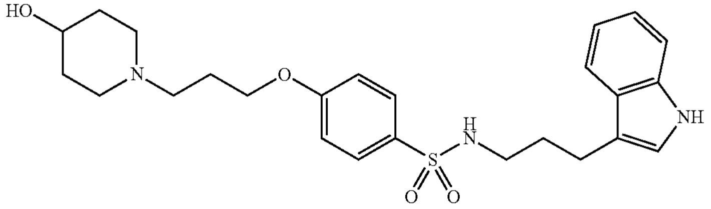 [SMILES: O=S(=O)(NCCCc1c[nH]c2ccccc12)c1ccc(OCCCN2CCC(O)CC2)cc1] | N-(3-(1H-indol-3-yl)propyl)-4-(3-(4-hydroxy-piperidin-1-yl)propoxy)benzene-sulfonamide | $^1$H NMR (400 MHz, $CDCl_3$) δ 8.12 (s, 1H), 7.71 (d, J = 8.9 Hz, 2H), 7.49 (d, J = 8.0 Hz, 1H), 7.35 (d, J = 8.1 Hz, 1H), 7.19 (t, J = 7.2 Hz, 1H), 7.09 (t, J = 7.1 Hz, 1H), 6.92 (d, J = 8.8 Hz, 3H), 4.25 (t, J = 6.2 Hz, 1H), 4.07 (t, J = 6.3 Hz, 2H), 3.73 (s, 1H), 3.00 (dd, J = 13.3, 6.8 Hz, 2H), 2.80 (ddd, J = 23.9, 12.3, 5.4 Hz, 4H), 2.52 (t, J = 7.1 Hz, 2H), 2.24-2.11 (m, 2H), 2.04-1.96 (m, 2H), 1.95-1.80 (m, 4H), 1.66-1.59 (m, 2H); 472 $[M + H]^+$ |
| 70 | 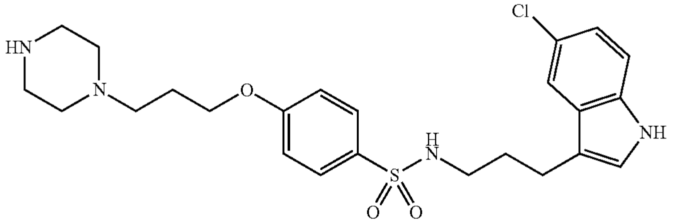 | N-(3-(5-chloro-1H-indol-3-yl)propyl)-4-(3-(piperazin-1-yl)propoxy)benzene-sulfonamide | $^1$H NMR (400 MHz, $CDCl_3$) δ 8.21 (s, 1H), 7.71 (d, J = 8.7 Hz, 2H), 7.44 (d, J = 1.3 Hz, 1H), 7.28 (s, 1H), 7.13 (dd, J = 8.5, 1.7 Hz, 1H), 6.94 (d, J = 8.9 Hz, 3H), 4.24 (t, J = 6.0 Hz, 1H), 4.08 (t, J = 6.3 Hz, 2H), 2.99 (dd, J = 13.4, 6.8 Hz, 2H), 2.91 (t, J = 4.8 Hz, 4H), 2.71 (t, J = 7.2 Hz, 2H), 2.56-2.49 (m, 2H), 2.49-2.36 (m, 4H), 2.04-1.94 (m, 2H), 1.83 (dt, J = 13.9, 7.0 Hz, 2H); 491 [M] |
| 71 | 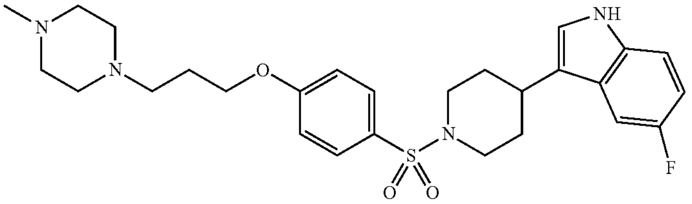 | 5-fluoro-3-(1-((4-(3-(4-methyl-piperazin-1-yl)propoxy)phenyl-sulfonyl)piperidin-4-yl)-1H-indole | $^1$H NMR (400 MHz, $CDCl_3$) δ 8.03 (s, 1H), 7.74 (d, J = 8.8 Hz, 2H), 7.27 (d, J = 8.7 Hz, 1H), 7.13 (dd, J = 9.7, 2.0 Hz, 1H), 7.02 (t, J = 7.4 Hz, 2H), 6.99 (t, J = 3.1 Hz, 1H), 6.93 (td, J = 9.1, 2.2 Hz, 1H), 4.11 (t, J = 6.3 Hz, 2H), 3.91 (d, J = 11.3 Hz, 2H), 2.73-2.65 (m, 1H), 2.63-2.34 (m, 12H), 2.31 (s, 3H), 2.03 (dt, J = 14.1, 9.8 Hz, 4H), 1.84 (ddd, J = 25.4, 12.5, 3.9 Hz, 2H); 502 $[M + H]^+$ |

TABLE 1-continued

| Example | Structure | Name | $^1H$ NMR, MS |
|---|---|---|---|
| 72 | 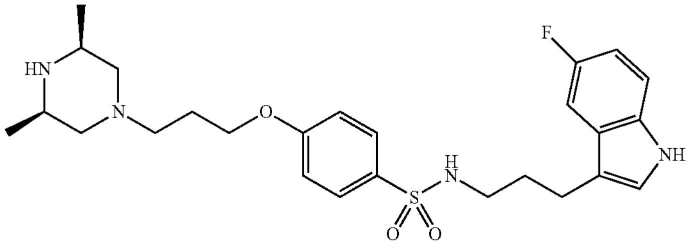 [SMILES: C[C@@H]1CN(CCCOc2ccc(S(=O)(=O)NCCCc3c[nH]c4ccc(F)cc34)cc2)C[C@H](C)N1] | 4-(3-((3S,5R)-3,5-dimethylpiperazin-1-yl)propoxy)-N-(3-(5-fluoro-1H-indol-3-yl)propyl)benzenesulfonamide | $^1H$ NMR (400 MHz, $CDCl_3$) δ 8.15 (s, 1H), 7.71 (d, J = 8.7 Hz, 2H), 7.30-7.22 (m, 1H), 7.10 (dd, J = 9.6, 2.1 Hz, 1H), 6.94 (dt, J = 12.5, 3.0 Hz, 4H), 4.24 (t, J = 6.2 Hz, 1H), 4.07 (t, J = 6.2 Hz, 2H), 3.00 (dd, J = 13.2, 6.6 Hz, 2H), 2.98-2.88 (m, 2H), 2.83 (d, J = 10.7 Hz, 2H), 2.70 (t, J = 7.2 Hz, 2H), 2.52 (t, J = 7.3 Hz, 2H), 2.01 (dt, J = 12.6, 6.4 Hz, 2H), 1.82 (dt, J = 13.8, 7.0 Hz, 2H), 1.07 (s, 3H), 1.06 (s, 13H); 502 [M] |
| 73 | 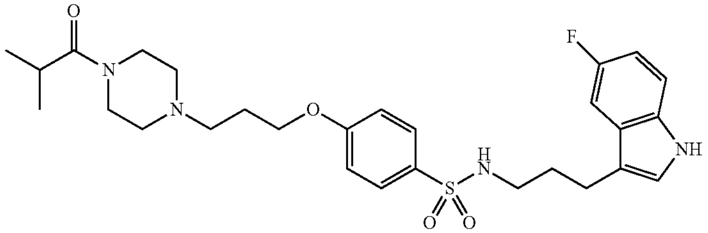 [SMILES: CC(C)C(=O)N1CCN(CCCOc2ccc(S(=O)(=O)NCCCc3c[nH]c4ccc(F)cc34)cc2)CC1] | N-(3-(5-fluoro-1H-indol-3-yl)propyl)-4-(3-(4-isobutyrylpiperazin-1-yl)propoxy)benzenesulfonamide | $^1H$ NMR (400 MHz, $CDCl_3$) δ 8.05 (s, 1H), 7.72 (d, J = 8.8 Hz, 2H), 7.30-7.24 (m, 1H), 7.09 (dd, J = 9.6, 2.2 Hz, 1H), 7.00 (s, 1H), 6.97-6.89 (m, 3H), 4.25 (t, J = 6.4 Hz, 1H), 4.09 (t, J = 6.2 Hz, 2H), 3.71-3.60 (m, 2H), 3.57-3.50 (m, 2H), 3.01 (dd, J = 13.4, 6.7 Hz, 2H), 2.79 (dt, J = 13.6, 6.9 Hz, 1H), 2.70 (d, J = 7.2 Hz, 2H), 2.55 (t, J = 7.1 Hz, 2H), 2.51-2.38 (m, 4H), 2.05-1.93 (m, 2H), 1.87-1.77 (m, 2H), 1.14 (s, 3H), 1.12 (s, 3H); 545 $[M + H]^+$ |
| 74 | 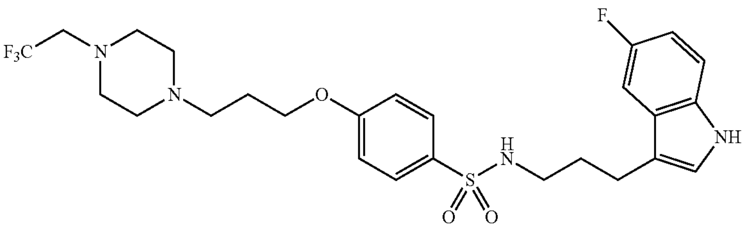 [SMILES: O=S(=O)(NCCCc1c[nH]c2ccc(F)cc12)c1ccc(OCCCN2CCN(CC(F)(F)F)CC2)cc1] | N-(3-(5-fluoro-1H-indol-3-yl)propyl)-4-(3-(4-(2,2,2-trifluoroethyl)piperazin-1-yl)propoxy)benzenesulfonamide | $^1H$ NMR (400 MHz, $CDCl_3$) δ 8.04 (s, 1H), 7.71 (d, J = 8.7 Hz, 2H), 7.30-7.22 (m, 1H), 7.10 (dd, J = 9.6, 2.2 Hz, 1H), 6.99 (t, J = 2.8 Hz, 1H), 6.94 (dd, J = 11.7, 5.5 Hz, 3H), 4.24 (t, J = 6.2 Hz, 1H), 4.07 (t, J = 6.3 Hz, 2H), 3.06-2.92 (m, 4H), 2.71 (t, J = 7.1 Hz, 6H), 2.53 (t, J = 7.1 Hz, 6H), 2.04-1.95 (m, 2H), 1.88-1.76 (m, 2H); 557 $[M + H]^+$ |

TABLE 1-continued

| Example | Structure | Name | $^1$H NMR, MS |
| --- | --- | --- | --- |
| 75 | 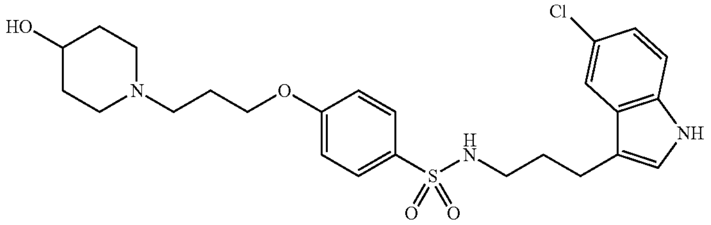 [SMILES: O=S(=O)(NCCCc1c[nH]c2ccc(Cl)cc12)c1ccc(OCCCN2CCC(O)CC2)cc1] | N-(3-(5-chloro-1H-indol-3-yl)propyl)-4-(3-(4-hydroxypiperidin-1-yl)propoxy)benzene-sulfonamide | $^1$H NMR (400 MHz, $CDCl_3$) δ 8.19 (s, 1H), 7.71 (d, J = 8.8 Hz, 2H), 7.44 (d, J = 1.5 Hz, 1H), 7.28 (s, 1H), 7.13 (dd, J = 8.6, 1.8 Hz, 1H), 6.97-6.90 (m, 3H), 4.28-4.19 (m, 1H), 4.08 (t, J = 6.3 Hz, 2H), 3.78-3.67 (m, 1H), 3.49 (s, 1H), 2.99 (dd, J = 13.3, 6.7 Hz, 2H), 2.85-2.76 (m, 2H), 2.71 (t, J = 7.3 Hz, 2H), 2.57-2.47 (m, 2H), 2.21-2.10 (m, 2H), 1.99 (dt, J = 13.1, 6.5 Hz, 2H), 1.95-1.87 (m, 2H), 1.87-1.76 (m, 2H), 1.65-1.59 (m, 2H); 506 [M] |
| 76 | 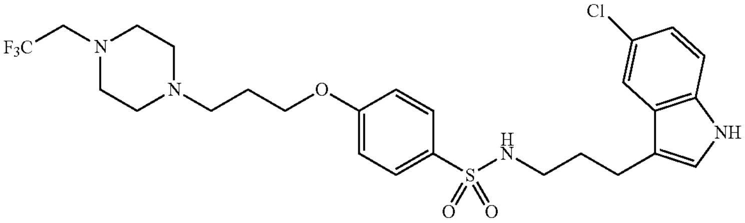 [SMILES: O=S(=O)(NCCCc1c[nH]c2ccc(Cl)cc12)c1ccc(OCCCN2CCN(CC(F)(F)F)CC2)cc1] | N-(3-(5-chloro-1H-indol-3-yl)propyl)-4-(3-(4-(2,2,2-trifluoroethyl)piperazin-1-yl)propoxy)benzene-sulfonamide | $^1$H NMR (400 MHz, $CDCl_3$) δ 8.10 (s, 1H), 7.71 (d, J = 8.8 Hz, 2H), 7.44 (s, 1H), 7.28 (s, 1H), 7.14 (d, J = 8.6 Hz, 1H), 6.97 (s, 1H), 6.93 (d, J = 8.7 Hz, 2H), 4.25-4.21 (m, 1H), 4.07 (t, J = 6.2 Hz, 2H), 3.06-2.91 (m, 4H), 2.71 (t, J = 7.1 Hz, 6H), 2.53 (s, 6H), 2.06-1.93 (m, 4H), 1.83 (dt, J = 14.1, 7.1 Hz, 2H); 573 [M] |
| 77 | 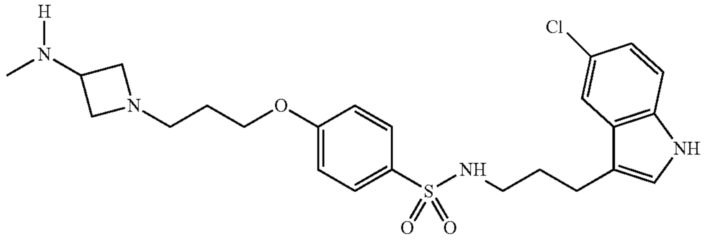 [SMILES: CNC1CN(CCCOc2ccc(S(=O)(=O)NCCCc3c[nH]c4ccc(Cl)cc34)cc2)C1] | N-(3-(5-chloro-1H-indol-3-yl)propyl)-4-(3-(3-(methylamino)azetidin-1-yl)propoxy)benzene-sulfonamide | $^1$H NMR (400 MHz, $CDCl_3$) δ 8.67 (s, 1H), 7.71 (d, J = 8.8 Hz, 2H), 7.44 (s, 1H), 7.25 (s, 1H), 7.13 (d, J = 7.3 Hz, 1H), 6.92 (d, J = 8.7 Hz, 2H), 6.82 (s, 1H), 4.23 (t, J = 6.4 Hz, 1H), 4.07 (t, J = 6.2 Hz, 2H), 3.61 (t, J = 6.8 Hz, 2H), 3.42-3.33 (m, 1H), 2.98 (dd, J = 13.2, 6.6 Hz, 2H), 2.78 (t, J = 6.5 Hz, 2H), 2.68 (t, J = 7.0 Hz, 2H), 2.64 (t, J = 7.0 Hz, 2H), 2.37 (s, 3H), 1.90-1.83 (m, 2H), 1.79 (dd, J = 14.1, 7.0 Hz, 2H); 491 [M] |

TABLE 1-continued

| Example | Structure | Name | $^1$H NMR, MS |
|---|---|---|---|
| 78 | 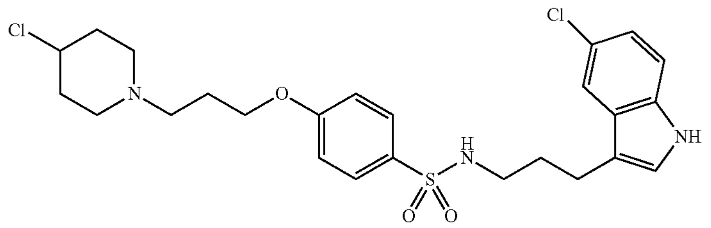 [SMILES: O=S(=O)(NCCCc1c[nH]c2ccc(Cl)cc12)c1ccc(OCCCN2CCC(Cl)CC2)cc1] | N-(3-(5-chloro-1H-indol-3-yl)propyl)-4-(3-(4-chloro-piperidin-1-yl)propoxy)benzene-sulfonamide | $^1$H NMR (400 MHz, $CDCl_3$) δ 8.11 (s, 1H), 7.71 (d, J = 8.7 Hz, 2H), 7.44 (s, 1H), 7.28 (s, 1H), 7.14 (d, J = 8.8 Hz, 1H), 6.97 (s, 1H), 6.93 (d, J = 8.7 Hz, 2H), 4.24 (t, J = 6.5 Hz, 1H), 4.07 (t, J = 6.3 Hz, 2H), 3.00 (dd, J = 13.2, 6.6 Hz, 2H), 2.78 (s, 2H), 2.72 (t, J = 7.2 Hz, 2H), 2.53 (t, J = 7.2 Hz, 2H), 2.36-2.16 (m, 3H), 2.14-2.09 (s, 2H), 2.03-1.94 (m, 2H), 1.94-1.87 (m, 2H), 1.87-1.78 (m, 2H); 524 [M] |
| 79 | 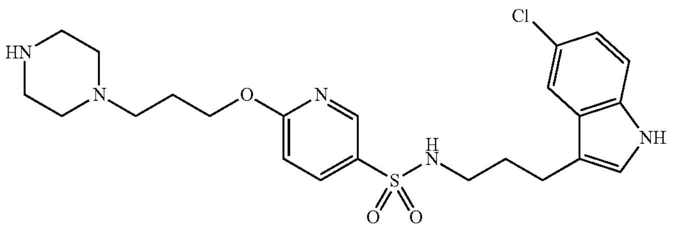 [SMILES: O=S(=O)(NCCCc1c[nH]c2ccc(Cl)cc12)c1ccc(OCCCN2CCNCC2)nc1] | N-(3-(5-chloro-1H-indol-3-yl)propyl)-6-(3-(piperazin-1-yl)pro-poxy)pyridin-3-sulfonamide | $^1$H NMR (400 MHz, MeOD) δ 8.56 (d, J = 1.9 Hz, 1H), 8.01 (dd, J = 8.7, 2.3 Hz, 1H), 7.42 (s, 1H), 7.29 (d, J = 8.6 Hz, 1H), 7.05 (d, J = 8.3 Hz, 2H), 6.90 (d, J = 8.8 Hz, 1H), 4.48 (t, J = 5.9 Hz, 2H), 3.50 (d, J = 4.4 Hz, 4H), 3.38 (s, 4H), 3.25-3.14 (m, 2H), 2.95 (t, J = 6.9 Hz, 2H), 2.71 (t, J = 7.4 Hz, 2H), 2.22 (dd, J = 12.8, 6.7 Hz, 2H), 2.05 (d, J = 5.5 Hz, 1H), 1.87-1.74 (m, 2H), 0.92 (t, J = 6.6 Hz, 1H); 492.06 [M] |
| 80 | 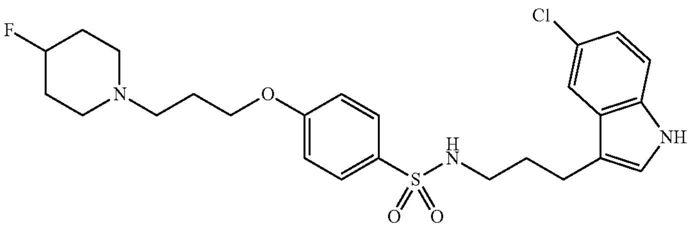 [SMILES: O=S(=O)(NCCCc1c[nH]c2ccc(Cl)cc12)c1ccc(OCCCN2CCC(F)CC2)cc1] | N-(3-(5-chloro-1H-indol-3-yl)propyl)-4-(3-(4-fluoro-piperidin-1-yl)propoxy)benzene-sulfonamide | $^1$H NMR (400 MHz, MeOD) δ 7.72 (d, J = 8.7 Hz, 2H), 7.42 (s, 1H), 7.29 (d, J = 8.6 Hz, 1H), 7.03 (dd, J = 10.2, 8.0 Hz, 4H), 4.75 (s, 1H), 4.62 (s, 1H), 4.11 (t, J = 6.1 Hz, 2H), 2.90 (t, J = 7.0 Hz, 2H), 2.69 (t, J = 7.3 Hz, 4H), 2.62-2.56 (m, 2H), 2.50 (s, 2H), 2.07-1.94 (m, 4H), 1.92-1.83 (m, 2H), 1.78 (dt, J = 14.3, 7.2 Hz, 2H); 508 [M] |
| 81 | 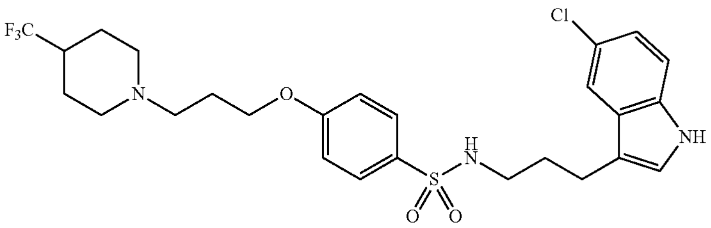 | N-(3-(5-chloro-1H-indol-3-yl)propyl)-4-(3-(4-(trifluoromethyl) piperidin-1-yl)propoxy) benzenesulfonamide | $^1$H NMR (400 MHz, $CDCl_3$) δ 8.04 (s, 1H), 7.72 (d, J = 8.7 Hz, 2H), 7.44 (s, 1H), 7.27 (d, J = 7.9 Hz, 2H), 7.14 (d, J = 8.7 Hz, 1H), 6.99 (s, 1H), 6.94 (d, J = 8.8 Hz, 2H), 4.24 (t, J = 6.3 Hz, 1H), 4.07 (t, J = 6.3 Hz, 2H), 3.00 (dd, J = 13.4, |

TABLE 1-continued

| Example | Structure | Name | $^1$H NMR, MS |
|---|---|---|---|
| | | | 6.6 Hz, 2H), 2.72 (t, J = 7.2 Hz, 2H), 2.58 (t, J = 6.9 Hz, 6H), 2.07-1.94 (m, 6H), 1.85-1.78 (m, 2H); 558 [M] |
| 82 | 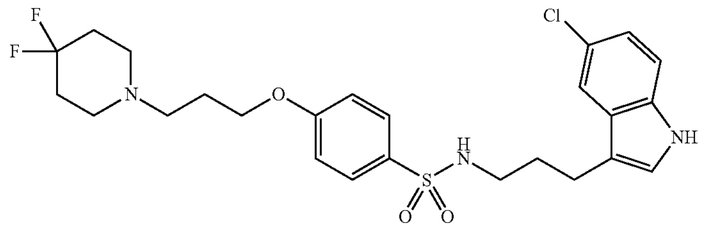 [SMILES: O=S(=O)(NCCCc1c[nH]c2ccc(Cl)cc12)c1ccc(OCCCN2CCC(F)(F)CC2)cc1] | N-(3-(5-chloro-1H-indol-3-yl)propyl)-4-(3-(4,4-difluoropiperidin-1-yl)propoxy) benzenesulfonamide | $^1$H NMR (400 MHz, MeOD) δ 7.73 (d, J = 8.8 Hz, 2H), 7.42 (s, 1H), 7.29 (d, J = 8.6 Hz, 1H), 7.04 (dd, J = 10.0, 7.3 Hz, 4H), 4.12 (t, J = 6.2 Hz, 2H), 2.91 (t, J = 6.9 Hz, 2H), 2.73-2.66 (m, 2H), 2.63 (t, J = 7.3 Hz, 6H), 2.20 (dd, J = 15.5, 7.0 Hz, 1H), 2.10-1.94 (m, 6H), 1.84-1.73 (m, 2H); 526 [M] |
| 83 | 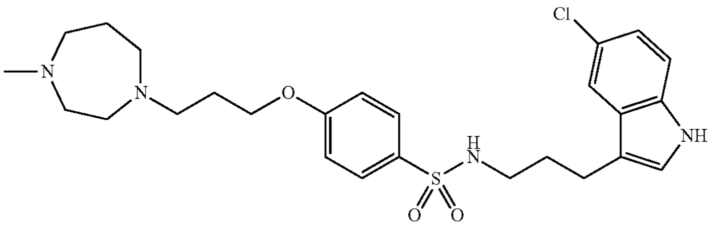 [SMILES: CN1CCCN(CCCOc2ccc(S(=O)(=O)NCCCc3c[nH]c4ccc(Cl)cc34)cc2)CC1] | N-(3-(5-chloro-1H-indol-3-yl)propyl)-4-(3-(4-methyl-1,4-diazepan-1-yl)propoxy)benzenesulfonamide | $^1$H NMR (400 MHz, $CDCl_3$) δ 8.37 (s, 1H), 7.71 (d, J = 8.8 Hz, 2H), 7.44 (d, J = 1.6 Hz, 1H), 7.29-7.22 (m, 1H), 7.13 (dd, J = 8.6, 1.8 Hz, 1H), 6.96-6.88 (m, 2H), 4.33 (t, J = 5.9 Hz, 1H), 4.08 (t, J = 6.3 Hz, 2H), 3.00 (q, J = 6.5 Hz, 2H), 2.80-2.73 (m, 4H), 2.69 (dd, J = 14.4, 7.3 Hz, 4H), 2.66-2.59 (m, 4H), 2.37 (s, 3H), 1.95 (dt, J = 13.3, 6.5 Hz, 2H), 1.87-1.78 (m, 4H); 519 [M] |
| 84 | 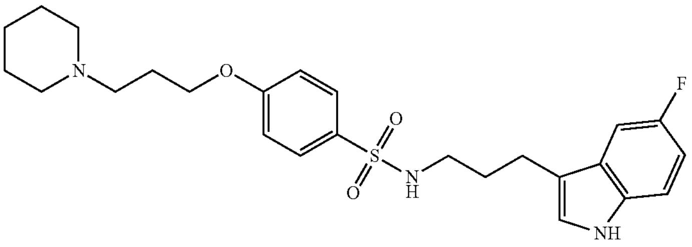 [SMILES: O=S(=O)(NCCCc1c[nH]c2ccc(F)cc12)c1ccc(OCCCN2CCCCC2)cc1] | N-(3-(5-fluoro-1H-indol-3-yl)propyl)-4-(3-(piperidin-1-yl)propoxy)benzenesulfonamide | $^1$H NMR (400 MHz, $CDCl_3$) δ 8.27 (br s, 1H), 7.70 (d, J = 8.7 Hz, 2H), 7.29-7.21 (m, 1H), 7.10 (dd, J = 9.6, 2.0 Hz, 1H), 6.97-6.88 (m, 4H), 4.29 (t, J = 6.2 Hz, 1H), 4.08 (t, J = 6.3 Hz, 2H), 2.99 (q, J = 6.6 Hz, 2H), 2.69 (t, J = 7.2 Hz, 2H), 2.56-2.49 (m, 2H), 2.49-2.35 (m, 4H), 2.02 (p, J = 13.3, 7.0 Hz, 2H), 1.82 (p, J = 13.3, 7.0 Hz, 2H), 1.64-1.60 (m, 4H), 1.46 (s, 2H); 474 [M + H]$^+$ |

TABLE 1-continued

| Example | Structure | Name | $^1$H NMR, MS |
|---|---|---|---|
| 85 | 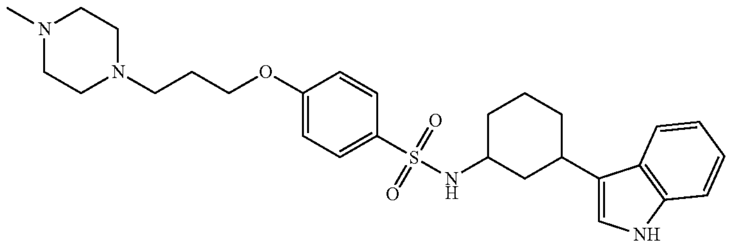 [SMILES: CN1CCN(CCCOc2ccc(S(=O)(=O)NC3CCCC(c4c[nH]c5ccccc45)C3)cc2)CC1] | N-(3-(1H-indol-3-yl)cyclohexyl)-4-(3-(4-methylpiperazin-1-yl)propoxy)benzene-sulfonamide | $^1$H NMR (400 MHz, $CDCl_3$) δ 8.14 (br s, 1H), 7.80 (d, J = 8.8 Hz, 2H), 7.47 (d, J = 8.0 Hz, 1H), 7.34 (d, J = 8.1 Hz, 1H), 7.17 (t, J = 7.6 Hz, 1H), 7.06 (t, J = 7.5 Hz, 1H), 6.91 (d, J = 8.8 Hz, 2H), 6.86-6.82 (m, 1H), 4.68 (d, J = 6.9 Hz, 1H), 4.03 (t, J = 6.3 Hz, 2H), 3.73-3.65 (m, 1H), 3.08-2.98 (m, 1H), 2.58-2.49 (m, 5H), 2.31 (s, 3H), 2.06-1.92 (m, 4H), 1.74-1.63 (m, 4H), 1.62-1.51 (m, 2H); 511 $[M + H]^+$ |
| 86 | 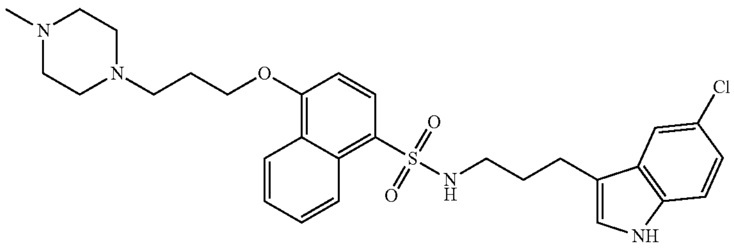 [SMILES: CN1CCN(CCCOc2ccc(S(=O)(=O)NCCCc3c[nH]c4ccc(Cl)cc34)c3ccccc23)CC1] | N-(3-(5-chloro-1H-indol-3-yl)propyl)-4-(3-(4-methylpiperazin-1-yl)propoxy)naphthalene-1-sulfonamide | $^1$H NMR (400 MHz, $CDCl_3$ δ 8.55 (d, J = 8.5 Hz, 1H), 8.37 (d, J = 8.3 Hz, 1H), 8.14 (d, J = 8.2 Hz, 2H), 7.66 (t, J = 7.7 Hz, 1H), 7.57 (t, J = 7.8 Hz, 1H), 7.31 (s, 1H), 7.21 (d, J = 8.5 Hz, 1H), 7.10-7.08 (m, 1H), 6.76 (d, J = 8.4 Hz, 1H), 6.70 (s, 1H), 4.52 (t, J = 6.2 Hz, 1H), 4.27 (t, J = 6.2 Hz, 2H), 2.91 (q, J = 6.5 Hz, 2H), 2.64 (t, J = 7.2 Hz, 2H), 2.56-2.48 (m, 10H), 2.30 (s, 3H), 2.15 (p, J = 6.4 Hz, 2H), 1.72 (p, J = 7.0 Hz, 2H); 556 $[M + H]^+$ |
| 87 | 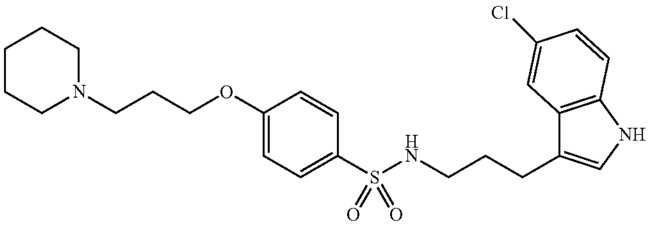 [SMILES: O=S(=O)(NCCCc1c[nH]c2ccc(Cl)cc12)c1ccc(OCCCN2CCCCC2)cc1] | N-(3-(5-chloro-1H-indol-3-yl)propyl)-4-(3-(piperidin-1-yl)propoxy)benzene-sulfonamide | $^1$H NMR (400 MHz, $CDCl_3$ δ 8.33 (br s, 1H), 7.70 (d, J = 8.7 Hz, 2H), 7.44 (s, 1H), 7.26-7.24 (m, 1H), 7.13-7.11 (m, 1H), 6.9 (d, J = 8.8 Hz, 3H), 4.28 (t, J = 6.2 Hz, 1H), 4.07 (t, J = 6.3 Hz, 2H), 2.98 (q, J = 6.6 Hz, 2H), 2.69 (t, J = 7.2 Hz, 2H), 2.49 (t, J = 7.2 Hz, 2H), 2.42 (br s, 4H), 1.99 (p, J = 6.5 Hz, 2H), 1.83 (p, J = 7.0 Hz, 2H), 1.62-1.57 (m, 4H), 1.46-1.45 (m, 2H); 491 $[M +H]^+$ |

TABLE 1-continued

| Example | Structure | Name | $^1$H NMR, MS |
|---|---|---|---|
| 88 | 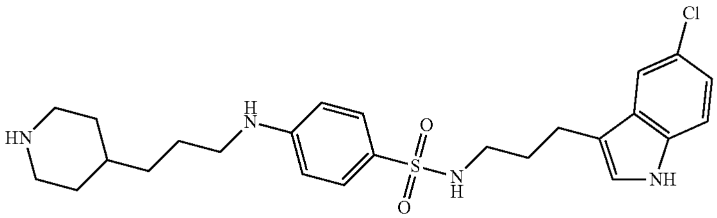 [SMILES: O=S(=O)(NCCCc1c[nH]c2ccc(Cl)cc12)c1ccc(NCCCC2CCNCC2)cc1] | N-(3-(5-chloro-1H-indol-3-yl)propyl)-4-((3-(piperidin-4-yl)propyl)amino)benzenesulfonamide | $^1$H NMR (400 MHz, DMSO δ 10.97 (s, 1H), 7.50 (s, 1H), 7.43 (d, J = 8.6 Hz, 2H), 7.32 (d, J = 8.6 Hz, 1H), 7.15-7.13 (m, 2H), 7.05-7.03 (m, 1H), 6.59 (d, J = 8.7 Hz, 2H), 6.44 (t, J = 5.0 Hz, 1H), 3.02 (q, J = 5.9 Hz, 2H), 2.92 (d, J = 11.7 Hz, 2H), 2.71-2.68 (m, 2H), 2.60 (t, J = 7.4 Hz, 2H), 2.45-2.42 (m, 1H), 1.67 (p, J = 7.1 Hz, 2H), 1.60-1.50 (m, 4H), 1.28-1.23 (m, 4H), 1.03-0.95 (m, 2H); 490 [M + H]$^+$ |
| 89 | 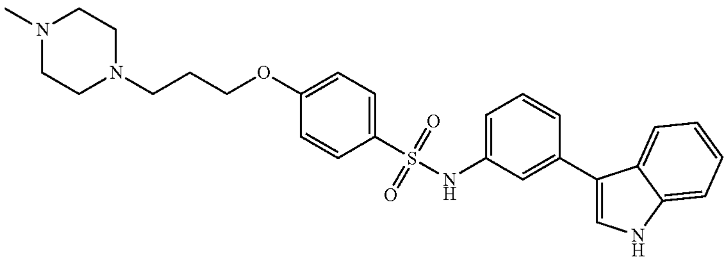 [SMILES: CN1CCN(CCCOc2ccc(S(=O)(=O)Nc3cccc(-c4c[nH]c5ccccc45)c3)cc2)CC1] | N-(3-(1H-indol-3-yl)phenyl)-4-(3-(4-methylpiperazin-1-yl)propoxy)benzenesulfonamide | $^1$H NMR 400 MHz, $CDCl_3$ 8.57 (br s, 1H), 7.73-7.71 (m, 3H), 7.42-7.40 (m, 2H), 7.33-7.28 (m, 4H), 7.26-7.21 (m, 1H), 7.15 (t, J = 7.8 Hz, 1H), 7.00 (d, J = 8.1 Hz, 1H), 6.88 (d, J = 8.8 Hz, 2H), 4.01 (t, J = 6.3 Hz, 2H), 2.51-2.47 (m, 10H), 2.29 (s, 3H), 1.94 (p, J = 6.9 Hz, 2H); 505 [M + H]$^+$ |
| 90 | 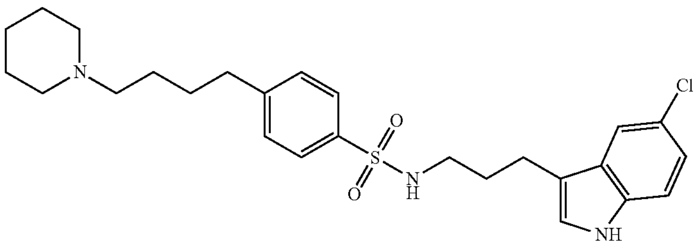 [SMILES: O=S(=O)(NCCCc1c[nH]c2ccc(Cl)cc12)c1ccc(CCCCN2CCCCC2)cc1] | N-(3-(5-chloro-1H-indol-3-yl)propyl)-4-(4-(piperidin-1-yl)butyl) benzenesulfonamide | $^1$H NMR (400 MHz, $CDCl_3$) δ 9.44 (br s, 1H), 7.66 (d, J = 8.1 Hz, 2H), 7.48-7.43 (m, 1H), 7.23 (d, J = 8.4 Hz, 3H), 7.26-7.20 (m, 1H), 6.79-6.72 (m, 1H), 4.29 (t, J = 6.1 Hz, 1H), 2.95 (q, J = 6.6 Hz, 2H), 2.69 (t, J = 7.0 Hz, 4H), 2.58-2.39 (m, 4H), 2.39-2.31 (m, 2H), 1.85-1.76 (m, 2H), 1.68-1.58 (m, 6H), 1.54-1.40 (m, 4H); 488 [M + H]$^+$ |
| 91 | 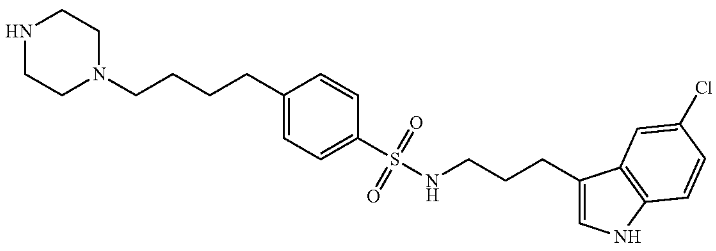 [SMILES: O=S(=O)(NCCCc1c[nH]c2ccc(Cl)cc12)c1ccc(CCCCN2CCNCC2)cc1] | N-(3-(5-chloro-1H-indol-3-yl)propyl)-4-(4-(piperazin-1-yl)butyl) benzenesulfonamide | $^1$H NMR (400 MHz, $CDCl_3$) δ 8.83 (br s, 1H), 7.69 (d, J = 8.1 Hz, 2H), 7.47-7.42 (m, 1H), 7.25-7.20 (m, 2H), 7.12 (dd, J = 8.7, 1.6 Hz, 1H), 6.89-6.83 (m, 1H), 4.39 (br s, 1H), 2.98 (t, J = 6.7 Hz, 2H), 2.92 (t, J = 4.8 Hz, 4H), 2.70 (t, J = 6.7 Hz, 4H), 2.57-2.40 (m, 4H), 2.40-2.32 (m, 2H), 1.99-1.84 (m, 4H), 1.84-1.76 |

TABLE 1-continued

| Example | Structure | Name | $^1$H NMR, MS |
|---|---|---|---|
| | | | (m, 2H), 1.70-1.58 (m, 2H), 1.55-1.42 (m, 2H); 489 [M + H]$^+$ |
| 92 | 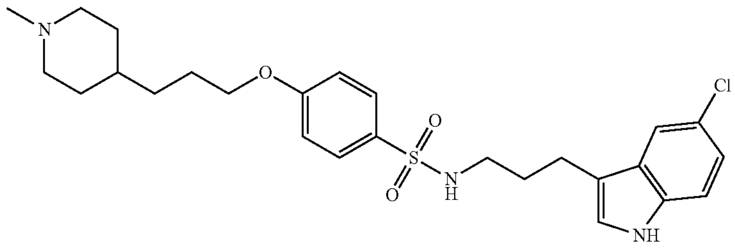 [SMILES: CN1CCC(CCCOc2ccc(S(=O)(=O)NCCCc3c[nH]c4ccc(Cl)cc34)cc2)CC1] | N-(3-(5-chloro-1H-indol-3-yl)propyl)-4-(3-(1-methylpiperidin-4-yl)propoxy)benzenesulfonamide | $^1$H NMR (400 MHz, $CDCl_3$ δ 8.16 (br s, 1H), 7.71 (d, J = 8.7 Hz, 2H), 7.44 (s, 1H), 7.28-7.26 (m, 1H), 7.13 (d, J = 8.6 Hz, 1H), 6.99 (s, 1H), 6.92 (d, J = 8.7 Hz, 2H), 4.29 (t, J = 5.8 Hz, 1H), 3.99 (t, J = 6.4 Hz, 2H), 2.99 (q, J = 6.6 Hz, 2H), 2.91 (t, J = 10.8 Hz, 2H), 2.30 (s, 3H), 2.05-1.93 (m, 4H), 1.86-1.78 (m, 4H), 1.72 (d, J = 9.4 Hz, 2H), 1.42-1.40 (m, 1H); 505 [M + H]$^+$ |
| 93 | 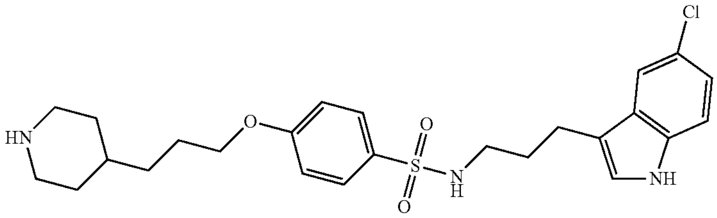 [SMILES: O=S(=O)(NCCCc1c[nH]c2ccc(Cl)cc12)c1ccc(OCCCC2CCNCC2)cc1] | N-(3-(5-chloro-1H-indol-3-yl)propyl)-4-(3-(piperidin-4-yl)propoxy)benzenesulfonamide | $^1$H NMR (400 MHz, $CDCl_3$ δ 8.13 (br s, 1H), 7.72 (d, J = 8.7 Hz, 2H), 7.45 (s, 1H), 7.28-7.26 (m, 1H), 7.14 (d, J = 8.6 Hz, 1H), 6.99 (s, 1H), 6.93 (d, J = 8.7 Hz, 2H), 4.31 (br s, 1H), 3.99 (t, J = 6.4 Hz, 2H), 3.09 (d, J = 12.1 Hz, 2H), 3.00 (t, J = 6.6 Hz, 2H), 2.72 (t, J = 7.2 Hz, 2H), 2.60 (t, J = 11.8 Hz, 2H), 1.85-1.81 (m, 4H), 1.71 (d, J = 12.5 Hz, 4H), 1.41-1.38 (m, 3H), 1.19-1.10 (m, 1H); 491 [M + H]$^+$ |
| 94 | 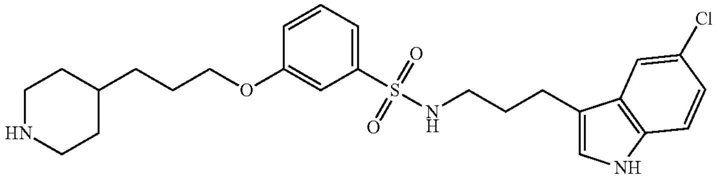 [SMILES: O=S(=O)(NCCCc1c[nH]c2ccc(Cl)cc12)c1cccc(OCCCC2CCNCC2)c1] | N-(3-(5-chloro-1H-indol-3-yl)propyl)-3-(3-(piperidin-4-yl)propoxy)benzenesulfonamide | $^1$H NMR (400 MHz, $CDCl_3$ δ 8.21 (br s, 1H), 7.44 (s, 1H), 7.39-7.37 (m, 2H), 7.32 (s, 1H), 7.28-7.26 (m, 1H), 7.13 (d, J = 8.4 Hz, 1H), 7.08-7.07 (m, 1H), 6.99 (s, 1H), 4.40 (br s, 1H), 3.96 (t, J = 6.4 Hz, 2H), 3.09 (d, J = 12.1 Hz, 2H), 3.03 (t, J = 6.8 Hz, 2H), 2.73 (t, J = 7.2 Hz, 2H), 2.60 (t, J = 11.4 Hz, 2H), 1.88-1.77 (m, 4H), 1.72-1.69 (m, 4H), 1.40-1.37 (m, 3H), 1.19-1.10 (m, 1H); 491 [M + H]$^+$ |

TABLE 1-continued

| Example | Structure | Name | $^1$H NMR, MS |
|---|---|---|---|
| 95 | 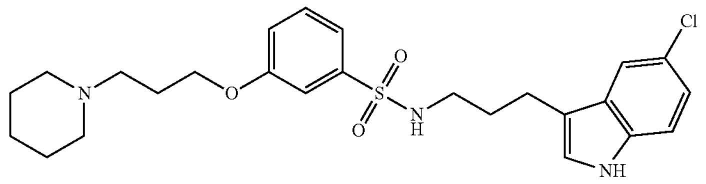 [SMILES: O=S(=O)(NCCCc1c[nH]c2ccc(Cl)cc12)c1cccc(OCCCN2CCCCC2)c1] | N-(3-(5-chloro-1H-indol-3-yl)propyl)-3-(3-(piperidin-1-yl)propoxy)benzenesulfonamide | $^1$H NMR (400 MHz, $CDCl_3$) δ 8.97 (br s, 1H), 7.42-7.39 (m, 1H), 7.36-7.28 (m, 2H), 7.25-7.22 (m, 2H), 7.14-7.09 (m, 1H), 7.01-6.96 (m, 1H), 6.94-6.91 (m, 1H), 4.36 (t, J = 6.0 Hz, 1H), 4.01 (t, J = 6.2 Hz, 2H), 2.98 (dd, J = 13.2, 6.7 Hz, 2H), 2.71 (t, J = 7.0 Hz, 2H), 2.66-2.59 (m, 2H), 2.59-2.44 (m, 4H), 2.10-2.00 (m, 2H), 1.87-1.80 (m, 2H), 1.71-1.56 (m, 4H), 1.54-1.42 (m, 2H).; 490 $[M + H]^+$ |
| 96 | 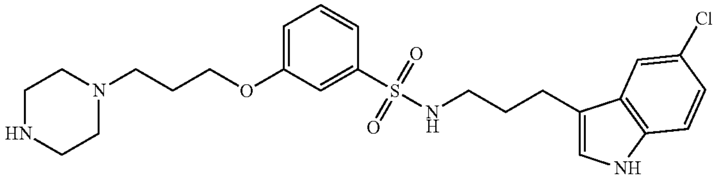 [SMILES: O=S(=O)(NCCCc1c[nH]c2ccc(Cl)cc12)c1cccc(OCCCN2CCNCC2)c1] | N-(3-(5-chloro-1H-indol-3-yl)propyl)-3-(3-(piperazin-1-yl)propoxy)benzenesulfonamide | $^1$H NMR (400 MHz, $CDCl_3$) δ 8.53 (br s, 1H), 7.44-7.40 (m, 1H), 7.38-7.31 (m, 2H), 7.28 (s, 1H), 7.26-7.22 (m, 1H), 7.15-7.10 (m, 1H), 7.07-7.00 (m, 1H), 6.98-6.94 (m, 1H), 4.40-4.28 (m, 1H), 4.03 (t, J = 6.2 Hz, 2H), 3.06-2.95 (m, 2H), 2.92 (t, J = 4.8 Hz, 4H), 2.72 (t, J = 7.1 Hz, 2H), 2.53 (t, J = 7.2 Hz, 2H), 2.51-2.40 (m, 4H), 1.99 (p, J = 13.4, 6.7 Hz, 2H), 1.84 (p, J = 13.7, 6.8 Hz, 2H); 491 $[M +H]^+$ |
| 97 | 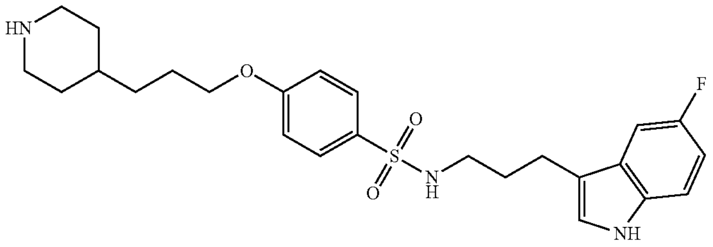 [SMILES: O=S(=O)(NCCCc1c[nH]c2ccc(F)cc12)c1ccc(OCCCC2CCNCC2)cc1] | N-(3-(5-fluoro-1H-indol-3-yl)propyl)-4-(3-(piperidin-4-yl)propoxy)benzenesulfonamide | $^1$H NMR (400 MHz, $CDCl_3$) δ 8.19 (br s, 1H), 7.72 (d, J = 8.7 Hz, 2H), 7.26-7.22 (m, 1H), 7.09 (dd, J = 9.6, 2.2 Hz, 1H), 6.99 (s, 1H), 6.95-6.88 (m, 3H), 3.98 (t, J = 6.4 Hz, 2H), 3.09 (d, J = 12.1 Hz, 2H), 2.99 (t, J = 6.9 Hz, 2H), 2.70 (t, J = 7.2 Hz, 2H), 2.60 (t, J = 11.5 Hz, 2H), 1.86-1.75 (m, 4H), 1.75-1.63 (m, 3H), 1.45-1.30 (m, 2H), 1.30-1.20 (m, 1H), 1.19-1.05 (m, 2H); 474 $[M + H]^+$ |
| 98 | 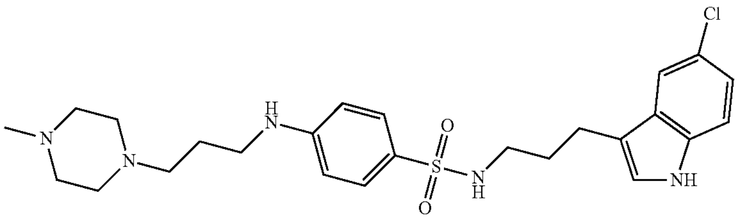 [SMILES: CN1CCN(CCCNc2ccc(S(=O)(=O)NCCCc3c[nH]c4ccc(Cl)cc34)cc2)CC1] | N-(3-(5-chloro-1H-indol-3-yl)propyl)-4-((3-(4-methylpiperazin-1-yl)propyl)amino)benzenesulfonamide | $^1$H NMR (400 MHz, $CDCl_3$ δ 8.31 (br s, 1H), 7.57 (d, J = 8.7 Hz, 2H), 7.44 (d, J = 1.7 Hz, 1H), 7.26-7.24 (m, 1H), 7.11 (dd, J = 8.6, 1.9 Hz, 1H), 6.95 (d, J = 1.9 Hz, 1H), 6.52 (d, J = 8.8 Hz, 2H), 5.74 (br s, 1H), 4.39 |

TABLE 1-continued

| Example | Structure | Name | $^1$H NMR, MS |
|---|---|---|---|
| | | | (t, J = 6.2 Hz, 1H), 3.23 (t, J = 6.2 Hz, 2H), 2.96 (q, J = 6.5 Hz, 2H), 2.69 (t, J = 7.2 Hz, 2H), 2.53-2.50 (m, 10H), 2.32 (s, 3H), 1.83-1.76 (m, 4H); 505 $[M + H]^+$ |
| 99 | 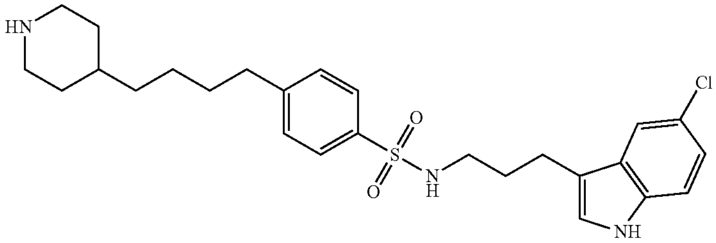 [SMILES: O=S(=O)(NCCCc1c[nH]c2ccc(Cl)cc12)c1ccc(CCCCC2CCNCC2)cc1] | N-(3-(5-chloro-1H-indol-3-yl)propyl)-4-(4-(piperidin-4-yl)butyl)benzene-sulfonamide | $^1$H NMR (400 MHz, $CDCl_3$) δ 8.25 (br s, 1H), 7.70 (d, J = 8.3 Hz, 2H), 7.43 (d, J = 1.9 Hz, 1H), 7.28 (d, J = 4.5 Hz, 2H), 7.26-7.24 (m, 1H), 7.13 (dd, J = 8.6, 1.9 Hz, 1H), 6.98 (s, 1H), 3.10-3.03 (m, 2H), 3.01 (t, J = 6.9 Hz, 2H), 2.71 (t, J = 7.2 Hz, 2H), 2.69-2.62 (m, 2H), 2.61-2.52 (m, 2H), 2.60-2.00 (m, 1H), 1.87-1.78 (m, 4H), 1.66-1.56 (m, 2H), 1.36-1.18 (m, 4H), 1.14-1.02 (m, 2H); 488 $[M + H]^+$ |
| 100 | 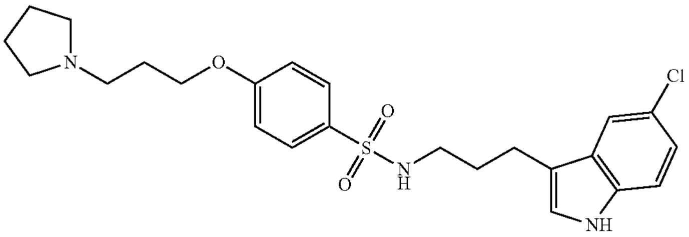 [SMILES: O=S(=O)(NCCCc1c[nH]c2ccc(Cl)cc12)c1ccc(OCCCN2CCCC2)cc1] | N-(3-(5-chloro-1H-indol-3-yl)propyl)-4-(3-(pyrrolidin-1-yl)propoxy)benzene-sulfonamide | $^1$H NMR (400 MHz, DMSO δ 10.94 (br s, 1H), 7.67 (d, J = 8.8 Hz, 2H), 7.48-7.44 (m, 2H), 7.32 (d, J = 8.6 Hz, 1H), 7.12 (d, J = 1.5 Hz, 1H), 7.07-7.02 (m, 3H), 4.07 (t, J = 6.4 Hz, 2H), 2.75 (br s, 2H), 2.60 (t, J = 7.4 Hz, 2H), 2.40 (br s, 4H), 1.89 (p, J = 6.7 Hz, 2H), 1.71-1.63 (m, 6H); 477 $[M + H]^+$ |
| 101 | 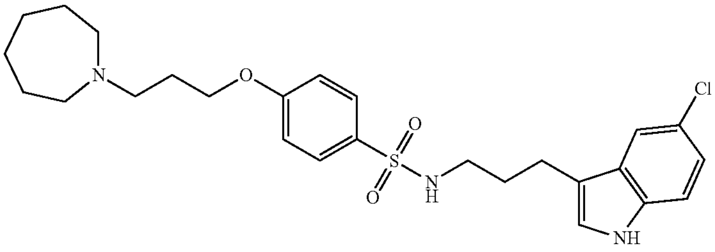 [SMILES: O=S(=O)(NCCCc1c[nH]c2ccc(Cl)cc12)c1ccc(OCCCN2CCCCCC2)cc1] | 4-(3-(azepan-1-yl)propoxy)-N-(3-(5-chloro-1H-indol-3-yl)propyl)benzene-sulfonamide | $^1$H NMR (400 MHz, $CDCl_3$) δ 8.53 (br s, 1H), 7.70 (d, J = 8.9 Hz, 2H), 7.42 (d, J = 1.8 Hz, 1H), 7.26 (d, J = 2.1 Hz, 1H), 7.10 (dd, J = 8.6, 1.9 Hz, 1H), 6.89 (d, J = 8.8 Hz, 3H), 4.72-4.58 (m, 1H), 4.05 (t, J = 6.2 Hz, 2H), 3.00-2.91 (m, 2H), 2.80-2.71 (m, 6H), 2.67 (t, J = 7.2 Hz, 2H), 2.06-1.97 (m, 2H), 1.79 (p, J = 7.0 Hz, 2H), 1.74-1.65 (m, 4H), 1.65-1.56 (m, 4H); 504 $[M + H]^+$ |

TABLE 1-continued

| Example | Structure | Name | $^1$H NMR, MS |
|---|---|---|---|
| 102 | 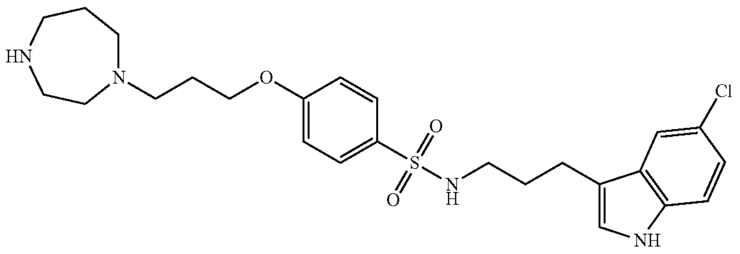 [SMILES: O=S(=O)(NCCCc1c[nH]c2ccc(Cl)cc12)c1ccc(OCCCN2CCCNCC2)cc1] | 4-(3-(1,4-diazepan-1-yl)propoxy)-N-(3-(5-chloro-1H-indol-3-yl)propyl)benzene-sulfonamide | $^1$H NMR (400 MHz, MeOD) δ 7.72 (d, J = 8.9 Hz, 2H), 7.41-7.38 (m, 1H), 7.28 (d, J = 8.6 Hz, 1H), 7.07-6.98 (m, 4H), 4.12 (t, J = 6.1 Hz, 2H), 3.30-3.20 (m, 4H), 2.96-2.86 (m, 4H), 2.84-2.73 (m, 4H), 2.67 (t, J = 7.4 Hz, 2H), 2.02-1.93 (m, 4H), 1.77 (p, J = 14.4, 7.2 Hz, 2H); 505 [M + H]$^+$ |
| 103 | 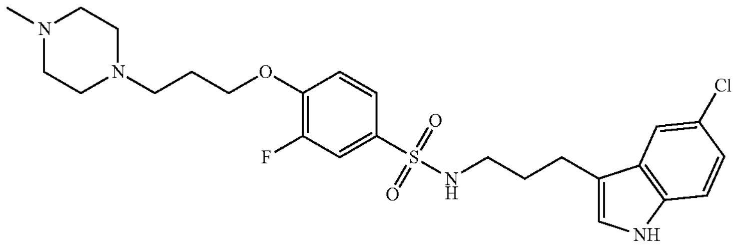 [SMILES: CN1CCN(CCCOc2ccc(S(=O)(=O)NCCCc3c[nH]c4ccc(Cl)cc34)cc2F)CC1] | N-(3-(5-chloro-1H-indol-3-yl)propyl)-3-fluoro-4-(3-(4-methyl-piperazin-1-yl)propoxy)benzene-sulfonamide | $^1$H NMR (400 MHz, $CDCl_3$ δ 8.20 (br s, 1H), 7.51-7.47 (m, 2H), 7.43 (d, J = 1.6 Hz, 1H), 7.26-7.25 (m, 1H), 7.12 (dd, J = 8.6, 1.9 Hz, 1H), 7.00 (d, J = 8.2 Hz, 1H), 6.96-6.95 (m, 1H), 4.34 (t, J = 6.2 Hz, 1H), 4.14 (t, J = 6.3 Hz, 2H), 2.99 (q, J = 6.5 Hz, 2H), 2.71 (t, J = 7.2 Hz, 2H), 2.56-2.47 (m, 10H), 2.28 (s, 3H), 2.02 (p, J = 6.6 Hz, 2H), 1.84 (p, J = 7.0 Hz, 2H); 524 [M + H]$^+$ |
| 104 | 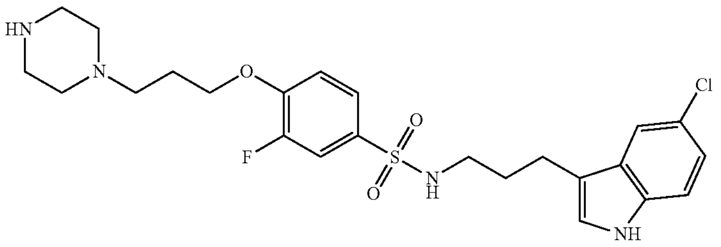 [SMILES: O=S(=O)(NCCCc1c[nH]c2ccc(Cl)cc12)c1ccc(OCCCN2CCNCC2)c(F)c1] | N-(3-(5-chloro-1H-indol-3-yl)propyl)-3-fluoro-4-(3-(piperazin-1-yl)propoxy)benzene-sulfonamide | $^1$H NMR (400 MHz, $CDCl_3$ δ 8.23 (br s, 1H), 7.52-7.48 (m, 2H), 7.44 (d, J = 1.7 Hz, 1H), 7.27-7.24 (m, 1H), 7.12 (dd, J = 8.6, 1.8 Hz, 1H), 7.01-6.95 (m, 2H), 4.33 (br s, 1H), 4.15 (t, J = 6.3 Hz, 2H), 3.00 (br s, 1H), 2.89 (t, J = 4.8 Hz, 4H), 2.72 (t, J = 7.2 Hz, 2H), 2.52 (t, J = 7.1 Hz, 2H), 2.44 (br s, 4H), 2.02 (p, J = 6.6 Hz, 2H), 1.84 (p, J = 7.0 Hz, 2H); 510 [M + H]$^+$ |
| 105 | 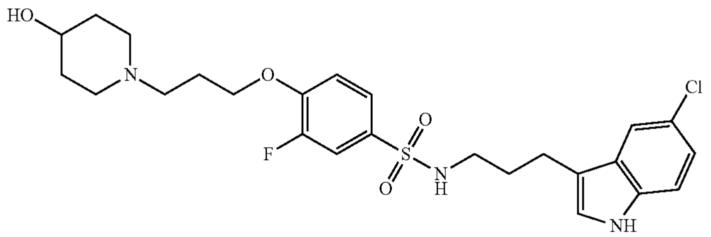 [SMILES: O=S(=O)(NCCCc1c[nH]c2ccc(Cl)cc12)c1ccc(OCCCN2CCC(O)CC2)c(F)c1] | N-(3-(5-chloro-1H-indol-3-yl)propyl)-3-fluoro-4-(3-(4-hydroxypiperidin-1-yl)propoxy)benzene-sulfonamide | $^1$H NMR (400 MHz, DMSO δ 10.95 (br s, 1H), 7.59-7.53 (m, 3H), 7.47 (d, J = 1.9 Hz, 1H), 7.34-7.29 (m, 2H), 7.12 (d, J = 2.1 Hz, 1H), 7.03 (dd, J = 8.6, 2.0 Hz, 1H), 4.52 (d, J = 6.9 Hz, 1H), 4.14 (t, J = 6.4 Hz, 2H), 3.45-3.38 (m, 1H), 2.77 (q, J = 6.3 Hz, 2H), 2.70-2.67 (m, 2H), 2.60 (t, J = 7.4 Hz, 2H), 2.37 (t, J = 7.0 Hz, 2H), 1.98 (t, J = 10.1 Hz, 2H), 1.88 (p, J = 6.5 Hz, |

TABLE 1-continued

| Example | Structure | Name | $^1$H NMR, MS |
|---|---|---|---|
| | | | 2H), 1.71-7.64 (m, 4H), 1.40-1.31 (m, 2H); 525 $[M + H]^+$ |
| 106 | 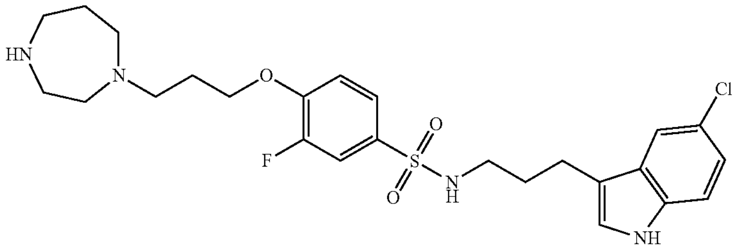 [SMILES: O=S(=O)(NCCCc1c[nH]c2ccc(Cl)cc12)c1ccc(OCCCN2CCCNCC2)c(F)c1] | 4-(3-(1,4-diazepan-1-yl)propoxy)-N-(3-(5-chloro-1H-indol-3-yl)propyl)-3-fluorobenzene-sulfonamide | $^1$H NMR (400 MHz, $CDCl_3$ δ 10.95 (br s, 1H), 7.56-7.53 (m, 2H), 7.47 (d, J = 1.7 Hz, 1H), 7.34-7.30 (m, 2H), 7.12 (d, J = 1.7 Hz, 1H), 7.03 (dd, J = 8.6, 1.9 Hz, 1H), 4.16 (t, J = 6.3 Hz, 2H), 2.79-2.70 (m, 6H), 2.63-2.54 (m, 9H), 1.86 (p, J = 6.4 Hz, 2H), 1.71-1.59 (m, 4H); 524 $[M + H]^+$ |
| 107 | 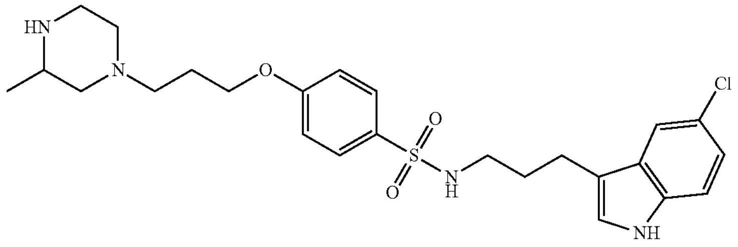 [SMILES: CC1CN(CCCOc2ccc(S(=O)(=O)NCCCc3c[nH]c4ccc(Cl)cc34)cc2)CCN1] | N-(3-(5-chloro-1H-indol-3-yl)propyl)-4-(3-(3-methyl-piperazin-1-yl)propoxy)benzene-sulfonamide | $^1$H NMR (400 MHz, $CDCl_3$) δ 8.23 (br s, 1H), 7.75-7.66 (m, 2H), 7.44 (d, J = 1.9 Hz, 1H), 7.30-7.23 (m, 1H), 7.13 (dd, J = 8.6, 2.0 Hz, 1H), 6.96-6.87 (m, 3H), 4.35-4.27 (m, 1H), 4.07 (t, J = 6.3 Hz, 2H), 3.04-2.79 (m, 7H), 2.71 (t, J = 7.2 Hz, 2H), 2.52 (t, J = 7.3 Hz, 2H), 2.10-1.93 (m, 4H), 1.82 (p, J = 14.1, 7.1 Hz, 2H), 1.06 (d, J = 6.3 Hz, 3H); 505 [ M + $H]^+$ |
| 108 | 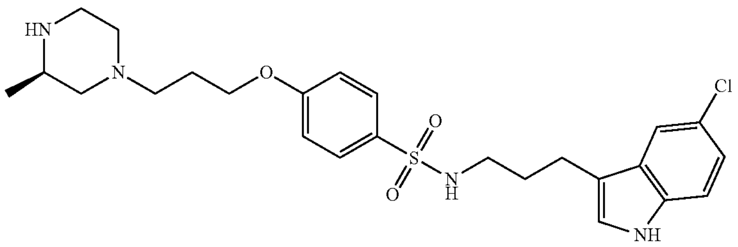 [SMILES: C[C@@H]1CN(CCCOc2ccc(S(=O)(=O)NCCCc3c[nH]c4ccc(Cl)cc34)cc2)CCN1] | (R)-N-(3-(5-chloro-1H-indol-3-yl)propyl)-4-(3-(3-methyl-piperazin-1-yl)propoxy)benzene-sulfonamide | $^1$H NMR (400 MHz, $CDCl_3$) δ 8.23 (br s, 1H), 7.75-7.68 (m, 2H), 7.44 (d, J = 1.9 Hz, 1H), 7.31-7.23 (m, 1H), 7.13 (dd, J = 8.6, 1.9 Hz, 1H), 6.97-6.90 (m, 3H), 4.35-4.26 (m, 1H), 4.07 (t, J = 6.3 Hz, 2H), 3.05-2.78 (m, 7H), 2.71 (t, J = 7.2 Hz, 2H), 2.52 (t, J = 7.3 Hz, 2H), 2.08-1.95 (m, 3H), 1.82 (p, J = 14.1, 7.1 Hz, 2H), 1.75-1.70 (m, 2H), 1.06 (d, J = 6.3 Hz, 3H); 505 [M + $H]^+$ |
| 109 | 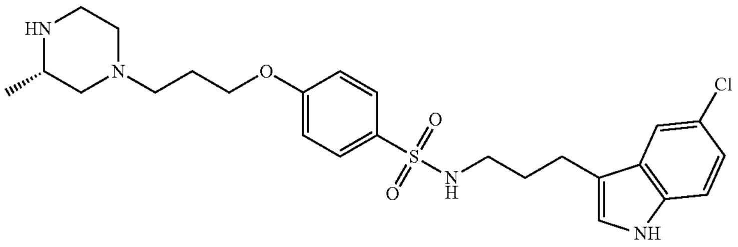 [SMILES: C[C@H]1CN(CCCOc2ccc(S(=O)(=O)NCCCc3c[nH]c4ccc(Cl)cc34)cc2)CCN1] | (S)-N-(3-(5-chloro-1H-indol-3-yl)propyl)-4-(3-(3-methylpipera-zin-1-yl)pro-poxy)benzene-sulfonamide | $^1$H NMR (400 MHz, $CDCl_3$) δ 8.23 (br s, 1H), 7.74-7.67 (m, 2H), 7.44 (d, J = 1.9 Hz, 1H), 7.28-7.23 (m, 1H), 7.13 (dd, J = 8.6, 2.0 Hz, 1H), 6.97-6.90 (m, 3H), 4.37-4.26 (m, 1H), 4.07 (t, J = 6.3 Hz, 2H), 3.03-2.79 (m, 7H), 2.71 (t, J = 7.2 Hz, 2H), 2.52 (t, J = 7.3 Hz, 2H), 2.09-1.94 (m, 3H), 1.82 |

TABLE 1-continued

| Example | Structure | Name | $^1$H NMR, MS |
| --- | --- | --- | --- |
| | | | (p, J = 7.0 Hz, 2H), 1.06 (d, J = 6.3 Hz, 3H); 505 [M + H]$^+$ |
| 110 | 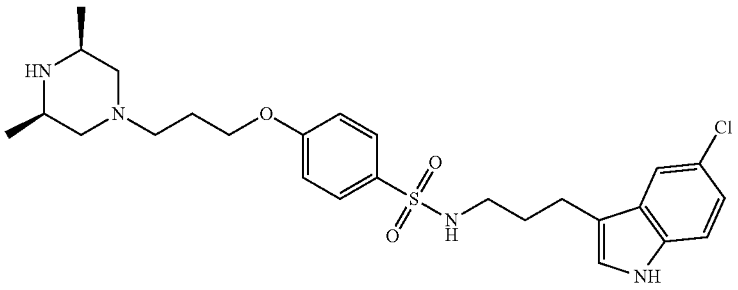 [SMILES: C[C@@H]1CN(CCCOc2ccc(S(=O)(=O)NCCCc3c[nH]c4ccc(Cl)cc34)cc2)C[C@H](C)N1] | N-(3-(5-chloro-1H-indol-3-yl)propyl)-4-(3-(3S,5R)-3,5-dimethyl-piperazin-1-yl)propoxy)benzene-sulfonamide | $^1$H NMR (400 MHz, $CDCl_3$) δ 8.26 (br s, 1H), 7.75-7.68 (m, 2H), 7.44 (d, J = 1.9 Hz, 1H), 7.27-7.24 (m, 1H), 7.13 (dd, J = 8.6, 2.0 Hz, 1H), 6.98-6.89 (m, 3H), 4.35 (t, J = 6.2 Hz, 1H), 4.07 (t, J = 6.3 Hz, 2H), 3.03-2.89 (m, 4H), 2.85-2.78 (m, 2H), 2.70 (t, J = 7.2 Hz, 2H), 2.56-2.46 (m, 2H), 2.07-1.95 (m, 2H), 1.82 (p, J = 7.1 Hz, 2H), 1.66-1.59 (m, 2H), 1.06 (d, J = 6.4 Hz, 6H); 520 [M + H]$^+$ |
| 111 | 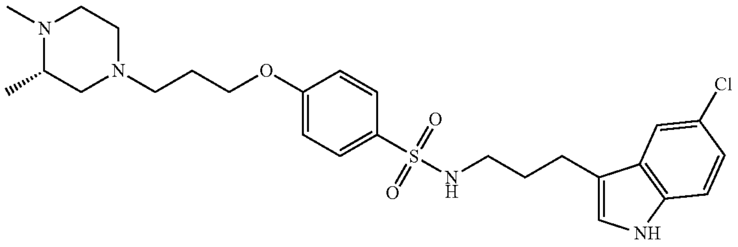 [SMILES: C[C@H]1CN(CCCOc2ccc(S(=O)(=O)NCCCc3c[nH]c4ccc(Cl)cc34)cc2)CCN1C] | (S)-N-(3-(5-chloro-1H-indol-3-yl)propyl)-4-(3-(3,4-dimethyl-piperazin-1-yl)propoxy)benzene-sulfonamide | $^1$H NMR (400 MHz, $CDCl_3$) δ 8.53-8.32 (m, 1H), 7.71 (d, J = 8.8 Hz, 2H), 7.42 (d, J = 1.3 Hz, 1H), 7.25 (d, J = 8.4 Hz, 1H), 7.10 (dd, J = 8.6, 1.8 Hz, 1H), 6.96-6.86 (m, 3H), 4.76-4.54 (m, 1H), 4.04 (t, J = 6.1 Hz, 2H), 3.03-2.92 (m, 3H), 2.92-2.78 (m, 2H), 2.68 (t, J = 7.2 Hz, 2H), 2.61-2.34 (m, 8H), 2.10 (t, J = 10.7 Hz, 1H), 1.98 (p, J = 13.3, 7.0 Hz, 2H), 1.81 (p, J = 14.7, 7.0 Hz, 2H), 1.15 (d, J = 6.3 Hz, 3H); 520 [M + H]$^+$ |
| 112 | 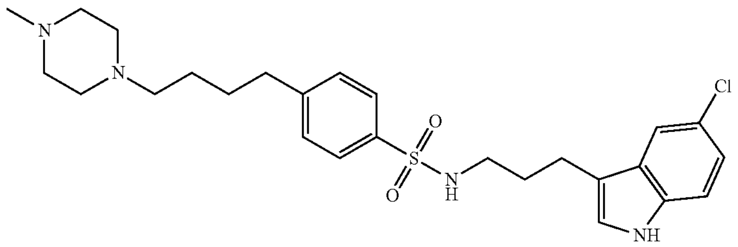 [SMILES: CN1CCN(CCCCc2ccc(S(=O)(=O)NCCCc3c[nH]c4ccc(Cl)cc34)cc2)CC1] | N-(3-(5-chloro-1H-indol-3-yl)propyl)-4-(4-(4-methylpiperazin-1-yl)butyl)benzene-sulfonamide | $^1$H NMR (400 MHz, $CDCl_3$) δ 8.73 (br s, 1H), 7.68 (d, J = 8.3 Hz, 2H), 7.45 (d, J = 1.9 Hz, 1H), 7.26-7.23 (m, 2H), 7.13 (dd, J = 8.6, 1.9 Hz, 1H), 6.86 (d, J = 2.2 Hz, 1H), 4.34-4.24 (m, 1H), 2.99 (q, J = 6.7 Hz, 2H), 2.74-2.66 (m, 4H), 2.66-2.40 (m, 8H), 2.41-2.35 (m, 2H), 2.29 (s, 3H), 1.83 (q, J = 14.7, 7.0 Hz, 2H), 1.69-1.60 (m, 2H), 1.54-1.45 (m, 2H); 505 [M + H]$^+$ |

TABLE 1-continued

| Example | Structure | Name | $^1H$ NMR, MS |
|---|---|---|---|
| 113 | 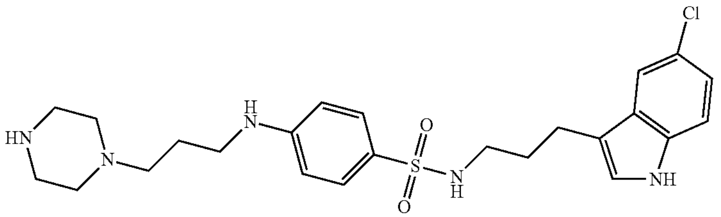 | N-(3-(5-chloro-1H-indol-3-yl)propyl)-4-((3-(piperazin-1-yl)propyl)amino)benzenesulfonamide | $^1H$ NMR (400 MHz, $CDCl_3$ δ 8.24 (br s, 1H), 7.57-7.55 (m, 2H), 7.44 (d, J = 1.9 Hz, 1H), 7.25-7.23 (m, 2H), 7.11 (dd, J = 8.6, 2.0 Hz, 1H), 6.95 (s, 1H), 6.54-6.50 (m, 2H), 5.76 (br s, 1H), 4.33 (br s, 1H), 3.22 (t, J = 6.2 Hz, 2H), 2.98-2.91 (m, 6H), 2.69 (t, J = 7.3 Hz, 2H), 2.50-2.45 (m, 6H), 1.84-1.71 (m, 4H); 491 $[M + H]^+$ |
| 114 | 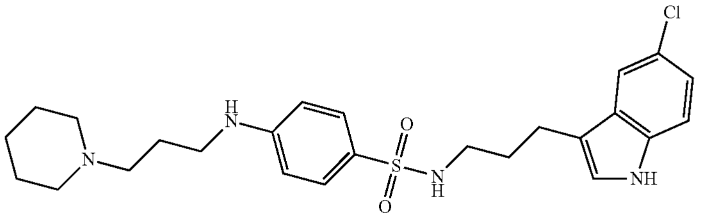 [SMILES: O=S(=O)(NCCCc1c[nH]c2ccc(Cl)cc12)c1ccc(NCCCN2CCCCC2)cc1] | N-(3-(5-chloro-1H-indol-3-yl)propyl)-4-((3-(piperidin-1-yl)propyl)amino)benzenesulfonamide | $^1H$ NMR (400 MHz, $CDCl_3$ δ 8.22 (br s, 1H), 7.57-7.55 (m, 2H), 7.45 (dd, J = 1.9 Hz, 1H), 7.25-7.23 (m, 2H), 7.11 (dd, J = 8.6, 2.0 Hz, 1H), 6.93 (d, J = 2.1 Hz, 1H), 6.51 (d, J = 8.8 Hz, 2H), 4.24 (t, J = 6.3 Hz, 1H), 3.21 (t, J = 6.2 Hz, 2H), 2.96 (d, J = 6.6 Hz, 2H), 2.69 (t, J = 7.3 Hz, 2H), 2.49-2.44 (m, 6H), 1.83-1.75 (m, 4H), 1.62 (p, J = 5.6 Hz, 4H), 1.49-1.48 (m, 2H); 490 $[M + H]^+$ |
| 115 | 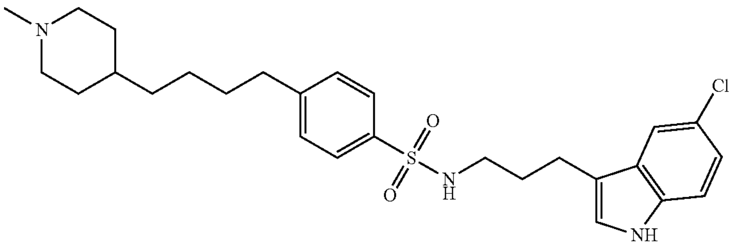 [SMILES: CN1CCC(CCCCc2ccc(S(=O)(=O)NCCCc3c[nH]c4ccc(Cl)cc34)cc2)CC1] | N-(3-(5-chloro-1H-indol-3-yl)propyl)-4-(4-(1-methylpiperidin-4-yl)butyl)benzenesulfonamide | $^1H$ NMR (400 MHz, MeOD) δ 7.70 (d, J = 8.3 Hz, 2H), 7.39 (d, J = 1.8 Hz, 1H), 7.33 (d, J = 8.2 Hz, 2H), 7.27 (d, J = 8.6 Hz, 1H), 7.02 (dd, J = 8.6, 2.0 Hz, 1H), 6.99 (s, 1H), 2.92 (t, J = 7.0 Hz, 2H), 2.87-2.77 (m, 2H), 2.72-2.59 (m, 4H), 2.23 (s, 3H), 2.00-1.90 (m, 2H), 1.78-1.70 (m, 2H), 1.68-1.58 (m, 4H), 1.37-1.14 (m, 7H); 502 $[M +H]^+$ |
| 116 | 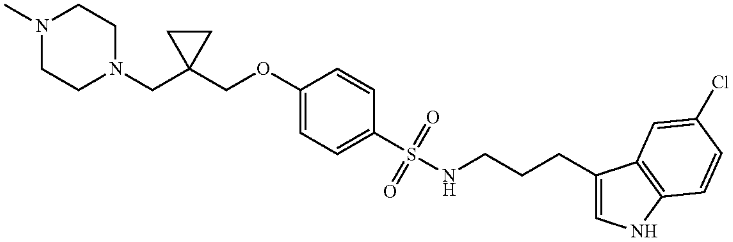 [SMILES: CN1CCN(CC2(COc3ccc(S(=O)(=O)NCCCc4c[nH]c5ccc(Cl)cc45)cc3)CC2)CC1] | N-(3-(5-chloro-1H-indol-3-yl)propyl)-4-((1-((4-methylpiperazin-1-yl)methyl)cyclopropyl)methoxy)benzenesulfonamide | $^1H$ NMR (400 MHz, $CDCl_3$) δ 8.25 (br s, 1H), 7.69 (d, J = 8.8 Hz, 2H), 7.47-7.41 (m, 1H), 7.26-7.22 (m, 1H), 7.16-7.10 (m, 1H), 7.00-6.88 (m, 3H), 4.30-4.21 (m, 1H), 3.94 (s, 2H), 2.99 (q, J = 6.7 Hz, 2H), 2.71 (t, J = 7.2 Hz, 2H), 2.63-2.38 (m, 8H), 2.38 (s, 2H), 2.27 (s, 3H), 1.88-1.78 (m, 2H), |

TABLE 1-continued

| Example | Structure | Name | $^1$H NMR, MS |
|---|---|---|---|
| | | | 0.65 (t, J = 5.1 Hz, 2H), 0.48 (t, J = 5.2 Hz, 2H); 531 [M + H]$^+$ |
| 117 | 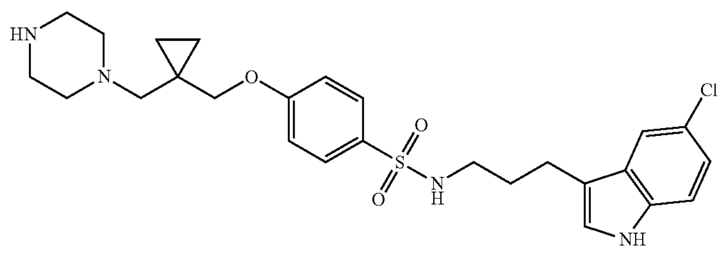 [SMILES: O=S(=O)(NCCCc1c[nH]c2ccc(Cl)cc12)c1ccc(OCC2(CN3CCNCC3)CC2)cc1] | N-(3-(5-chloro-1H-indol-3-yl)propyl)-4-((1-(piperazin-1-ylmethyl)cyclopropyl)methoxy)benzenesulfonamide | $^1$H NMR (400 MHz, $CDCl_3$) δ 8.45 (br s, 1H), 7.72-7.65 (m, 2H), 7.44 (d, J = 1.8 Hz, 1H), 7.26-7.22 (m, 1H), 7.13 (dd, J = 8.6, 1.9 Hz, 1H), 6.97-6.93 (m, 2H), 6.91 (s, 1H), 4.45-4.21 (m, 1H), 3.94 (s, 2H), 2.98 (t, J = 6.9 Hz, 2H), 2.85 (t, J = 4.8 Hz, 4H), 2.70 (t, J = 7.1 Hz, 2H), 2.52-2.39 (m, 4H), 2.36 (s, 2H), 1.89-1.78 (m, 3H), 0.65 (t, J = 5.3 Hz, 2H), 0.47 (t, J = 5.4 Hz, 2H); 517 [M + H]$^+$ |
| 118 | 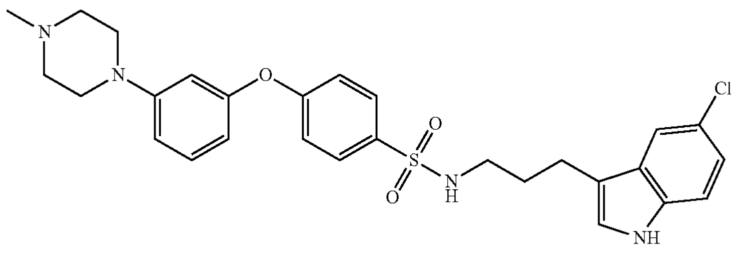 [SMILES: CN1CCN(c2cccc(Oc3ccc(S(=O)(=O)NCCCc4c[nH]c5ccc(Cl)cc45)cc3)c2)CC1] | N-(3-(5-chloro-1H-indol-3-yl)propyl)-4-(3-(4-methylpiperazin-1-yl)phenoxy)benzenesulfonamide | $^1$H NMR (400 MHz, $CDCl_3$) δ 8.15 (br s, 1H), 7.73 (d, J = 8.8 Hz, 2H), 7.46 (d, J = 1.7 Hz, 1H), 7.29-7.22 (m, 4H), 7.13 (dd, J = 8.6, 1.9 Hz, 1H), 7.04-6.97 (m, 3H), 6.77 (dd, J = 8.3, 2.1 Hz, 1H), 6.60 (t, J = 2.2 Hz, 1H), 6.51 (dd, J = 7.9, 1.8 Hz, 1H), 4.36 (t, J = 6.2 Hz, 1H), 3.27-3.14 (m, 4H), 3.01 (q, J = 6.7 Hz, 2H), 2.73 (t, J = 7.2 Hz, 2H), 2.60-2.51 (m, 2H), 2.35 (s, 3H), 1.91-1.80 (m, 2H),; 540 [M + H]$^+$ |
| 119 | 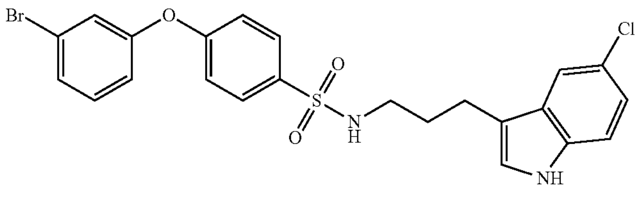 [SMILES: O=S(=O)(NCCCc1c[nH]c2ccc(Cl)cc12)c1ccc(Oc2cccc(Br)c2)cc1] | 4-(3-bromophenoxy)-N-(3-(5-chloro-1H-indol-3-yl)propyl)benzenesulfonamide | $^1$H NMR (400 MHz, $CDCl_3$) δ 8.01 (br s, 1H), 7.81-7.74 (m, 2H), 7.46 (d, J = 1.8 Hz, 1H), 7.37-7.32 (m, 1H), 7.30-7.23 (m, 3H), 7.21 (t, J = 2.0 Hz, 1H), 7.13 (dd, J = 8.6, 1.9 Hz, 1H), 7.06-6.96 (m, 4H), 4.40 (t, J = 6.0 Hz, 1H), 3.03 (q, J = 6.7 Hz, 2H), 2.74 (t, J = 7.2 Hz, 2H), 1.87 (p, J = 7.1 Hz, 2H); 521 [M + H]$^+$ |

TABLE 1-continued

| Example | Structure | Name | $^1$H NMR, MS |
|---|---|---|---|
| 120 | 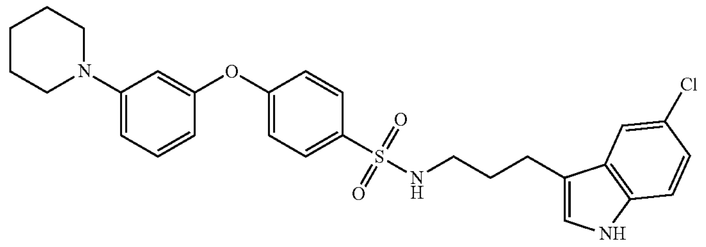 [SMILES: O=S(=O)(NCCCc1c[nH]c2ccc(Cl)cc12)c1ccc(Oc2cccc(N3CCCCC3)c2)cc1] | N-(3-(5-chloro-1H-indol-3-yl)propyl)-4-(3-(piperidin-1-yl)phenoxy)benzenesulfonamide | $^1$H NMR (400 MHz, $CDCl_3$) δ 8.06 (br s, 1H), 7.77-7.69 (m, 2H), 7.46 (d, J = 1.8 Hz, 1H), 7.26-7.21 (m, 2H), 7.13 (dd, J = 8.6, 1.9 Hz, 1H), 7.05-6.96 (m, 3H), 6.78 (dd, J = 8.3, 2.1 Hz, 1H), 6.61 (t, J = 2.2 Hz, 1H), 6.46 (dd, J = 7.9, 1.8 Hz, 1H), 4.36 (t, J = 6.3 Hz, 1H), 3.21-3.11 (m, 4H), 3.01 (q, J = 6.7 Hz, 2H), 2.74 (t, J = 7.2 Hz, 2H), 1.86 (p, J = 14.1, 7.1 Hz, 2H), 1.72-1.64 (m, 4H), 1.64-1.52 (m, 4H); 524 $[M + H]^+$ |
| 121 | 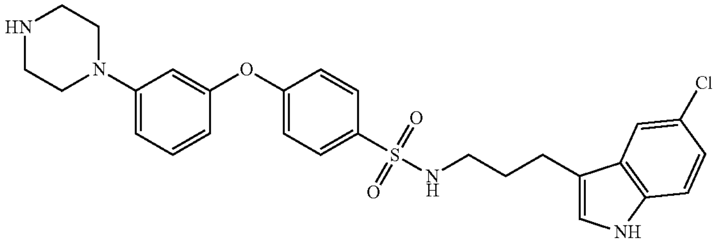 [SMILES: O=S(=O)(NCCCc1c[nH]c2ccc(Cl)cc12)c1ccc(Oc2cccc(N3CCNCC3)c2)cc1] | N-(3-(5-chloro-1H-indol-3-yl)propyl)-4-(3-(piperazin-1-yl)phenoxy)benzenesulfonamide | $^1$H NMR (400 MHz, MeOD) δ 7.78-7.70 (m, 2H), 7.42 (d, J = 1.8 Hz, 1H), 7.30-7.23 (m, 2H), 7.02 (d, J = 8.7 Hz, 4H), 6.83 (dd, J = 8.3, 2.2 Hz, 1H), 6.64 (t, J = 2.2 Hz, 1H), 6.49 (dd, J = 7.8, 1.8 Hz, 1H), 3.16-3.09 (m, 4H), 3.00-2.88 (m, 6H), 2.68 (t, J = 7.4 Hz, 2H), 1.78 (p, J = 14.4, 7.2 Hz, 2H); 525 $[M + H]^+$ |
| 122 | 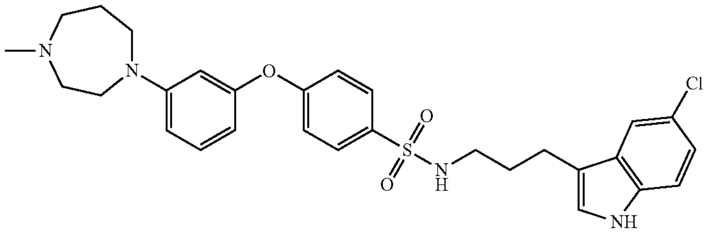 [SMILES: CN1CCCN(c2cccc(Oc3ccc(S(=O)(=O)NCCCc4c[nH]c5ccc(Cl)cc45)cc3)c2)CC1] | N-(3-(3-5-chloro-1H-indol-3-yl)propyl)-4-(3-(4-methyl-1,4-diazepan-1-yl)phenoxy)benzenesulfonamide | $^1$H NMR (400 MHz, MeOD) δ 7.78-7.70 (m, 2H), 7.42 (d, J = 1.8 Hz, 1H), 7.27 (d, J = 8.6 Hz, 1H), 7.19 (t, J = 8.2 Hz, 1H), 7.05-6.99 (m, 4H), 6.59 (dd, J = 8.4, 2.2 Hz, 1H), 6.38 (t, J = 2.2 Hz, 1H), 6.29 (dd, J = 7.9, 1.7 Hz, 1H), 3.55-3.48 (m, 2H), 3.43 (t, J = 6.3 Hz, 2H), 2.92 (t, J = 7.0 Hz, 2H), 2.71-2.63 (m, 4H), 2.60-2.53 (m, 2H), 2.34 (s, 3H), 2.00-1.92 (m, 2H), 1.78 (p, J = 14.5, 7.2 Hz, 2H); 553 $[M + H]^+$ |
| 123 | 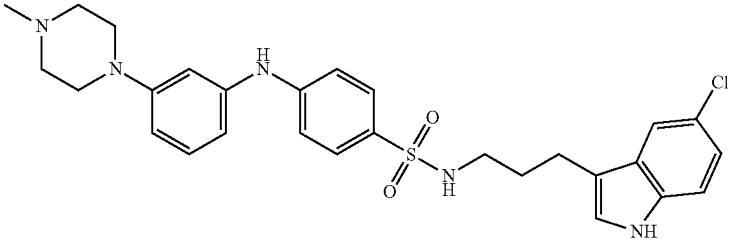 [SMILES: CN1CCN(c2cccc(Nc3ccc(S(=O)(=O)NCCCc4c[nH]c5ccc(Cl)cc45)cc3)c2)CC1] | N-(3-(5-chloro-1H-indol-3-yl)propyl)-4-((3-(4-methyl-piperazin-1-yl)phenyl)amino)benzenesulfonamide | $^1$H NMR 400 MHz, $CDCl_3$ δ 8.09 (br s, 1H), 7.61 (d, J = 8.6 Hz, 2H), 7.44 (s, 1H), 7.23-7.19 (m, 2H), 7.11 (d, J = 8.0 Hz, 1H), 6.97-6.95 (m, 3H), 6.68-6.63 (m, 3H), 6.01 (s, 1H), 4.29 (t, J = 6.2 Hz, 1H), 3.20-3.18 (m, 4H), 3.00 (q, J = 6.0 Hz, 2H), 2.71 (t, |

TABLE 1-continued

| Example | Structure | Name | $^1$H NMR, MS |
|---|---|---|---|
| | | | J = 7.3 Hz, 2H), 2.57-2.55 (m, 4H), 2.34 (s, 3H), 1.82 (p, J = 7.1 Hz, 2H); 539 [M + H]$^+$ |
| 124 | 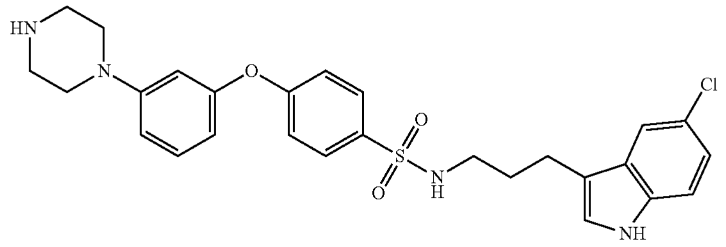 [SMILES: O=S(=O)(NCCCc1c[nH]c2ccc(Cl)cc12)c1ccc(Oc2cccc(N3CCNCC3)c2)cc1] | N-(3-(5-chloro-1H-indol-3-yl)propyl)-4-((3-(piperazin-1-yl)phenyl)amino)benzenesulfonamide | $^1$H NMR 400 MHz, $CDCl_3$ δ 8.05 (br s, 1H), 7.61 (d, J = 8.8 Hz, 2H), 7.44 (d, J = 1.7 Hz, 1H), 7.23-7.20 (m, 3H), 7.11 (dd, J = 8.6, 1.9 Hz, 1H), 6.97-6.95 (m, 3H), 6.68-6.64 (m, 3H), 6.00 (s, 1H), 4.26 (t, J = 6.0 Hz, 1H), 3.14-3.12 (m, 4H), 3.03-2.98 (m, 6H), 2.71 (t, J = 7.2 Hz, 2H), 1.82 (p, J = 7.1 Hz, 2H); 525 [M + H]$^+$ |
| 125 | 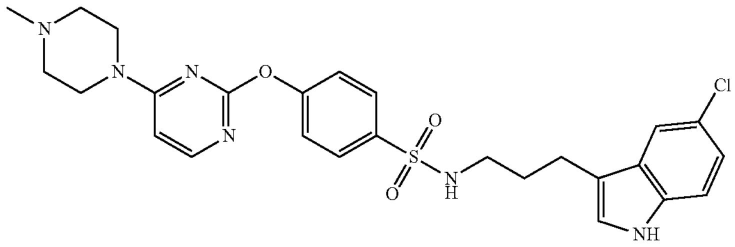 [SMILES: CN1CCN(c2ccnc(Oc3ccc(S(=O)(=O)NCCCc4c[nH]c5ccc(Cl)cc45)cc3)n2)CC1] | N-(3-(5-chloro-1H-indol-3-yl)propyl)-4-((4-(4-methylpiperazin-1-yl)pyrimidin-2-yl)amino)benzenesulfonamide | $^1$H NMR 400 MHz, $CDCl_3$ δ 8.30 (br s, 1H), 8.01 (br s, 1H), 7.71 (d, J = 8.9 Hz, 2H), 7.66 (d, J = 8.9 Hz, 2H), 7.43 (d, J = 1.8 Hz, 1H), 7.37 (br s, 1H), 7.21 (d, J = 8.6 Hz, 1H), 7.09 (dd, J = 8.6, 1.9 Hz, 1H), 6.81 (d, J = 1.7 Hz, 1H), 6.11 (d, J = 5.8 Hz, 1H), 4.65 (br s, 1H), 3.67-3.64 (m, 4H), 2.99-2.94 (m, 2H), 2.69 (t, J = 7.1 Hz, 2H), 2.49-2.47 (m, 4H), 2.34 (s, 3H), 1.82 (p, J = 6.9 Hz, 2H); 541 [M + H]$^+$ |
| 126 | 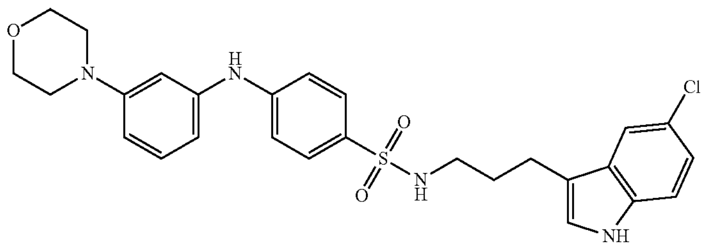 [SMILES: O=S(=O)(NCCCc1c[nH]c2ccc(Cl)cc12)c1ccc(Nc2cccc(N3CCOCC3)c2)cc1] | N-(3-(5-chloro-1H-indol-3-yl)propyl)-4-((3-morpholinophenyl)amino)benzenesulfonamide | $^1$H NMR 400 MHz, $CDCl_3$ δ 8.00 (br s, 1H), 7.63-7.61 (m, 2H), 7.44 (d, J = 2.0 Hz, 1H), 7.26-7.21 (m, 2H), 7.12 (dd, J = 8.6, 2.0 Hz, 1H), 6.98-6.95 (m, 3H), 6.68-6.64 (m, 3H), 6.01 (s, 1H), 4.26 (t, J = 6.3 Hz, 1H), 3.85-3.83 (m, 4H), 3.15-3.13 (m, 4H), 3.01 (q, J = 5.5 Hz, 2H), 2.71 (t, J = 7.2 Hz, 2H), 1.83 (p, J = 7.0 Hz, 2H); 526 [M + H]$^+$ |

TABLE 1-continued

| Example | Structure | Name | $^1$H NMR, MS |
|---|---|---|---|
| 127 | 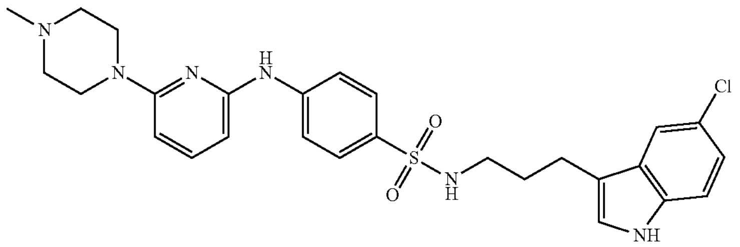 [SMILES: CN1CCN(c2cccc(Nc3ccc(S(=O)(=O)NCCCc4c[nH]c5ccc(Cl)cc45)cc3)n2)CC1] | N-(3-(5-chloro-1H-indol-3-yl)propyl)-4-((4-(piperazin-1-yl)pyrimidin-2-yl)amino)benzene-sulfonamide | $^1$H NMR 400 MHz, $CDCl_3$ δ 8.26 (br s, 1H), 8.02 (d, J = 6.2 Hz, 1H), 7.72-7.70 (m, 2H), 7.67-7.65 (m, 2H), 7.44 (d, J = 1.8 Hz, 1H), 7.22 (d, J = 8.6 Hz, 1H), 7.13-7.09 (m, 2H), 6.81 (d, J = 2.2 Hz, 1H), 6.11 (d, J = 6.2 Hz, 1H), 4.32 (br s, 1H), 3.62 (t, J = 4.8 Hz, 4H), 3.00-2.94 (m, 6H), 2.71 (t, J = 7.1 Hz, 2H), 1.83 (p J = 7.0 Hz, 2H); 540 $[M+H]^+$ |
| 128 | 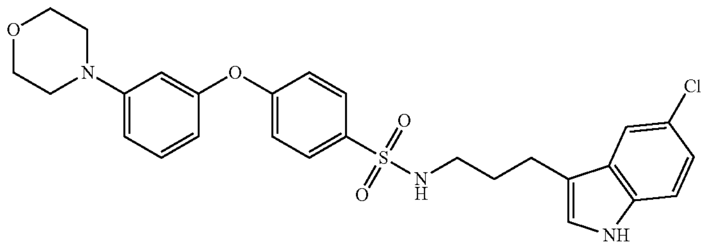 [SMILES: O=S(=O)(NCCCc1c[nH]c2ccc(Cl)cc12)c1ccc(Oc2cccc(N3CCOCC3)c2)cc1] | N-(3-(5-chloro-1H-indol-3-yl)propyl)-4-(3-morpholino-phenoxy)benzene-sulfonamide | $^1$H NMR (400 MHz, $CDCl_3$) δ 8.01 (br s, 1H), 7.77-7.71 (m, 2H), 7.46 (d, J = 1.9 Hz, 1H), 7.30-7.24 (m, 2H), 7.13 (dd, J = 8.6, 2.0 Hz, 1H), 7.07-6.97 (m, 3H), 6.75 (dd, J = 8.3, 1.9 Hz, 1H), 6.59 (t, J = 2.3 Hz, 1H), 6.56-6.50 (m, 1H), 4.38-4.28 (m, 1H), 3.92-3.80 (m, 4H), 3.19-3.11 (m, 4H), 3.02 (q, J = 6.7 Hz, 2H), 2.74 (t, J = 7.3 Hz, 2H), 1.86 (p, J = 7.1 Hz, 2H); 526 $[M+H]^+$ |
| 129 | 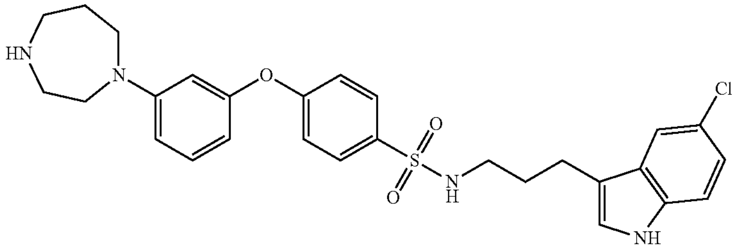 [SMILES: O=S(=O)(NCCCc1c[nH]c2ccc(Cl)cc12)c1ccc(Oc2cccc(N3CCCNCC3)c2)cc1] | 4-(3-(1,4-diazepan-1-yl)phenoxy)-N-(3-(5-chloro-1H-indol-3-yl)propyl)benzene-sulfonamide | $^1$H NMR (400 MHz, $CDCl_3$) δ 8.11 (br s, 1H), 7.77-7.68 (m, 2H), 7.46 (d, J = 1.9 Hz, 1H), 7.27-7.24 (m, 2H), 7.20 (t, J = 8.2 Hz, 1H), 7.13 (dd, J = 8.6, 2.0 Hz, 1H), 7.05-7.00 (m, 2H), 7.00-6.97 (m, 1H), 6.54 (dd, J = 8.4, 2.4 Hz, 1H), 6.37 (t, J = 2.3 Hz, 1H), 6.32 (dd, J = 7.9, 1.7 Hz, 1H), 4.93-4.81 (m, 1H), 4.38-4.26 (m, 1H), 3.61-3.46 (m, 4H), 3.06-2.98 (m, 4H), 2.91-2.82 (m, 2H), 2.74 (t, J = 7.3 Hz, 2H), 1.94-1.82 (m, 4H); 539 $[M+H]^+$ |

TABLE 1-continued

| Example | Structure | Name | $^1$H NMR, MS |
|---|---|---|---|
| 130 | 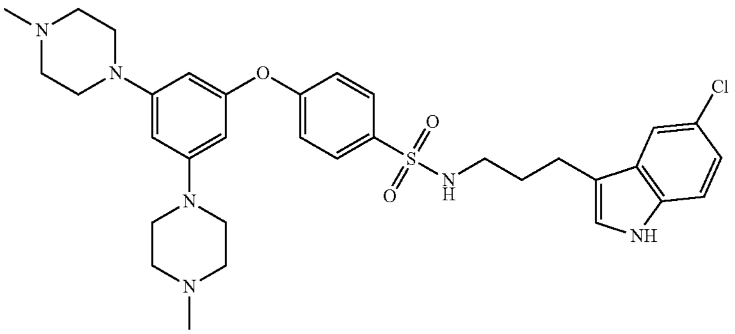 [SMILES: CN1CCN(c2cc(Oc3ccc(S(=O)(=O)NCCCc4c[nH]c5ccc(Cl)cc45)cc3)cc(N3CCN(C)CC3)c2)CC1] | 4-(3,5-bis(4-methylpiperazin-1-yl)phenoxy)-N-(3-(5-chloro-1H-indol-3-yl)propyl)benzenesulfonamide | $^1$H NMR (400 MHz, $CDCl_3$) δ 8.29 (br s, 1H), 7.72 (d, J = 8.8 Hz, 2H), 7.46 (d, J = 1.6 Hz, 1H), 7.24 (d, J = 8.7 Hz, 1H), 7.12 (dd, J = 8.6, 1.9 Hz, 1H), 7.02 (d, J = 8.8 Hz, 2H), 6.96 (s, 1H), 6.30 (s, 1H), 6.13 (d, J = 1.9 Hz, 2H), 4.36-4.28 (m, 1H), 3.23-3.14 (m, 8H), 3.06-2.98 (m, 2H), 2.73 (t, J = 7.2 Hz, 2H), 2.60-2.51 (m, 8H), 2.34 (s, 6H), 1.89-1.81 (m, 2H); 637 $[M + H]^+$ |
| 131 | 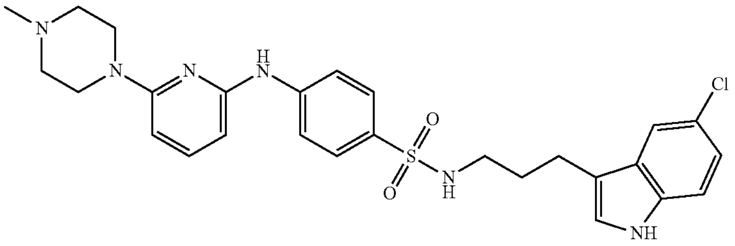 [SMILES: CN1CCN(c2cccc(Nc3ccc(S(=O)(=O)NCCCc4c[nH]c5ccc(Cl)cc45)cc3)n2)CC1] | N-(3-(5-chloro-1H-indol-3-yl)propyl)-4-((6-(4-methylpiperazin-1-yl)pyridin-2-yl)amino)benzenesulfonamide | $^1$H NMR 400 MHz, $CDCl_3$ δ 8.15 (br s, 1H), 7.70-7.68 (m, 2H), 7.48-7.39 (m, 4H), 7.22 (d, J = 8.6 Hz, 1H), 7.10 (dd, J = 6.7 Hz, 1H), 6.90 (d, J = 2.1 Hz, 1H), 6.58 (s, 1H), 6.21 (dd, J = 12.1, 8.2 Hz, 2H), 4.41 (t, J = 6.2 Hz, 1H), 3.57-3.54 (m, 4H), 3.00 (q, J = 6.5 Hz, 2H), 2.70 (t, J = 7.2 Hz, 2H), 2.54-2.51 (m, 4H), 2.35 (s, 3H), 1.82 (p, J = 7.0 Hz, 2H); 540 $[M + H]^+$ |
| 132 | 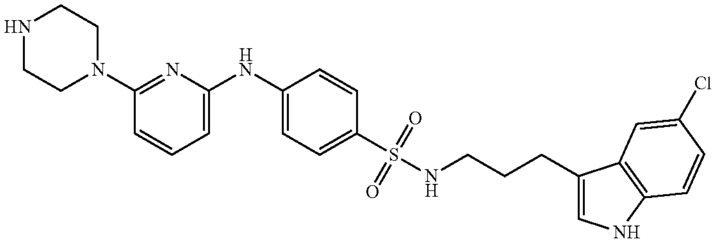 [SMILES: O=S(=O)(NCCCc1c[nH]c2ccc(Cl)cc12)c1ccc(Nc2cccc(N3CCNCC3)n2)cc1] | N-(3-(5-chloro-1H-indol-3-yl)propyl)-4-((6-(piperazin-1-yl)pyridin-2-yl)amino)benzenesulfonamide | $^1$H NMR 400 MHz, $CDCl_3$ δ 8.07 (br s, 1H), 7.71-7.69 (m, 2H), 7.50-7.40 (m, 4H), 7.25-7.23 (m, 1H), 7.12 (dd, J = 8.6, 2.0 Hz, 1H), 6.92 (d, J = 2.1 Hz, 1H), 6.53 (s, 1H), 6.21 (dd, J = 11.6, 8.2 Hz, 2H), 4.25 (t, J = 6.1 Hz, 1H), 3.52-3.49 (m, 4H), 3.02-2.98 (m, 6H, 2.72 (t, J = 14.3 Hz, 2H), 2.04-2.02 (m, 1H), 1.84 (p, J = 7.0 Hz, 2H); 526 $[M + H]^+$ |
| 133 | 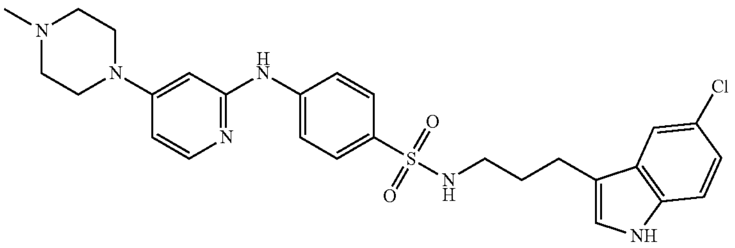 [SMILES: CN1CCN(c2ccnc(Nc3ccc(S(=O)(=O)NCCCc4c[nH]c5ccc(Cl)cc45)cc3)c2)CC1] | N-(3-(5-chloro-1H-indol-3-yl)propyl)-4-((4-(4-methylpiperazin-1-yl)pyridin-2-yl)amino)benzenesulfonamide | $^1$H NMR (400 MHz, $CDCl_3$ δ 8.86 (br s, 1H), 8.01 (d, J = 5.9 Hz, 1H), 7.68-7.65 (m, 2H), 7.43-7.37 (m, 3H), 7.20 (d, J = 8.6 Hz, 1H), 7.08 (dd, J = 8.6, 2.0 Hz, 1H), 6.70 (br s, 1H), 6.61 (d, J = 2.0 Hz, 2H), 6.41 (dd, J = 6.0, 2.0 Hz, 1H), 6.21 (s, 1H), 4.37 (br s, 1H), 3.35-3.32 (m, 4H), 2.93 (t, J = |

TABLE 1-continued

| Example | Structure | Name | $^1$H NMR, MS |
| --- | --- | --- | --- |
| | | | 6.1 Hz, 2H), 2.68 (t, J = 7.0 Hz, 2H), 2.54-2.51 (m, 4H), 2.35 (s, 3H), 1.83 (p, J = 6.8 Hz, 2H); 540 [M + H]$^+$ |
| 134 | 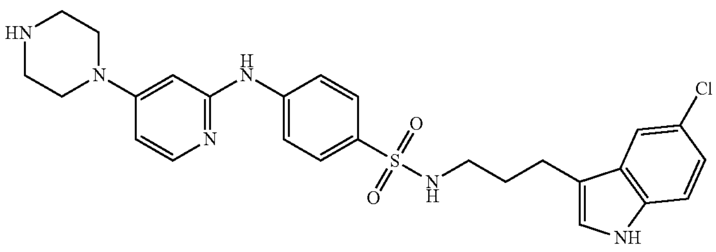 [SMILES: O=S(=O)(NCCCc1c[nH]c2ccc(Cl)cc12)c1ccc(Nc2cc(N3CCNCC3)ccn2)cc1] | N-(3-(5-chloro-1H-indol-3-yl)propyl)-4-((4-(piperazin-1-yl)pyridin-2-yl)amino)benzene-sulfonamide | $^1$H NMR 400 MHz, $CDCl_3$ δ 8.86 (br s, 1H), 8.02 (d, J = 5.9 Hz, 1H), 7.68-7.66 (m, 2H), 7.43-7.37 (m, 3H), 7.20 (d, J = 8.6 Hz, 1H), 7.09 (dd, J = 8.6, 1.9 Hz, 1H), 6.66 (br s, 1H), 6.61 (d, J = 1.9 Hz, 1H), 6.41 (dd, J = 6.1, 2.0 Hz, 1H), 6.21 (s, 1H), 4.27 (br s, 1H), 3.30-3.28 (m, 4H), 3.01-2.99 (m, 4H), 2.94 (br s, 2H), 2.69 (t, J = 7.0 Hz, 2H), 1.83 (p, J = 6.8 Hz, 2H); 526 [M + H]$^+$ |
| 135 | 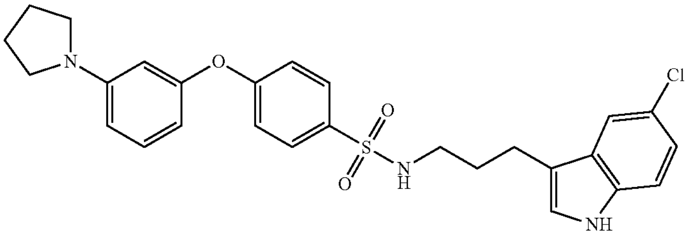 [SMILES: O=S(=O)(NCCCc1c[nH]c2ccc(Cl)cc12)c1ccc(Oc2cccc(N3CCCC3)c2)cc1] | N-(3-(5-chloro-1H-indol-3-yl)propyl)-4-(3-(pyrrolidin-1-yl)phenoxy)benzene-sulfonamide | $^1$H NMR (400 MHz, $CDCl_3$) δ 8.00 (br s, 1H), 7.77-7.68 (m, 2H), 7.47 (d, J = 1.9 Hz, 1H), 7.28-7.24 (m, 1H), 7.21 (t, J = 8.1 Hz, 1H), 7.13 (dd, J = 8.6, 1.9 Hz, 1H), 7.07-7.01 (m, 2H), 6.99 (d, J = 2.2 Hz, 1H), 6.41 (dd, J = 8.1, 2.0 Hz, 1H), 6.31 (dd, J = 8.0, 1.7 Hz, 1H), 6.24 (t, J = 2.3 Hz, 1H), 4.32-4.25 (m, 1H), 3.26 (t, J = 6.6 Hz, 4H), 3.02 (q, J = 6.7 Hz, 2H), 2.74 (t, J = 7.2 Hz, 2H), 2.03-1.96 (m, 4H), 1.87 (p, J = 13.3, 7.0 Hz, 2H); 510 [M + H]$^+$ |
| 136 | 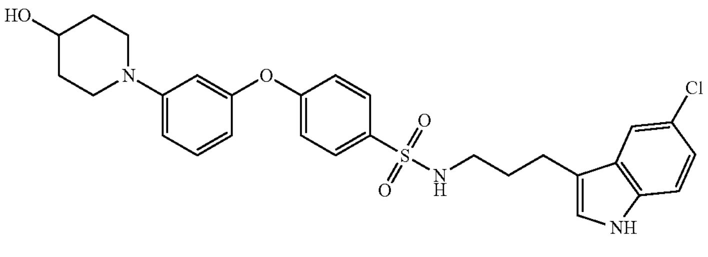 [SMILES: O=S(=O)(NCCCc1c[nH]c2ccc(Cl)cc12)c1ccc(Oc2cccc(N3CCC(O)CC3)c2)cc1] | N-(3-(5-chloro-1H-indol-3-yl)propyl)-4-(3-(4-hydroxy-piperidin-1-yl)phenoxy)benzene-sulfonamide | $^1$H NMR (400 MHz, $CDCl_3$) δ 8.04 (br s, 1H), 7.76-7.70 (m, 2H), 7.46 (d, J = 2.0 Hz, 1H), 7.28-7.21 (m, 1H), 7.13 (dd, J = 8.6, 2.0 Hz, 1H), 7.05-6.97 (m, 3H), 6.78 (dd, J = 8.2, 2.1 Hz, 1H), 6.61 (t, J = 2.3 Hz, 1H), 6.48 (dd, J = 8.0, 1.6 Hz, 1H), 4.30 (t, J = 6.3 Hz, 1H), 3.91-3.84 (m, 1H), 3.59-3.51 (m, 2H), 3.02 (q, J = 6.7 Hz, 2H), 2.96 (ddd, J = 12.8, 9.8, 3.2 Hz, 2H), 2.74 (t, J = 7.2 Hz, 2H), 2.03-1.95 (m, 2H), 1.86 (p, J = 7.1 Hz, 2H), 1.72-1.61 (m, 2H); 540 [M + H]$^+$ |

TABLE 1-continued

| Example | Structure | Name | $^1$H NMR, MS |
|---|---|---|---|
| 137 | 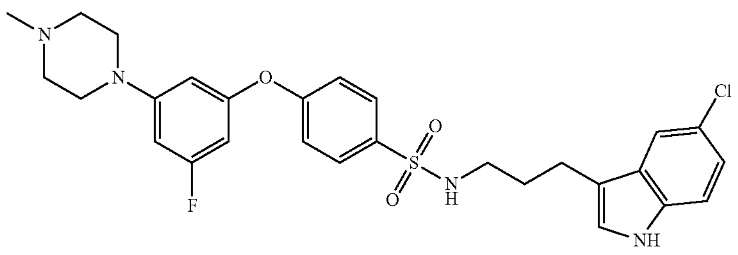 [SMILES: CN1CCN(c2cc(F)cc(Oc3ccc(S(=O)(=O)NCCCc4c[nH]c5ccc(Cl)cc45)cc3)c2)CC1] | N-(3-(5-chloro-1H-indol-3-yl)propyl)-4-(3-fluoro-5-(4-methylpiperazin-1-yl)phenoxy-benzenesulfonamide | $^1$H NMR (400 MHz, $CDCl_3$) δ 8.05 (br s, 1H), 7.79-7.73 (m, 2H), 7.46 (d, J = 1.8 Hz, 1H), 7.30-7.23 (m, 1H), 7.13 (dd, J = 8.6, 2.0 Hz, 1H), 7.07-7.01 (m, 2H), 6.99 (d, J = 2.1 Hz, 1H), 6.43 (td, J = 12.0, 2.0 Hz, 1H), 6.37-6.34 (m, 1H), 6.19 (td, J = 10.7, 2.0 Hz, 1H), 4.29 (t, J = 6.3 Hz, 2H), 3.24-3.13 (m, 4H), 3.03 (q, J = 8.0 Hz, 2H), 2.74 (t, J = 7.2 Hz, 2H), 2.58-2.47 (m, 4H), 2.34 (s, 2H), 1.87 (p, J = 14.7, 7.0 Hz, 2H); 557 [M + H]$^+$ |
| 138 | 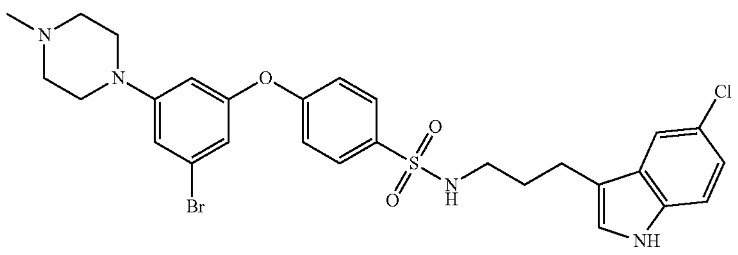 [SMILES: CN1CCN(c2cc(Br)cc(Oc3ccc(S(=O)(=O)NCCCc4c[nH]c5ccc(Cl)cc45)cc3)c2)CC1] | 4-(3-bromo-5-(4-methylpiperazin-1-yl)phenoxy)-N-(3-(5-chloro-1H-indol-3-yl)propyl)benzene-sulfonamide | $^1$H NMR (400 MHz, $CDCl_3$) δ 8.09 (br s, 1H), 7.78-7.72 (m, 2H), 7.46 (d, J = 1.9 Hz, 1H), 7.28-7.23 (m, 1H), 7.15-7.10 (m, 1H), 7.05-7.00 (m, 2H), 6.99 (d, J = 2.1 Hz, 1H), 6.88-6.85 (m, 1H), 6.62 (t, J = 1.8 Hz, 1H), 6.50 (t, = 2.1 Hz, 1H), 4.44-4.33 (m, 1H), 3.24-3.17 (m, 4H), 3.03 (q, J = 6.7 Hz, 2H), 2.74 (t, J = 7.2 Hz, 2H), 2.58-2.50 (m, 4H), 2.35 (s, 3H), 1.91-1.82 (m, 2H); 619 [M + H]$^+$ |
| 139 | 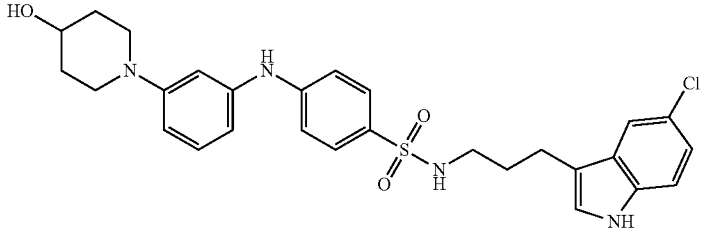 [SMILES: O=S(=O)(NCCCc1c[nH]c2ccc(Cl)cc12)c1ccc(Nc2cccc(N3CCC(O)CC3)c2)cc1] | N-(3-(5-chloro-1H-indol-3-yl)propyl)-4-((3-(4-hydroxy-piperidin-1-yl)phenyl)amino)benzene-sulfonamide | $^1$H NMR 400 MHz, $CDCl_3$ δ 8.09 (br s, 1H), 7.61 (d, J = 8.8 Hz, 2H), 7.44 (d, J = 1.4 Hz, 1H), 7.24-7.18 (m, 2H), 7.10 (dd, J = 8.6, 1.8 Hz, 1H), 6.96-6.94 (m, 3H), 6.69-6.67 (m, 2H), 6.62 (d, J = 7.3 Hz, 1H), 6.03 (s, 1H), 4.36 (t, J = 6.2 Hz, 1H), 4.07-3.97 (m, 1H), 3.89-3.83 (m, 1H), 3.56-3.50 (m, 2H), 3.02-2.89 (m, 4H), 2.70 (t, J = 7.2 Hz, 2H), 2.00-1.96 (m, 2H), 1.81 (p, J = 7.0 Hz, 2H), 1.71-1.54 (m, 2H); 540 [M +H]$^+$ |

TABLE 1-continued

| Example | Structure | Name | $^1$H NMR, MS |
|---|---|---|---|
| 140 | 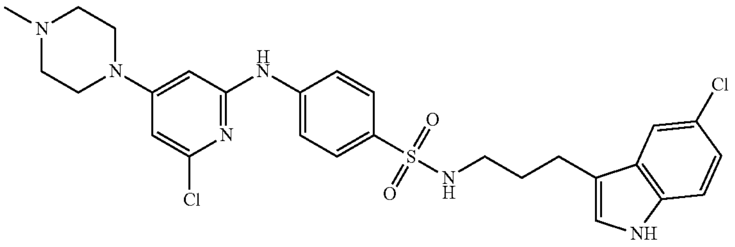 [SMILES: CN1CCN(c2cc(Cl)nc(Nc3ccc(S(=O)(=O)NCCCc4c[nH]c5ccc(Cl)cc45)cc3)c2)CC1] | N-(3-(5-chloro-1H-indol-3-yl)propyl)-4-((6-chloro-4-(4-methylpiperazin-1-yl)pyridin-2-yl)amino)benzenesulfonamide | $^1$H NMR 400 MHz, $CDCl_3$ δ 8.31 (br s, 1H), 7.68 (d, J = 8.8 Hz, 2H), 7.43 (d, J = 1.8 Hz, 1H), 7.37 (d, J = 8.8 Hz, 2H), 7.25-7.23 (m, 1H), 7.09 (dd, J = 6.6 Hz, 1H), 6.74 (d, J = 2.1 Hz, 1H), 6.69 (s, 1H), 6.37 (d, J = 1.8 Hz, 1H), 6.11 (d, J = 1.8 Hz, 1H), 5.29 (s, 1H), 4.40 (t, J = 6.1 Hz, 1H), 3.33-3.31 (m, 4H), 2.97 (p, J = 6.4 Hz, 2H), 2.69 (t, J = 7.0 Hz, 2H), 2.52-2.49 (m, 4H), 2.34 (s, 3H), 1.83 (p, J = 6.8 Hz, 2H); 574 [M + H]$^+$ |
| 141 | 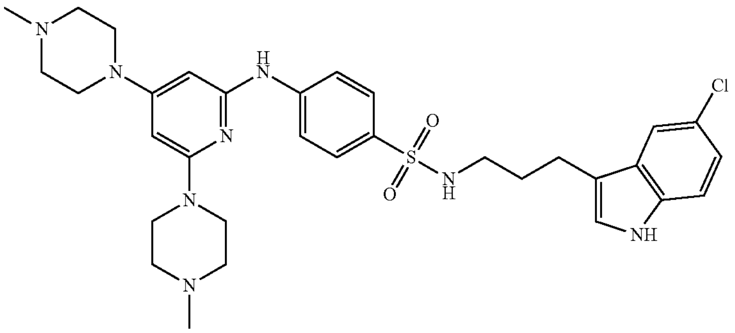 [SMILES: CN1CCN(c2cc(Nc3ccc(S(=O)(=O)NCCCc4c[nH]c5ccc(Cl)cc45)cc3)nc(N3CCN(C)CC3)c2)CC1] | 4-((4,6-bis(4-methylpiperazin-1-yl)pyridin-2-yl)amino)-N-(3-(5-chloro-1H-indol-3-yl)propyl)benzenesulfonamide | $^1$H NMR 400 MHz, $CDCl_3$ δ 8.24 (br s, 1H), 7.67 (d, J = 8.8 Hz, 2H), 7.43-7.40 (m, 3H), 7.21 (d, J = 8.6 Hz, 1H), 7.09 (dd, J = 8.6, 2.0 Hz, 1H), 6.81 (d, J = 2.0 Hz, 1H), 6.47 (br s, 1H), 5.75-5.67 (m, 2H), 4.34 (t, J = 6.2 Hz, 1H), 3.52-3.49 (m, 4H), 3.30-3.27 (m, 4H), 2.98 (q, J = 6.4 Hz, 2H), 2.69 (t, J = 7.1 Hz, 2H), 2.50 (br s, 8H), 2.33 (s, 6H), 1.81 (p, J = 6.9 Hz, 2H); 638 [M + H]$^+$ |
| 142 | 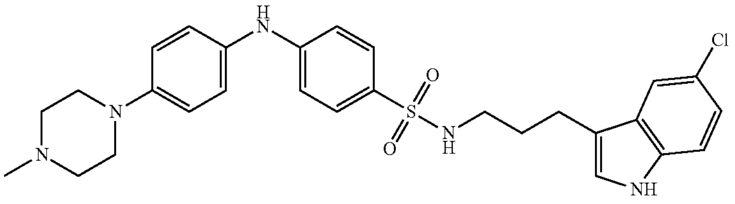 [SMILES: CN1CCN(c2ccc(Nc3ccc(S(=O)(=O)NCCCc4c[nH]c5ccc(Cl)cc45)cc3)cc2)CC1] | N-(3-(5-chloro-1H-indol-3-yl)propyl)-4-((4-(4-methylpiperazin-1-yl)phenyl)amino)benzenesulfonamide | $^1$H NMR 400 MHz, $CDCl_3$ δ 10.93 (br s, 1H), 8.39 (br s, 1H), 7.50-7.48 (m, 3H), 7.31 (d, J = 8.6 Hz, 1H), 7.22 (t, J = 5.8 Hz, 1H), 7.13 (d, J = 1.8 Hz, 1H), 7.04-7.02 (m, 3H), 6.91-6.87 (m, 4H), 3.09-3.06 (m, 4H), 2.73 (q, J = 6.4 Hz, 2H), 2.61 (t, J = 7.4 Hz, 2H), 2.45-2.43 (m, 4H), 2.21 (s, 3H), 1.68 (p, J = 7.4 Hz, 2H); 539 [M + H]$^+$ |
| 143 | 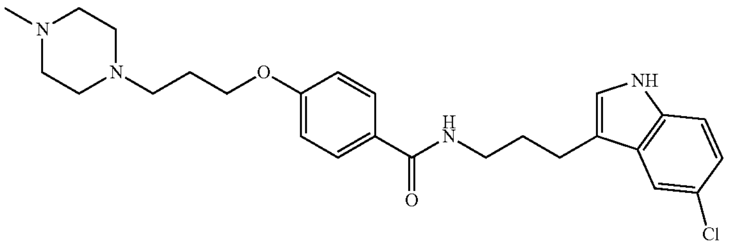 [SMILES: CN1CCN(CCCOc2ccc(C(=O)NCCCc3c[nH]c4ccc(Cl)cc34)cc2)CC1] | N-(3-(5-chloro-1H-indol-3-yl)propyl)-4-(3-(4-methylpiperazin-1-yl)propoxy)benzamide | $^1$H NMR (400 MHz, $CDCl_3$) δ 8.06 (br s, 1H), 7.60-7.53 (m, 3H), 7.31-7.27 (m, 1H), 7.17-7.12 (m, 1H), 7.08 (s, 1H), 6.87 (d, J = 8.7 Hz, 2H), 6.01-5.93 (m, 1H), 4.04 (t, J = 6.3 Hz, 2H), 3.52 (q, J = 6.6 Hz, 2H), 2.83 (t, J = 7.2 Hz, 2H), 2.70-2.40 (m, |

| Example | Structure | Name | $^1$H NMR, MS |
|---|---|---|---|
| | | | 10H), 2.33 (s, 3H), 2.05-1.96 (m, 4H); 469 $[M + H]^+$ |
| 144 | 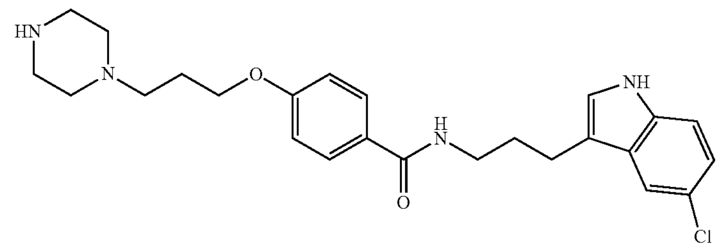 [SMILES: O=C(NCCCc1c[nH]c2ccc(Cl)cc12)c1ccc(OCCCN2CCNCC2)cc1] | N-(3-(5-chloro-1H-indol-3-yl)propyl)-4-(3-(piperazin-1-yl)propoxy)benzamide | $^1$H NMR (400 MHz, MeOD) δ 7.79-7.70 (m, 2H), 7.54-7.46 (m, 1H), 7.28 (d, J = 8.6 Hz, 1H), 7.12 (s, 1H), 7.03 (dd, J = 8.6, 1.9 Hz, 1H), 6.99-6.91 (m, 2H), 4.54 (br s, 2H), 4.11 (t, J = 6.1 Hz, 2H), 3.44 (t, J = 7.1 Hz, 2H), 3.19-3.09 (m, 4H), 2.80 (t, J = 7.3 Hz, 2H), 2.73-2.66 (m, 4H), 2.64 (t, J = 7.2 Hz, 2H), 2.06-1.94 (m, 4H); 455 $[M + H]^+$ |
| 145 | 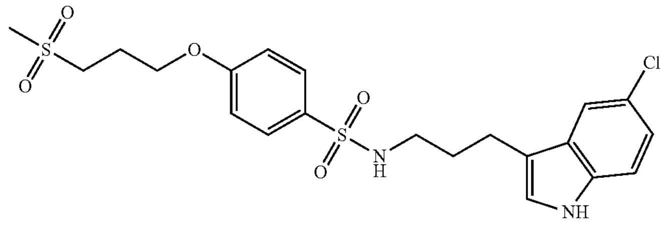 [SMILES: CS(=O)(=O)CCCOc1ccc(S(=O)(=O)NCCCc2c[nH]c3ccc(Cl)cc23)cc1] | N-(3-(5-chloro-1H-indol-3-yl)propyl)-4-(3-(methylsulfonyl)propoxy)benzenesulfonamide | $^1$H NMR (400 MHz, $CDCl_3$) δ 8.14 (br s, 1H), 7.75-7.68 (m, 2H), 7.42 (d, J = 2.0 Hz, 1H), 7.30-7.26 (m, 1H), 7.12 (dd, J = 8.6, 2.1 Hz, 1H), 6.96-.687 (m, 3H), 4.43 (t, J = 6.2 Hz, 1H), 4.17 (t, J = 5.8 Hz, 2H), 3.32-3.23 (m, 2H), 3.03-2.95 (m, 5H), 2.69 (t, J = 7.2 Hz, 2H), 2.44-2.34 (m, 2H), 1.81 (p, J = 7.1 Hz, 2H); 486 $[M + H]^+$ |
| 146 | 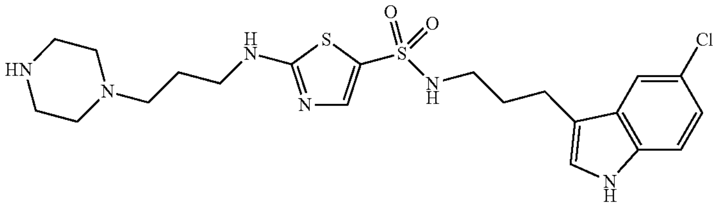 [SMILES: O=S(=O)(NCCCc1c[nH]c2ccc(Cl)cc12)c1cnc(NCCCN2CCNCC2)s1] | N-(3-(5-chloro-1H-indol-3-yl)propyl)-2-((3-(piperazin-1-yl)propyl)amino)thiazol-5-sulfonamide | $^1$H NMR (400 MHz, $CDCl_3$) δ 8.17 (br s, 1H), 8.11 (br s, 1H), 7.57 (s, 1H), 7.50 (s, 1H), 7.13 (d, J = 7.7 Hz, 1H), 7.01 (s, 1H), 4.49 (br s, 1H), 3.45-3.31 (m, 2H), 3.15-3.02 (m, 2H), 2.77 (t, J = 7.2 Hz, 2H), 2.67-2.21 (m, 6H), 2.02-1.86 (m, 2H), 1.86-1.73 (m, 2H), 1.68-1.44 (m, 4H); 497 $[M + H]^+$ |
| 147 | 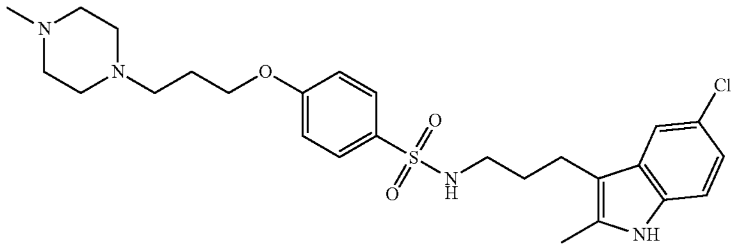 [SMILES: Cc1[nH]c2ccc(Cl)cc2c1CCCNS(=O)(=O)c1ccc(OCCCN2CCN(C)CC2)cc1] | N-(3-(5-chloro-2-methyl-1H-indol-3-yl)propyl)-4-(3-(4-methylpiperazin-1-yl)propoxy)benzenesulfonamide | $^1$H NMR (400 MHz, $CDCl_3$) δ 7.93 (s, 1H), 7.66 (d, J = 8.8 Hz, 2H), 7.31 (s, 1H), 7.16 (d, J = 8.6 Hz, 1H), 7.05 (d, J = 8.6 z, 1H), 6.92 (d, J = 8.8 Hz, 2H), 4.15 (t, J = 6.2 Hz, 1H), 4.07 (t, J = 6.2 Hz, 2H), 2.93 (dd, J = 13.3, 6.6 Hz, 2H), 2.70-2.36 (m, 8H), 2.32 (s, 3H), 2.30 (s, 3H), 2.05-1.95 (m, 2H), 1.79-1.70 (m, 2H), 1.70-1.50 (m, 4H); 519 $[M +H]^+$ |

TABLE 1-continued

| Example | Structure | Name | $^1$H NMR, MS |
|---|---|---|---|
| 148 | 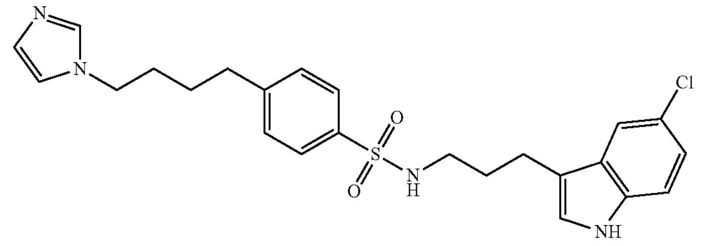 [SMILES: O=S(=O)(NCCCc1c[nH]c2ccc(Cl)cc12)c1ccc(CCCCn2ccnc2)cc1] | 4-(4-(1H-imidazol-1-yl)butyl)-N-(3-(5-chloro-1H-indol-3-yl)propyl)benzene-sulfonamide | $^1$H NMR (400 MHz, DMSO) δ 10.95 (s, 1H), 7.67 (d, J = 8.3 Hz, 2H), 7.59 (s, 1H), 7.55 (br s, 1H), 7.47 (d, J = 2.0 Hz, 1H), 7.36 (d, J = 8.2 Hz, 2H), 7.32 (d, J = 8.6 Hz, 1H), 7.12 (s, 1H), 7.11 (d, J = 2.1 Hz, 1H), 7.04 (dd, J = 8.6, 2.0 Hz, 1H), 6.86 (s, 1H), 3.96 (t, J = 7.0 Hz, 2H), 2.78 (t, J = 6.5 Hz, 2H), 2.69-2.62 (m, 2H), 2.59 (t, J = 7.5 Hz, 2H), 1.75-1.60 (m, 4H), 1.56-1.43 (m, 2H); 471 [M + H]$^+$ |
| 149 | 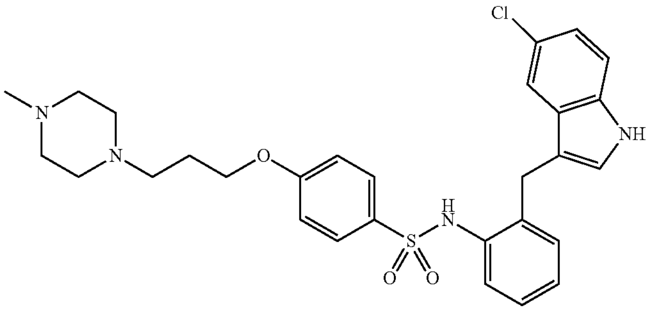 [SMILES: CN1CCN(CCCOc2ccc(S(=O)(=O)Nc3ccccc3Cc3c[nH]c4ccc(Cl)cc34)cc2)CC1] | N-(2-((5-chloro-1H-indol-3-yl)methyl)phenyl)-4-(3-(4-methyl-piperazin-1-yl)propoxy)benzene-sulfonamide | $^1$H NMR (400 MHz, $CDCl_3$) δ 8.17 (br s, 1H), 8.11 (br s, 1H), 7.57 (s, 1H), 7.50 (s, 1H), 7.13 (d, J = 7.7 Hz, 1H), 7.01 (s, 1H), 4.49 (br s, 1H), 3.45-3.31 (m, 2H), 3.15-3.02 (m, 2H), 2.77 (t, J = 7.2 Hz, 2H), 2.67-2.21 (m, 6H), 2.02-1.86 (m, 2H), 1.86-1.73 (m, 2H), 1.68-1.44 (m, 4H); 497 [M + H]$^+$ |
| 150 | 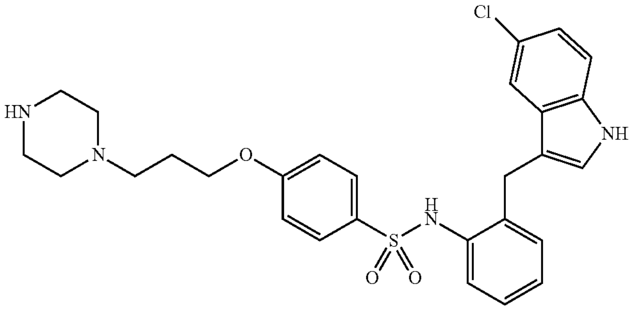 [SMILES: O=S(=O)(Nc1ccccc1Cc1c[nH]c2ccc(Cl)cc12)c1ccc(OCCCN2CCNCC2)cc1] | N-(2-((5-chloro-1H-indol-3-yl)methyl)phenyl)-1)-4-(3-(piperazin-1-yl)propoxy)benzene-sulfonamide | $^1$H NMR (400 MHz, $CDCl_3$) δ 7.93 (s, 1H), 7.66 (d, J = 8.8 Hz, 2H), 7.31 (s, 1H), 7.16 (d, J = 8.6 Hz, 1H), 7.05 (d, J = 8.6 Hz, 1H), 6.92 (d, J = 8.8 Hz, 2H), 4.15 (t, J = 6.2 Hz, 1H), 4.07 (t, J = 6.2 Hz, 2H), 2.93 (dd, J = 13.3, 6.6 Hz, 2H), 2.70-2.36 (m, 8H), 2.32 (s, 3H), 2.30 (s, 3H), 2.05-1.95 (m, 2H), 1.79-1.70 (m, 2H), 1.70-1.50 (m, 4H); 519 [M +H]$^+$ |
| 151 | 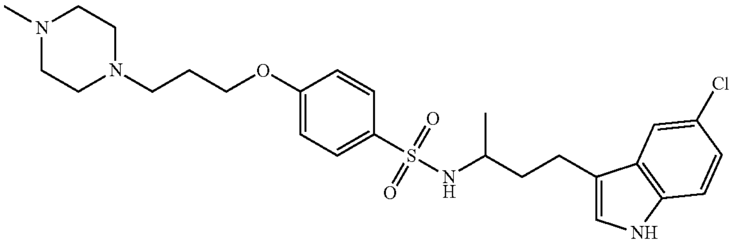 [SMILES: CC(CCc1c[nH]c2ccc(Cl)cc12)NS(=O)(=O)c1ccc(OCCCN2CCN(C)CC2)cc1] | N-(4-(5-chloro-1H-indol-3-yl)butan-2-yl)-4-(3-(4-methyl-piperazin-1-yl)propoxy)benzene-sulfonamide | $^1$H NMR (400 MHz, DMSO) δ 10.95 (s, 1H), 7.67 (d, J = 8.3 Hz, 2H), 7.59 (s, 1H), 7.55 (br s, 1H), 7.47 (d, J = 2.0 Hz, 1H), 7.36 (d, J = 8.2 Hz, 2H), 7.32 (d, J = 8.6 Hz, 1H), 7.12 (s, 1H), 7.11 (d, J = 2.1 Hz, 1H), 7.04 (dd, J = 8.6, 2.0 Hz, 1H), 6.86 (s, 1H), 3.96 (t, J = 7.0 Hz, 2H), 2.78 (t, J = 6.5 Hz, 2H), 2.69-2.62 (m, 2H), 2.59 (t, J = 7.5 |

TABLE 1-continued

| Example | Structure | Name | $^1$H NMR, MS |
|---|---|---|---|
| | | | Hz, 2H), 1.75-1.60 (m, 4H), 1.56-1.43 (m, 2H); 471 [M + H]$^+$ |
| 152 | 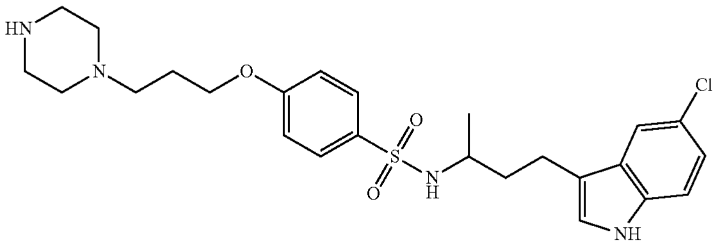 | N-(4-(5-chloro-1H-indol-3-yl)butan-2-yl)-4-(3-(piperazin-1-yl)propoxy)benzenesulfonamide | $^1$H NMR (400 MHz, $CDCl_3$) δ 8.28 (br s, 1H), 7.50-7.42 (m, 3H), 7.29 (d, J = 8.6 Hz, 1H), 7.24 (dd, J = 7.9, 1.7 Hz, 1H), 7.21-7.11 (m, 4H), 6.83-6.76 (m, 2H), 6.75 (d, J = 2.3 Hz, 1H), 6.45 (br s, 1H), 4.05 (t, J = 6.3 Hz, 2H), 3.67 (s, 2H), 2.77-2.33 (m, 10H), 2.30 (s, 3H), 2.03-1.95 (m, 2H); 553 [M + H]$^+$ |
| 153 | 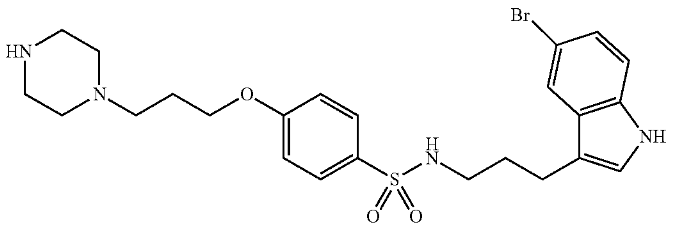 [SMILES: O=S(=O)(NCCCc1c[nH]c2ccc(Br)cc12)c1ccc(OCCCN2CCNCC2)cc1] | N-(3-(5-bromo-1H-indol-3-yl)propyl)-4-(3-(piperazin-1-yl)propoxy)benzenesulfonamide | $^1$H NMR (400 MHz, $CDCl_3$) δ 8.44 (br s, 1H), 7.80-7.66 (m, 2H), 7.64-7.54 (m, 1H), 7.26-7.18 (m, 2H), 6.96-6.88 (m, 3H), 4.64 (br s, 1H), 4.06 (t, J = 6.3 Hz, 2H), 2.97 (t, J = 6.9 Hz, 2H), 2.90 (t, J = 4.9 Hz, 4H), 2.69 (t, J = 7.2 Hz, 2H), 2.59-2.35 (m, 6H), 2.05-1.93 (m, 2H), 1.90-1.78 (m, 3H); 536 [M + H]$^+$ |
| 154 | 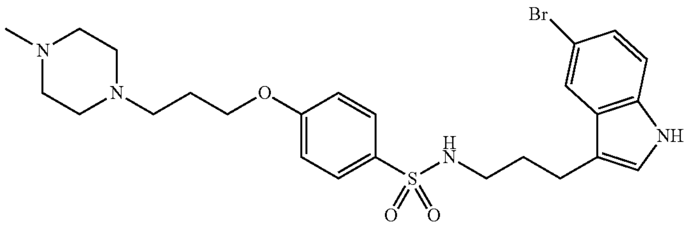 [SMILES: CN1CCN(CCCOc2ccc(S(=O)(=O)NCCCc3c[nH]c4ccc(Br)cc34)cc2)CC1] | N-(3-(5-bromo-1H-indol-3-yl)propyl)-4-(3-(4-(3-(4-methyl-piperazin-1-yl)propoxy)benzenesulfonamide | $^1$H NMR (400 MHz, $CDCl_3$) δ 8.48 (br s, 1H), 7.75-7.67 (m, 2H), 7.63-7.56 (m, 1H), 7.25-7.18 (m, 2H), 6.95-6.88 (m, 3H), 4.67 (t, J = 6.2 Hz, 1H), 4.05 (t, J = 6.3 Hz, 2H), 2.96 (q, J = 6.5 Hz, 2H), 2.68 (t, J = 7.2 Hz, 2H), 2.60-2.41 (m, 8H), 2.29 (s, 3H), 2.08 (br s, 1H), 2.04-1.91 (m, 3H), 1.80 (p, J = 7.1 Hz, 2H); 550 [M +H]$^+$ |
| 155 | 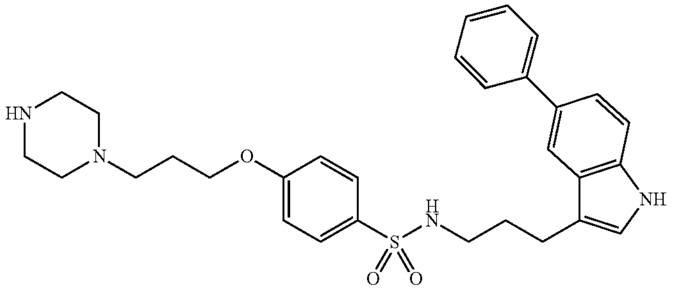 [SMILES: O=S(=O)(NCCCc1c[nH]c2ccc(-c3ccccc3)cc12)c1ccc(OCCCN2CCNCC2)cc1] | N-(3-(5-phenyl-1H-indol-3-yl)propyl)-4-(3-(piperazin-1-yl)propoxy)benzenesulfonamide | $^1$H NMR (400 MHz, $CDCl_3$) δ 8.21 (br s, 1H), 7.71-7.66 (m, 3H), 7.66-7.61 (m, 2H), 7.47-7.39 (m, 4H), 7.34-7.28 (m, 1H), 6.96 (s, 1H), 6.88-6.83 (m, 2H), 4.36 (br s, 1H), 3.99 (t, J = 6.2 Hz, 2H), 3.05-2.99 (m, 2H), 2.96 (t, J = 4.9 Hz, 4H), 2.80 (t, J = 7.2 Hz, 2H), 2.57-2.44 (m, 6H), 1.99-1.91 (m, 3H), 1.90-1.83 (m, 2H); 533 [M + H]$^+$ |

TABLE 1-continued

| Ex-am-ple | Structure | Name | $^1$H NMR, MS |
|---|---|---|---|
| 156 | 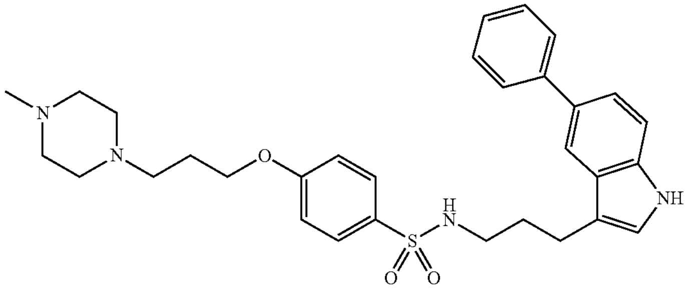 [SMILES: CN1CCN(CCCOc2ccc(S(=O)(=O)NCCCc3c[nH]c4ccc(-c5ccccc5)cc34)cc2)CC1] | 4-(3-(4-methyl-piperazin-1-yl)propoxy)-N-(3-(5-phenyl-1H-indol-3-yl)propyl)benzene-sulfonamide | $^1$H NMR (400 MHz, $CDCl_3$) δ 8.21 (br s, 1H), 7.72-7.66 (m, 3H), 7.66-7.61 (m, 2H), 7.48-7.39 (m, 4H), 7.32 (t, J = 7.4 Hz, 1H), 6.98-6.94 (m, 1H), 6.90-6.83 (m, 2H), 4.32 (t, J = 6.3 Hz, 1H), 4.00 (t, J = 6.4 Hz, 2H), 3.02 (q, J = 6.6 Hz, 2H), 2.80 (t, J = 7.2 Hz, 2H), 2.69-2.34 (m, 10H), 2.30 (s, 3H), 1.96 (p, J = 6.7 Hz, 2H), 1.88 (p, J = 7.0 Hz, 2H); 547 [M + H]$^+$ |
| 157 | 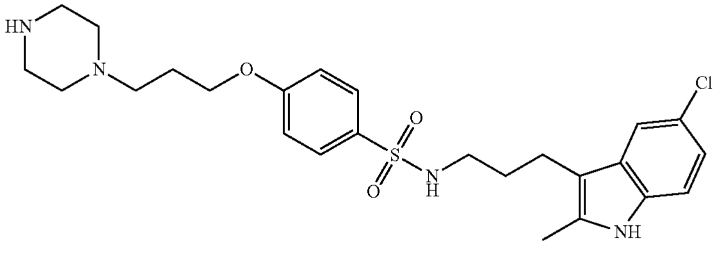 [SMILES: Cc1[nH]c2ccc(Cl)cc2c1CCCNS(=O)(=O)c1ccc(OCCCN2CCNCC2)cc1] | N-(3-(5-chloro-2-methyl-1H-indol-3-yl)propyl)-4-(3-(piperazin-1-yl)propoxybenzene-sulfonamide | $^1$H NMR (400 MHz, $CDCl_3$) δ 7.99 (br s, 1H), 7.70-7.62 (m, 2H), 7.30 (d, J = 1.9 Hz, 1H), 7.16 (d, J = 8.5 Hz, 1H), 7.04 (dd, J = 8.5, 2.0 Hz, 1H), 6.96-6.88 (m, 2H), 4.23 (br s, 1H), 4.07 (t, J = 6.3 Hz, 2H), 3.00-2.79 (m, 6H), 2.64 (t, J = 7.2 Hz, 2H), 2.56-2.37 (m, 6H), 2.32 (s, 3H), 2.06-1.94 (m, 2H), 1.80-1.67 (m, 6H); 505 [M + H]$^+$ |
| 158 | 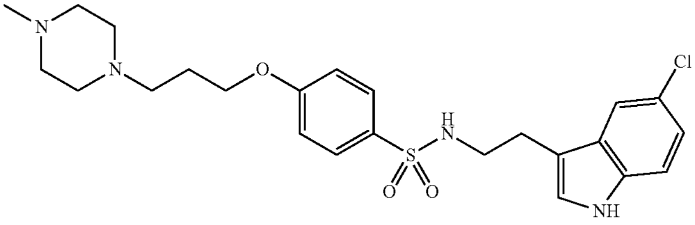 [SMILES: CN1CCN(CCCOc2ccc(S(=O)(=O)NCCc3c[nH]c4ccc(Cl)cc34)cc2)CC1] | N-(2-(5-chloro-1H-indol-3-yl)ethyl)-4-(3-(4-methyl piperazin-1-yl)pro-poxy)benzene-sulfonamide | $^1$H NMR (400 MHz, $CDCl_3$) δ 8.17 (s, 1H), 7.68-7.60 (m, 2H), 7.32 (d, J = 1.9 Hz, 1H), 7.28-7.25 (m, 1H), 7.13 (dd, J = 8.6, 2.0 Hz, 1H), 7.01 (d, J = 2.3 Hz, 1H), 6.92-6.84 (m, 2H), 4.27 (t, J = 6.1 Hz, 1H), 4.07 (t, J = 6.3 Hz, 2H), 3.25 (q, J = 6.5 Hz, 2H), 2.88 (t, J = 6.6 Hz, 2H), 2.69-2.32 (m, 10H), 2.29 (s, 3H), 2.05-1.93 (m, 2H); 491 [M + H]$^+$ |
| 159 | 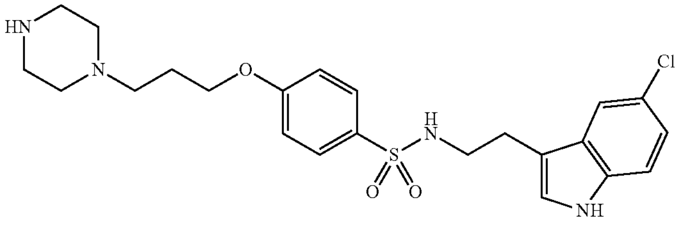 [SMILES: O=S(=O)(NCCc1c[nH]c2ccc(Cl)cc12)c1ccc(OCCCN2CCNCC2)cc1] | N-(2-(5-chloro-1H-indol-3-yl)ethyl)-4-(3-(piperazin-1-yl)propoxy)benzene-sulfonamide | $^1$H NMR (400 MHz, $CDCl_3$) δ 8.22 (br s, 1H), 7.64 (d, J = 8.8 Hz, 2H), 7.32 (d, J = 1.7 Hz, 1H), 7.28-7.24 (m, 1H), 7.13 (dd, J = 8.6, 1.8 Hz, 1H), 7.01 (s, 1H), 6.88 (d, J = 8.8 Hz, 2H), 4.30 (br s, 1H), 4.07 (t, J = 6.3 Hz, 2H), 3.25 (t, J = 6.4 Hz, 2H), 3.01-2.80 (m, 6H), 2.55-2.42 (m, 6H), 2.00 (dt, J = 13.3, 6.5 Hz, 2H); 477 [M + H]$^+$ |

TABLE 1-continued

| Example | Structure | Name | $^1$H NMR, MS |
|---|---|---|---|
| 160 | 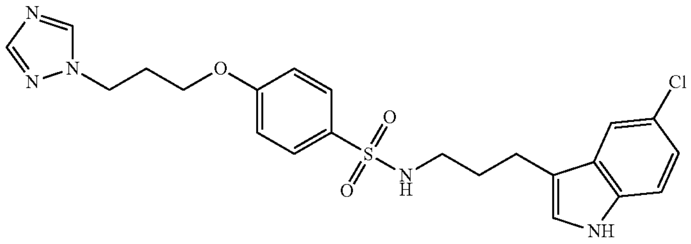 [SMILES: O=S(=O)(NCCCc1c[nH]c2ccc(Cl)cc12)c1ccc(OCCCn2cncn2)cc1] | 4-(3-(1H-1,2,4-triazol-1-yl)propoxy)-N-(3-(5-chloro-1H-indol-3-yl)propyl)benzene-sulfonamide | $^1$H NMR (400 MHz, $CDCl_3$) δ 8.44 (br s, 1H), 8.01 (d, J = 18.3 Hz, 2H), 7.77-7.68 (m, 2H), 7.44 (d, J = 2.0 Hz, 1H), 7.27-7.24 (m, 1H), 7.12 (dd, J = 8.6, 2.0 Hz, 1H), 6.92-6.86 (m, 3H), 4.44 (t, J = 6.5 Hz, 2H), 4.32 (t, J = 6.1 Hz, 1H), 3.95 (t, J = 5.7 Hz, 2H), 3.03-2.94 (m, 2H), 2.70 (t, J = 7.2 Hz, 2H), 2.44-2.37 (m, 2H), 1.82 (p, J = 7.0 Hz, 2H); 474 $[M + H]^+$ |
| 161 | 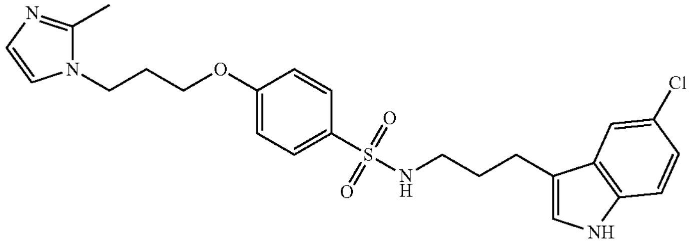 [SMILES: Cc1nccn1CCCOc1ccc(S(=O)(=O)NCCCc2c[nH]c3ccc(Cl)cc23)cc1] | N-(3-(5-chloro-1H-indol-3-yl)propyl)-4-(3-(2-methyl-1H-imidazol-1-yl)propoxy)benzene-sulfonamide | $^1$H NMR (400 MHz, MeOD) δ 7.71 (d, J = 1.9 Hz, 2H), 7.39 (d, J = 2.0 Hz, 1H), 7.34 (s, 1H), 7.27 (d, J = 8.6 Hz, 1H), 7.21 (br s, 1H), 7.06-6.95 (m, 4H), 4.29 (t, J = 6.8 Hz, 2H), 4.07 (t, J = 5.5 Hz, 2H), 2.90 (t, J = 7.0 Hz, 2H), 2.67 (t, J = 7.4 Hz, 2H), 2.50 (s, 3H), 2.31 (p, J = 12.3, 6.2 Hz, 2H), 1.76 (p, J = 14.4, 7.2 Hz, 2H); 487 $[M + H]^+$ |
| 162 | 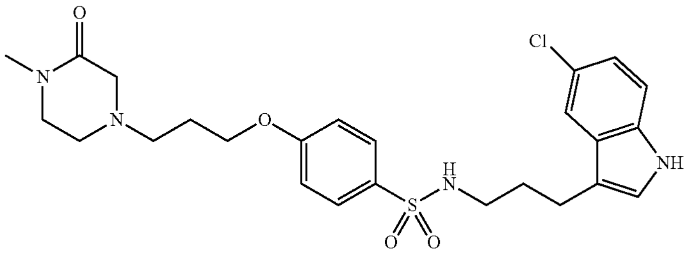 [SMILES: CN1CCN(CCCOc2ccc(S(=O)(=O)NCCCc3c[nH]c4ccc(Cl)cc34)cc2)CC1=O] | N-(3-(5-chloro-1H-indol-3-yl)propyl)-4-(3-(4-methyl-3-oxo-piperazin-1-yl)propoxy)benzene-sulfonamide | $^1$H NMR (400 MHz, $CDCl_3$) δ 8.26 (br s, 1H), 7.74-7.68 (m, 2H), 7.46-7.42 (m, 1H), 7.28-7.26 (m, 1H), 7.13 (dd, J = 8.6, 2.0 Hz, 1H), 6.97-6.88 (m, 3H), 4.29 (t, J = 6.3 Hz, 1H), 4.08 (t, J = 6.1 Hz, 2H), 3.35-3.30 (m, 2H), 3.15 (s, 2H), 3.04-2.93 (m, 5H), 2.74-2.67 (m, 4H), 2.58 (t, J = 6.9 Hz, 2H), 1.98 (p, J = 6.5 Hz, 2H), 1.82 (p, J = 7.1 Hz, 2H); 520 $[M + H]^+$ |
| 163 | 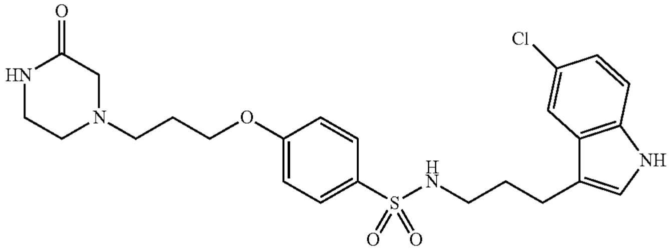 [SMILES: O=C1CN(CCCOc2ccc(S(=O)(=O)NCCCc3c[nH]c4ccc(Cl)cc34)cc2)CCN1] | N-(3-(5-chloro-1H-indol-3-yl)propyl)-4-(3-(3-oxopipera-zin-1-yl)pro-poxyl)benzene-sulfonamide | $^1$H NMR (400 MHz, $CDCl_3$) δ 8.17 (br s, 1H), 7.76-7.68 (m, 2H), 7.46-7.42 (m, 1H), 7.29-7.26 (m, 1H), 7.16-7.10 (m, 1H), 6.97-6.90 (m, 3H), 5.77 (s, 1H), 4.29 (t, J = 6.3 Hz, 1H), 4.09 (t, J = 6.2 Hz, 2H), 3.41-3.35 (m, 2H), 3.17 (s, 2H), 3.00 (q, J = 6.7 Hz, 2H), 2.74-2.67 |

TABLE 1-continued

| Example | Structure | Name | $^1$H NMR, MS |
|---|---|---|---|
| | | | (m, 4H), 2.62 (t, J = 6.9 Hz, 2H), 1.99 (p, J = 6.5 Hz, 2H), 1.82 (p, J = 7.1 Hz, 2H); 506 [M + H]$^+$ |
| 164 | 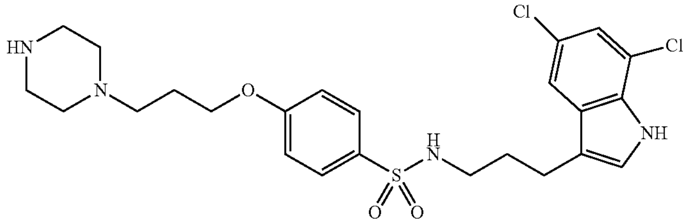 [SMILES: O=S(=O)(NCCCc1c[nH]c2c(Cl)cc(Cl)cc12)c1ccc(OCCCN2CCNCC2)cc1] | N-(3-(5,7-dichloro-1H-indol-3-yl)propyl)-4-(3-(piperazin-1-yl)propoxy)benzenesulfonamide | $^1$H NMR (400 MHz, $CDCl_3$) δ 8.45 (br s, 1H), 7.76-7.67 (m, 2H), 7.39-7.33 (m, 1H), 7.21-7.15 (m, 1H), 7.02 (s, 1H), 6.96-6.89 (m, 2H), 4.43 (s, 1H), 4.06 (t, J = 6.3 Hz, 2H), 3.48 (s, 1H), 2.97 (t, J = 6.9 Hz, 2H), 2.90 (t, J = 4.9 Hz, 4H), 2.70 (m, J = 7.3, 0.9 Hz, 2H), 2.54-2.34 (m, 6H), 2.05-1.93 (m, 2H), 1.82 (p, J = 7.1 Hz, 2H); 526 [M + H]$^+$ |
| 165 | 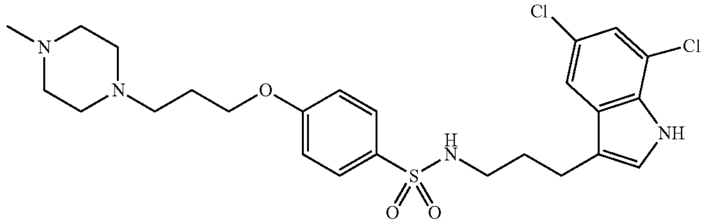 [SMILES: CN1CCN(CCCOc2ccc(S(=O)(=O)NCCCc3c[nH]c4c(Cl)cc(Cl)cc34)cc2)CC1] | N-(3-(5,7-dichloro-1H-indol-3-yl)propyl)-4-(3-(4-methylpiperazin-1-yl)propoxy)benzenesulfonamide | $^1$H NMR (400 MHz, $CDCl_3$) δ 8.30 (br s, 1H), 7.76-7.68 (m, 2H), 7.40-7.34 (m, 1H), 7.21-7.16 (m, 1H), 7.05-7.01 (m, 1H), 6.97-6.89 (m, 2H), 4.31 (t, J = 6.3 Hz, 1H), 4.07 (t, J = 6.4 Hz, 2H), 2.98 (q, J = 6.7 Hz, 2H), 2.75-2.67 (m, 2H), 2.64-2.33 (m, 10H), 2.29 (s, 3H), 2.06-1.93 (m, 2H), 1.83 (p, J = 7.1 Hz, 2H); 540 [M + H]$^+$ |
| 166 | 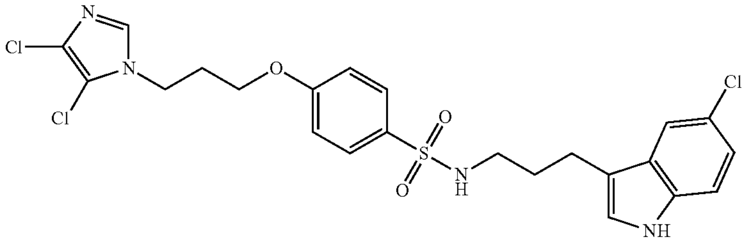 [SMILES: O=S(=O)(NCCCc1c[nH]c2ccc(Cl)cc12)c1ccc(OCCCn2cnc(Cl)c2Cl)cc1] | N-(3-(5-chloro-1H-indol-3-yl)propyl)-4-(3-(4,5-dichoro-1H-imidazol-1-yl)propoxy)benzenesulfonamide | $^1$H NMR (400 MHz, $CDCl_3$) δ 8.60 (br s, 1H), 7.78-7.69 (m, 2H), 7.44 (d, J = 2.0 Hz, 1H), 7.29 (d, J = 5.6 Hz, 1H), 7.12 (dd, J = 8.6, 2.0 Hz, 1H), 6.94-6.87 (m, 2H), 6.85 (d, J = 2.3 Hz, 1H), 4.30 (t, J = 6.2 Hz, 1H), 4.20 (t, J = 6.5 Hz, 2H), 3.93 (t, J = 5.6 Hz, 2H), 3.00 (q, J = 6.8 Hz, 2H), 2.70 (t, J = 7.1 Hz, 2H), 2.33-2.22 (m, 2H), 1.82 (p, J = 7.0 Hz, 2H); 541 [M + H]$^+$ |
| 167 | 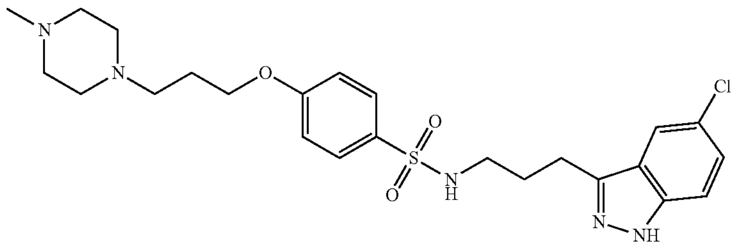 [SMILES: CN1CCN(CCCOc2ccc(S(=O)(=O)NCCCc3n[nH]c4ccc(Cl)cc34)cc2)CC1] | N-(3-(5-chloro-1H-indazol-3-yl)propyl)-4-(3-(4-methylpiperazin-1-yl)propoxybenzenesulfonamide | $^1$H NMR (400 MHz, $CDCl_3$) δ 7.74-7.67 (m, 2H), 7.57 (dd, J = 1.8, 0.6 Hz, 1H), 7.37 (dd, J = 8.8, 0.6 Hz, 1H), 7.32 (dd, J = 8.8, 1.8 Hz, 1H), 6.92-6.84 (m, 2H), 5.22-5.13 (m, 1H), 4.05 (t, J = 6.3 Hz, 2H), 3.05 (q, J = 6.5 Hz, 2H), 2.93 (t, J = 7.1 Hz, 2H), 2.67- |

TABLE 1-continued

| Ex-am-ple | Structure | Name | $^1H$ NMR, MS |
|---|---|---|---|
| | | | 2.38 (m, 10H), 2.32 (s, 3H), 2.04-1.90 (m, 4H); 506 [M + H]$^+$ |
| 168 | 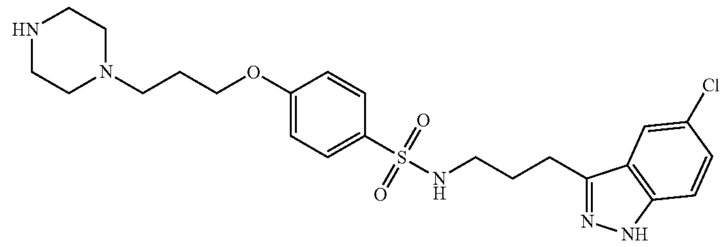 [SMILES: O=S(=O)(NCCCc1n[nH]c2ccc(Cl)cc12)c1ccc(OCCCN2CCNCC2)cc1] | N-(3-(5-chloro-1H-indazol-3-yl)propyl)-4-(3-(piperazin-1-yl)propoxy)benzene-sulfonamide | $^1H$ NMR (400 MHz, $CDCl_3$) δ 7.74-7.66 (m, 2H), 7.57 (d, J = 1.1 Hz, 1H), 7.40-7.30 (m, 2H), 6.93-6.84 (m, 2H), 4.06 (t, J = 6.3 Hz, 2H), 3.05 (t, J = 6.7 Hz, 2H), 2.96-2.88 (m, 6H), 2.55-2.40 (m, 6H), 2.30-1.98 (m, 4H); 492 [M + H]$^+$ |
| 169 | 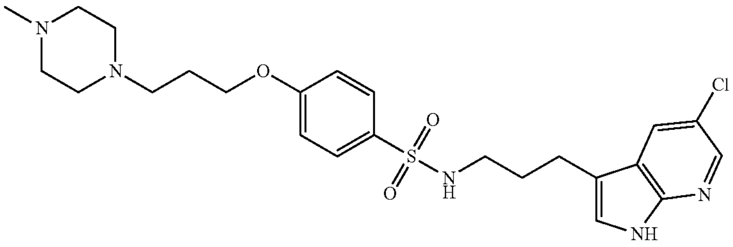 [SMILES: CN1CCN(CCCOc2ccc(S(=O)(=O)NCCCc3c[nH]c4ncc(Cl)cc34)cc2)CC1] | N-(3-(5-chloro-1H-pyrrolo[2,3-b]pyridin-3-yl)propyl)-4-(3-(4-methylpiperazin-1-yl)pro-poxy)benzene-sulfonamide | $^1H$ NMR (400 MHz, $CDCl_3$) δ 9.02 (br s, 1H), 8.21 (d, J = 2.2 Hz, 1H), 7.76 (d, J = 2.2 Hz, 1H), 7.75-7.68 (m, 2H), 7.00 (d, J = 1.9 Hz, 1H), 6.95-6.86 (m, 2H), 4.42 (t, J = 6.2 Hz, 1H), 4.08 (t, J = 6.2 Hz, 2H), 2.98 (dd, J = 13.1, 6.7 Hz, 2H), 2.76-2.57 (m, 10H), 2.43 (s, 3H), 2.06-1.97 (m, 2H), 1.87-1.79 (m, 2H); 506 [M + H]$^+$ |
| 170 | 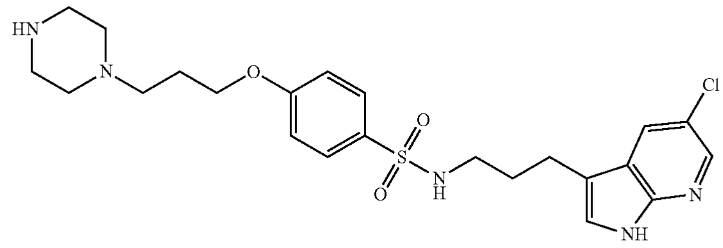 [SMILES: O=S(=O)(NCCCc1c[nH]c2ncc(Cl)cc12)c1ccc(OCCCN2CCNCC2)cc1] | N-(3-(5-chloro-1H-pyrrolo[2,3-b]pyridin-3-yl)propyl)-4-(3-(4-piperazin-1-yl)pro-poxy)benzene-sulfonamide | $^1H$ NMR (400 MHz, $CDCl_3$) δ 8.21 (d, J = 2.2 Hz, 1H), 7.77 (d, J = 2.2 Hz, 1H), 7.75-7.68 (m, 2H), 7.02 (s, 1H), 6.94-6.86 (m, 2H), 4.42 (br s, 1H), 4.08 (t, J = 6.2 Hz, 2H), 3.03-2.94 (m, 4H), 2.70 (t, J = 7.3 Hz, 2H), 2.60-2.53 (m, 4H), 2.60-1.95 (m, 2H), 1.90-1.75 (m, 6H); 492 [M + H]$^+$ |
| 171 | 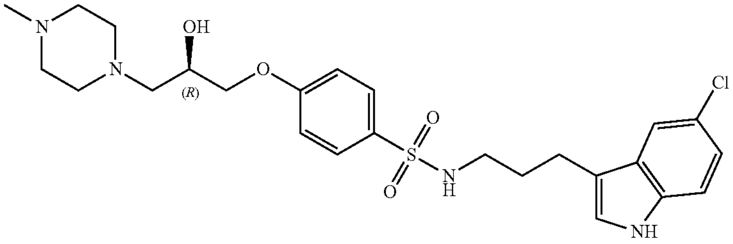 | (R)-N-(3-(5-chloro-1H-indol-3-yl)propyl)-4-(2-hydroxy-3-(4-methylpipera-zin-1-yl)pro-poxy)benzene-sulfonamide | $^1H$ NMR (400 MHz, $CDCl_3$) δ 8.18 (s, 1H), 7.76-7.68 (m, 2H), 7.47-7.40 (m, 1H), 7.27-7.24 (m, 1H), 7.12 (dd, J = 8.6, 2.0 Hz, 1H), 6.99-6.93 (m, 2H), 6.93-6.88 (m, 1H), 4.38 (t, J = 6.0 Hz, 1H), 4.16-4.08 (m, 1H), 4.08-3.98 (m, 2H), 2.98 (q, J = 6.5 Hz, 2H), 2.81-2.65 (m, 4H), 2.64-2.37 (m, 8H), 2.32 (s, 3H), 1.81 (p, J = 7.0 Hz, 2H); 522 [M + H]$^+$ |

TABLE 1-continued

| Example | Structure | Name | $^1$H NMR, MS |
|---|---|---|---|
| 172 | 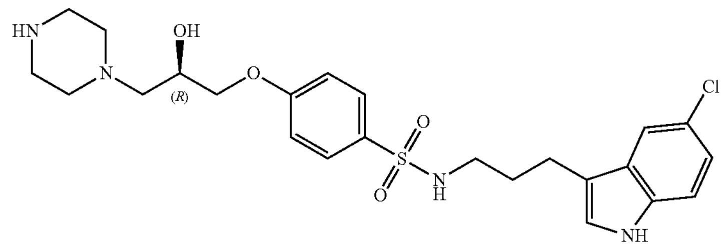 | (R)-N-(3-(5-chloro-1H-indol-3-yl)propyl)-4-(2-hydroxy-3-(piperazin-1-yl)propoxy)benzenesulfonamide | $^1$H NMR (400 MHz, $CDCl_3$) δ 8.12 (br s, 1H), 7.76-7.67 (m, 2H), 7.46-7.42 (m, 1H), 7.28-7.24 (m, 1H), 7.13 (dd, J = 8.6, 2.0 Hz, 1H), 7.00-6.94 (m, 2H), 6.93-6.89 (m, 1H), 4.26 (br s, 1H), 4.16-4.09 (m, 1H), 4.09-3.99 (m, 2H), 3.04-2.96 (m, 2H), 2.96-2.87 (m, 4H), 2.74-2.62 (m, 4H), 2.59-2.51 (m, 2H), 2.49-2.39 (m, 2H), 1.82 (p, J = 7.0 Hz, 2H); 508 [M +H]$^+$ |
| 173 | 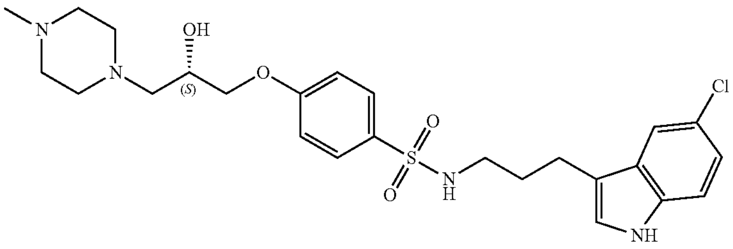 | (S)-N-(3-(5-chloro-1H-indol-3-yl)propyl)-4-(2-hydroxy-3-(4-methylpiperazin-1-yl)propoxy)benzenesulfonamide | $^1$H NMR (400 MHz, $CDCl_3$) δ 8.17 (br s, 1H), 7.76-7.67 (m, 2H), 7.47-7.40 (m, 1H), 7.28-7.23 (m, 1H), 7.12 (dd, J = 8.6, 2.0 Hz, 1H), 6.99-6.92 (m, 2H), 6.91 (d, J = 2.4 Hz, 1H), 4.36 (t, J = 6.3 Hz, 1H), 4.16-4.07 (m, 1H), 4.07-3.98 (m, 2H), 2.98 (q, J = 6.6 Hz, 2H), 2.81-2.66 (m, 4H), 2.64-2.38 (m, 8H), 2.32 (s, 3H), 1.81 (p, J = 7.0 Hz, 2H); 522 [M + H]$^+$ |
| 174 | 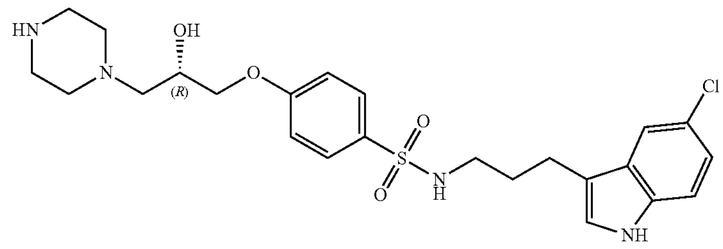 | (S)-N-(3-(5-chloro-1H-indol-3-yl)propyl)-4-(2-hydroxy-3-(piperazin-1-yl)propoxy)benzenesulfonamide | $^1$H NMR (400 MHz, $CDCl_3$) δ 8.15 (br s, 1H), 7.75-7.68 (m, 2H), 7.46-7.41 (m, 1H), 7.27-7.24 (m, 1H), 7.13 (dd, J = 8.6, 2.0 Hz, 1H), 6.99-6.93 (m, 2H), 6.92-6.89 (m, 1H), 4.32 (br s, 1H), 4.17-4.09 (m, 1H), 4.08-3.99 (m, 2H), 3.03-2.90 (m, 6H), 2.73-2.63 (m, 4H), 2.56-2.51 (m, 2H), 2.48-2.39 (m, 2H), 1.82 (p, J = 7.0 Hz, 2H); 508 [M +H]$^+$ |
| 175 | 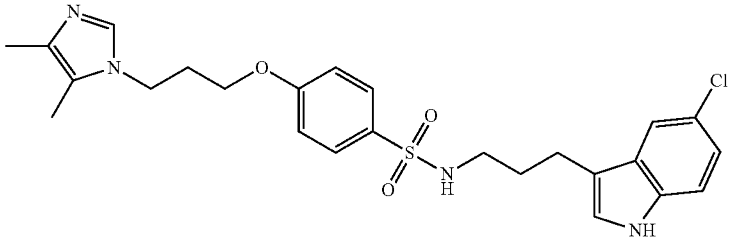 [SMILES: Cc1ncn(CCCOc2ccc(S(=O)(=O)NCCCc3c[nH]c4ccc(Cl)cc34)cc2)c1C] | N-(3-(5-chloro-1H-indol-3-yl)propyl)-4-(3-(4,5-dimethyl-1H-imidazol-1-yl)propoxy)benzenesulfonamide | $^1$H NMR (400 MHz, $CDCl_3$) δ 9.97 (br s, 1H), 7.75-7.68 (m, 2H), 7.44 (d, J = 1.9 Hz, 1H), 7.26-7.21 (m, 2H), 7.08 (dd, J = 8.6, 2.0 Hz, 1H), 6.90-6.82 (m, 2H), 6.70 (d, J = 1.7 Hz, 1H), 4.38 (br s, 1H), 4.10 (t, J = 6.4 Hz, 2H), 3.84 (t, J = 5.5 Hz, 2H), 3.01-2.91 |

TABLE 1-continued

| Example | Structure | Name | $^1$H NMR, MS |
|---|---|---|---|
| | | | (m, 2H), 2.69 (t, J = 7.0 Hz, 2H), 2.23-2.10 (m, 8H), 1.80-1.77 (m, 2H); 501 [M + H]$^+$ |
| 176 | 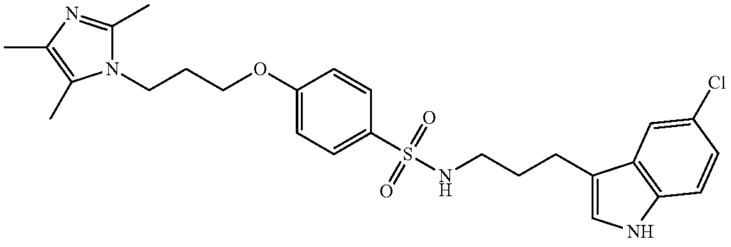 [SMILES: Cc1nc(C)n(CCCOc2ccc(S(=O)(=O)NCCCc3c[nH]c4ccc(Cl)cc34)cc2)c1C] | N-(3-(5-chloro-1H-indol-3-yl)propyl)-4-(3-(2,4,5-trimethyl-1H-imidazol-1-yl)propoxy)benzenesulfonamide | $^1$H NMR (400 MHz, $CDCl_3$) δ 9.31 (br s, 1H), 7.75-7.67 (m, 2H), 7.44 (d, J = 1.9 Hz, 1H), 7.24-7.21 (m, 1H), 7.10 (dd, J = 8.6, 2.0 Hz, 1H), 6.88-6.81 (m, 3H), 4.29 (t, J = 6.2 Hz, 1H), 4.00 (t, J = 6.7 Hz, 2H), 3.87 (t, J = 5.5 Hz, 2H), 2.97 (q, J = 6.7 Hz, 2H), 2.69 (t, J = 7.1 Hz, 2H), 2.21 (s, 3H), 2.18-2.07 (m, 8H), 1.84-1.74 (m, 2H); 515 [M + H]$^+$ |
| 177 | 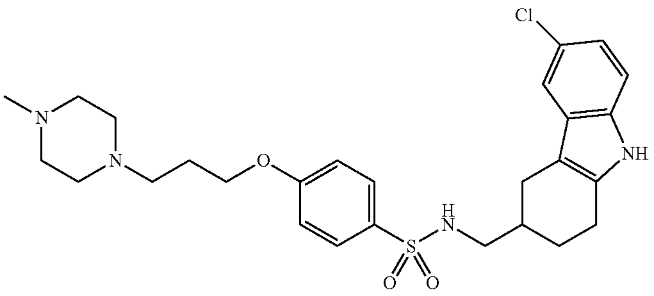 [SMILES: CN1CCN(CCCOc2ccc(S(=O)(=O)NCC3CCc4[nH]c5ccc(Cl)cc5c4C3)cc2)CC1] | N-(6-chloro-2,3,4,9-tetrahydro-1H-carbazol-3-yl)methyl)-4-(3-(4-methylpiperazin-1-yl)propoxy)benzenesulfonamide | $^1$H NMR (400 MHz, $CDCl_3$) δ 7.86-7.76 (m, 3H), 7.32 (d, J = 1.9 Hz, 1H), 7.16 (d, J = 8.5 Hz, 1H), 7.05 (dd, J = 8.5, 2.0 Hz, 1H), 7.01-6.94 (m, 2H), 4.54-4.46 (m, 1H), 4.07 (t, J = 6.3 Hz, 2H), 3.09-2.94 (m, 2H), 2.79-2.68 (m, 3H), 2.64-2.33 (m, 9H), 2.29 (s, 3H), 2.27-2.14 (m, 1H), 2.07-1.91 (m, 4H).; 531 [M + H]$^+$ |
| 178 | 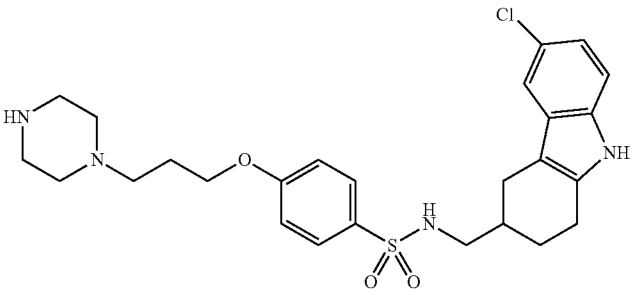 [SMILES: O=S(=O)(NCC1CCc2[nH]c3ccc(Cl)cc3c2C1)c1ccc(OCCCN2CCNCC2)cc1] | N-(6-chloro-2,3,4,9-tetrahydroxy-1H-carbazol-3-yl)methyl)-4-(3-(piperazin-1-yl)propoxy)benzenesulfonamide | $^1$H NMR (400 MHz, $CDCl_3$) δ 7.88-7.76 (m, 3H), 7.32 (d, J = 1.9 Hz, 1H), 7.16 (d, J = 8.5 Hz, 1H), 7.05 (dd, J = 8.5, 2.0 Hz, 1H), 7.01-6.94 (m, J = 8.9 Hz, 2H), 4.49 (br s, 1H), 4.08 (t, J = 6.3 Hz, 2H), 3.06-2.97 (m, 2H), 2.90 (t, J = 4.9 Hz, 4H), 2.78-2.68 (m, 3H), 2.54-2.37 (m, 6H), 2.26-2.18 (m, 1H), 2.07-1.93 (m, 4H); 517 [M + H]$^+$ |
| 179 | 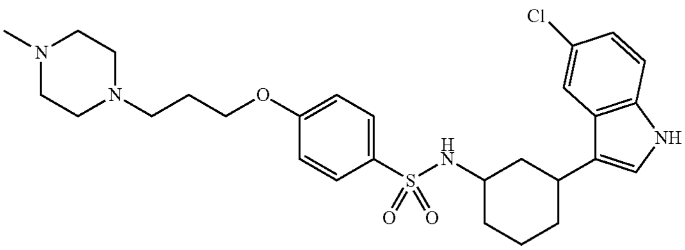 [SMILES: CN1CCN(CCCOc2ccc(S(=O)(=O)NC3CCCC(c4c[nH]c5ccc(Cl)cc45)C3)cc2)CC1] | N-(5-(3-(5-chloro-1H-indol-3-yl)cyclohexyl)-4-(3-(4-methylpiperazin-1-yl)propoxy)benzenesulfonamide | $^1$H NMR (400 MHz, MeOD) δ 7.81-7.74 (m, 2H), 7.46 (d, J = 1.9 Hz, 1H), 7.27 (d, J = 8.6 Hz, 1H), 7.02 (dd, J = 8.6, 2.0 Hz, 1H), 7.00-6.93 (m, 3H), 4.03 (t, J = 6.1 Hz, 2H), 3.57-3.47 (m, 1H), 3.16-3.06 (m, 1H), 2.74-2.50 (m, 8H), 2.39 (s, 3H), 2.02-1.91 (m, 4H), 1.87-1.80 (m, 1H), 1.78-1.68 |

TABLE 1-continued

| Example | Structure | Name | $^1$H NMR, MS |
|---|---|---|---|
| | | | (m, 1H), 1.67-1.52 (m, 5H); 545 [M + H]$^+$ |
| 180 | 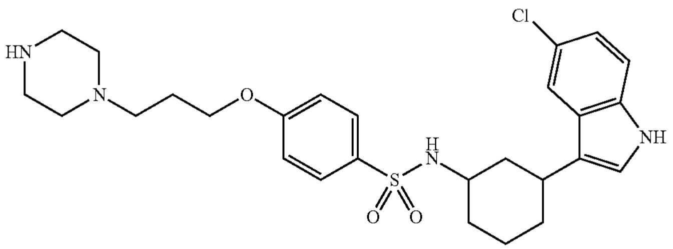 [SMILES: O=S(=O)(NC1CCCC(c2c[nH]c3ccc(Cl)cc23)C1)c1ccc(OCCCN2CCNCC2)cc1] | N-(3-(5-chloro-1H-indol-3-yl)cyclohexyl)-4-(3-(piperazin-1-yl)propoxy)benzene-sulfonamide | $^1$H NMR (400 MHz, MeOD) δ 7.78 (d, J = 8.9 Hz, 2H), 7.46 (d, J = 1.9 Hz, 1H), 7.27 (d, J = 8.6 Hz, 1H), 7.02 (dd, J = 8.6, 2.0 Hz, 1H), 7.00-6.92 (m, 3H), 4.04 (t, J = 6.1 Hz, 2H), 3.53-3.48 (m, 1H), 3.15-3.10 (m, 1H), 2.97 (t, J = 5.0 Hz, 4H), 2.63-2.44 (m, 6H), 2.01-1.91 (m, 3H), 1.87-1.80 (m, 1H), 1.77-1.69 (m, 1H), 1.67-1.53 (m, 5H).; 531 [M + H]$^+$ |
| 181 | 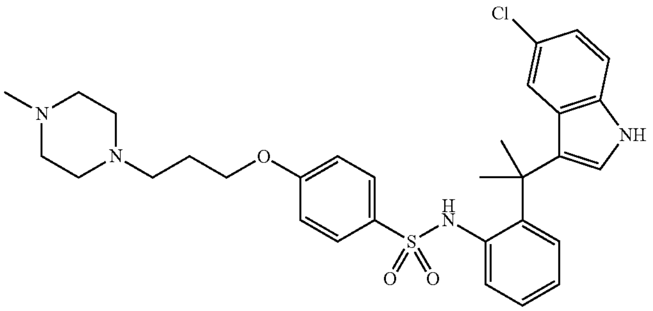 [SMILES: CN1CCN(CCCOc2ccc(S(=O)(=O)Nc3ccccc3C(C)(C)c3c[nH]c4ccc(Cl)cc34)cc2)CC1] | N-(2-(2-(5-chloro-1H-indol-3-yl)propan-2-yl)phenyl)-4-(3-(4-methylpiperazin-1-yl)propoxy)benzene-sulfonamide | $^1$H NMR (400 MHz, MeOD) δ 7.69-7.63 (m, 1H), 7.56 (s, 1H), 7.45 (d, J = 8.7 Hz, 1H), 7.28-7.22 (m, 1H), 7.18-7.07 (m, 3H), 6.82-6.76 (m, 2H), 6.63-6.55 (m, 2H), 6.49 (d, J = 1.9 Hz, 1H), 4.02 (t, J = 6.1 Hz, 2H), 2.86-2.35 (m, 10H), 2.31 (s, 3H), 2.02-1.92 (m, 2H); 583 [M + H]$^+$ |
| 182 | 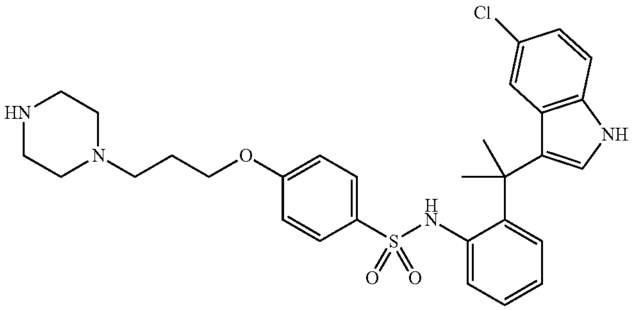 [SMILES: CC(C)(c1ccccc1NS(=O)(=O)c1ccc(OCCCN2CCNCC2)cc1)c1c[nH]c2ccc(Cl)cc12] | N-(2-(2-(5-chloro-1H-indol-3-yl)propan-2-yl)phenyl)-4-(3-(piperazin-1-yl)propoxy)benzene-sulfonamide | $^1$H NMR (400 MHz, MeOD) δ 7.68-7.62 (m, 1H), 7.56 (s, 1H), 7.46 (d, J = 8.7 Hz, 1H), 7.28-7.21 (m, 1H), 7.18-7.07 (m, 3H), 6.82-6.75 (m, 2H), 6.63-6.56 (m, 2H), 6.49 (d, J = 1.9 Hz, 1H), 4.03 (t, J = 6.1 Hz, 2H), 3.01 (t, J = 5.0 Hz, 4H), 2.66-2.46 (m, 6H), 2.03-1.92 (m, 2H), 1.73 (s, 6H); 567 [M + H]$^+$ |
| 183 | 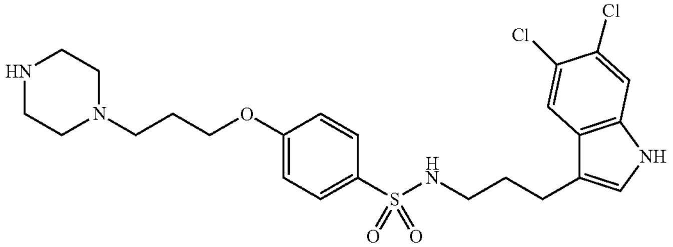 [SMILES: O=S(=O)(NCCCc1c[nH]c2cc(Cl)c(Cl)cc12)c1ccc(OCCCN2CCNCC2)cc1] | N-(3-(5,6-dichloro-1H-indol-3-yl)propyl)-4-(3-(piperazin-1-yl)propoxybenzene-sulfonamide | $^1$H NMR (400 MHz, $CDCl_3$) δ 8.45 (br s, 1H), 7.75-7.65 (m, 2H), 7.53 (s, 1H), 7.43 (s, 1H), 6.96-6.87 (m, 3H), 4.52 (br s, 1H), 4.06 (t, J = 6.3 Hz, 2H), 2.97 (t, J = 6.8 Hz, 2H), 2.90 (t, J = 4.9 Hz, 4H), 2.68 (t, J = 7.2 Hz, 2H), 2.55-2.37 (m, 6H), 2.05-1.96 (m, 2H), 1.85-1.75 (m, 2H); 526 [M + H]$^+$ |

TABLE 1-continued

| Example | Structure | Name | $^1$H NMR, MS |
|---|---|---|---|
| 184 | 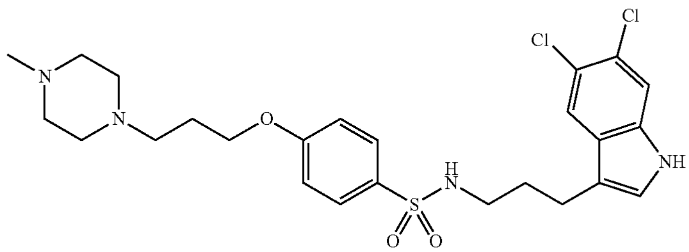 [SMILES: CN1CCN(CCCOc2ccc(S(=O)(=O)NCCCc3c[nH]c4cc(Cl)c(Cl)cc34)cc2)CC1] | N-(3-(5,6-dichloro-1H-indol-3-yl)propyl)-4-(3-(4-methylpiperazin-1-yl)propoxy)benzene-sulfonamide | $^1$H NMR (400 MHz, $CDCl_3$) δ 8.54 (br s, 1H), 7.75-7.66 (m, 2H), 7.52 (s, 1H), 7.42 (s, 1H), 6.96-6.86 (m, 3H), 4.65 (t, J = 6.3 Hz, 1H), 4.05 (t, J = 6.3 Hz, 2H), 2.96 (q, J = 6.6 Hz, 2H), 2.67 (t, J = 7.3 Hz, 2H), 2.62-2.34 (m, 9H), 2.29 (s, 3H), 2.07-1.93 (m, 3H), 1.79 (p, J = 7.1 Hz, 2H); 540 $[M + H]^+$ |
| 185 | 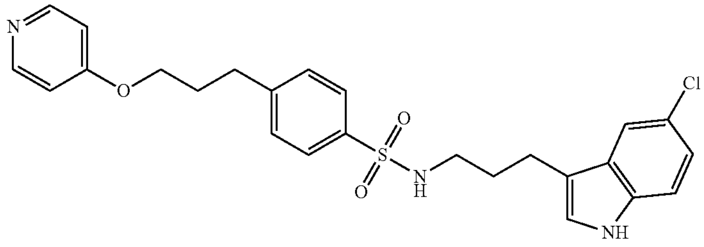 [SMILES: O=S(=O)(NCCCc1c[nH]c2ccc(Cl)cc12)c1ccc(CCCOc2ccncc2)cc1] | N-(3-(5-chloro-1H-indol-3-yl)propyl)-4-(3-(pyridin-4-yl)oxy)propyl)benzene-sulfonamide | $^1$H NMR (400 MHz, $CDCl_3$) δ 8.11 (br s, 1H), 7.75-7.70 (m, 2H), 7.40 (d, J = 1.9 Hz, 1H), 7.28-7.22 (m, 3H), 7.18-7.10 (m, 3H), 7.01 (d, J = 2.2 Hz, 1H), 6.37-6.32 (m, 2H), 4.47 (t, J = 5.8 Hz, 1H), 3.74 (t, J = 7.1 Hz, 2H), 3.07 (q, J = 6.7 Hz, 2H), 2.71 (q, J = 7.5 Hz, 2H), 2.12 (p, J = 14.8, 7.4 Hz, 2H), 1.81 (p, J = 14.2, 7.1 Hz, 2H); 489 $[M + H]^+$ |
| 186 | 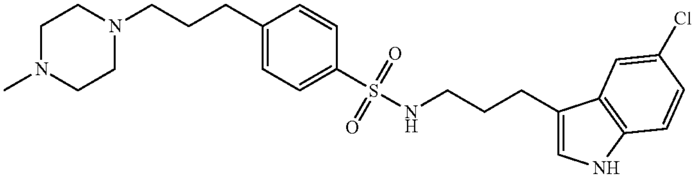 | N-(3-(5-chloro-1H-indol-3-yl)propyl)-4-(3-(4-methylpiperazin-1-yl)propyl)benzene-sulfonamide | $^1$H NMR (400 MHz, $CDCl_3$) δ 8.62 (br s, 1H), 7.71 (d, J = 8.3 Hz, 2H), 7.44 (d, J = 1.9 Hz, 1H), 7.32-7.21 (m, 2H), 7.12 (dd, J = 8.6, 2.0 Hz, 1H), 6.85 (d, J = 1.8 Hz, 1H), 4.33 (t, J = 6.2 Hz, 1H), 3.01 (q, J = 6.7 Hz, 2H), 2.70 (t, J = 7.3 Hz, 4H), 2.66-2.24 (m, 13H), 1.88-1.75 (m, 4H); 484 $[M + H]^+$ |
| 187 | 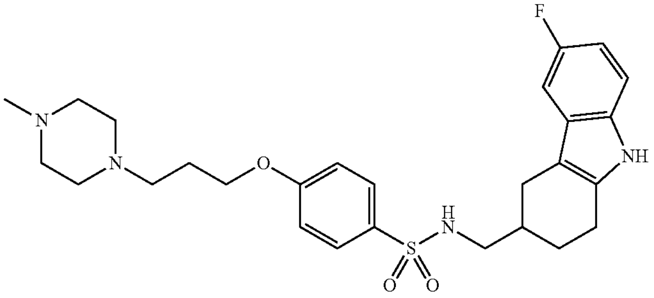 [SMILES: CN1CCN(CCCOc2ccc(S(=O)(=O)NCC3CCc4[nH]c5ccc(F)cc5c4C3)cc2)CC1] | N-(6-fluoro-2,3,4,9-tetrahydro-1H-carbazol-3-yl)methyl)-4-(3-(4-methylpiperazin-1-yl)propoxy)benzene-sulfonamide | $^1$H NMR (400 MHz, MeOD) δ 7.84-7.75 (m, 2H), 7.14 (dd, J = 8.7, 4.4 Hz, 1H), 7.11-7.02 (m, 2H), 6.92 (dd, J = 9.8, 2.5 Hz, 1H), 6.77-6.69 (m, 1H), 4.10 (t, J = 6.1 Hz, 2H), 2.98-2.85 (m, 2H), 2.82-2.34 (m, 12H), 2.31 (s, 3H), 2.19-2.11 (m, 1H), 2.07-1.96 (m, 3H), 1.96-1.87 (m, 1H), 1.59-1.47 (m, 1H); 515 $[M + H]^+$ |

TABLE 1-continued

| Example | Structure | Name | $^1$H NMR, MS |
|---|---|---|---|
| 188 | 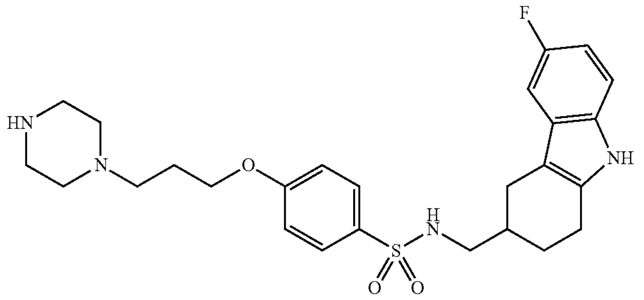 [SMILES: O=S(=O)(NCC1CCc2[nH]c3ccc(F)cc3c2C1)c1ccc(OCCCN2CCNCC2)cc1] | N-(6-(fluoro-2,3,4,9-tetrahydro-1H-carbazol-3-yl)methyl)-4-(3-(piperazin-1-yl)propoxy)benzenesulfonamide | $^1$H NMR (400 MHz, MeOD) δ 7.83-7.76 (m, 2H), 7.14 (dd, J = 8.7, 4.4 Hz, 1H), 7.10-7.04 (m, 2H), 6.92 (dd, J = 9.8, 2.5 Hz, 1H), 6.77-6.68 (m, 1H), 4.11 (t, J = 6.1 Hz, 2H), 2.97-2.84 (m, 6H), 2.78-2.63 (m, 3H), 2.63-2.43 (m, 6H), 2.20-2.08 (m, 1H), 2.08-1.86 (m, 4H), 1.59-1.47 (m, 1H); 501 [M + H]$^+$ |
| 189 | 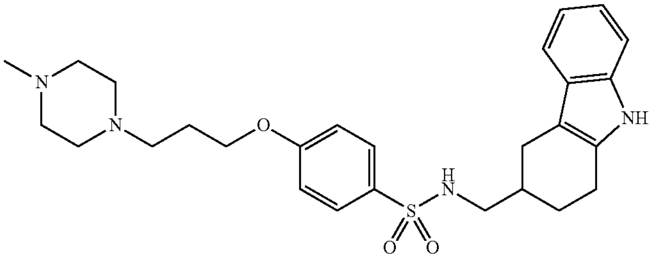 [SMILES: CN1CCN(CCCOc2ccc(S(=O)(=O)NCC3CCc4[nH]c5ccccc5c4C3)cc2)CC1] | 4-(3-(4-methyl-piperazin-1-yl)propoxy)-N-((2,3,4,9-tetrahydro-1H-carbazol-3-yl)methyl)benzenesulfonamide | $^1$H NMR (400 MHz, MeOD) δ 7.83-7.76 (m, 2H), 7.29 (d, J = 7.6 Hz, 1H), 7.20 (d, J = 7.9 Hz, 1H), 7.09-7.03 (m, 2H), 7.01-6.95 (m, 1H), 6.95-6.89 (m, 1H), 4.14-4.06 (m, 2H), 2.96-2.87 (m, 2H), 2.84-2.34 (m, 12H), 2.30 (s, 3H), 2.24-2.15 (m, 1H), 2.08-1.86 (m, 5H), 1.60-1.48 (m, 1H); 497 [M + H]$^+$ |
| | 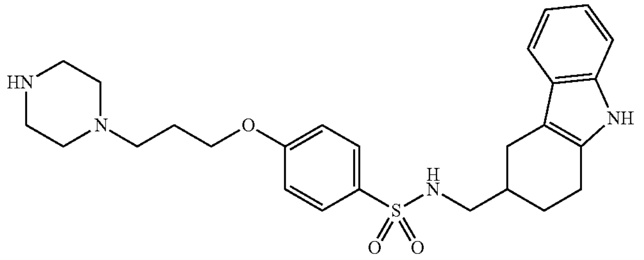 [SMILES: O=S(=O)(NCC1CCc2[nH]c3ccccc3c2C1)c1ccc(OCCCN2CCNCC2)cc1] | 4-(3-(piperazin-1-yl)propoxy)-N-(2,3,4,9-tetrahydro-1H-carbazol-3-yl)methyl)benzenesulfonamide | $^1$H NMR (400 MHz, MeOD) δ 7.84-7.74 (m, 2H), 7.29 (d, J = 7.7 Hz, 1H), 7.20 (d, J = 7.9 Hz, 1H), 7.10-7.03 (m, 2H), 7.01-6.95 (m, 1H), 6.95-6.89 (m, 1H), 4.10 (t, J = 6.1 Hz, 2H), 2.95-2.86 (m, 6H), 2.80-2.67 (m, 3H), 2.62-2.40 (m, 6H), 2.24-2.15 (m, 1H), 2.07-1.88 (m, 4H), 1.59-1.49 (m, 1H); 484 [M + H]$^+$ |

<Analysis and Purification Conditions>

[LC-MS analysis conditions]

Device name: Shimadzu LCMS-2020

Column: ACE Excel2 C18, 75×2.1 mm

Moving phase: acetonitrile/$H_2O$+0.1% TFA

Flow rate: 0.5 mL/min

UV detector: 254 nm

[MPLC purification conditions]

Device name: CombiFlash® Rf+

UV detector: 254 nm

[Prep-HPLC purification conditions]

Device name: Gilson GX-281, 321 pump, UV/VIS-155

Column: Luna® 10 vM C18 (2) 100 Å, 250×21.2 mm

Moving phase: acetonitrile/0.1% TFA $H_2O$

Flow rate: 18 mL/min

UV detector: 254 nm

[$^1$H NMR]

Device name: Bruker Avance (400 MHz)

<Experimental Example 1> Evaluation of Pin1 Enzyme Inhibitory Activity

In order to evaluate the Pin1 enzyme inhibitory activity of the compound represented by formula 1 according to the present invention, the following experiment was performed, and the results are shown in Table 2 below.

The enzyme activity of Pin1 protein was measured using a sensolyte Green Pin1 assay kit of Anaspec. The substrate was diluted in a buffer at a ratio of 1:100 to prepare a concentration of 1 μM, and the protein was diluted in a buffer at a ratio of 1:20 to prepare a concentration of 50 μg/ml. In addition, a developing solution was prepared by diluting thereof in a buffer at a ratio of 1:100.

The compound prepared in each example was diluted with DMSO and prepared at a concentration of 100 μM, 10 μM, 1 μM or 0.1 μM using a buffer. After sequentially adding 10 μl of the compound prepared in each Example diluted to four concentrations according to the above method, 10 μl of Pin1 protein, and 30 μl of the developing solution to each well of a black 96-well plate, 50 μl of the substrate was finally added. Finally, 50 μl of the substrate was added to each well of the plate, and the enzyme reaction was carried out after shaking the plate for 10 seconds.

Then, the plate was incubated for 2 hours at room temperature in an environment without light, and the fluorescence values at 490 nm/520 nm wavelength were measured using a device of Synergy Neo (Tecan). The results are shown in Table 2 below by dividing the grades of A to D for each concentration (μM) at which the Pin1 enzyme activity is inhibited.

TABLE 2

| Example | Pin 1 inhibition |
|---|---|
| 1 | D |
| 2 | D |
| 3 | D |
| 4 | D |
| 5 | D |
| 6 | D |
| 7 | D |
| 8 | D |
| 9 | D |
| 10 | D |
| 11 | C |
| 12 | C |
| 13 | D |
| 14 | D |
| 15 | D |
| 16 | D |
| 17 | D |
| 18 | D |
| 19 | D |
| 20 | C |
| 21 | C |
| 22 | C |
| 23 | D |
| 24 | D |
| 25 | D |
| 26 | C |
| 27 | C |
| 28 | D |
| 29 | D |
| 30 | D |
| 31 | B |
| 32 | D |
| 33 | D |
| 34 | C |
| 35 | C |
| 36 | B |
| 37 | D |
| 38 | D |
| 39 | D |
| 40 | D |
| 41 | D |
| 42 | D |
| 43 | C |
| 44 | D |
| 45 | B |
| 46 | D |
| 47 | D |
| 48 | C |
| 49 | C |
| 50 | C |
| 51 | D |
| 52 | C |
| 53 | C |
| 54 | C |
| 55 | C |
| 56 | A |
| 57 | C |
| 58 | B |
| 59 | B |
| 60 | B |
| 61 | A |
| 62 | B |
| 63 | B |
| 64 | C |
| 65 | C |
| 66 | A |
| 67 | B |
| 68 | B |
| 69 | B |
| 70 | A |
| 71 | C |
| 72 | C |
| 73 | C |
| 74 | B |
| 75 | A |
| 76 | B |
| 77 | A |
| 78 | B |
| 79 | A |
| 80 | B |
| 81 | B |
| 82 | B |
| 83 | A |
| 84 | B |
| 85 | C |
| 86 | A |
| 87 | A |
| 88 | A |
| 89 | C |
| 90 | A |
| 91 | A |
| 92 | A |
| 93 | A |
| 94 | B |
| 95 | B |
| 96 | B |
| 97 | B |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | B |
| 111 | B |
| 112 | A |
| 113 | A |
| 114 | A |
| 115 | A |
| 116 | A |
| 117 | A |
| 118 | A |
| 119 | B |
| 120 | B |
| 121 | A |
| 122 | B |
| 123 | A |
| 124 | A |
| 125 | A |
| 126 | B |
| 127 | A |
| 128 | B |
| 128 | B |
| 129 | B |
| 130 | A |

TABLE 2-continued

| Example | Pin 1 inhibition |
|---|---|
| 131 | B |
| 132 | B |
| 133 | A |
| 134 | A |
| 135 | B |
| 136 | B |
| 137 | A |
| 138 | A |
| 139 | B |
| 140 | A |
| 141 | A |
| 142 | B |
| 143 | A |
| 144 | B |
| 145 | A |
| 146 | A |
| 147 | A |
| 148 | A |
| 149 | A |
| 150 | A |
| 151 | A |
| 152 | A |
| 153 | A |
| 154 | A |
| 155 | B |
| 156 | B |
| 157 | B |
| 158 | A |
| 159 | A |
| 160 | A |
| 161 | A |
| 162 | B |
| 163 | B |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | B |
| 180 | B |
| 181 | B |
| 182 | B |
| 183 | A |
| 184 | A |
| 185 | A |
| 186 | A |
| 187 | A |
| 188 | A |
| 189 | A |
| 190 | A |

* A < 1 μM, 1 μM < B < 10 μM, 10 μM < C < 100 μM, 100 μM < D.

As shown in Table 2, it was confirmed that when the compound of Example 56, 61, 66, 70, 75, 77, 79, 83, 86, 87, 88, 90, 91, 92, 93, 98, 99, 100, 101, 102, 103, 104, 105, 106, 107, 108, 109, 112, 113, 114, 115, 116, 117, 118, 121, 123, 124, 125, 127, 130, 133, 134, 137, 138, 140, 141, 143, 145, 146, 147, 148, 149, 150, 151, 152, 153, 154, 158, 159, 160, 161, 164, 165, 166, 167, 168, 169, 170, 171, 172, 173, 174, 175, 176, 177, 178, 183, 184, 185, 186, 187, 188, 189 or 190 was treated, Pin1 inhibitory activity was exhibited at the concentration of less than 1 μM.

The above results indicate that the compounds of Examples of the present invention are excellent in inhibiting the Pin1 enzyme, and therefore, it can be seen that the benzenesulfonamide derivative compound according to the present invention can be effectively used as a pharmaceutical composition for preventing or treating cancer.

<Experimental Example 2> Evaluation of MDA-MB 231 Triple Negative Breast Cancer Cell Line Protein Expression Inhibitory Ability In order to confirm the ability of the compound represented by formula 1 according to the present invention to inhibit the protein expression of MDA-MB 231 triple negative breast cancer cell line, the following experiment was performed, and the results are shown in Table 3 below.

MDA-MB-231 cells were cultured in a 5% $CO_2$ incubator at 37° C. using RPMI medium supplemented with 10% FBS and 1% penicillin/streptomycin.

The cells were washed with PBS once a day, and then replaced with a new medium. The cells grown at the density of at least 90% 1 day before the experiment were detached using trypsin/EDTA, and then plated at the density of 100,000 per well in a 6-well plate.

On the next day of culture, the compound prepared in each example was treated at a concentration of 10 μM, and DMSO was treated at a concentration of 0.1% of the total as the control, followed by incubation for 72 hours. After 72 hours, the cells were washed twice with PBS, collected by scraping, and centrifuged at 13,000 rpm for 3 minutes to remove all the supernatant and only cells were taken.

RIPA buffer (containing 1× protease inhibitor and phosphatase inhibitor) was added to the prepared cells (80 μl/well), and the plate was shaken once every 5 minutes to disrupt the cells for a total of 15 minutes. The disrupted cells were centrifuged at 13,000 rpm for 15 minutes to collect only the supernatant protein. The obtained protein was quantified using a BCA protein quantification kit (Pierece, MA, USA), and a total of 10 μg of the protein was used for Western blotting.

The protein sample was isolated by 10% SDS-PAGE, and transferred to a PVDF membrane. Anti-human cycline D1 antibody (Cell signal) and anti-Vinculin antibody were bound to the protein sample, and the expression of the protein was measured by using an ECL reagent and LAS4000 equipment. The measurement results were quantified and generalized using ImageJ. The results are shown in Table 3 below by dividing the grades A to D according to the amount of the protein compared to the DMSO-treated control group.

TABLE 3

| Example | MBA-MB-231 |
|---|---|
| 22 | D |
| 31 | C |
| 34 | D |
| 35 | A |
| 36 | D |
| 44 | D |
| 45 | D |
| 55 | D |
| 56 | B |
| 57 | D |
| 58 | D |
| 59 | B |
| 60 | C |
| 61 | A |
| 66 | A |
| 70 | A |
| 75 | A |

TABLE 3-continued

| Example | MBA-MB-231 |
|---|---|
| 77 | A |
| 78 | A |
| 79 | A |
| 80 | B |
| 81 | A |
| 82 | D |
| 83 | A |
| 86 | D |
| 88 | C |
| 90 | B |
| 91 | A |
| 92 | A |
| 93 | A |
| 98 | A |
| 99 | A |
| 103 | B |
| 104 | D |
| 105 | D |
| 106 | C |
| 118 | C |
| 121 | A |
| 123 | D |

* 0 < A < 35%, 35% < B < 50%, 50% < C < 70%, 70% < D < 100%.

As shown in Table 3, when the compound of Example 35, 61, 66, 70, 75, 77, 78, 79, 81, 83, 91, 92, 93, 98, 99 or 121 was treated, the expression level of MDA-MB 231 triple-negative breast cancer cell line protein was found to be less than 35% compared to the DMSO-treated control group.

The above results indicate that the compounds of Examples of the present invention have excellent ability to inhibit the expression of MDA-MB 231 triple negative breast cancer cell line protein, and therefore, it can be seen that the benzenesulfonamide derivative compound according to the present invention can be effectively used as a pharmaceutical composition for preventing or treating cancer.

<Experimental Example 3> Evaluation of Cell Viability of MCF7, MCF7-SP, A2780 or A2780-SP Cells In order to confirm the inhibitory effect of the compound represented by formula 1 according to the present invention on the growth of MCF7, MCF7-SP, A2780 or A2780-SP cells, the following experiment was performed, and the results are shown in Tables 4 and 5 below.

MCF7 cells (breast cancer cells) were plated in a 96-well plate at the density of 3000 viable cells per well, and cultured in DMEM/High glucose medium supplemented with 10% FBS and 1% penicillin/streptomycin.

On the next day of culture, the cells were treated with the compound of Example 71, 76, 80, 84, 92, 99, 100 or 119, followed by culture for 3 days. Cell viability was evaluated by Cell-titer Glo (Promega, WC, USA), and luciferase activity was detected using a Tecan plate reader (Biocompare, USA).

On the other hand, MCF7-SP cells (breast cancer stem cells) were plated in an Ultra-Low Attachment round bottom 96-well plate (corning) at the density of 1,500 viable cells per well, and cultured in cancer stem cell medium. The cancer stem cell medium is composed of the neurobasal medium supplemented with 20 ng/ml of bFGF, 10 ng/ml of EGF, 2.5 ng/ml of amphotericin B, HEPES, Glutamax and B27.

On the next day of culture, the cells were treated with the compound of Example 71, 76, 80, 84, 92, 99, 100 or 119, followed by culture for 8 days. The medium containing the compound was added thereto once again on the 4th day. Sphere cell viability was evaluated by Cell-titer Glo (Promega, WC, USA), and luciferase activity was detected using a Tecan plate reader (Biocompare, USA).

In addition, A2780 cells (ovarian cancer cells) were plated in a 96-well plate at the density of 3000 viable cells per well, and cultured in RPMI-1640 medium supplemented with 10% FBS and 1% penicillin/streptomycin.

On the next day of culture, the cells were treated with the compound of Examples 57, and 69 to 144, followed by culture for 3 days. Cell viability was evaluated by Cell-titer Glo (Promega, WC, USA), and luciferase activity was detected using a Tecan plate reader (Biocompare, USA).

On the other hand, A2780-SP cells (ovarian cancer stem cells) were plated in an Ultra-Low Attachment round bottom 96-well plate (corning) at the density of 1,500 viable cells per well, and cultured in cancer stem cell medium. The cancer stem cell medium is composed of the neurobasal medium supplemented with 20 ng/ml of bFGF, 10 ng/ml of EGF, 2.5 ng/ml of amphotericin B, HEPES, Glutamax and B27.

On the next day of culture, the cells were treated with the compound of Examples 57, and 69 to 144, followed by culture for 8 days. The medium containing the compound was added thereto once again on the 4th day. Sphere cell viability was evaluated by Cell-titer Glo (Promega, WC, USA), and luciferase activity was detected using a Tecan plate reader (Biocompare, USA).

TABLE 4

| Example | MCF7 | MCF7-SP |
|---|---|---|
| 70 | B | B |
| 75 | B | C |
| 79 | C | C |
| 83 | B | B |
| 91 | B | B |
| 98 | C | C |
| 99 | B | B |
| 118 | B | B |

* A < 1 μM, 1 μM < B < 10 μM, 10 μM < C.

TABLE 5

| Example | A2780 | A2780-SP |
|---|---|---|
| 56 | B | A |
| 59 | B | A |
| 61 | B | A |
| 66 | B | A |
| 70 | B | A |
| 75 | B | B |
| 77 | C | B |
| 79 | C | A |
| 83 | B | A |
| 88 | C | A |
| 90 | C | A |
| 91 | C | A |
| 92 | C | A |
| 93 | B | A |
| 95 | C | B |
| 98 | B | B |
| 99 | B | A |
| 100 | B | A |
| 103 | C | A |
| 104 | C | A |
| 105 | C | A |
| 106 | B | A |
| 108 | B | A |
| 109 | B | A |

TABLE 5-continued

| Example | A2780 | A2780-SP |
|---|---|---|
| 110 | C | A |
| 111 | C | A |
| 112 | C | A |
| 113 | — | B |
| 114 | — | B |
| 115 | — | A |
| 117 | — | B |
| 118 | C | A |
| 121 | B | A |
| 123 | B | B |
| 124 | B | B |
| 125 | C | B |
| 127 | C | B |
| 130 | B | B |
| 133 | C | B |
| 134 | C | A |
| 137 | C | B |
| 138 | C | B |
| 140 | — | B |
| 141 | — | B |
| 143 | — | B |
| 145 | C | C |
| 146 | C | B |
| 147 | C | C |
| 148 | C | B |
| 149 | C | C |
| 150 | C | A |
| 151 | C | A |
| 152 | C | A |
| 153 | B | A |
| 154 | B | A |
| 157 | C | A |
| 158 | C | A |
| 159 | C | A |
| 160 | C | C |
| 161 | C | A |
| 164 | B | A |
| 165 | B | A |
| 166 | C | B |
| 167 | B | A |
| 168 | C | A |
| 169 | B | A |
| 170 | B | A |
| 171 | C | A |
| 172 | C | A |
| 173 | B | A |
| 174 | C | A |
| 175 | B | A |
| 176 | B | A |
| 177 | B | A |
| 178 | B | A |
| 183 | C | A |
| 184 | C | A |
| 185 | C | C |
| 186 | C | A |
| 187 | C | A |
| 188 | C | A |
| 189 | C | A |
| 190 | C | A |

* A < 1 μM, 1 μM < B < 10 μM, 10 μM < C,
—: not tested.

As shown in Table 4, the MCF7 cell concentration was less than 10 μM when the compound of Example 70, 75, 83, 91, 99 or 118 was treated, and the MCF7-SP cell concentration was less than 10 μM when the compound of Example 70, 83, 91, 99 or 118 was treated.

As shown in Table 5, the A2780 cell concentration was less than 10 μM when the compound of Example 56, 59, 61, 66, 70, 75, 83, 93, 98, 99, 100, 106, 108, 109, 121, 123, 124, 130, 153, 154, 164, 165, 167, 169, 170, 173, 175, 176, 177 or 178 was treated, and the concentration was less than 1 μM when the compound of Example 56, 59, 61, 66, 70, 79, 83, 88, 90, 91, 92, 93, 99, 100, 103, 104, 105, 106, 108, 109, 110, 111, 112, 115, 118, 121, 134, 150, 151, 152, 153, 154, 157, 158, 159, 161, 164, 165, 167, 168, 169, 170, 171, 172, 173, 174, 175, 176, 177, 178, 183, 184, 186, 187, 188, 189 or 190 was treated.

The above results indicate that the compounds of Examples of the present invention have excellent inhibitory effect on the growth of MCF7, MCF7-SP, A2780 or A2780-SP cells, and therefore, it can be seen that the benzenesulfonamide derivative compound according to the present invention can be effectively used as a pharmaceutical composition for preventing or treating cancer.

The invention claimed is:

1. A compound represented by formula 1, a stereoisomer thereof or a pharmaceutically acceptable salt thereof:

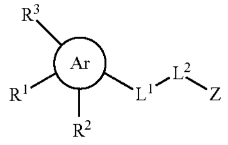

(1)

wherein Ar is 6-10 membered aryl or 5-6 membered heteroaryl containing one to two heteroatoms selected from the group consisting of N, S and O;

$R^1$ and $R^2$ are independently hydrogen or halogen;

$R^3$ is substituted straight or branched $C_{1-8}$ alkyl, $NR^{a1}R^{a2}$, $OR^{a3}$,

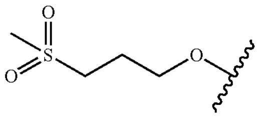

or

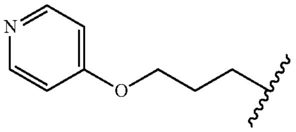

, wherein $R^{a1}$ is hydrogen, $R^{a2}$ and $R^{a3}$ are independently substituted straight or branched $C_{1-8}$ alkyl, nonsubstituted or substituted phenyl or nonsubstituted or substituted 5-6 membered heteroaryl containing one to three heteroatoms selected from the group consisting of N, S and O, wherein the substituted alkyl is substituted with one substituent selected from the group consisting of nonsubstituted or substituted 4-8 membered heterocycloalkyl containing one to two heteroatoms selected from the group consisting of N, S and O, and nonsubstituted or substituted 4-6 membered heteroaryl containing one to three heteroatoms selected from the group consisting of N, S and O, and the substituted alkyl is optionally further substituted with hydroxy or to form 3-6 membered cycloalkyl with substituted carbon, the substituted phenyl and the substituted 5-6 membered heteroaryl are independently substituted with one to three substituents selected from the group consisting of 4-8 membered nonsubstituted or substituted heterocycloalkyl containing one to two heteroatoms selected from the group consisting of N, S and O, and halogen, and the substituted 4-8 membered heterocycloalkyl and the substituted 4-6 membered heteroaryl are substituted with one to three substituents selected from the group consisting of straight or branched $C_{1-5}$ alkyl nonsubstituted or substituted with one or more straight or branched $C_{1-5}$ alkylcarbonyl, $NR^{b1}R^{b2}$, halogen, hydroxy and oxo, $R^{b1}$ and $R^{b2}$ are independently hydrogen, or straight or branched $C_{1-6}$ alkyl;

$L^1$ is

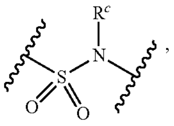

wherein $R^c$ is hydrogen;

$L^2$ is straight or branched $C_{1-8}$ alkylene nonsubstituted or substituted with hydroxy;

Z is $C_{3-8}$ cycloalkyl fused with nonsubstituted or substituted 9 membered heteroaryl containing one or two heteroatoms of N, substituted 9 membered heteroaryl containing one or two heteroatoms of N, or substituted 9 membered heteroaryl $C_{1-5}$ alkyl containing one or two heteroatoms of N, wherein the substituted 9 membered heteroaryl and the substituted 9 membered heteroaryl $C_{1-5}$ alkyl are independently substituted with halogen and optionally further substituted with straight or branched $C_{1-5}$ alkyl.

2. The compound, the thereof or the pharmaceutically acceptable salt stereoisomer thereof according to claim 1, wherein:

Ar is 6-10 membered aryl or 5-6 membered heteroaryl containing one or two heteroatoms selected from the group consisting of N, S and O;

$R^1$ and $R^2$ are independently hydrogen or fluorine;

$R^3$ is substituted straight or branched $C_{1-6}$ alkyl, $NR^{a1}R^{a2}$, $OR^{a3}$,

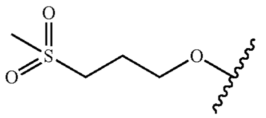

or

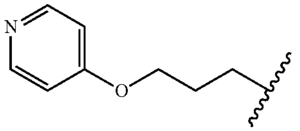

wherein $R^{a1}$ is hydrogen, $R^{a2}$ and $R^{a3}$ are independently substituted straight or branched $C_{1-6}$ alkyl, nonsubstituted or substituted phenyl or nonsubstituted or substituted 5-6 membered heteroaryl containing one or two heteroatoms selected from the group consisting of N, S and O, wherein the substituted alkyl is substituted with one substituent selected from the group consisting of nonsubstituted or substituted 4-7 membered heterocycloalkyl containing one or two heteroatoms selected from the group consisting of N, S and O, and nonsubstituted or substituted 4-6 membered heteroaryl containing one to three heteroatoms selected from the group consisting of N, S and O, and the substituted alkyl is optionally further substituted with hydroxy or to form 3-5 membered cycloalkyl with substituted carbon, the substituted phenyl and the substituted 5-6 membered heteroaryl are independently substituted with one to three substituents selected from the group consisting of 4-7 membered nonsubstituted or substituted heterocycloalkyl containing one to two heteroatoms selected from the group consisting of N, S and O, and halogen, and the substituted 4-7 membered heterocycloalkyl and the substituted 4-6 membered heteroaryl are independently substituted with one to three substituents selected from the group consisting of straight or branched $C_{1-4}$ alkyl nonsubstituted or substituted with one or more straight or branched $C_{1-4}$ alkylcarbonyl, $NR^{b1}R^{b2}$, chlorine, fluorine, bromine, hydroxy and oxo, $R^{b1}$ and $R^{b2}$ are independently hydrogen, or straight or branched $C_{1-3}$ alkyl;

$L^1$ is

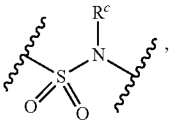

wherein $R^c$ is hydrogen;

$L^2$ is straight or branched $C_{1-6}$ alkylene nonsubstituted or substituted with a hydroxy;

Z is $C_{4-7}$ cycloalkyl fused with nonsubstituted or substituted 9 membered heteroaryl containing one or two heteroatoms of N, substituted 9 membered heteroaryl containing one or two heteroatoms of N, or substituted 9 membered heteroaryl $C_{1-4}$ alkyl containing one or two heteroatoms of N, wherein the substituted 9 membered heteroaryl and the substituted 9 membered heteroaryl $C_{1-4}$ alkyl are independently substituted with one or more substituents selected from the group consisting of fluorine, chlorine, and bromine, and optionally further substituted with straight or branched $C_{1-4}$ alkyl.

3. The compound, the stereoisomer thereof or the pharmaceutically acceptable salt thereof according to claim 1, wherein:

Ar is phenyl, naphthyl, pyridyl or thiazolyl;

$R^1$ and $R^2$ are independently hydrogen or fluorine;

$R^3$ is substituted straight or branched $C_{1-5}$ alkyl, $NR^{a1}R^{a2}$, $OR^{a3}$,

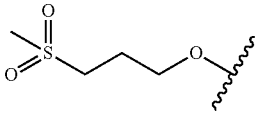

or

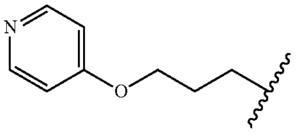

wherein $R^{a1}$ is hydrogen, $R^{a2}$ and $R^{a3}$ are independently substituted straight or branched $C_{1-5}$ alkyl, nonsubstituted or substituted phenyl or nonsubstituted or substituted 5-6 membered containing one to three heteroatoms selected from the group consisting of N, S and O, wherein the substituted alkyl is substituted with one substituent selected from the group consisting of nonsubstituted or substituted 4-7 membered heterocycloalkyl containing one or two heteroatoms selected from the group consisting of N, S and O, and nonsubstituted or substituted 5-6 membered heteroaryl containing one to three heteroatoms selected from the group consisting of N, S and O, and the substituted alkyl is optionally further substituted with hydroxy or to form cyclopropyl with substituted carbon, the substituted phenyl and the substituted 5-6 membered heteroaryl are independently substituted with one to three substituents selected from the group consisting of nonsubstituted or substituted 4-7 membered heterocycloalkyl containing one to two heteroatoms selected from the group consisting of N, S and O, and halogen, and the substituted 4-7 membered heterocycloalkyl and the substituted 5-6 membered heteroaryl are substituted with one to three substituents selected from the group consisting of straight or branched $C_{1-3}$ alkyl nonsubstituted or substituted with one or more straight or branched $C_{1-4}$ alkylcarbonyl, $NR^{b1}R^{b2}$, chlorine, fluorine, bromine, hydroxy and oxo, $R^{b1}$ and $R^{b2}$ are independently hydrogen, methyl or ethyl;

$L^1$ is

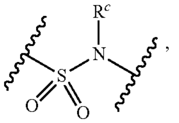

wherein $R^c$ is hydrogen;

$L^2$ is straight or branched $C_{1-4}$ alkylene nonsubstituted or substituted with hydroxy;

Z is $C_{5-6}$ cycloalkyl fused with nonsubstituted or substituted 9 membered heteroaryl containing one or two heteroatoms of N, substituted 9 membered heteroaryl containing one or two heteroatoms selected of N, or substituted 9 membered heteroaryl $C_{1-3}$ alkyl containing one or two heteroatoms N, wherein the substituted 9 membered heteroaryl and the substituted 9 membered heteroaryl $C_{1-3}$ alkyl are independently substituted with one to three substituents selected from the group consisting of fluorine, chlorine, and bromine, optionally further substituted with straight or branched $C_{1-3}$ alkyl.

4. The compound, the stereoisomer thereof or the pharmaceutically acceptable salt thereof according to claim 1, wherein:

Ar is phenyl, naphthyl, pyridine or thiazole;

$R^1$ and $R^2$ are independently hydrogen or fluorine;

$R^3$ is

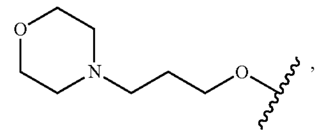 [SMILES: *OCCCN1CCOCC1]

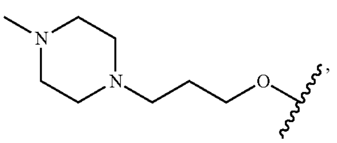

-continued

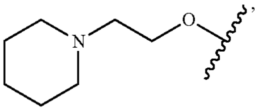

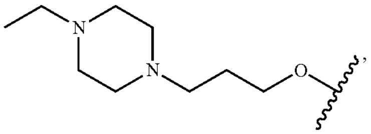

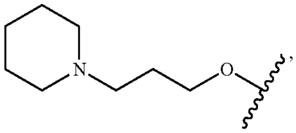

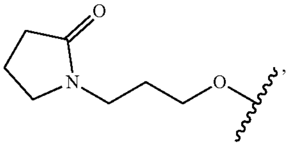

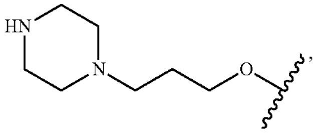

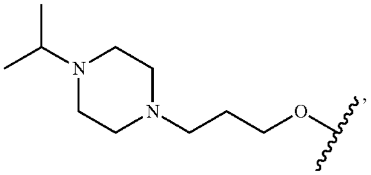

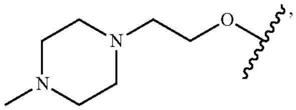

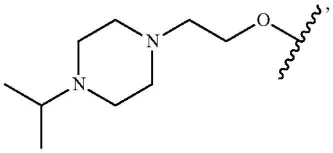

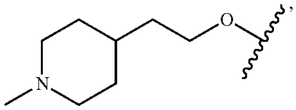

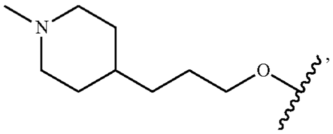

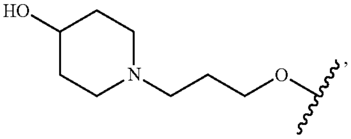

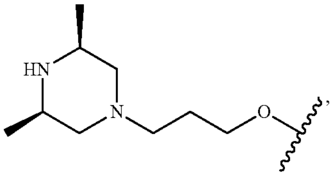

-continued
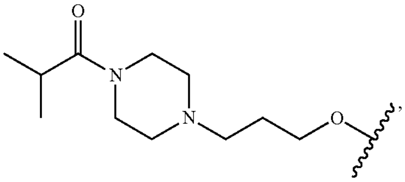,
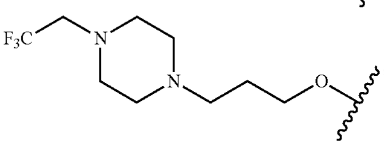,
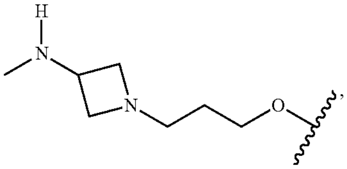,
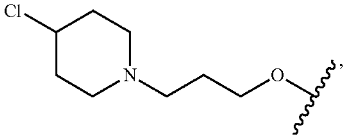,
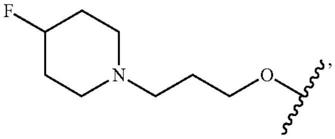,
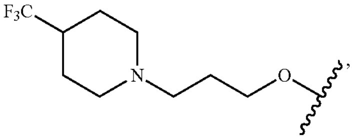,
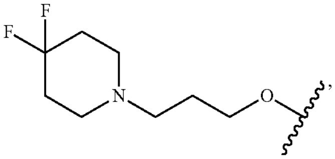,
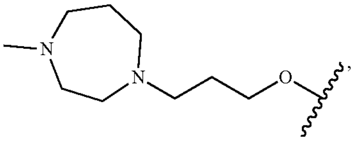,
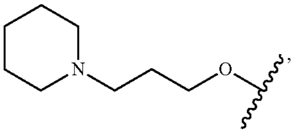,
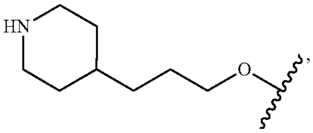,
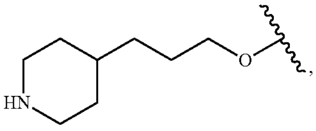,
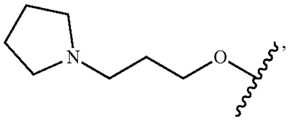,
-continued
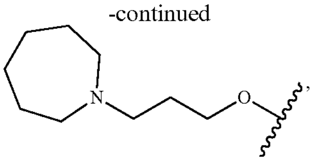,
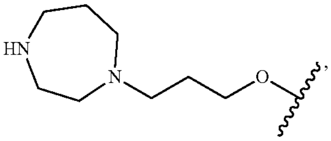,
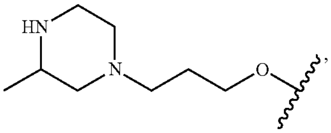,
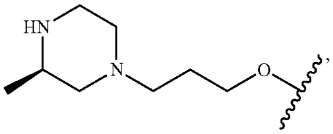,
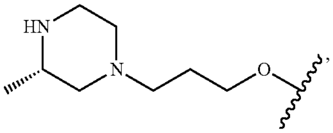,
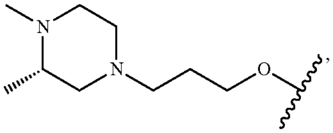,
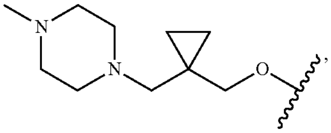,
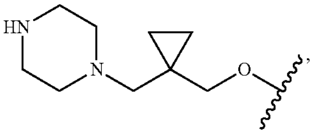,
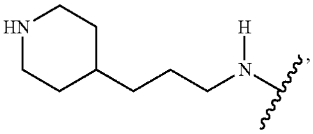,
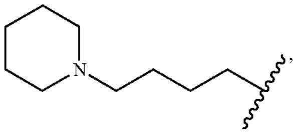,
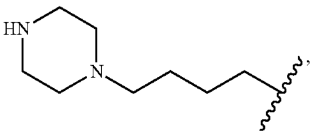,
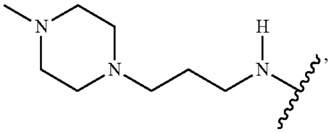,
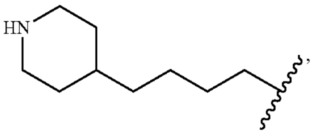, -continued
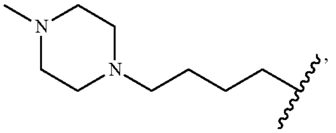
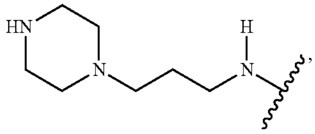
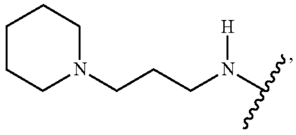
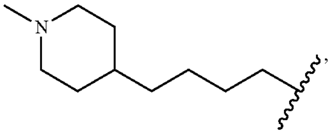
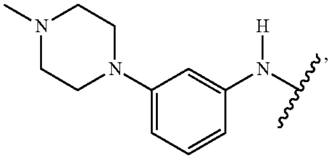
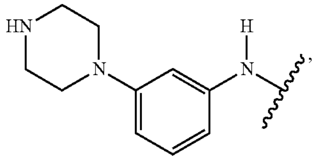
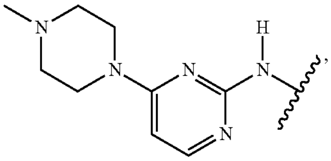
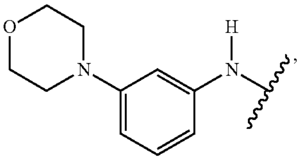
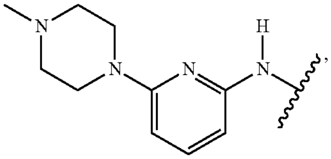
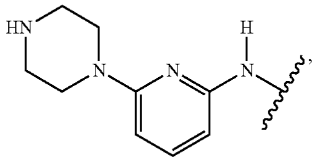
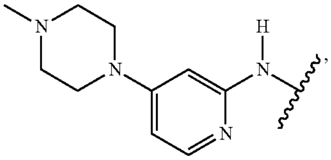
-continued
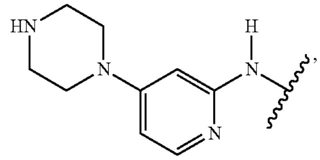
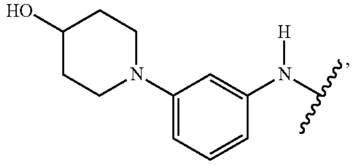
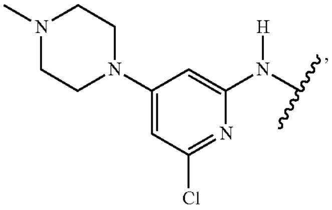
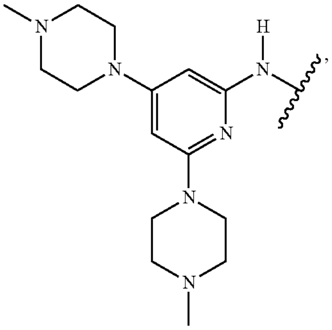
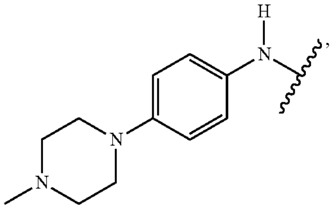
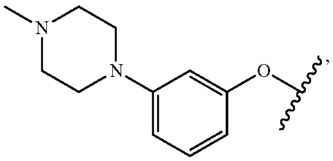
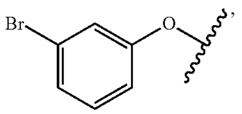
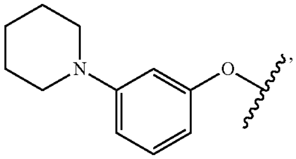
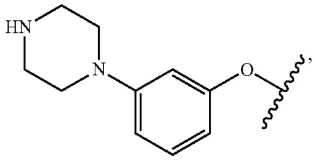

-continued
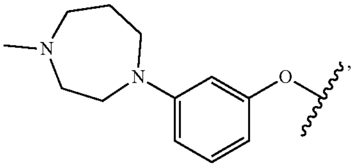,
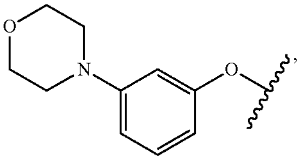,
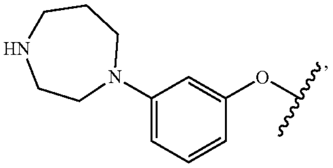,
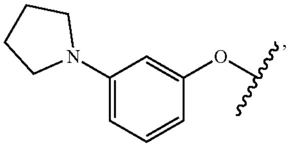,
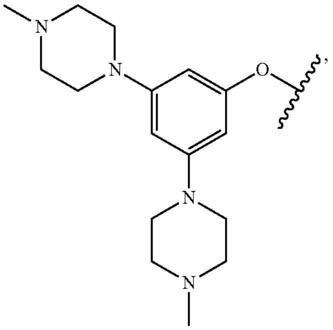,
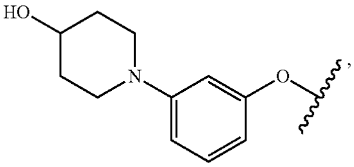,
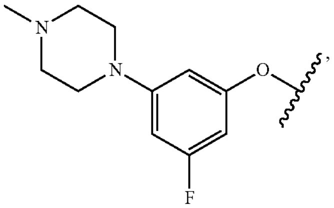,
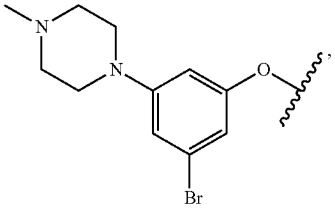,
-continued
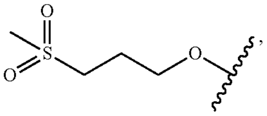,
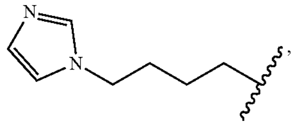,
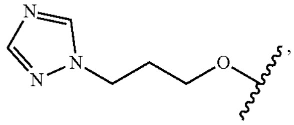,
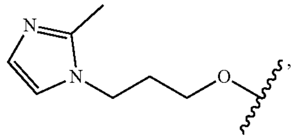,
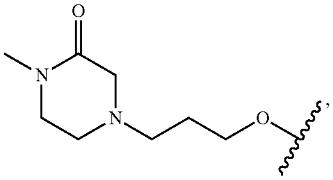,
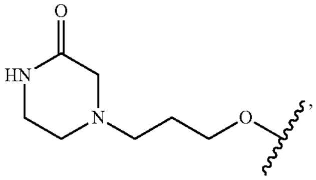,
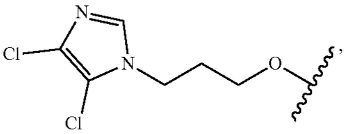,
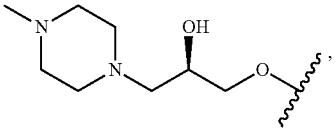,
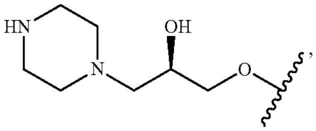,
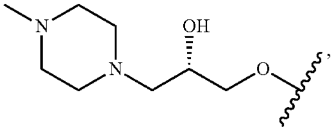,
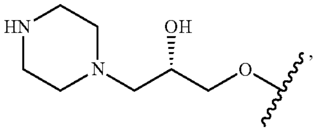,
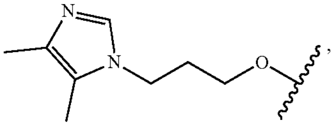, -continued

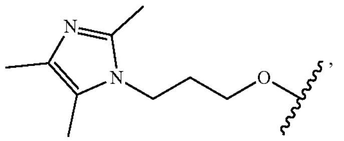,

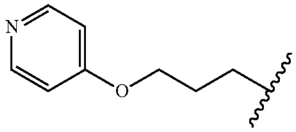 or

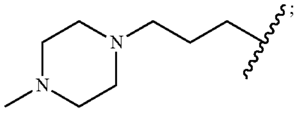;

$L^1$ is

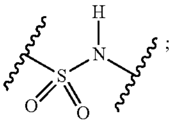 [SMILES: *NS(*)(=O)=O];

$L^2$ is

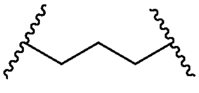, 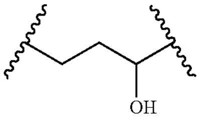, 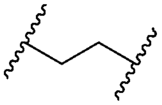, 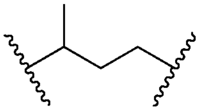 or 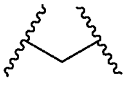;

Z is

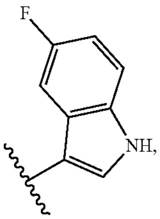 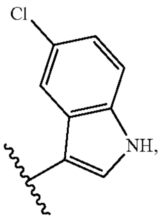 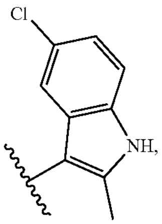 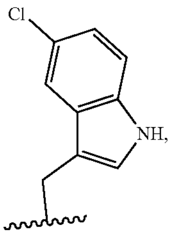 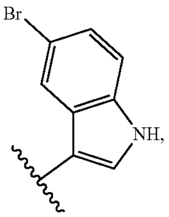 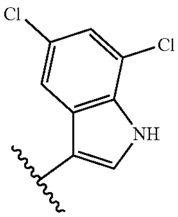,

-continued

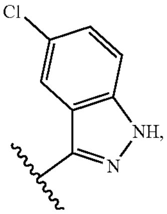 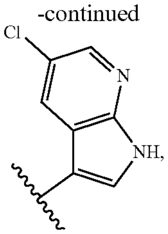 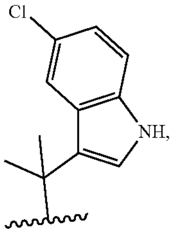 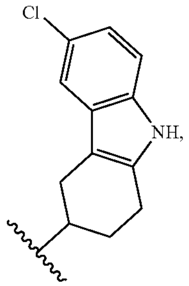 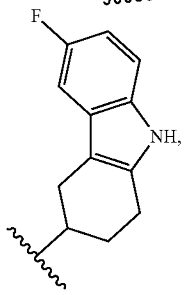 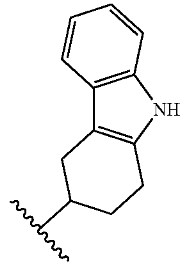 or 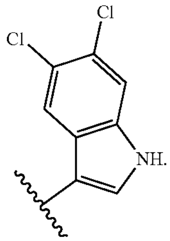

5. The compound, the stereoisomer thereof or the pharmaceutically acceptable salt thereof according to claim 1, wherein the compound represented by formula 1 is selected from the group consisting of the following compounds:

<56> N-(3-(5-fluoro-1H-indol-3-yl)propyl)-4-(3-(4-methylpiperazin-1-yl)propoxy)benzenesulfonamide;

<59> N-(3-(5-fluoro-1H-indol-3-yl)propyl)-4-(3-(1-methylpiperidin-4-yl)propoxy)benzenesulfonamide;

<61> N-(3-(5-fluoro-1H-indol-3-yl)propyl)-4-(3-(piperazin-1-yl) propoxy)benzenesulfonamide;

<63> 4-(3-(4-ethylpiperazin-1-yl)propoxy)-N-(3-(5-fluoro-1H-indol-3-yl)propyl)benzenesulfonamide;

<66> N-(3-(5-chloro-1H-indol-3-yl)propyl)-4-(3-(4-methylpiperazin-1-yl)propoxy)benzenesulfonamide;

<70> N-(3-(5-chloro-1H-indol-3-yl)propyl)-4-(3-(piperazin-1-yl) propoxy)benzenesulfonamide;

<72> 4-(3-((3S,5R)-3,5-dimethylpiperazin-1-yl) propoxy)-N-(3-(5-fluoro-1H-indol-3-yl)propyl)benzenesulfonamide;

<73> N-(3-(5-fluoro-1H-indol-3-yl)propyl)-4-(3-(4-isobutyrylpiperazin-1-yl)propoxy)benzenesulfonamide;

<74> N-(3-(5-fluoro-1H-indol-3-yl)propyl)-4-(3-(4-(2,2,2-trifluoroethyl)piperazin-1-yl)propoxy)benzenesulfonamide;

<75> N-(3-(5-chloro-1H-indol-3-yl)propyl)-4-(3-(4-hydroxypiperidin-1-yl)propoxy)benzenesulfonamide;

<76> N-(3-(5-chloro-1H-indol-3-yl)propyl)-4-(3-(4-(2,2,2-trifluoroethyl)piperazin-1-yl)propoxy)benzenesulfonamide;

<77> N-(3-(5-chloro-1H-indol-3-yl)propyl)-4-(3-(3-(methylamino)azetidin-1-yl)propoxy)benzenesulfonamide;

<78> N-(3-(5-chloro-1H-indol-3-yl)propyl)-4-(3-(4-chloropiperidin-1-yl)propoxy)benzenesulfonamide;

<79> N-(3-(5-chloro-1H-indol-3-yl)propyl)-6-(3-(piperazin-1-yl) propoxy)pyridin-3-sulfonamide;
<80> N-(3-(5-chloro-1H-indol-3-yl)propyl)-4-(3-(4-fluoropiperidin-1-yl)propoxy)benzenesulfonamide;
<81> N-(3-(5-chloro-1H-indol-3-yl)propyl)-4-(3-(4-(trifluoromethyl)piperidin-1-yl)propoxy)benzenesulfonamide;
<82> N-(3-(5-chloro-1H-indol-3-yl)propyl)-4-(3-(4,4-difluoropiperidin-1-yl)propoxy)benzenesulfonamide;
<83> N-(3-(5-chloro-1H-indol-3-yl)propyl)-4-(3-(4-methyl-1,4-diazepan-1-yl)propoxy)benzenesulfonamide;
<84> N-(3-(5-fluoro-1H-indol-3-yl)propyl)-4-(3-(piperidin-1-yl)propoxy)benzenesulfonamide;
<86> N-(3-(5-chloro-1H-indol-3-yl)propyl)-4-(3-(4-methylpiperazin-1-yl)propoxy)naphthalene-1-sulfonamide;
<87> N-(3-(5-chloro-1H-indol-3-yl)propyl)-4-(3-(piperidin-1-yl)propoxy)benzenesulfonamide;
<88> N-(3-(5-chloro-1H-indol-3-yl)propyl)-4-((3-(piperidin-4-yl)propyl)amino)benzenesulfonamide;
<90> N-(3-(5-chloro-1H-indol-3-yl)propyl)-4-(4-(piperidin-1-yl)butyl)benzenesulfonamide;
<91> N-(3-(5-chloro-1H-indol-3-yl)propyl)-4-(4-(piperazin-1-yl)butyl)benzenesulfonamide;
<92> N-(3-(5-chloro-1H-indol-3-yl)propyl)-4-(3-(1-methylpiperidin-4-yl)propoxy)benzenesulfonamide;
<93> N-(3-(5-chloro-1H-indol-3-yl)propyl)-4-(3-(piperidin-4-yl)propoxy)benzenesulfonamide;
<94> N-(3-(5-chloro-1H-indol-3-yl)propyl)-3-(3-(piperidin-4-yl)propoxy)benzenesulfonamide;
<95> N-(3-(5-chloro-1H-indol-3-yl)propyl)-3-(3-(piperidin-1-yl)propoxy)benzenesulfonamide;
<96> N-(3-(5-chloro-1H-indol-3-yl)propyl)-3-(3-(piperazin-1-yl)propoxy)benzenesulfonamide;
<97> N-(3-(5-fluoro-1H-indol-3-yl)propyl)-4-(3-(piperidin-4-yl)propoxy)benzenesulfonamide;
<98> N-(3-(5-chloro-1H-indol-3-yl)propyl)-4-((3-(4-methylpiperazin-1-yl)propyl)amino)benzenesulfonamide;
<99> N-(3-(5-chloro-1H-indol-3-yl)propyl)-4-(4-(piperidin-4-yl)butyl)benzenesulfonamide;
<100> N-(3-(5-chloro-1H-indol-3-yl)propyl)-4-(3-(pyrrolidin-1-yl)propoxy)benzenesulfonamide;
<101> 4-(3-(azepan-1-yl)propoxy)-N-(3-(5-chloro-1H-indol-3-yl)propyl)benzenesulfonamide;
<102> 4-(3-(1,4-diazepan-1-yl)propoxy)-N-(3-(5-chloro-1H-indol-3-yl)propyl)benzenesulfonamide;
<103> N-(3-(5-chloro-1H-indol-3-yl)propyl)-3-fluoro-4-(3-(4-methylpiperazin-1-yl)propoxy)benzenesulfonamide;
<104> N-(3-(5-chloro-1H-indol-3-yl)propyl)-3-fluoro-4-(3-(piperazin-1-yl)propoxy)benzenesulfonamide;
<105> N-(3-(5-chloro-1H-indol-3-yl)propyl)-3-fluoro-4-(3-(4-hydroxypiperidin-1-yl)propoxy)benzenesulfonamide;
<106> 4-(3-(1,4-diazepan-1-yl)propoxy)-N-(3-(5-chloro-1H-indol-3-yl)propyl)-3-fluorobenzenesulfonamide;
<107> N-(3-(5-chloro-1H-indol-3-yl)propyl)-4-(3-(3-methylpiperazin-1-yl)propoxy)benzenesulfonamide;
<108> (R)—N-(3-(5-chloro-1H-indol-3-yl)propyl)-4-(3-(3-methylpiperazin-1-yl)propoxy)benzenesulfonamide;
<109> (S)—N-(3-(5-chloro-1H-indol-3-yl)propyl)-4-(3-(3-methylpiperazin-1-yl)propoxy)benzenesulfonamide;
<110> N-(3-(5-chloro-1H-indol-3-yl)propyl)-4-(3-((3S,5R)-3,5-dimethylpiperazin-1-yl)propoxy)benzenesulfonamide;
<111> (S)—N-(3-(5-chloro-1H-indol-3-yl)propyl)-4-(3-(3,4-dimethylpiperazin-1-yl)propoxy)benzenesulfonamide;
<112> N-(3-(5-chloro-1H-indol-3-yl)propyl)-4-(4-(4-methylpiperazin-1-yl)butyl)benzenesulfonamide;
<113> N-(3-(5-chloro-1H-indol-3-yl)propyl)-4-((3-(piperazin-1-yl)propyl)amino)benzenesulfonamide;
<114> N-(3-(5-chloro-1H-indol-3-yl)propyl)-4-((3-(piperidin-1-yl)propyl)amino)benzenesulfonamide;
<115> N-(3-(5-chloro-1H-indol-3-yl)propyl)-4-(4-(1-methylpiperidin-4-yl)butyl)benzenesulfonamide;
<116> N-(3-(5-chloro-1H-indol-3-yl)propyl)-4-((1-((4-methylpiperazin-1-yl)methyl)cyclopropyl)methoxy)benzenesulfonamide;
<117> N-(3-(5-chloro-1H-indol-3-yl)propyl)-4-((1-(piperazin-1-ylmethyl)cyclopropyl)methoxy)benzenesulfonamide;
<118> N-(3-(5-chloro-1H-indol-3-yl)propyl)-4-(3-(4-methylpiperazin-1-yl)phenoxy)benzenesulfonamide;
<119> 4-(3-bromophenoxy)-N-(3-(5-chloro-1H-indol-3-yl)propyl)benzenesulfonamide;
<120> N-(3-(5-chloro-1H-indol-3-yl)propyl)-4-(3-(piperidin-1-yl)phenoxy)benzenesulfonamide;
<121> N-(3-(5-chloro-1H-indol-3-yl)propyl)-4-(3-(piperazin-1-yl)phenoxy)benzenesulfonamide;
<122> N-(3-(5-chloro-1H-indol-3-yl)propyl)-4-(3-(4-methyl-1,4-diazepan-1-yl)phenoxy)benzenesulfonamide;
<123> N-(3-(5-chloro-1H-indol-3-yl)propyl)-4-((3-(4-methylpiperazin-1-yl)phenyl)amino)benzenesulfonamide;
<124> N-(3-(5-chloro-1H-indol-3-yl)propyl)-4-((3-(piperazin-1-yl)phenyl)amino)benzenesulfonamide;
<125> N-(3-(5-chloro-1H-indol-3-yl)propyl)-4-((4-(4-methylpiperazin-1-yl)pyrimidin-2-yl)amino)benzenesulfonamide;
<126> N-(3-(5-chloro-1H-indol-3-yl)propyl)-4-((3-morpholinophenyl)amino)benzenesulfonamide;
<127> N-(3-(5-chloro-1H-indol-3-yl)propyl)-4-((4-(piperazin-1-yl)pyrimidin-2-yl)amino)benzenesulfonamide;
<128> N-(3-(5-chloro-1H-indol-3-yl)propyl)-4-(3-morpholinophenoxy)benzenesulfonamide;
<129> 4-(3-(1,4-diazepan-1-yl)phenoxy)-N-(3-(5-chloro-1H-indol-3-yl)propyl)benzenesulfonamide;
<130> 4-(3,5-bis(4-methylpiperazin-1-yl)phenoxy)-N-(3-(5-chloro-1H-indol-3-yl)propyl)benzenesulfonamide;
<131> N-(3-(5-chloro-1H-indol-3-yl)propyl)-4-((6-(4-methylpiperazin-1-yl)pyridin-2-yl)amino)benzenesulfonamide;
<132> N-(3-(5-chloro-1H-indol-3-yl)propyl)-4-((6-(piperazin-1-yl)pyridin-2-yl)amino)benzenesulfonamide;
<133> N-(3-(5-chloro-1H-indol-3-yl)propyl)-4-((4-(4-methylpiperazin-1-yl)pyridin-2-yl)amino)benzenesulfonamide;
<134> N-(3-(5-chloro-1H-indol-3-yl)propyl)-4-((4-(piperazin-1-yl)pyridin-2-yl)amino)benzenesulfonamide;
<135> N-(3-(5-chloro-1H-indol-3-yl)propyl)-4-(3-(pyrrolidin-1-yl)phenoxy)benzenesulfonamide;
<136> N-(3-(5-chloro-1H-indol-3-yl)propyl)-4-(3-(4-hydroxypiperidin-1-yl)phenoxy)benzenesulfonamide;

<137> N-(3-(5-chloro-1H-indol-3-yl)propyl)-4-(3-fluoro-5-(4-methylpiperazin-1-yl)phenoxy)benzenesulfonamide;

<138> 4-(3-bromo-5-(4-methylpiperazin-1-yl)phenoxy)-N-(3-(5-chloro-1H-indol-3-yl)propyl)benzenesulfonamide;

<139> N-(3-(5-chloro-1H-indol-3-yl)propyl)-4-((3-(4-hydroxypiperidin-1-yl)phenyl)amino)benzenesulfonamide;

<140> N-(3-(5-chloro-1H-indol-3-yl)propyl)-4-((6-chloro-4-(4-methylpiperazin-1-yl)pyridin-2-yl)amino)benzenesulfonamide;

<141> 4-((4,6-bis(4-methylpiperazin-1-yl)pyridin-2-yl)amino)-N-(3-(5-chloro-1H-indol-3-yl)propyl)benzenesulfonamide;

<142> N-(3-(5-chloro-1H-indol-3-yl)propyl)-4-((4-(4-methylpiperazin-1-yl)phenyl)amino)benzenesulfonamide;

<145> N-(3-(5-chloro-1H-indol-3-yl)propyl)-4-(3-(methylsulfonyl)propoxy)benzenesulfonamide;

<146> N-(3-(5-chloro-1H-indol-3-yl)propyl)-2-((3-(piperazin-1-yl)propyl)amino)thiazole-5-sulfonamide;

<147> N-(3-(5-chloro-2-methyl-1H-indol-3-yl)propyl)-4-(3-(4-methylpiperazin-1-yl)propoxy)benzenesulfonamide;

<148> 4-(4-(1H-imidazol-1-yl)butyl)-N-(3-(5-chloro-1H-indol-3-yl)propyl)benzenesulfonamide;

<151> N-(4-(5-chloro-1H-indol-3-yl)butan-2-yl)-4-(3-(4-methylpiperazin-1-yl)propoxy)benzenesulfonamide;

<152> N-(4-(5-chloro-1H-indol-3-yl)butan-2-yl)-4-(3-(piperazin-1-yl)propoxy)benzenesulfonamide;

<153> N-(3-(5-bromo-1H-indol-3-yl)propyl)-4-(3-(piperazin-1-yl)propoxy)benzenesulfonamide;

<154> N-(3-(5-bromo-1H-indol-3-yl)propyl)-4-(3-(4-methylpiperazin-1-yl)propoxy)benzenesulfonamide;

<157> N-(3-(5-chloro-2-methyl-1H-indol-3-yl)propyl)-4-(3-(piperazin-1-yl)propoxy)benzenesulfonamide;

<158> N-(2-(5-chloro-1H-indol-3-yl)ethyl)-4-(3-(4-methylpiperazin-1-yl)propoxy)benzenesulfonamide;

<159> N-(2-(5-chloro-1H-indol-3-yl)ethyl)-4-(3-(piperazin-1-yl)propoxy)benzenesulfonamide;

<160> 4-(3-(1H-1,2,4-triazol-1-yl)propoxy)-N-(3-(5-chloro-1H-indol-3-yl)propyl)benzenesulfonamide;

<161> N-(3-(5-chloro-1H-indol-3-yl)propyl)-4-(3-(2-methyl-1H-imidazol-1-yl)propoxy)benzenesulfonamide;

<162> N-(3-(5-chloro-1H-indol-3-yl)propyl)-4-(3-(4-methyl-3-oxopiperazin-1-yl)propoxy)benzenesulfonamide;

<163> N-(3-(5-chloro-1H-indol-3-yl)propyl)-4-(3-(3-oxopiperazin-1-yl)propoxy)benzenesulfonamide;

<164> N-(3-(5,7-dichloro-1H-indol-3-yl)propyl)-4-(3-(piperazin-1-yl)propoxy)benzenesulfonamide;

<165> N-(3-(5,7-dichloro-1H-indol-3-yl)propyl)-4-(3-(4-methylpiperazin-1-yl)propoxy)benzenesulfonamide;

<166> N-(3-(5-chloro-1H-indol-3-yl)propyl)-4-(3-(4,5-dichloro-1H-imidazol-1-yl)propoxy)benzenesulfonamide;

<167> N-(3-(5-chloro-1H-indazol-3-yl)propyl)-4-(3-(4-methylpiperazin-1-yl)propoxy)benzenesulfonamide;

<168> N-(3-(5-chloro-1H-indazol-3-yl)propyl)-4-(3-(piperazin-1-yl)propoxy)benzenesulfonamide;

<169> N-(3-(5-chloro-1H-pyrrolo[2,3-b]pyridin-3-yl)propyl)-4-(3-(4-methylpiperazin-1-yl)propoxy)benzenesulfonamide;

<170> N-(3-(5-chloro-1H-pyrrolo[2,3-b]pyridin-3-yl)propyl)-4-(3-(piperazin-1-yl)propoxy)benzenesulfonamide;

<171> (R)—N-(3-(5-chloro-1H-indol-3-yl)propyl)-4-(2-hydroxy-3-(4-methylpiperazin-1-yl)propoxy)benzenesulfonamide;

<172> (R)—N-(3-(5-chloro-1H-indol-3-yl)propyl)-4-(2-hydroxy-3-(piperazin-1-yl)propoxy)benzenesulfonamide;

<173> (S)—N-(3-(5-chloro-1H-indol-3-yl)propyl)-4-(2-hydroxy-3-(4-methylpiperazin-1-yl)propoxy)benzenesulfonamide;

<174> (S)—N-(3-(5-chloro-1H-indol-3-yl)propyl)-4-(2-hydroxy-3-(piperazin-1-yl)propoxy)benzenesulfonamide;

<175> N-(3-(5-chloro-1H-indol-3-yl)propyl)-4-(3-(4,5-dimethyl-1H-imidazol-1-yl)propoxy)benzenesulfonamide;

<176> N-(3-(5-chloro-1H-indol-3-yl)propyl)-4-(3-(2,4,5-trimethyl-1H-imidazol-1-yl)propoxy)benzenesulfonamide;

<177> N-((6-chloro-2,3,4,9-tetrahydro-1H-carbazol-3-yl)methyl)-4-(3-(4-methylpiperazin-1-yl)propoxy)benzenesulfonamide;

<178> N-((6-chloro-2,3,4,9-tetrahydro-1H-carbazol-3-yl)methyl)-4-(3-(piperazin-1-yl)propoxy)benzenesulfonamide;

<181> N-(2-(2-(5-chloro-1H-indol-3-yl)propan-2-yl)phenyl)-4-(3-(4-methylpiperazin-1-yl)propoxy)benzenesulfonamide;

<183> N-(3-(5,6-dichloro-1H-indol-3-yl)propyl)-4-(3-(piperazin-1-yl)propoxy)benzenesulfonamide;

<184> N-(3-(5,6-dichloro-1H-indol-3-yl)propyl)-4-(3-(4-methylpiperazin-1-yl)propoxy)benzenesulfonamide;

<185> N-(3-(5-chloro-1H-indol-3-yl)propyl)-4-(3-(pyridin-4-yloxy)propyl)benzenesulfonamide;

<186> N-(3-(5-chloro-1H-indol-3-yl)propyl)-4-(3-(4-methylpiperazin-1-yl)propyl)benzenesulfonamide;

<187> N-((6-fluoro-2,3,4,9-tetrahydro-1H-carbazol-3-yl)methyl)-4-(3-(4-methylpiperazin-1-yl)propoxy)benzenesulfonamide;

<188> N-((6-fluoro-2,3,4,9-tetrahydro-1H-carbazol-3-yl)methyl)-4-(3-(piperazin-1-yl)propoxy)benzenesulfonamide;

<189> 4-(3-(4-methylpiperazin-1-yl)propoxy)-N-((2,3,4,9-tetrahydro-1H-carbazol-3-yl)methyl)benzenesulfonamide;

<190> 4-(3-(piperazin-1-yl)propoxy)-N-((2,3,4,9-tetrahydro-1H-carbazol-3-yl)methyl)benzenesulfonamide.

6. A preparation method of a compound represented by formula 1 comprising a step of preparing a compound represented by formula 1 by reacting a compound represented by formula 2 with a compound represented by formula 3 as shown in reaction formula 1:

[Reaction Formula 1]

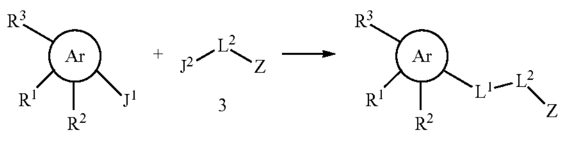

2 3 1 wherein in reaction formula 1, Ar, $R^1$, $R^2$, $R^3$, $L^1$, $L^2$ and Z are as defined in formula 1 of claim 1, $J^1$ is chlorosulfone; and $J^2$ is amine.

7. A pharmaceutical composition comprising a compound represented by formula 1, a stereoisomer thereof or a pharmaceutically acceptable salt thereof of claim 1 as an active ingredient for the treatment of Pin-1 related cancer, Pin-1 related inflammatory disease or Pin-1 related metabolic disease.

8. The pharmaceutical composition according to claim 7, wherein the compound inhibits Pin1 (Peptidyl-prolyl cis-trans isomerase NIMA-interacting 1).

9. The pharmaceutical composition according to claim 7, wherein the Pin-1 related cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell cancer, ovarian epithelial carcinoma, ovarian germ cell carcinoma, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal cancer, kidney cancer, heart Cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal interstitial cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, rectal cancer, rectal carcinoid tumor, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer and thymus cancer.

10. The pharmaceutical composition according to claim 7, wherein the Pin-1 related inflammatory disease is at least one selected from the group consisting of arthritis, encephalomyelitis, meningitis, peritonitis, osteomyelitis, encephalitis, ankylosing spondylitis, vasculitis, uveitis, ileitis, atherosclerosis, myositis, leukocyte damage, inflammatory bowel disease, ulcerative colitis, retinal detachment, retinitis pigmentosa, macular degeneration, pancreatitis, atopic dermatitis, gout, vasculitis, non-alcoholic steatohepatitis, primary sclerosing cholangitis, nephritis, intraperitoneal disease, sepsis, systemic inflammatory reaction syndrome, myocardial infarction, allergic disease, asthma, atopic dermatitis, Wegener's granulomatosis, pulmonary sarcoidosis, Behcet's disease, chronic obstructive pulmonary disease and periodontitis.

11. The pharmaceutical composition according to claim 7, wherein the Pin-1 related metabolic disease is at least one selected from the group consisting of obesity, diabetes, hypertension, hyperlipidemia, hypercholesterolosis, arteriosclerosis, fatty liver, gout, stroke and heart disease.

12. A method for treating Pin-1 related cancer, Pin-1 related inflammatory disease or Pin-1 related metabolic disease comprising administering a compound represented by formula 1 of claim 1, a stereoisomer thereof or a pharmaceutically acceptable salt thereof to a subject in need thereof.

13. The method according to claim 12, wherein the compound inhibits Pin1 (Peptidyl-prolyl cis-trans isomerase NIMA-interacting 1).

14. The method according to claim 12, wherein the Pin-1 related cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell cancer, ovarian epithelial carcinoma, ovarian germ cell carcinoma, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal cancer, kidney cancer, heart Cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal interstitial cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, rectal cancer, rectal carcinoid tumor, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer and thymus cancer.

15. The method according to claim 12, wherein the Pin-1 related inflammatory disease is at least one selected from the group consisting of arthritis, encephalomyelitis, meningitis, peritonitis, osteomyelitis, encephalitis, ankylosing spondylitis, vasculitis, uveitis, ileitis, atherosclerosis, myositis, leukocyte damage, inflammatory bowel disease, ulcerative colitis, retinal detachment, retinitis pigmentosa, macular degeneration, pancreatitis, atopic dermatitis, gout, vasculitis, non-alcoholic steatohepatitis, primary sclerosing cholangitis, nephritis, intraperitoneal disease, sepsis, systemic inflammatory reaction syndrome, myocardial infarction, allergic disease, asthma, atopic dermatitis, Wegener's granulomatosis, pulmonary sarcoidosis, Behcet's disease, chronic obstructive pulmonary disease and periodontitis.

16. The method according to claim 12, wherein the Pin-1 related metabolic disease is at least one selected from the group consisting of obesity, diabetes, hypertension, hyperlipidemia, hypercholesterolosis, arteriosclerosis, fatty liver, gout, stroke and heart disease.

* * * * *